(12) United States Patent
Karafin et al.

(10) Patent No.: US 11,789,288 B2
(45) Date of Patent: *Oct. 17, 2023

(54) LIGHT FIELD VISION-CORRECTION DEVICE

(71) Applicant: LIGHT FIELD LAB, INC., San Jose, CA (US)

(72) Inventors: Jonathan Sean Karafin, San Jose, CA (US); Brendan Elwood Bevensee, San Jose, CA (US)

(73) Assignee: Light Field Lab, Inc., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/075,696

(22) Filed: Dec. 6, 2022

(65) Prior Publication Data
US 2023/0176395 A1 Jun. 8, 2023

Related U.S. Application Data

(63) Continuation of application No. 17/391,454, filed on Aug. 2, 2021, now Pat. No. 11,556,015, which is a
(Continued)

(51) Int. Cl.
*G02B 30/10* (2020.01)
*G02B 30/26* (2020.01)
(Continued)

(52) U.S. Cl.
CPC ............ *G02B 30/10* (2020.01); *A61B 3/032* (2013.01); *A61B 3/036* (2013.01); *A61M 21/00* (2013.01);
(Continued)

(58) Field of Classification Search
CPC ........ G02B 30/10; G02B 30/26; G02B 30/27; G02B 6/0005; B33Y 30/00; B33Y 50/02;
(Continued)

(56) References Cited

U.S. PATENT DOCUMENTS

| 8,149,265 B2 | 4/2012 | Smalley et al. |
| 10,331,207 B1 | 6/2019 | Simmons |

(Continued)

FOREIGN PATENT DOCUMENTS

| CN | 104618710 A | 5/2015 |
| CN | 104837003 A | 8/2015 |

(Continued)

OTHER PUBLICATIONS

CN201980018333.8 First Office Action of the Chinese Patent Office dated Jul. 23, 2021.
(Continued)

*Primary Examiner* — Sunghyoun Park
(74) *Attorney, Agent, or Firm* — Charles C. Yang

(57) ABSTRACT

Devices utilizing holographic 4D plenoptic capture and display technologies to generate a light field function to provide glasses-less vision correction for observers with imperfect vision, and to project an image according to the generated light field function, and methods for calibrating a four-dimensional light field for a user with an uncorrected visual acuity.

23 Claims, 60 Drawing Sheets

Related U.S. Application Data continuation of application No. 16/634,533, filed as application No. PCT/US2019/013410 on Jan. 13, 2019, now Pat. No. 11,163,176.

(60) Provisional application No. 62/617,293, filed on Jan. 14, 2018.

(51) Int. Cl.

| | |
|---|---|
| *A61B 3/032* | (2006.01) |
| *A61B 3/036* | (2006.01) |
| *G03H 1/00* | (2006.01) |
| *G03H 1/26* | (2006.01) |
| *H04N 13/344* | (2018.01) |
| *G02B 30/27* | (2020.01) |
| *F21V 8/00* | (2006.01) |
| *B33Y 30/00* | (2015.01) |
| *B33Y 50/02* | (2015.01) |
| *B29C 64/282* | (2017.01) |
| *B29C 64/232* | (2017.01) |
| *B29C 64/255* | (2017.01) |
| *B29C 64/393* | (2017.01) |
| *B29C 64/236* | (2017.01) |
| *B29C 64/241* | (2017.01) |
| *B29C 64/135* | (2017.01) |
| *A61M 21/00* | (2006.01) |
| *G06F 3/01* | (2006.01) |
| *G06F 3/03* | (2006.01) |
| *G06F 3/04815* | (2022.01) |
| *G06T 19/00* | (2011.01) |

(52) U.S. Cl.
CPC .......... *B29C 64/135* (2017.08); *B29C 64/232* (2017.08); *B29C 64/236* (2017.08); *B29C 64/241* (2017.08); *B29C 64/255* (2017.08); *B29C 64/282* (2017.08); *B29C 64/393* (2017.08); *B33Y 30/00* (2014.12); *B33Y 50/02* (2014.12); *G02B 6/0005* (2013.01); *G02B 30/26* (2020.01); *G02B 30/27* (2020.01); *G03H 1/0005* (2013.01); *G03H 1/268* (2013.01); *G06F 3/011* (2013.01); *G06F 3/0325* (2013.01); *G06F 3/04815* (2013.01); *G06T 19/006* (2013.01); *H04N 13/344* (2018.05); *A61B 2503/12* (2013.01); *A61M 2021/005* (2013.01); *G03H 2222/34* (2013.01); *G03H 2223/16* (2013.01)

(58) Field of Classification Search
CPC ... B29C 64/282; B29C 64/232; B29C 64/255; B29C 64/393; B29C 64/236; B29C 64/241; B29C 64/135; H04N 13/344; A61B 3/032; A61B 3/036; A61B 2503/12; A61M 21/00; A61M 2021/005; G03H 1/0005; G03H 1/268; G03H 2222/34; G03H 2223/16; G06F 3/011; G06F 3/0325; G06F 3/04815; G06T 19/006

See application file for complete search history.

(56) References Cited

U.S. PATENT DOCUMENTS

| | | |
|---|---|---|
| 10,432,919 B2 | 10/2019 | Lapstun |
| 10,560,689 B2 | 2/2020 | Lapstun |
| 2006/0028400 A1 | 2/2006 | Lapstun et al. |
| 2007/0285554 A1 | 12/2007 | Givon |
| 2008/0144174 A1 | 6/2008 | Lucente et al. |
| 2008/0170293 A1 | 7/2008 | Lucente et al. |
| 2009/0040294 A1 | 2/2009 | Smalley et al. |
| 2011/0012895 A1 | 1/2011 | Lucente et al. |
| 2011/0027766 A1 | 2/2011 | Yoo et al. |
| 2011/0157180 A1 | 6/2011 | Burger et al. |
| 2011/0164065 A1 | 7/2011 | Mate et al. |
| 2012/0327490 A1 | 12/2012 | Barbastathis et al. |
| 2013/0120980 A1 | 5/2013 | Eichenholz |
| 2014/0035959 A1 | 2/2014 | Lapstun |
| 2014/0036361 A1* | 2/2014 | Woodgate ............... G02B 30/33 385/9 |
| 2014/0293385 A1 | 10/2014 | Smithwick |
| 2014/0300694 A1 | 10/2014 | Smalley et al. |
| 2014/0300695 A1 | 10/2014 | Smalley et al. |
| 2015/0201186 A1 | 7/2015 | Smithwick |
| 2015/0277378 A1 | 10/2015 | Smithwick et al. |
| 2016/0042501 A1 | 2/2016 | Huang et al. |
| 2016/0103419 A1 | 4/2016 | Callagy et al. |
| 2016/0139402 A1 | 5/2016 | Lapstun |
| 2016/0170372 A1 | 6/2016 | Smithwick |
| 2016/0262608 A1* | 9/2016 | Krueger ................. G16H 40/63 |
| 2016/0274539 A1 | 9/2016 | Smithwick |
| 2016/0282808 A1 | 9/2016 | Smalley |
| 2017/0060399 A1 | 3/2017 | Hough et al. |
| 2017/0214907 A1 | 7/2017 | Lapstun |
| 2017/0289530 A1 | 10/2017 | Smithwick et al. |
| 2017/0347874 A1 | 12/2017 | Novik |
| 2018/0008141 A1* | 1/2018 | Krueger ............... A61B 3/0025 |
| 2018/0063519 A1 | 3/2018 | Smithwick et al. |
| 2018/0084232 A1 | 3/2018 | Belenkii et al. |
| 2018/0084245 A1 | 3/2018 | Lapstun |
| 2019/0011621 A1* | 1/2019 | Karafin ............... G02B 27/0955 |

FOREIGN PATENT DOCUMENTS

| | | |
|---|---|---|
| JP | 2009530661 A | 8/2009 |
| WO | 2008048360 A2 | 4/2008 |
| WO | 2017127897 A1 | 8/2017 |

OTHER PUBLICATIONS

CN201980018333.8 Second Office Action of the Chinese Patent Office dated Feb. 15, 2022.
EP-19739114.7 European Extended Search Report of European Patent Office dated Oct. 15, 2021.
International Search Report and Written Opinion of PCT/US2019/013410 dated Apr. 1, 2019.
Levoy et al., "Light Field rendering", Computer Graphics and Interactive Techniques, ACM, 2 Penn Plaza, Suite 701 New York NY 10121-0701 USA, Aug. 1, 1996 (Aug. 1, 1996), pp. 31-42.
Pamplona et al., "Tailored displays to compensate for visual aberrations", ACM Transactions on Graphics, vol. 31, No. 4, Jul. 1, 2012 (Jul. 1, 2012), pp. 1-12.
Pamplona et al., "Tailored Displays to Compensate for Visual Aberrations", ACM Transactions on Graphics, vol. 31, No. 4, Article 81, Publication Date: Jul. 2012.

* cited by examiner

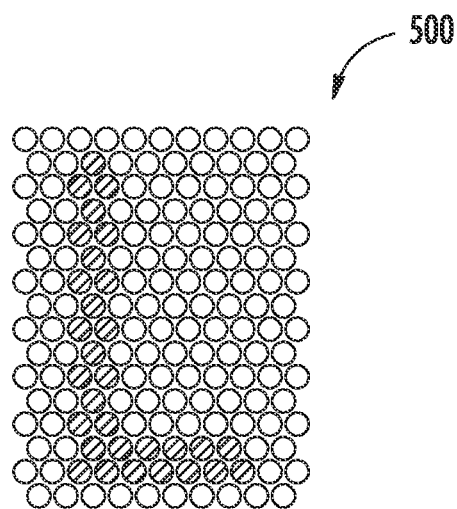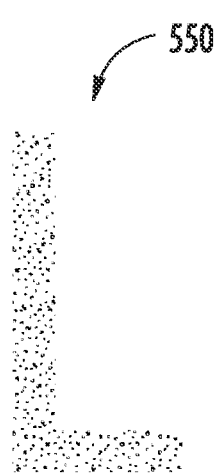
FIG. 5A  FIG. 5B
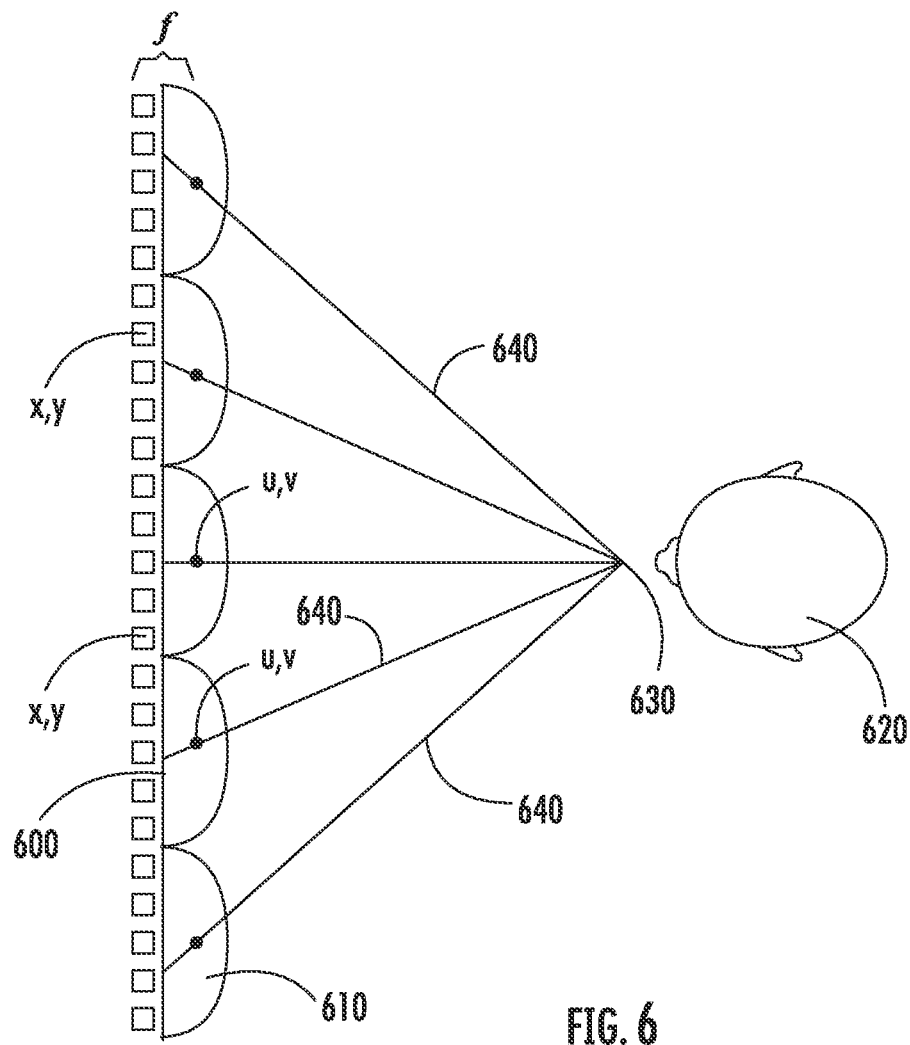
FIG. 6

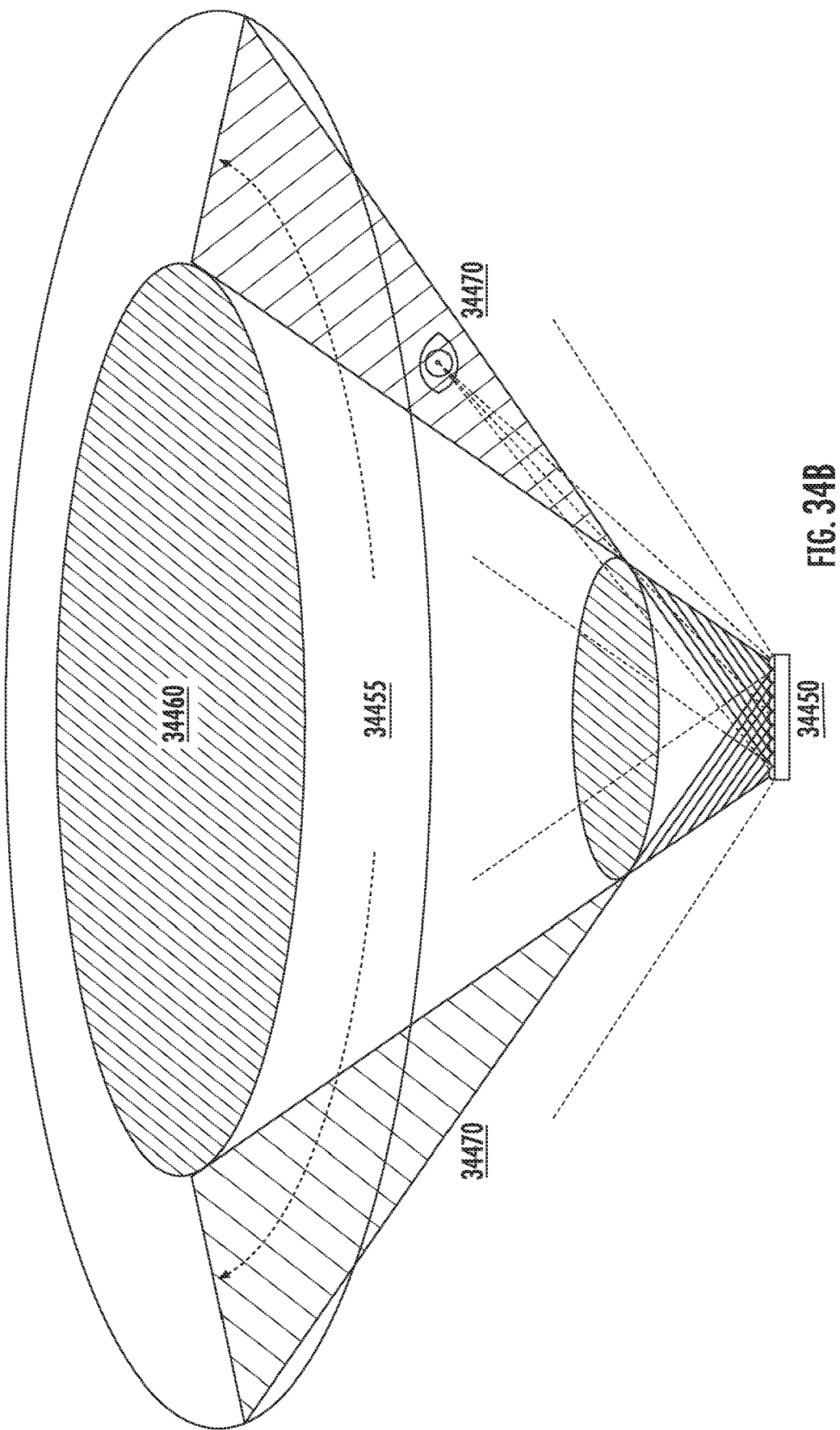

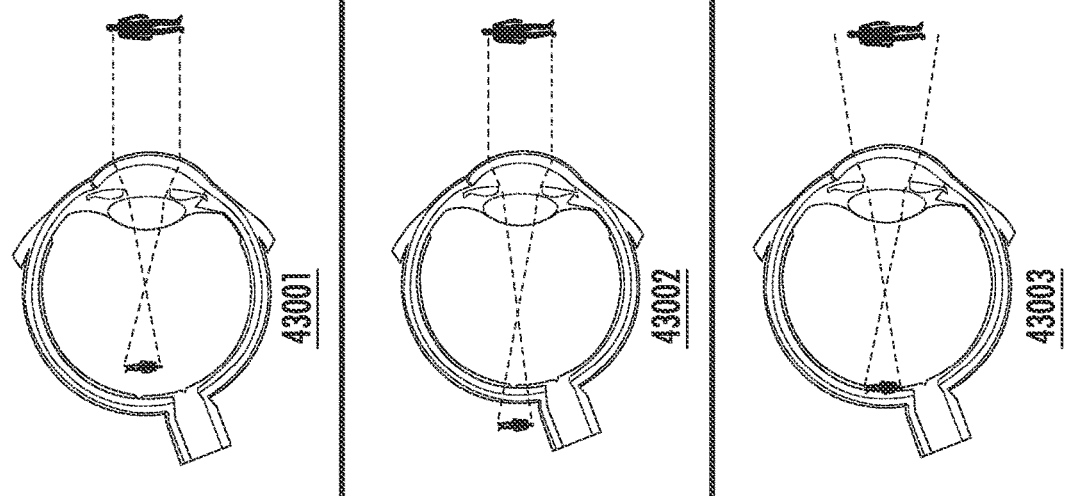
FIG. 43

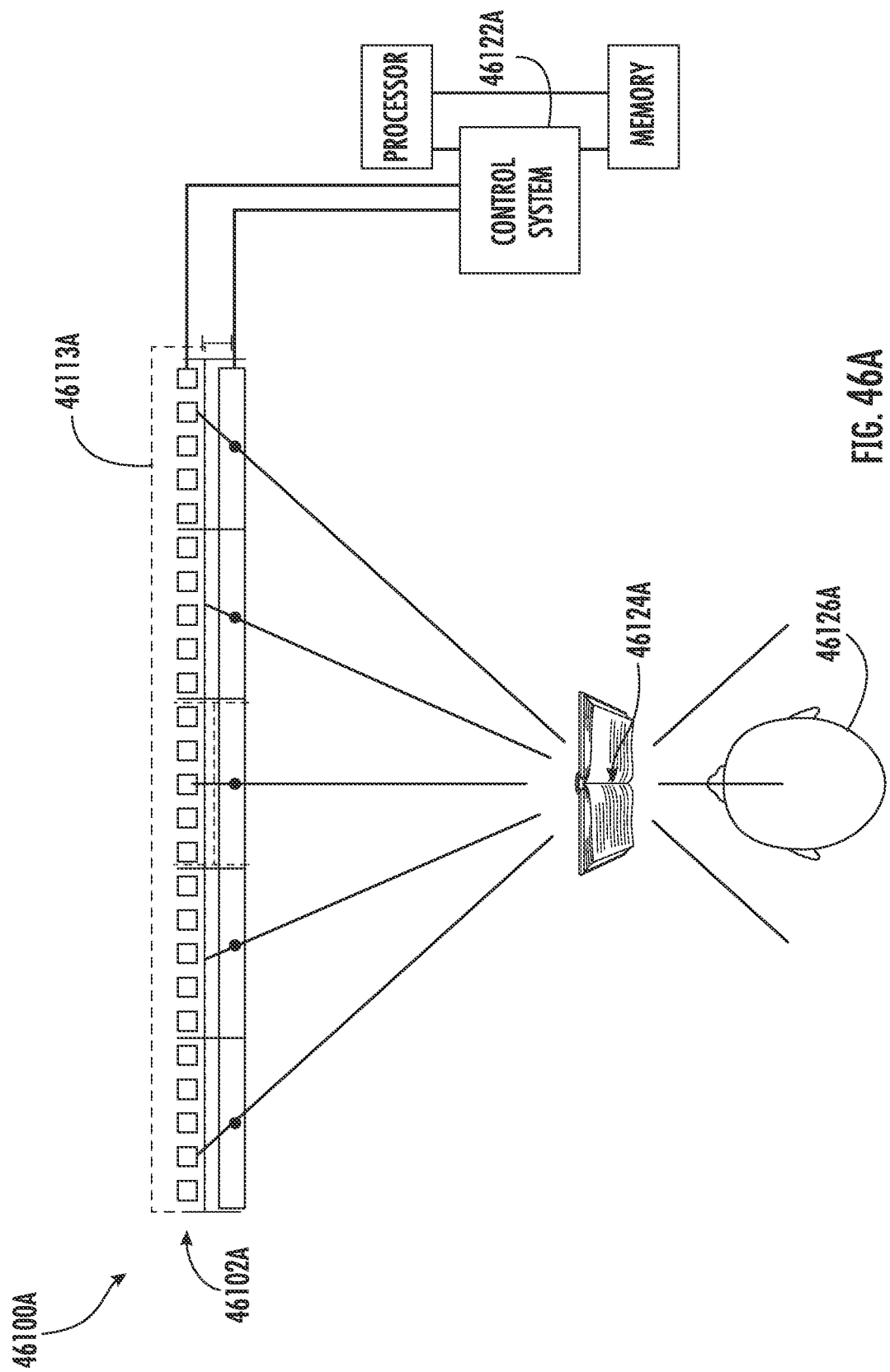

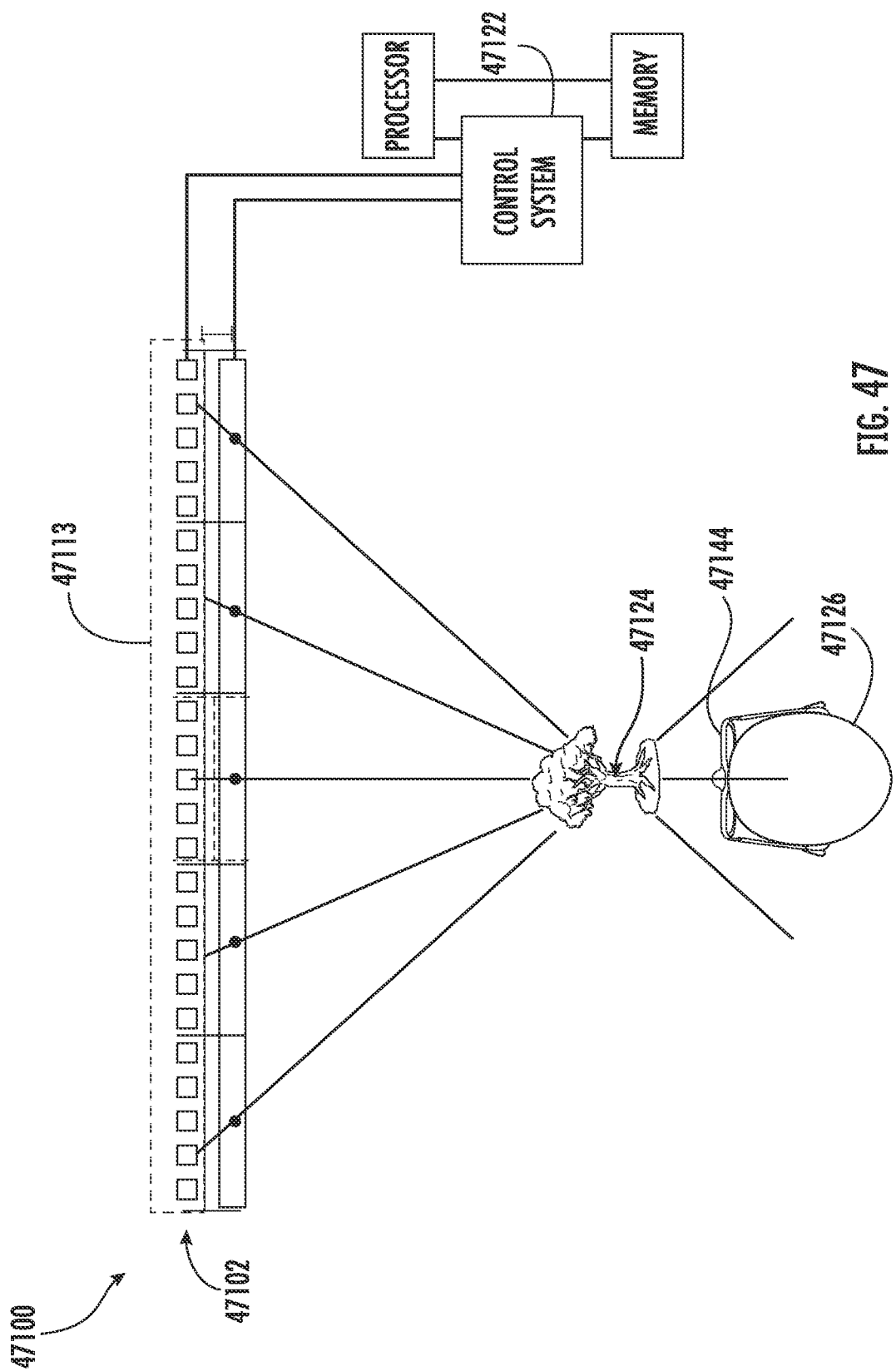

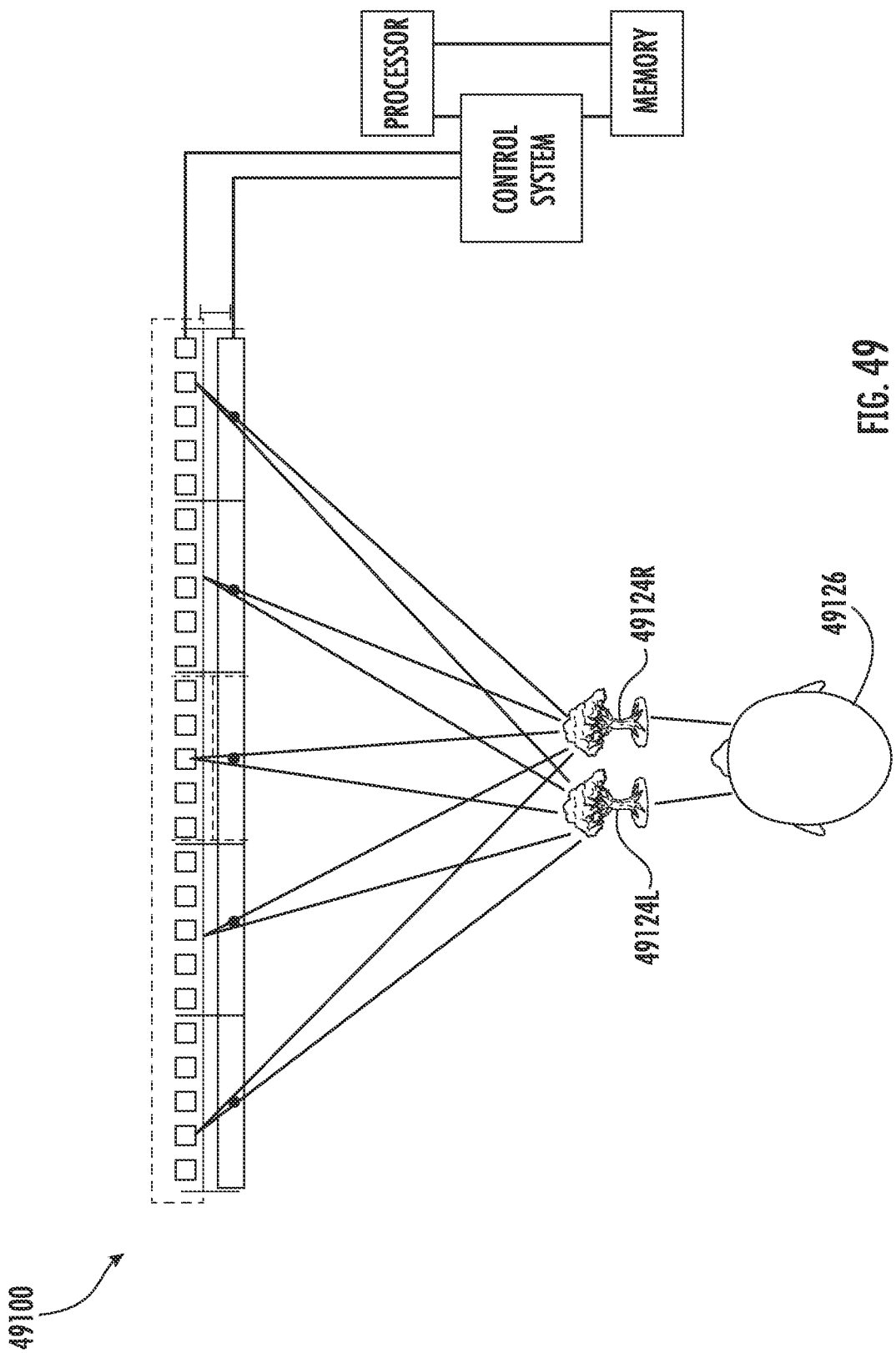

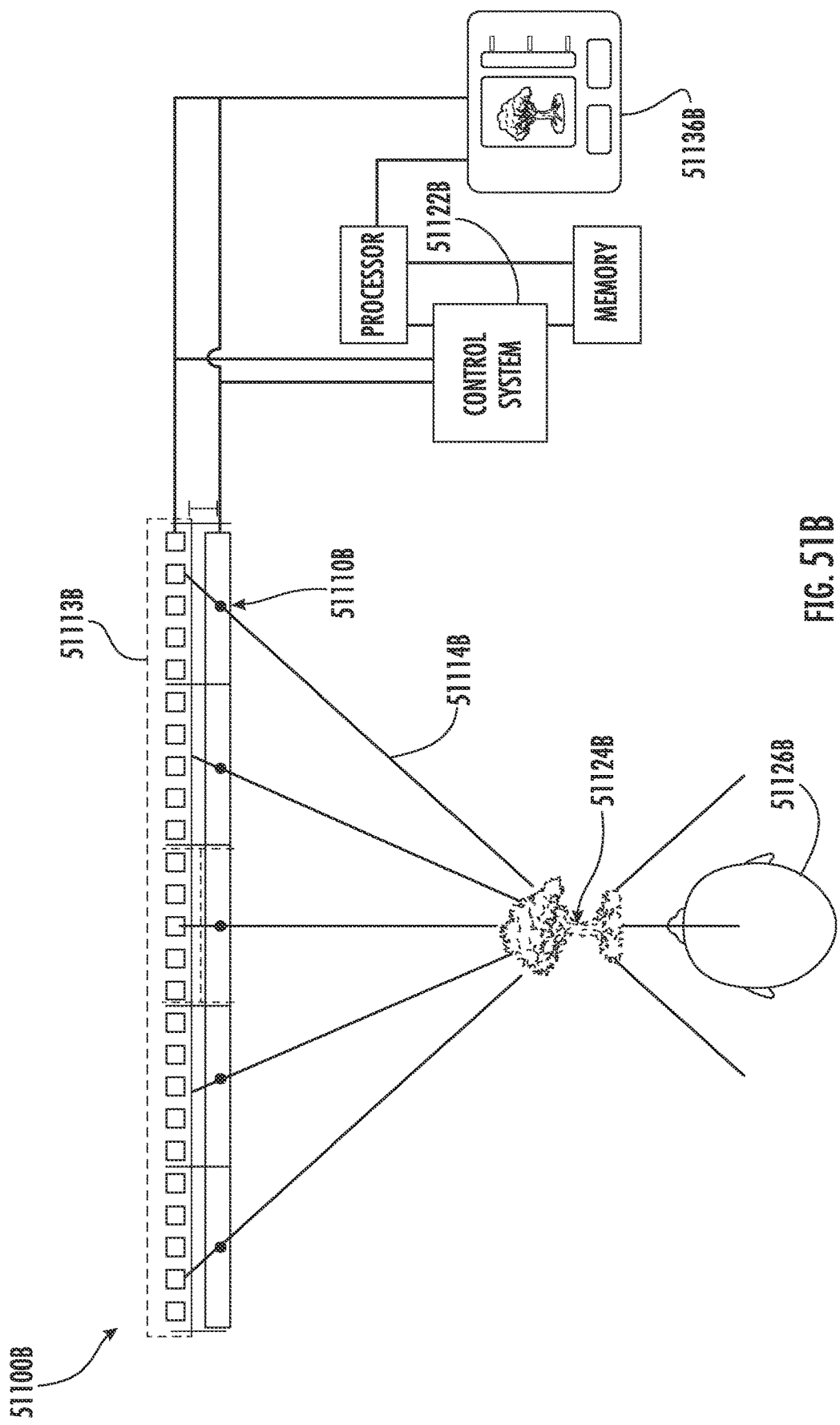

LIGHT FIELD VISION-CORRECTION DEVICE

CROSS-REFERENCE TO RELATED APPLICATIONS

This application claims the benefit of priority to U.S. Provisional Patent Application No. 62/617,293, entitled "Novel Application of Holographic and Light Field Technology," filed Jan. 14, 2018, which are both herein incorporated by reference in their entirety.

TECHNICAL FIELD

This disclosure generally relates to light field energy systems, and more specifically, to systems incorporating novel syntheses and applications of holographic and light field technology to calibrate a light field display system for the vision of individual users.

BACKGROUND

The dream of an interactive virtual world within a "holodeck" chamber as popularized by Gene Roddenberry's Star Trek and originally envisioned by author Alexander Moszkowski in the early 1900s has been the inspiration for science fiction and technological innovation for nearly a century. However, no compelling implementation of this experience exists outside of literature, media, and the collective imagination of children and adults alike.

SUMMARY

Disclosed are light field energy devices and systems having novel syntheses and application of holographic and light field technology for calibrating a light field display system for the vision of individual users, and methods thereof.

In one embodiment, a vision-correction device includes a light-source system able to provide light to a plurality of light locations and having a plurality of light sources, and a light-directing system having an array of waveguides able to direct light emitted by the plurality of light sources along a plurality of propagation paths where each propagation path extends through one of the plurality of light locations. A first waveguide of the array of waveguides is able to direct light from a first light location through the first waveguide along a first propagation path of the plurality of propagation paths where the first propagation path extends from the first waveguide in a unique direction determined at least by the first light location. In one embodiment, the device further includes a control system able to operate the plurality of light sources to direct light through the light-directing system to project a first holographic object along the plurality of propagation paths according to a four-dimensional ("4D") light field function that has been determined to account for an uncorrected visual acuity of a first user, whereby the first holographic object is perceivable by the first user with a first corrected visual acuity.

In another embodiment, the first waveguide defines a two-dimensional (2D) spatial coordinate, and where the unique direction determined at least by the first light location includes a two-dimensional angular coordinate, where the 2D spatial coordinate and the 2D angular coordinate form a 4D light field coordinate set. In one embodiment, the control system is further able to operate the plurality of light sources to direct light through the light-directing system to project a first 2D object according to the 4D light field function that has been determined to account for the uncorrected visual acuity of the first user, where the projected object is perceivable by the first user with the first corrected visual acuity. In some embodiments, the first 2D object includes a page of a book or a Snellen eye chart.

In one embodiment, the control system is further able to operate the plurality of light sources to direct light through the light-directing system to project a first stereoscopic object according to the 4D light field function that has been determined to account for the uncorrected visual acuity of the first user, where the first stereoscopic object is perceivable by the first user with the first corrected visual acuity. In some embodiments, the 4D light field function accounts for myopia in the uncorrected visual acuity of the first user, hyperopia in the uncorrected visual acuity of the first user, astigmatism in the uncorrected visual acuity of the first user, presbyopia in the uncorrected visual acuity of the first user, a plurality of visual imperfections in the uncorrected visual acuity of the first user, among others.

In one embodiment, the 4D light field function accounts for the uncorrected visual acuity of the first user, where the uncorrected visual acuity is correctable by an optical power correction. In another embodiment, the uncorrected visual acuity includes a plurality of uncorrected visual sub-acuities of the first user where the first user perceives all visible objects equidistant to the first user with the same uncorrected visual sub-acuity, and where the 4D light field function further simultaneously accounts for the plurality of uncorrected visual sub-acuities by a plurality of simultaneous optical power corrections, each optical power correction corresponding to an uncorrected visual sub-acuity. In one embodiment, the light directed along the first propagation path through the first waveguide substantially fills a first aperture of the first waveguide. In another embodiment, the light-directing system further includes a first light-inhibiting element positioned to limit propagation of light along a portion of the plurality of propagation paths that do not extend through the first aperture. In yet another embodiment, the first light-inhibiting element includes a baffle structure for attenuating or modifying the portion of propagation paths that do not extend through the first aperture.

In one embodiment, the light-directing system further includes a second waveguide of the array of waveguides able to direct light from a second light location through the second waveguide along a second propagation path of the plurality of propagation paths, where the second propagation path extends from the second waveguide in a unique direction determined at least by the second light location.

In one embodiment, the light directed along the second propagation path through the second waveguide substantially fills a second aperture of the second waveguide, and the light-directing system further includes a second light-inhibiting element positioned to limit propagation of light along a portion of propagation paths that do not extend through the second aperture. In one embodiment, the second light-inhibiting element includes a baffle structure for attenuating or modifying propagation paths. In one embodiment, the light directed along the first propagation path converges with light directed along the second propagation path.

In one embodiment, the vision-correction device further includes an energy-sensing system able to sense energy data, and a tracking processor able to determine the location of the first user based on the energy data received from the energy-sensing system. In some embodiments, the 4D light field function has also been determined to account for the location of the first user so the first holographic object is perceivable by the first user with the first corrected visual acuity when the first user is at one of a continuum of distances from the device for vision correction. In other embodiments, the tracking processor tracks the location of the eyes of the one or more users. In some other embodiments, the uncorrected visual acuity includes a left uncorrected visual acuity for the left eye of a first user, and a right uncorrected visual acuity for the right eye of a first user, where the 4D light field function accounts for the left uncorrected visual acuity and the right uncorrected visual acuity.

In one embodiment, the control system is able to operate the plurality of light sources to direct light through the light-directing system to project a second holographic object according to a second 4D light field function that has been determined to account for an uncorrected visual acuity of a second user, whereby the second holographic object is perceivable by the second user with a second corrected visual acuity.

In one embodiment, the control system is configured to project the first holographic object to a first-viewing zone and project the second holographic object to a second-viewing zone. In one embodiment, the location of the first-viewing zone and the location of the second-viewing zone are determined by the location of the first user and the second user. In one embodiment, the tracking processor is able to dynamically track the location of the first and second users based on energy data received from an energy-sensing system, and where the location of the first-viewing zone follows the movement of the first user and the location of the second-viewing zone follows the movement of the second user.

In one embodiment, the vision-correction device further includes an energy-sensing system able to sense energy data, and a tracking processor configured to determine the location of the first and second users based on the energy data received from the energy-sensing system. In one embodiment, the energy-sensing system includes a plurality of cameras that capture image data, and where the tracking processor further analyzes the image data to determine the location of the first and second users. In one embodiment, the second 4D light field function has also been determined to account for the location of the second user so the second holographic object is perceivable by the second user with the second corrected visual acuity when the second user is at one of a continuum of distances from the device for vision correction. In one embodiment, the energy-sensing system includes at least one depth sensor, and where the tracking processor further analyzes data generated by the depth sensor to determine the location of the first and second users. In one embodiment, the energy-sensing system is able to generate data describing a 4D light field by sensing light received at an interface, and where the tracking processor further analyzes the data describing a 4D light field to determine the location of the first and second users. In some embodiments, the tracking processor tracks the location of the eyes of the first and second users. In other embodiments, the uncorrected visual acuity includes a left uncorrected visual acuity for the left eye of the first user, and a right uncorrected visual acuity for the right eye of the first user, and the 4D light field function further simultaneously accounts for the left uncorrected visual acuity and for the right uncorrected visual acuity.

In one embodiment, the vision-correction device further includes the light-source system having a relay system, where the relay system includes one or more relay elements, where each of the one or more relay elements includes a first surface and a second surface, and where the plurality of light sources are disposed at the second surface of the one or more relay elements, the one or more relay elements able to direct light emitted by the plurality of light sources through the first and second surfaces to the plurality of light locations.

In one embodiment, the second surfaces of the one or more relay elements are arranged to form a singular seamless energy surface. In another embodiment, the device further includes a light-sensing system able to generate data describing a 4D light field by sensing light received at an interface. In one embodiment, the light-sensing system and the light-directing system form a bi-directional energy surface able to simultaneously sense energy and project the first holographic object. In another embodiment, the device further includes a memory in communication with a processor and where the processor instructs the memory to store the 4D light field function in the memory.

In one embodiment, a device for determining a visually corrective 4D function includes a light-source system able to provide light to a plurality of light locations and having a plurality of light sources, a light-directing system having an array of waveguides able to direct light from the plurality of light sources along a plurality of propagation paths where each propagation path extends through one of the plurality of light locations, and where a first waveguide is able to direct light from a first light location through the first waveguide along a first propagation path of the plurality of propagation paths where the first propagation path extends from the first waveguide in a unique direction determined at least by the first light location. The device further includes a control system in communication with the plurality of light sources able to operate the plurality of light sources to direct light through the light-directing system to project a test object along the plurality of propagation paths, an interactive user interface able to receive a progression of user inputs from a first user ranking the visual clarity of the test object, and a processor able to generate a 4D light field function from the progression of user inputs where the 4D light field function is determined to account for a first uncorrected visual acuity of the first user.

In one embodiment, the control system is able to iteratively adjust the test object in a progression of successive diopter and astigmatism corrections determined by the progression of user inputs ranking the visual clarity of the test object. In another embodiment, the first test object includes a plurality of sub-objects perceivable to the first user at a corresponding plurality of perceived distances, where the progression of user inputs from the first user ranks the visual clarity of the plurality of sub-objects.

In some embodiments, the test object includes a 2D image, a page of a book, a Snellen eye chart, a stereoscopic image, among others. In other embodiments, light is directed from the first waveguide that defines two-dimensional (2D) spatial coordinate, and where the unique direction determined at least by the first light location includes a two-dimensional angular coordinate, where the 2D spatial coordinate and the 2D angular coordinate form a four-dimensional (4D) coordinate set. In one embodiment, light directed along the first propagation path through the first waveguide substantially fills a first aperture of the first waveguide. In some embodiments, the light-directing system further includes a light-inhibiting element positioned to limit propagation of light along a portion of propagation paths that do not extend through the first aperture. In another embodiment, the light-inhibiting element includes a baffle structure for attenuating or modifying propagation paths.

In some embodiment, the light-directing system further includes a second waveguide able to direct light from a second light location through the second waveguide along a second propagation path of the plurality of propagation paths where the second propagation path extends from the second waveguide in a unique direction determined at least by the second light location. In other embodiments, the light directed along the second propagation path through the second waveguide substantially fills a second aperture of the second waveguide, and the light-directing system further includes a second light-inhibiting element positioned to limit propagation of light along a portion of propagation paths that do not extend through the second aperture.

In one embodiment, the second light-inhibiting element includes a baffle structure for attenuating or modifying propagation paths. In one embodiment, light directed along the first propagation path converges with light directed along the second propagation path. In some embodiments, the light-source system further includes a relay system, where the relay system includes one or more relay elements, where each of the one or more relay elements includes a first surface and a second surface, where the plurality of light locations are disposed at the second surface of the one the one or more relay elements and the relay elements are able to direct light emitted by the plurality of light sources through the first and second surfaces to the plurality of light locations.

In one embodiment, the second surfaces of the one or more relay elements are arranged to form a singular seamless energy surface. In another embodiment, the device further includes a memory in communication with the processor and where the processor is configured to instruct the memory to store the 4D light field function. In yet another embodiment, the processor is able to instruct the memory to associate at least one of a user name of the first user, a user profile of the first user, and a user identification of the first user with the 4D light field function stored in the memory.

In one embodiment, the processor is able to instruct the memory to store at least one additional 4D light field function where the at least one additional 4D light field function is determined to account for a first uncorrected visual acuity of at least one additional user, and where the processor is configured to instruct the memory to associate at least one of a user name of the least one additional user, a user profile of the least one additional user, and a user identification of the least one additional user with the least one additional 4D light field function stored in the memory.

In one embodiment, the control system is further able to operate the plurality of light sources to direct light through the light-directing system to project a first holographic object according to the 4D light field function, whereby the first holographic object is perceivable by the first user with a first corrected visual acuity. In some embodiments, the device further includes an energy-sensing system able to sense energy data, and a tracking processor able to determine the location of the first user based on the energy data received from the energy-sensing system.

In one embodiment, the 4D light field function has also been determined to account for the location of the first user so the first holographic object is perceivable by the first user with the first corrected visual acuity when the first user is at one of a continuum of distances from the device for vision correction. In another embodiment, the tracking processor tracks the location of the eyes of the one or more users. In yet another embodiment, the uncorrected visual acuity includes a left uncorrected visual acuity for the left eye of a first user, and a right uncorrected visual acuity for the right eye of a first user, where the 4D light field function accounts for the left uncorrected visual acuity and the right uncorrected visual acuity.

In one embodiment, the control system is able to operate the plurality of light sources to direct light through the light-directing system to project a second holographic object according to a second 4D light field function that has been determined to account for an uncorrected visual acuity of a second user, whereby the second holographic object is perceivable by the second user with a second corrected visual acuity. In another embodiment, the control system is configured to project the first holographic object to a first-viewing zone and project the second holographic object to a second-viewing zone. In yet another embodiment, the location of the first-viewing zone and the location of the second-viewing zone are determined by the location of the first user and the second user. In one embodiment, a tracking processor is able to dynamically track the location of the first and second users based on energy data received from an energy-sensing system, and where the location of the first-viewing zone follows the movement of the first user and the location of the second-viewing zone follows the movement of the second user.

In one embodiment, the device further includes an energy-sensing system able to sense energy data related to the location of the first and second users, and a tracking processor able to determine the location of the first and second users based on the energy data received from the energy-sensing system. In one embodiment, the energy-sensing system includes a plurality of cameras that capture image data, and where the tracking processor analyzes the image data to determine the location of the first and second users. In another embodiment, the second 4D light field function has also been determined to account for the location of the second user so the second holographic object is perceivable by the second user with the second corrected visual acuity when the second user is at one of a continuum of distances from the device for vision correction.

In one embodiment, the energy-sensing system includes at least one depth sensor, and where the tracking processor analyzes data generated by the depth sensor to determine the location of the first and second users. In another embodiment, the energy-sensing system is able to generate data describing a 4D light field by sensing light received at an interface, and where the tracking processor analyzes the data describing a 4D light field to determine the location of the first and second users.

In one embodiment, the tracking processor tracks the location of the eyes of the first and second users. In another embodiment, the uncorrected visual acuity includes a left uncorrected visual acuity for the left eye of the first user, and a right uncorrected visual acuity for the right eye of the first user, and where the 4D light field function simultaneously accounts for the left uncorrected visual acuity and for the right uncorrected visual acuity.

In one embodiment, the light-source system includes a relay system, where the relay system includes one or more relay elements, where each of the one or more relay elements includes a first surface and a second surface, and where the plurality of light sources are disposed at the second surface of the one or more relay elements, the one or more relay elements configured to direct light emitted by the plurality of light sources through the first and second surfaces to the plurality of light locations.

In one embodiment, the second surfaces of the one or more relay elements are arranged to form a singular seamless energy surface. In another embodiment, the device further includes a light-sensing system able to generate data describing a 4D light field by sensing light received at an interface. In one embodiment, the light-sensing system and the light-directing system form a bi-directional energy surface able to simultaneously sense energy and project the first holographic object.

In one embodiment, the control system is further able to operate the plurality of light sources to direct light through the light-directing system to project a first 2D object along the plurality of propagation paths according to the 4D light field function that has been determined to account for the uncorrected visual acuity of the first user, whereby the first 2D object is perceivable by the first user with the first corrected visual acuity.

In some embodiments, the first 2D object includes a page of a book, or a Snellen eye chart, among others. In other embodiments, the control system is further able to operate the plurality of light sources to direct light through the light-directing system to project a first stereoscopic object according to the 4D light field function that has been determined to account for the uncorrected visual acuity of the first user, whereby the first stereoscopic object is perceivable by the first user with the first corrected visual acuity.

In some embodiments, the 4D light field function accounts for myopia in the uncorrected visual acuity of the first user, hyperopia in the uncorrected visual acuity of the first user, astigmatism in the uncorrected visual acuity of the first user, presbyopia in the uncorrected visual acuity of the first user, among others. In other embodiments, the 4D light field function simultaneously accounts for a plurality of visual imperfections in the uncorrected visual acuity of the first user.

In one embodiment, the 4D light field function accounts for the uncorrected visual acuity of the first user, where the uncorrected visual acuity is correctable by an optical power correction. In another embodiment, the uncorrected visual acuity includes a plurality of uncorrected visual sub-acuities of the first user where the first user perceives all visible objects equidistant to the user with the same the visual sub-acuity, and where the 4D light field function simultaneously accounts for the plurality of uncorrected visual sub-acuities by a plurality of simultaneous optical power corrections, each optical power correction corresponding to an uncorrected visual sub-acuity.

In one embodiment, a method for calibrating a four dimensional (4D") light field display to project a holographic object according to a 4D light field function for a user with an uncorrected visual acuity includes the steps of: projecting a test object, iteratively adjusting the projection of the test object according to a progression of user inputs evaluating the clarity of the test object, generating a 4D light field function according to the progression of user inputs evaluating the clarity of the test objects that compensates for vision problems of the user, and using the 4D light field function to project a holographic object calibrated to correct vision problems of the user.

In one embodiment, adjusting the test object step includes a progression of successive diopter and astigmatism corrections. In some embodiments, the test object includes a two-dimensional ("2D") object or a Snellen eye chart, among others. In one embodiment, the method includes the user evaluating the clarity of the test object by reading lines on the Snellen eye chart. In some embodiments, the test object includes a plurality of sub-objects, each sub-object being projected at a unique depth in the user's field of view.

In other embodiments, evaluating the clarity of the test object includes evaluating the clarity of each sub-object.

In some embodiments, the 4D light field function accounts for a user with myopia, a user with hyperopia, a user with astigmatism in the uncorrected visual acuity of the user, a user with presbyopia, a user with a plurality of visual imperfections in the uncorrected visual acuity of the user, among others. In other embodiment, the method may be repeated for additional users to project additional holographic objects calibrated to account for vision problems of the additional users.

In one embodiment, the 4D light field display includes a tracking processor able to dynamically track users based on data received from an energy-sensing system to project the holographic objects. In another embodiment, the 4D light field display is able to project each holographic object to a viewing zone for a corresponding user. In yet another embodiment, the viewing zones follow the movement of the user. In one embodiment, the 4D light field function also accounts for the location of the users to correct vision problems when the users are located at different distances form the 4D light field display. In another embodiment, the tracking processor is able to track the location of the eyes of the users. In yet another embodiment, the 4D light field function accounts for users with a vision problem that varies from the right eye to the left eye. In another embodiment, the 4D light field function is able to project a 2D object calibrated to correct for vision problems of the users. In one embodiment, the 4D light field function is able to project a stereoscopic object calibrated to correct for vision problems of the users.

BRIEF DESCRIPTION OF THE DRAWINGS

FIG. 5A is a schematic diagram illustrating an example of a relayed image through multi-core optical fibers;

FIG. 5B is a schematic diagram illustrating an example of a relayed image through an optical relay that exhibits the properties of the Transverse Anderson Localization principle;

FIG. 6 is a schematic diagram showing rays propagated from an energy surface to a viewer;

FIG. 34B illustrates an orthogonal view of a table-mounted energy waveguide system, in accordance with one embodiment of the present disclosure;

FIG. 43 illustrates a comparison between the perceived images seen by viewers with nearsightedness and farsightedness, and with vision correction applied;

FIG. 46A illustrates an embodiment of a vision-correction device calibrated to project a two-dimensional object;

FIG. 47 illustrates an embodiment of a vision-correction device calibrated to project a stereoscopic object;

FIG. 49 illustrates an embodiment of a vision-correcting device that projects different objects to different eyes;

FIG. 51B illustrates a first iteration of a test object;

DETAILED DESCRIPTION

Figure 1:
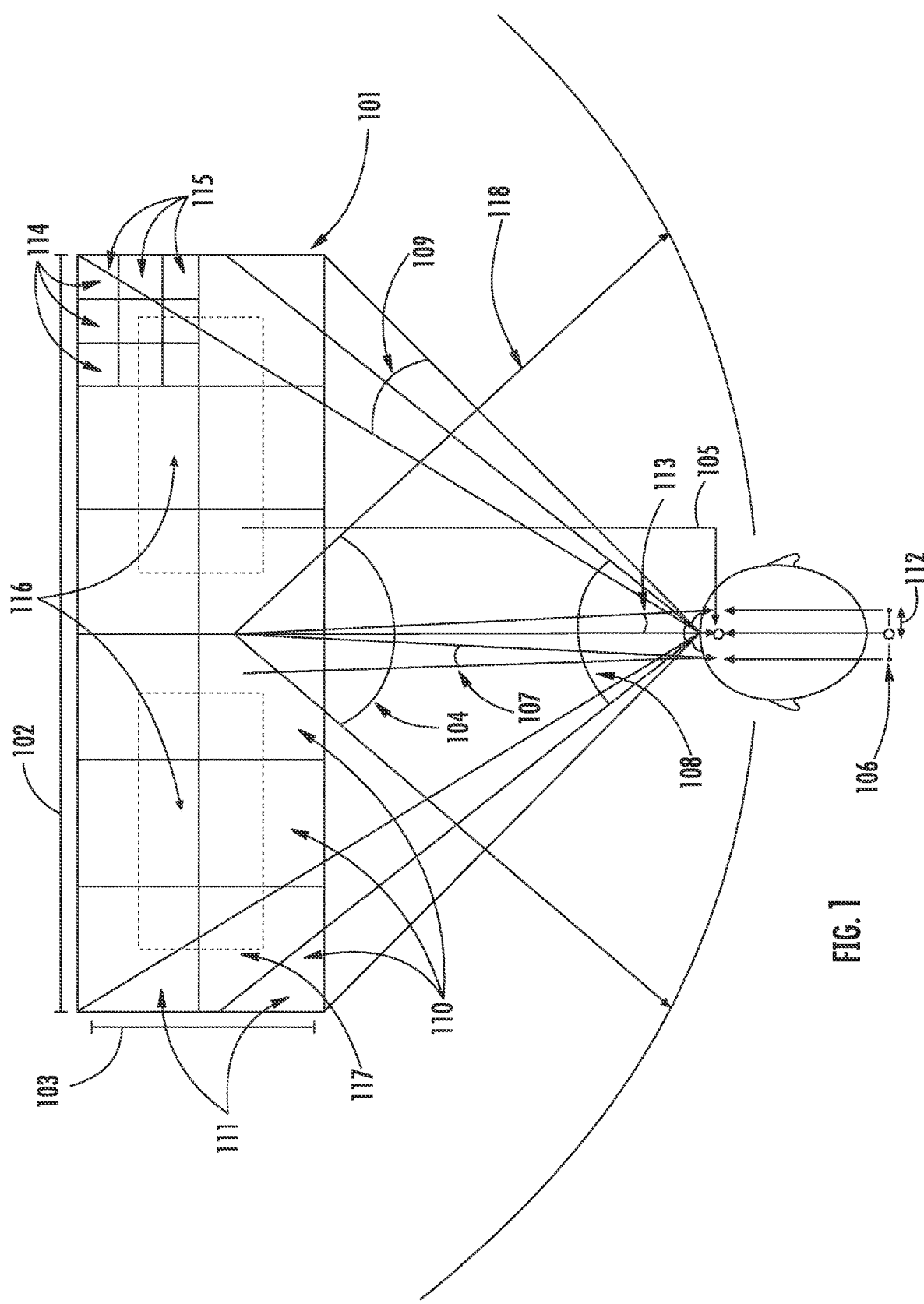
FIG. 1 is a schematic diagram illustrating design parameters for an energy directing system.

An embodiment of a Holodeck (collectively called "Holodeck Design Parameters") provide sufficient energy stimulus to fool the human sensory receptors into believing that received energy impulses within a virtual, social and interactive environment are real, providing: 1) binocular disparity without external accessories, head-mounted eyewear, or other peripherals; 2) accurate motion parallax, occlusion and opacity throughout a viewing volume simultaneously for any number of viewers; 3) visual focus through synchronous convergence, accommodation and miosis of the eye for all perceived rays of light; and 4) converging energy wave propagation of sufficient density and resolution to exceed the human sensory "resolution" for vision, hearing, touch, taste, smell, and/or balance.

Based upon conventional technology to date, we are decades, if not centuries away from a technology capable of providing for all receptive fields in a compelling way as suggested by the Holodeck Design Parameters including the visual, auditory, somatosensory, gustatory, olfactory, and vestibular systems.

In this disclosure, the terms light field and holographic may be used interchangeably to define the energy propagation for stimulation of any sensory receptor response. While initial disclosures may refer to examples of electromagnetic and mechanical energy propagation through energy surfaces for holographic imagery and volumetric haptics, all forms of sensory receptors are envisioned in this disclosure. Furthermore, the principles disclosed herein for energy propagation along propagation paths may be applicable to both energy emission and energy capture.

Many technologies exist today that are often unfortunately confused with holograms including lenticular printing, Pepper's Ghost, glasses-free stereoscopic displays, horizontal parallax displays, head-mounted VR and AR displays (HMD), and other such illusions generalized as "fauxlography." These technologies may exhibit some of the desired properties of a true holographic display; however, lack the ability to stimulate the human visual sensory response in any way sufficient to address at least two of the four identified Holodeck Design Parameters.

These challenges have not been successfully implemented by conventional technology to produce a seamless energy surface sufficient for holographic energy propagation. There are various approaches to implementing volumetric and direction multiplexed light field displays including parallax barriers, hogels, voxels, diffractive optics, multi-view projection, holographic diffusers, rotational mirrors, multilayered displays, time sequential displays, head mounted display, etc., however, conventional approaches may involve a compromise on image quality, resolution, angular sampling density, size, cost, safety, frame rate, etc., ultimately resulting in an unviable technology.

To achieve the Holodeck Design Parameters for the visual, auditory, somatosensory systems, the human acuity of each of the respective systems is studied and understood to propagate energy waves to sufficiently fool the human sensory receptors. The visual system is capable of resolving to approximately 1 arc min, the auditory system may distinguish the difference in placement as little as three degrees, and the somatosensory system at the hands are capable of discerning points separated by 2-12 mm. While there are various and conflicting ways to measure these acuities, these values are sufficient to understand the systems and methods to stimulate perception of energy propagation.

Of the noted sensory receptors, the human visual system is by far the most sensitive given that even a single photon can induce sensation. For this reason, much of this introduction will focus on visual energy wave propagation, and vastly lower resolution energy systems coupled within a disclosed energy waveguide surface may converge appropriate signals to induce holographic sensory perception. Unless otherwise noted, all disclosures apply to all energy and sensory domains.

When calculating for effective design parameters of the energy propagation for the visual system given a viewing volume and viewing distance, a desired energy surface may be designed to include many gigapixels of effective energy location density. For wide viewing volumes, or near field viewing, the design parameters of a desired energy surface may include hundreds of gigapixels or more of effective energy location density. By comparison, a desired energy source may be designed to have 1 to 250 effective megapixels of energy location density for ultrasonic propagation of volumetric haptics or an array of 36 to 3,600 effective energy locations for acoustic propagation of holographic sound depending on input environmental variables. What is important to note is that with a disclosed bi-directional energy surface architecture, all components may be configured to form the appropriate structures for any energy domain to enable holographic propagation.

However, the main challenge to enable the Holodeck today involves available visual technologies and electromagnetic device limitations. Acoustic and ultrasonic devices are less challenging given the orders of magnitude difference in desired density based upon sensory acuity in the respective receptive field, although the complexity should not be underestimated. While holographic emulsion exists with resolutions exceeding the desired density to encode interference patterns in static imagery, state-of-the-art display devices are limited by resolution, data throughput and manufacturing feasibility. To date, no singular display device has been able to meaningfully produce a light field having near holographic resolution for visual acuity.

Production of a single silicon-based device capable of meeting the desired resolution for a compelling light field display may not practical and may involve extremely complex fabrication processes beyond the current manufacturing capabilities. The limitation to tiling multiple existing display devices together involves the seams and gap formed by the physical size of packaging, electronics, enclosure, optics and a number of other challenges that inevitably result in an unviable technology from an imaging, cost and/or a size standpoint.

The embodiments disclosed herein may provide a real-world path to building the Holodeck.

Example embodiments will now be described hereinafter with reference to the accompanying drawings, which form a part hereof, and which illustrate example embodiments which may be practiced. As used in the disclosures and the appended claims, the terms "embodiment", "example embodiment", and "exemplary embodiment" do not necessarily refer to a single embodiment, although they may, and various example embodiments may be readily combined and interchanged, without departing from the scope or spirit of example embodiments. Furthermore, the terminology as used herein is for the purpose of describing example embodiments only and is not intended to be limitations. In this respect, as used herein, the term "in" may include "in" and "on", and the terms "a," "an" and "the" may include singular and plural references. Furthermore, as used herein, the term "by" may also mean "from", depending on the context. Furthermore, as used herein, the term "if" may also mean "when" or "upon," depending on the context. Furthermore, as used herein, the words "and/or" may refer to and encompass any and all possible combinations of one or more of the associated listed items.

Holographic System Considerations:

Overview of Light Field Energy Propagation Resolution

Light field and holographic display is the result of a plurality of projections where energy surface locations provide angular, color and intensity information propagated within a viewing volume. The disclosed energy surface provides opportunities for additional information to coexist and propagate through the same surface to induce other sensory system responses. Unlike a stereoscopic display, the viewed position of the converged energy propagation paths in space do not vary as the viewer moves around the viewing volume and any number of viewers may simultaneously see propagated objects in real-world space as if it was truly there. In some embodiments, the propagation of energy may be located in the same energy propagation path but in opposite directions. For example, energy emission and energy capture along an energy propagation path are both possible in some embodiments of the present disclosed.

FIG. 1 is a schematic diagram illustrating variables relevant for stimulation of sensory receptor response. These variables may include surface diagonal 101, surface width 102, surface height 103, a determined target seating distance 118, the target seating field of view field of view from the center of the display 104, the number of intermediate samples demonstrated here as samples between the eyes 105, the average adult inter-ocular separation 106, the average resolution of the human eye in arcmin 107, the horizontal field of view formed between the target viewer location and the surface width 108, the vertical field of view formed between the target viewer location and the surface height 109, the resultant horizontal waveguide element resolution, or total number of elements, across the surface 110, the resultant vertical waveguide element resolution, or total number of elements, across the surface 111, the sample distance based upon the inter-ocular spacing between the eyes and the number of intermediate samples for angular projection between the eyes 112, the angular sampling may be based upon the sample distance and the target seating distance 113, the total resolution Horizontal per waveguide element derived from the angular sampling desired 114, the total resolution Vertical per waveguide element derived from the angular sampling desired 115, device Horizontal is the count of the determined number of discreet energy sources desired 116, and device Vertical is the count of the determined number of discreet energy sources desired 117.

A method to understand the desired minimum resolution may be based upon the following criteria to ensure sufficient stimulation of visual (or other) sensory receptor response: surface size (e.g., 84" diagonal), surface aspect ratio (e.g., 16:9), seating distance (e.g., 128" from the display), seating field of view (e.g., 120 degrees or +/−60 degrees about the center of the display), desired intermediate samples at a distance (e.g., one additional propagation path between the eyes), the average inter-ocular separation of an adult (approximately 65 mm), and the average resolution of the human eye (approximately 1 arcmin). These example values should be considered placeholders depending on the specific application design parameters.

Further, each of the values attributed to the visual sensory receptors may be replaced with other systems to determine desired propagation path parameters. For other energy propagation embodiments, one may consider the auditory system's angular sensitivity as low as three degrees and the somatosensory system's spatial resolution of the hands as small as 2-12 mm.

While there are various and conflicting ways to measure these sensory acuities, these values are sufficient to understand the systems and methods to stimulate perception of virtual energy propagation. There are many ways to consider the design resolution, and the below proposed methodology combines pragmatic product considerations with the biological resolving limits of the sensory systems. As will be appreciated by one of ordinary skill in the art, the following overview is a simplification of any such system design, and should be considered for exemplary purposes only.

With the resolution limit of the sensory system understood, the total energy waveguide element density may be calculated such that the receiving sensory system cannot discern a single energy waveguide element from an adjacent element, given:

- Surface Aspect Ratio = $\frac{Widt(W)}{Heigh(H)}$

- Surface Horizontal Size = Surface Diagonal $* \left( \frac{1}{\sqrt{1 + \left(\frac{H}{W}\right)^2}} \right)$

- Surface Vertical Size = Surface Diagonal $* \left( \frac{1}{\sqrt{1 + \left(\frac{H}{W}\right)^2}} \right)$

- Horizontal Field of View = $2 * atan\left(\frac{\text{Surface Horizontal Size}}{2 * \text{Seating Distance}}\right)$

- Vertical Field of View = $2 * atan\left(\frac{\text{Surface Vertical Size}}{2 * \text{Seating Distance}}\right)$

- Horizontal Element Resolution = Horizontal $FoV * \frac{60}{\text{Eye Resolution}}$

- Vertical Element Resolution = Vertical $FoV * \frac{60}{\text{Eye Resolution}}$ The above calculations result in approximately a 32×18° field of view resulting in approximately 1920×1080 (rounded to nearest format) energy waveguide elements being desired. One may also constrain the variables such that the field of view is consistent for both (u, v) to provide a more regular spatial sampling of energy locations (e.g. pixel aspect ratio). The angular sampling of the system assumes a defined target viewing volume location and additional propagated energy paths between two points at the optimized distance, given:

- Sample Distance = $\dfrac{\text{Inter} - \text{Ocular Distance}}{(\text{Number of Desired Intermediate Samples} + 1)}$

- Angular Sampling = $a\tan\left(\dfrac{\text{Sample Distance}}{\text{Seating Distance}}\right)$ In this case, the inter-ocular distance is leveraged to calculate the sample distance although any metric may be leveraged to account for appropriate number of samples as a given distance. With the above variables considered, approximately one ray per 0.57° may be desired and the total system resolution per independent sensory system may be determined, given:

- Locations Per Element $(N) = \dfrac{\text{Seating } FoV}{\text{Angular Sampling}}$

- Total Resolution $H = N * \text{Horizontal Element Resolution}$

- Total Resolution $V = N * \text{Vertical Element Resolution}$

With the above scenario given the size of energy surface and the angular resolution addressed for the visual acuity system, the resultant energy surface may desirably include approximately 400 k×225 k pixels of energy resolution locations, or 90 gigapixels holographic propagation density. These variables provided are for exemplary purposes only and many other sensory and energy metrology considerations should be considered for the optimization of holographic propagation of energy. In an additional embodiment, 1 gigapixel of energy resolution locations may be desired based upon the input variables. In an additional embodiment, 1,000 gigapixels of energy resolution locations may be desired based upon the input variables.

Current Technology Limitations:

Active Area, Device Electronics, Packaging, and the Mechanical Envelope

Figure 2:
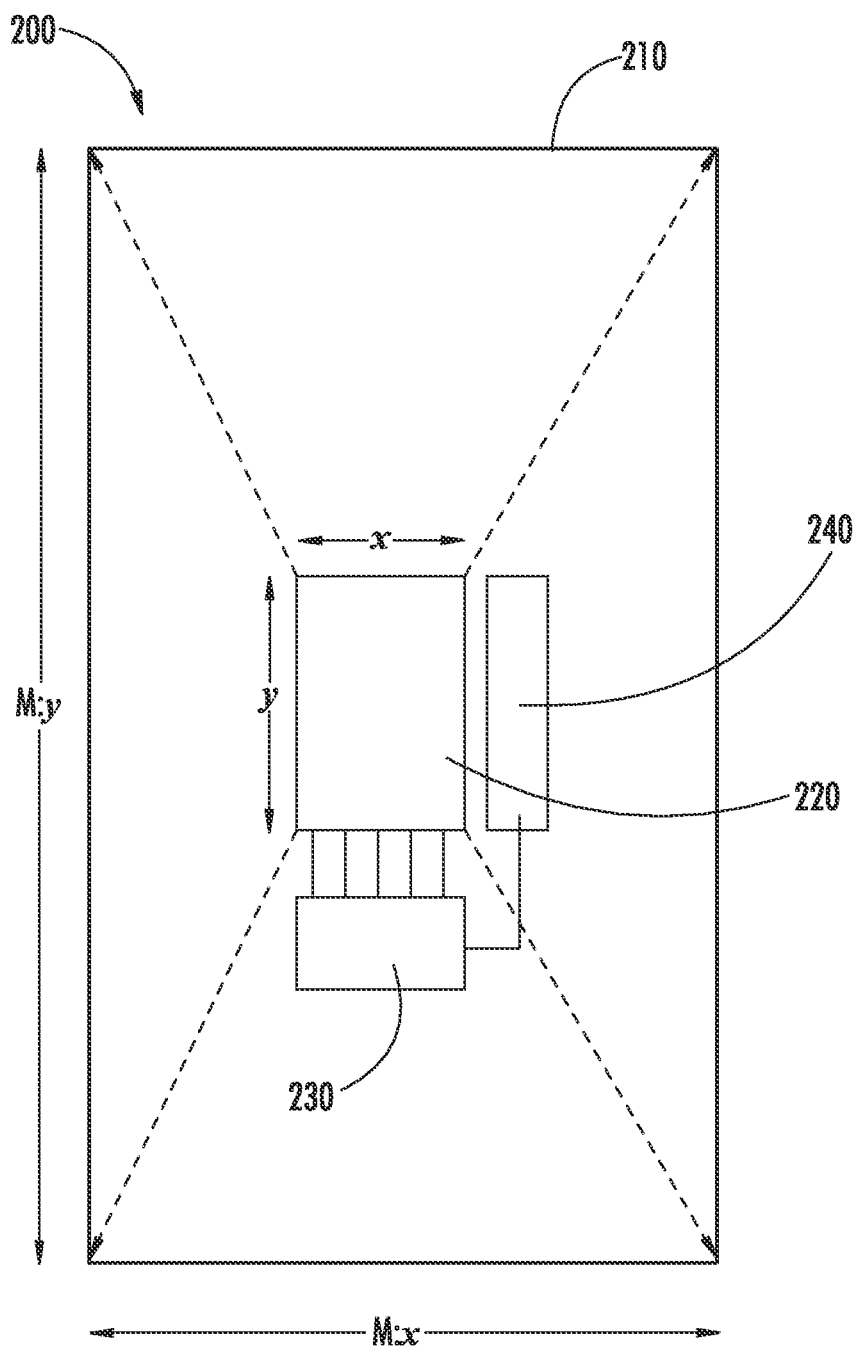
FIG. 2 is a schematic diagram illustrating an energy system having an active device area with a mechanical envelope.

FIG. 2 illustrates a device 200 having an active area 220 with a certain mechanical form factor. The device 200 may include drivers 230 and electronics 240 for powering and interface to the active area 220, the active area having a dimension as shown by the x and y arrows. This device 200 does not take into account the cabling and mechanical structures to drive, power and cool components, and the mechanical footprint may be further minimized by introducing a flex cable into the device 200. The minimum footprint for such a device 200 may also be referred to as a mechanical envelope 210 having a dimension as shown by the M:x and M:y arrows. This device 200 is for illustration purposes only and custom electronics designs may further decrease the mechanical envelope overhead, but in almost all cases may not be the exact size of the active area of the device. In an embodiment, this device 200 illustrates the dependency of electronics as it relates to active image area 220 for a micro OLED, DLP chip or LCD panel, or any other technology with the purpose of image illumination.

In some embodiments, it may also be possible to consider other projection technologies to aggregate multiple images onto a larger overall display. However, this may come at the cost of greater complexity for throw distance, minimum focus, optical quality, uniform field resolution, chromatic aberration, thermal properties, calibration, alignment, additional size or form factor. For most practical applications, hosting tens or hundreds of these projection sources 200 may result in a design that is much larger with less reliability.

For exemplary purposes only, assuming energy devices with an energy location density of 3840×2160 sites, one may determine the number of individual energy devices (e.g., device 100) desired for an energy surface, given:

- Devices $H = \dfrac{\text{Total Resolution } H}{\text{Device Resolution } H}$

- Devices $V = \dfrac{\text{Total Resolution } V}{\text{Device Resolution } V}$

Given the above resolution considerations, approximately 105×105 devices similar to those shown in FIG. 2 may be desired. It should be noted that many devices consist of various pixel structures that may or may not map to a regular grid. In the event that there are additional sub-pixels or locations within each full pixel, these may be exploited to generate additional resolution or angular density. Additional signal processing may be used to determine how to convert the light field into the correct (u,v) coordinates depending on the specified location of the pixel structure(s) and can be an explicit characteristic of each device that is known and calibrated. Further, other energy domains may involve a different handling of these ratios and device structures, and those skilled in the art will understand the direct intrinsic relationship between each of the desired frequency domains. This will be shown and discussed in more detail in subsequent disclosure.

The resulting calculation may be used to understand how many of these individual devices may be desired to produce a full resolution energy surface. In this case, approximately 105×105 or approximately 11,080 devices may be desired to achieve the visual acuity threshold. The challenge and novelty exists within the fabrication of a seamless energy surface from these available energy locations for sufficient sensory holographic propagation.

Summary of Seamless Energy Surfaces:

Configurations and Designs for Arrays of Energy Relays

In some embodiments, approaches are disclosed to address the challenge of generating high energy location density from an array of individual devices without seams due to the limitation of mechanical structure for the devices. In an embodiment, an energy propagating relay system may allow for an increase in the effective size of the active device area to meet or exceed the mechanical dimensions to configure an array of relays and form a singular seamless energy surface.

Figure 3:
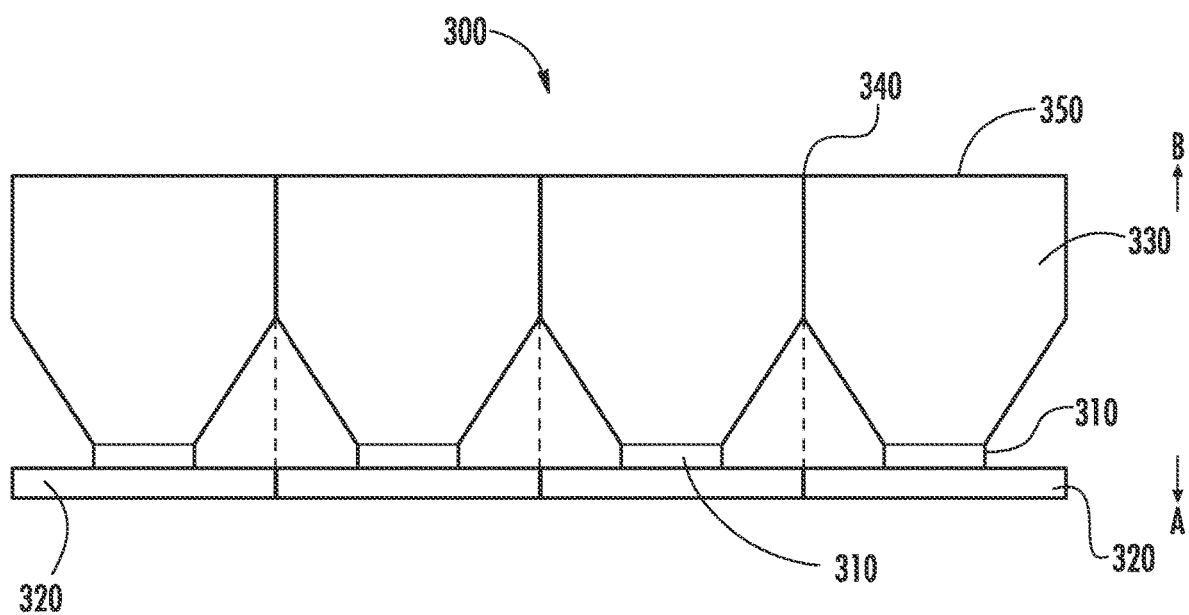
FIG. 3 is a schematic diagram illustrating an energy relay system.

FIG. 3 illustrates an embodiment of such an energy relay system 300. As shown, the relay system 300 may include a device 310 mounted to a mechanical envelope 320, with an energy relay element 330 propagating energy from the device 310. The relay element 330 may be configured to provide the ability to mitigate any gaps 340 that may be produced when multiple mechanical envelopes 320 of the device are placed into an array of multiple devices 310.

For example, if a device's active area 310 is 20 mm×10 mm and the mechanical envelope 320 is 40 mm×20 mm, an energy relay element 330 may be designed with a magnification of 2:1 to produce a tapered form that is approximately 20 mm×10 mm on a minified end (arrow A) and 40 mm×20 mm on a magnified end (arrow B), providing the ability to align an array of these elements 330 together seamlessly without altering or colliding with the mechanical envelope 320 of each device 310. Mechanically, the relay elements 330 may be bonded or fused together to align and polish ensuring minimal seam gap 340 between devices 310. In one such embodiment, it is possible to achieve a seam gap 340 smaller than the visual acuity limit of the eye.

Figure 4:
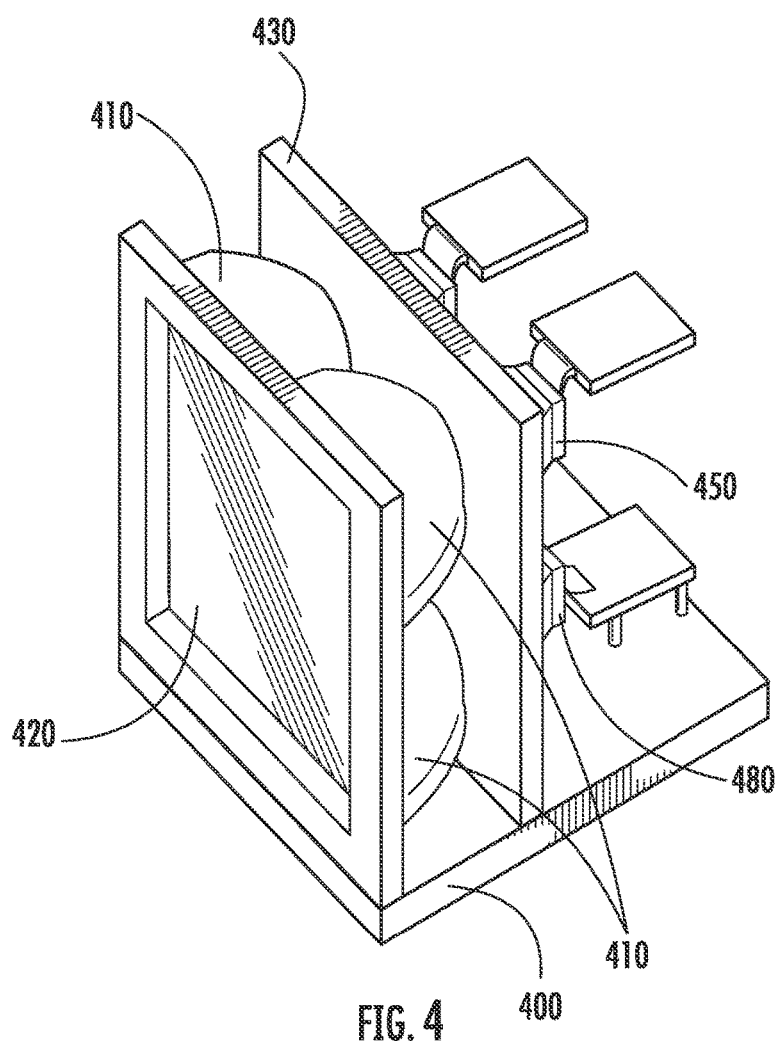
FIG. 4 is a schematic diagram illustrating an embodiment of energy relay elements adhered together and fastened to a base structure.

FIG. 4 illustrates an example of a base structure 400 having energy relay elements 410 formed together and securely fastened to an additional mechanical structure 430. The mechanical structure of the seamless energy surface 420 provides the ability to couple multiple energy relay elements 410, 450 in series to the same base structure through bonding or other mechanical processes to mount relay elements 410, 450. In some embodiments, each relay element 410 may be fused, bonded, adhered, pressure fit, aligned or otherwise attached together to form the resultant seamless energy surface 420. In some embodiments, a device 480 may be mounted to the rear of the relay element 410 and aligned passively or actively to ensure appropriate energy location alignment within the determined tolerance is maintained.

In an embodiment, the seamless energy surface comprises one or more energy locations and one or more energy relay element stacks comprise a first and second side and each energy relay element stack is arranged to form a singular seamless display surface directing energy along propagation paths extending between one or more energy locations and the seamless display surface, and where the separation between the edges of any two adjacent second sides of the terminal energy relay elements is less than the minimum perceptible contour as defined by the visual acuity of a human eye having better than 20/40 vision at a distance greater than the width of the singular seamless display surface.

In an embodiment, each of the seamless energy surfaces comprise one or more energy relay elements each with one or more structures forming a first and second surface with a transverse and longitudinal orientation. The first relay surface has an area different than the second resulting in positive or negative magnification and configured with explicit surface contours for both the first and second surfaces passing energy through the second relay surface to substantially fill a +/−10-degree angle with respect to the normal of the surface contour across the entire second relay surface.

In an embodiment, multiple energy domains may be configured within a single energy relay, or between multiple energy relays to direct one or more sensory holographic energy propagation paths including visual, acoustic, tactile or other energy domains.

In an embodiment, the seamless energy surface is configured with energy relays that comprise two or more first sides for each second side to both receive and emit one or more energy domains simultaneously to provide bi-directional energy propagation throughout the system.

In an embodiment, the energy relays are provided as loose coherent elements.

Introduction to Component Engineered Structures:

Disclosed Advances in Transverse Anderson Localization Energy Relays

The properties of energy relays may be significantly optimized according to the principles disclosed herein for energy relay elements that induce Transverse Anderson Localization. Transverse Anderson Localization is the propagation of a ray transported through a transversely disordered but longitudinally consistent material.

This implies that the effect of the materials that produce the Anderson Localization phenomena may be less impacted by total internal reflection than by the randomization between multiple-scattering paths where wave interference can completely limit the propagation in the transverse orientation while continuing in the longitudinal orientation.

Of significant additional benefit is the elimination of the cladding of traditional multi-core optical fiber materials. The cladding is to functionally eliminate the scatter of energy between fibers, but simultaneously act as a barrier to rays of energy thereby reducing transmission by at least the core to clad ratio (e.g., a core to clad ratio of 70:30 will transmit at best 70% of received energy transmission) and additionally forms a strong pixelated patterning in the propagated energy.

FIG. 5A illustrates an end view of an example of one such non-Anderson Localization energy relay 500, wherein an image is relayed through multi-core optical fibers where pixilation and fiber noise may be exhibited due to the intrinsic properties of the optical fibers. With traditional multi-mode and multi-core optical fibers, relayed images may be intrinsically pixelated due to the properties of total internal reflection of the discrete array of cores where any cross-talk between cores will reduce the modulation transfer function and increase blurring. The resulting imagery produced with traditional multi-core optical fiber tends to have a residual fixed noise fiber pattern similar to those shown in FIG. 5A.

FIG. 5B, illustrates an example of the same relayed image 550 through an energy relay comprising materials that exhibit the properties of Transverse Anderson Localization, where the relayed pattern has a greater density grain structures as compared to the fixed fiber pattern from FIG. 5A. In an embodiment, relays comprising randomized microscopic component engineered structures induce Transverse Anderson Localization and transport light more efficiently with higher propagation of resolvable resolution than commercially available multi-mode glass optical fibers.

In an embodiment, a relay element exhibiting Transverse Anderson Localization may comprise a plurality of at least two different component engineered structures in each of three orthogonal planes arranged in a dimensional lattice and the plurality of structures form randomized distributions of material wave propagation properties in a transverse plane within the dimensional lattice and channels of similar values of material wave propagation properties in a longitudinal plane within the dimensional lattice, wherein energy waves propagating through the energy relay have higher transport efficiency in the longitudinal orientation versus the transverse orientation and are spatially localized in the transverse orientation.

In an embodiment, a randomized distribution of material wave propagation properties in a transverse plane within the dimensional lattice may lead to undesirable configurations due to the randomized nature of the distribution. A randomized distribution of material wave propagation properties may induce Anderson Localization of energy on average across the entire transverse plane, however limited areas of similar material wave propagation properties may form inadvertently as a result of the uncontrolled random distribution. For example, if the size of these local areas of similar wave propagation properties become too large relative to their intended energy transport domain, there may be a potential reduction in the efficiency of energy transport through the material.

In an embodiment, a relay may be formed from a randomized distribution of component engineered structures to transport visible light of a certain wavelength range by inducing Transverse Anderson Localization of the light. However, due to their random distribution, the structures may inadvertently arrange such that a continuous area of a single component engineered structure forms across the transverse plane which is multiple times larger than the wavelength of visible light. As a result, visible light propagating along the longitudinal axis of the large, continuous, single-material region may experience a lessened Transverse Anderson Localization effect and may suffer degradation of transport efficiency through the relay.

In an embodiment, it may be desirable to design an ordered distribution of material wave propagation properties in the transverse plane of an energy relay material. Such an ordered distribution would ideally induce an energy localization effect through methods similar to Transverse Anderson Localization, while minimizing potential reductions in transport efficiency due to abnormally distributed material properties inherently resulting from a random property distribution. Using an ordered distribution of material wave propagation properties to induce a transverse energy localization effect similar to that of Transverse Anderson Localization in an energy relay element will hereafter be referred to as Ordered Energy Localization.

In an embodiment, multiple energy domains may be configured within a single, or between multiple Ordered Energy Localization energy relays to direct one or more sensory holographic energy propagation paths including visual, acoustic, tactile or other energy domains.

In an embodiment, the seamless energy surface is configured with Ordered Energy Localization energy relays that comprise two or more first sides for each second side to both receive and emit one or more energy domains simultaneously to provide bi-directional energy propagation throughout the system.

In an embodiment, the Ordered Energy Localization energy relays are configured as loose coherent or flexible energy relay elements.

Considerations for 4D Plenoptic Functions:

Selective Propagation of Energy through Holographic Waveguide Arrays

As discussed above and herein throughout, a light field display system generally includes an energy source (e.g., illumination source) and a seamless energy surface configured with sufficient energy location density as articulated in the above discussion. A plurality of relay elements may be used to relay energy from the energy devices to the seamless energy surface. Once energy has been delivered to the seamless energy surface with the requisite energy location density, the energy can be propagated in accordance with a 4D plenoptic function through a disclosed energy waveguide system. As will be appreciated by one of ordinary skill in the art, a 4D plenoptic function is well known in the art and will not be elaborated further herein.

The energy waveguide system selectively propagates energy through a plurality of energy locations along the seamless energy surface representing the spatial coordinate of the 4D plenoptic function with a structure configured to alter an angular direction of the energy waves passing through representing the angular component of the 4D plenoptic function, wherein the energy waves propagated may converge in space in accordance with a plurality of propagation paths directed by the 4D plenoptic function.

Reference is now made to FIG. 6 illustrating an example of light field energy surface in 4D image space in accordance with a 4D plenoptic function. The figure shows ray traces of an energy surface 600 to a viewer 620 in describing how the rays of energy converge in space 630 from various positions within the viewing volume. As shown, each waveguide element 610 defines four dimensions of information describing energy propagation 640 through the energy surface 600. Two spatial dimensions (herein referred to as x and y) are the physical plurality of energy locations that can be viewed in image space, and the angular components theta and phi (herein referred to as u and v), which is viewed in virtual space when projected through the energy waveguide array. In general, and in accordance with a 4D plenoptic function, the plurality of waveguides (e.g., lenslets) are able to direct an energy location from the x, y dimension to a unique location in virtual space, along a direction defined by the u, v angular component, in forming the holographic or light field system described herein.

However, one skilled in the art will understand that a significant challenge to light field and holographic display technologies arises from uncontrolled propagation of energy due designs that have not accurately accounted for any of diffraction, scatter, diffusion, angular direction, calibration, focus, collimation, curvature, uniformity, element crosstalk, as well as a multitude of other parameters that contribute to decreased effective resolution as well as an inability to accurately converge energy with sufficient fidelity.

In an embodiment, an approach to selective energy propagation for addressing challenges associated with holographic display may include energy inhibiting elements and substantially filling waveguide apertures with near-collimated energy into an environment defined by a 4D plenoptic function.

In an embodiment, an array of energy waveguides may define a plurality of energy propagation paths for each waveguide element configured to extend through and substantially fill the waveguide element's effective aperture in unique directions defined by a prescribed 4D function to a plurality of energy locations along a seamless energy surface inhibited by one or more elements positioned to limit propagation of each energy location to only pass through a single waveguide element.

In an embodiment, multiple energy domains may be configured within a single, or between multiple energy waveguides to direct one or more sensory holographic energy propagations including visual, acoustic, tactile or other energy domains.

In an embodiment, the energy waveguides and seamless energy surface are configured to both receive and emit one or more energy domains to provide bi-directional energy propagation throughout the system.

In an embodiment, the energy waveguides are configured to propagate non-linear or non-regular distributions of energy, including non-transmitting void regions, leveraging digitally encoded, diffractive, refractive, reflective, grin, holographic, Fresnel, or the like waveguide configurations for any seamless energy surface orientation including wall, table, floor, ceiling, room, or other geometry based environments. In an additional embodiment, an energy waveguide element may be configured to produce various geometries that provide any surface profile and/or tabletop viewing allowing users to view holographic imagery from all around the energy surface in a 360-degree configuration.

In an embodiment, the energy waveguide array elements may be reflective surfaces and the arrangement of the elements may be hexagonal, square, irregular, semi-regular, curved, non-planar, spherical, cylindrical, tilted regular, tilted irregular, spatially varying and/or multi-layered.

For any component within the seamless energy surface, waveguide, or relay components may include, but not limited to, optical fiber, silicon, glass, polymer, optical relays, diffractive, holographic, refractive, or reflective elements, optical face plates, energy combiners, beam splitters, prisms, polarization elements, spatial light modulators, active pixels, liquid crystal cells, transparent displays, or any similar materials exhibiting Anderson localization or total internal reflection.

Realizing the Holodeck:

Aggregation of Bi-directional Seamless Energy Surface Systems to Stimulate Human Sensory Receptors within Holographic Environments It is possible to construct large-scale environments of seamless energy surface systems by tiling, fusing, bonding, attaching, and/or stitching multiple seamless energy surfaces together forming arbitrary sizes, shapes, contours or form-factors including entire rooms. Each energy surface system may comprise an assembly having a base structure, energy surface, relays, waveguide, devices, and electronics, collectively configured for bi-directional holographic energy propagation, emission, reflection, or sensing.

In an embodiment, an environment of tiled seamless energy systems are aggregated to form large seamless planar or curved walls including installations comprising up to all surfaces in a given environment, and configured as any combination of seamless, discontinuous planar, faceted, curved, cylindrical, spherical, geometric, or non-regular geometries.

In an embodiment, aggregated tiles of planar surfaces form wall-sized systems for theatrical or venue-based holographic entertainment. In an embodiment, aggregated tiles of planar surfaces cover a room with four to six walls including both ceiling and floor for cave-based holographic installations. In an embodiment, aggregated tiles of curved surfaces produce a cylindrical seamless environment for immersive holographic installations. In an embodiment, aggregated tiles of seamless spherical surfaces form a holographic dome for immersive Holodeck-based experiences.

In an embodiment, aggregate tiles of seamless curved energy waveguides provide mechanical edges following the precise pattern along the boundary of energy inhibiting elements within the energy waveguide structure to bond, align, or fuse the adjacent tiled mechanical edges of the adjacent waveguide surfaces, resulting in a modular and seamless energy waveguide system.

In a further embodiment of an aggregated tiled environment, energy is propagated bi-directionally for multiple simultaneous energy domains. In an additional embodiment, the energy surface provides the ability to both display and capture simultaneously from the same energy surface with waveguides designed such that light field data may be projected by an illumination source through the waveguide and simultaneously received through the same energy surface. In an additional embodiment, additional depth sensing and active scanning technologies may be leveraged to allow for the interaction between the energy propagation and the viewer in correct world coordinates. In an additional embodiment, the energy surface and waveguide are operable to emit, reflect, or converge frequencies to induce tactile sensation or volumetric haptic feedback. In some embodiments, any combination of bi-directional energy propagation and aggregated surfaces are possible.

In an embodiment, the system comprises an energy waveguide capable of bi-directional emission and sensing of energy through the energy surface with one or more energy devices independently paired with two-or-more-path energy combiners to pair at least two energy devices to the same portion of the seamless energy surface, or one or more energy devices are secured behind the energy surface, proximate to an additional component secured to the base structure, or to a location in front and outside of the FOV of the waveguide for off-axis direct or reflective projection or sensing, and the resulting energy surface provides for bi-directional transmission of energy allowing the waveguide to converge energy, a first device to emit energy and a second device to sense energy, and where the information is processed to perform computer vision related tasks including, but not limited to, 4D plenoptic eye and retinal tracking or sensing of interference within propagated energy patterns, depth estimation, proximity, motion tracking, image, color, or sound formation, or other energy frequency analysis. In an additional embodiment, the tracked positions actively calculate and modify positions of energy based upon the interference between the bi-directional captured data and projection information.

In some embodiments, a plurality of combinations of three energy devices comprising an ultrasonic sensor, a visible electromagnetic display, and an ultrasonic emitting device are configured together for each of three first relay surfaces propagating energy combined into a single second energy relay surface with each of the three first surfaces comprising engineered properties specific to each device's energy domain, and two engineered waveguide elements configured for ultrasonic and electromagnetic energy respectively to provide the ability to direct and converge each device's energy independently and substantially unaffected by the other waveguide elements that are configured for a separate energy domain.

In some embodiments, disclosed is a calibration procedure to enable efficient manufacturing to remove system artifacts and produce a geometric mapping of the resultant energy surface for use with encoding/decoding technologies as well as dedicated integrated systems for the conversion of data into calibrated information appropriate for energy propagation based upon the calibrated configuration files.

In some embodiments, additional energy waveguides in series and one or more energy devices may be integrated into a system to produce opaque holographic pixels.

In some embodiments, additional waveguide elements may be integrated comprising energy inhibiting elements, beam-splitters, prisms, active parallax barriers or polarization technologies in order to provide spatial and/or angular resolutions greater than the diameter of the waveguide or for other super-resolution purposes.

In some embodiments, the disclosed energy system may also be configured as a wearable bi-directional device, such as virtual reality (VR) or augmented reality (AR). In other embodiments, the energy system may include adjustment optical element(s) that cause the displayed or received energy to be focused proximate to a determined plane in space for a viewer. In some embodiments, the waveguide array may be incorporated to holographic head-mounted-display. In other embodiments, the system may include multiple optical paths to allow for the viewer to see both the energy system and a real-world environment (e.g., transparent holographic display). In these instances, the system may be presented as near field in addition to other methods.

In some embodiments, the transmission of data comprises encoding processes with selectable or variable compression ratios that receive an arbitrary dataset of information and metadata; analyze said dataset and receive or assign material properties, vectors, surface IDs, new pixel data forming a more sparse dataset, and wherein the received data may comprise: 2D, stereoscopic, multi-view, metadata, light field, holographic, geometry, vectors or vectorized metadata, and an encoder/decoder may provide the ability to convert the data in real-time or off-line comprising image processing for: 2D; 2D plus depth, metadata or other vectorized information; stereoscopic, stereoscopic plus depth, metadata or other vectorized information; multi-view; multi-view plus depth, metadata or other vectorized information; holographic; or light field content; through depth estimation algorithms, with or without depth metadata; and an inverse ray tracing methodology appropriately maps the resulting converted data produced by inverse ray tracing from the various 2D, stereoscopic, multi-view, volumetric, light field or holographic data into real world coordinates through a characterized 4D plenoptic function. In these embodiments, the total data transmission desired may be multiple orders of magnitudes less transmitted information than the raw light field dataset.

System and Methods for Production of Ordered Energy Localization Energy Relays

While the Anderson localization principle was introduced in the 1950s, it wasn't until recent technological breakthroughs in materials and processes that allowed the principle to be explored practically in optical transport. Transverse Anderson localization is the propagation of a wave transported through a transversely disordered but longitudinally invariant material without diffusion of the wave in the transverse plane.

Within the prior art, Transverse Anderson localization has been observed through experimentation in which a fiber optic face plate is fabricated through drawing millions of individual strands of fiber with different refractive index (RI) that were mixed randomly and fused together. When an input beam is scanned across one of the surfaces of the face plate, the output beam on the opposite surface follows the transverse position of the input beam. Since Anderson localization exhibits in disordered mediums an absence of diffusion of waves, some of the fundamental physics are different when compared to optical fiber relays. This implies that the effect of the optical fibers that produce the Anderson localization phenomena are less impacted by total internal reflection than by the randomization of between multiple-scattering paths where wave interference can completely limit the propagation in the transverse orientation while continuing in the longitudinal path. Further to this concept, it is introduced herein that an ordered distribution of material wave propagation properties may be used in place of a randomized distribution in the transverse plane of an energy transport device. Such an ordered distribution may induce Ordered Energy Localization in a transverse plane of the device while reducing the occurrence of localized grouping of similar material properties, which can arise due to the nature of random distributions, and which may degrade the overall efficacy of energy transport through the device.

In an embodiment, it may be possible for Ordered Energy Localization materials to transport light as well as or better than, the highest quality commercially available multimode glass image fibers with a higher MTF. With multimode and multicore optical fibers, the relayed images are intrinsically pixelated due to the properties of total internal reflection of the discrete array of cores where any cross-talk between cores will reduce MTF and increase blurring. The resulting imagery produced with multicore optical fiber tends to have a residual fixed noise fiber pattern, as illustrated in FIG. 5A. By contrast, FIG. 5B illustrates the same relayed image through an example material sample that exhibits properties similar to that of the Transverse Anderson Localization principle, referred to herein as Ordered Energy Localization, where the noise pattern appears much more like a grain structure than a fixed fiber pattern.

Another advantage to optical relays that exhibit the Ordered Energy localization phenomena is that it they can be fabricated from a polymer material, resulting in reduced cost and weight. A similar optical grade material generally made of glass or other similar materials may cost ten to a hundred (or more) times more than the cost of the same dimension of material generated with polymers. Further, the weight of the polymer relay optics can be 10-100× less given that up to a majority of the density of the material is air and other light weight plastics. For the avoidance of doubt, any material that exhibits the Anderson localization property, or the Ordered Energy Localization property as described herein, may be included in this disclosure herein, even if it does not meet the above cost and weight suggestions. As one skilled in the art will understand that the above suggestion is a single embodiment that lends itself to significant commercial viabilities that similar glass products exclude. Of additional benefit is that for Ordered Energy Localization to work, optical fiber cladding may not be needed, which for traditional multicore fiber optics is required to prevent the scatter of light between fibers, but simultaneously blocks a portion of the rays of light and thus reduces transmission by at least the core to clad ratio (e.g. a core to clad ratio of 70:30 will transmit at best 70% of received illumination).

Another benefit is the ability to produce many smaller parts that can be bonded or fused without seams as the material fundamentally has no edges in the traditional sense and the merger of any two pieces is nearly the same as generating the component as a singular piece depending on the process to merge the two or more pieces together. For large scale applications, this is a significant benefit for the ability to manufacturer without massive infrastructure or tooling costs, and it provides the ability to generate single pieces of material that would otherwise be impossible with other methods. Traditional plastic optical fibers have some of these benefits but due to the cladding, generally still involve a seam line of some distances.

The present disclosure includes methods of manufacturing materials exhibiting the Ordered Energy Localization phenomena. A process is proposed to construct relays of electromagnetic energy, acoustic energy, or other types of energy using building blocks that consist of one or more component engineered structures (CES). The term CES refers to a building block component with specific engineered properties (EP) that include, but are not limited to, material type, size, shape, refractive index, center-of-mass, charge, weight, absorption, magnetic moment, among other properties. The size scale of the CES may be on the order of wavelength of the energy wave being relayed, and can vary across the milli-scale, the micro-scale, or the nano-scale. The other EP's are also highly dependent on the wavelength of the energy wave.

Within the scope of the present disclosure, a particular arrangement of multiple CES may form an ordered pattern, which may be repeated in the transverse direction across a relay to effectively induce Ordered Energy Localization. A single instance of such an ordered pattern of CES is referred to herein as a module. A module may comprise two or more CES. A grouping of two or more modules within a relay is referred to herein as a cluster.

Ordered Energy Localization is a general wave phenomenon that applies to the transport of electromagnetic waves, acoustic waves, quantum waves, energy waves, among others. The one or more building block structures required to form an energy wave relay that exhibits Ordered Energy Localization each have a size that is on the order of the corresponding wavelength. Another critical parameter for the building blocks is the speed of the energy wave in the materials used for those building blocks, which includes refractive index for electromagnetic waves, and acoustic impedance for acoustic waves. For example, the building block sizes and refractive indices can vary to accommodate any frequency in the electromagnetic spectrum, from X-rays to radio waves.

For this reason, discussions in this disclosure about optical relays can be generalized to not only the full electromagnetic spectrum, but to acoustical energy and other types of energy. For this reason, the use of the terms energy source, energy surface, and energy relay will be used often, even if the discussion is focused on one particular form of energy such as the visible electromagnetic spectrum.

For the avoidance of doubt, the material quantities, process, types, refractive index, and the like are merely exemplary and any optical material that exhibits the Ordered Energy localization property is included herein. Further, any use of ordered materials and processes is included herein.

It should be noted that the principles of optical design noted in this disclosure apply generally to all forms of energy relays, and the design implementations chosen for specific products, markets, form factors, mounting, etc. may or may not need to address these geometries but for the purposes of simplicity, any approach disclosed is inclusive of all potential energy relay materials.

In one embodiment, for the relay of visible electromagnetic energy, the size of the CES should be on the order of 1 micron. The materials used for the CES can be any optical material that exhibits the optical qualities desired to include, but not limited to, glass, plastic, resin and the like. The index of refraction of the materials are higher than 1, and if two CES types are chosen, the difference in refractive index becomes a key design parameter. The aspect ratio of the material may be chosen to be elongated, in order to assist wave propagation in a longitudinal direction.

The formation of a CES may be completed as a destructive process that takes formed materials and cuts the pieces into a desired shaped formation or any other method known in the art, or additive, where the CES may be grown, printed, formed, melted, or produced in any other method known in the art. Additive and destructive processes may be combined for further control over fabrication. These pieces are now constructed to a specified structure size and shape.

In one embodiment, for electromagnetic energy relays, it may be possible to use optical grade bonding agents, epoxies, or other known optical materials that may start as a liquid and form an optical grade solid structure through various means including but not limited to UV, heat, time, among other processing parameters. In another embodiment, the bonding agent is not cured or is made of index matching oils for flexible applications. Bonding agent may be applied to solid structures and non-curing oils or optical liquids. These materials may exhibit certain refractive index (RI) properties. The bonding agent needs to match the RI of either CES material type 1 or CES material type 2. In one embodiment, the RI of this optical bonding agent is 1.59, the same as PS. In a second embodiment, the RI of this optical bonding agent is 1.49, the same as PMMA.

In one embodiment, for energy waves, the bonding agent may be mixed into a blend of CES material type 1 and CES material type 2 in order to effectively cancel out the RI of the material that the bonding agent RI matches. The bonding agent may be thoroughly intermixed such that no regions are unsaturated which may require a certain amount of time for saturation and desired viscous properties. Additional constant agitation may be implemented to ensure the appropriate mixture of the materials to counteract any separation that may occur due to various densities of materials or other material properties.

It may be required to perform this process in a vacuum or in a chamber to evacuate any air bubbles that may form. An additional methodology may be to introduce vibration during the curing process.

An alternate method provides for three or more CES with additional form characteristics and EPs.

In one embodiment, for electromagnetic energy relays, an additional method provides for only a single CES to be used with only the bonding agent, where the RI of the CES and the bonding agent differ.

An additional method provides for any number of CESs and includes the intentional introduction of air bubbles.

In one embodiment, for electromagnetic energy relays, a method provides for multiple bonding agents with independent desired RIs, and a process to intermix the zero, one, or more CES's as they cure either separately or together to allow for the formation of a completely intermixed structure. Two or more separate curing methodologies may be leveraged to allow for the ability to cure and intermix at different intervals with different tooling and procedural methodologies. In one embodiment, a UV cure epoxy with a RI of 1.49 is intermixed with a heat cure second epoxy with a RI of 1.59 where constant agitation of the materials is provisioned with alternating heat and UV treatments with only sufficient duration to begin to see the formation of solid structures from within the larger mixture, but not long enough for any large particles to form, until such time that no agitation can be continued once the curing process has nearly completed, whereupon the curing processes are implemented simultaneously to completely bond the materials together. In a second embodiment, CES with a RI of 1.49 are added. In a third embodiment, CES with both a RI of 1.49 and 1.59 both added.

In another embodiment, for electromagnetic energy relays, glass and plastic materials are intermixed based upon their respective RI properties.

In an additional embodiment, the cured mixture is formed in a mold and after curing is cut and polished. In another embodiment, the materials leveraged will re-liquefy with heat and are cured in a first shape and then pulled into a second shape to include, but not limited to, tapers or bends.

Figure 7A:
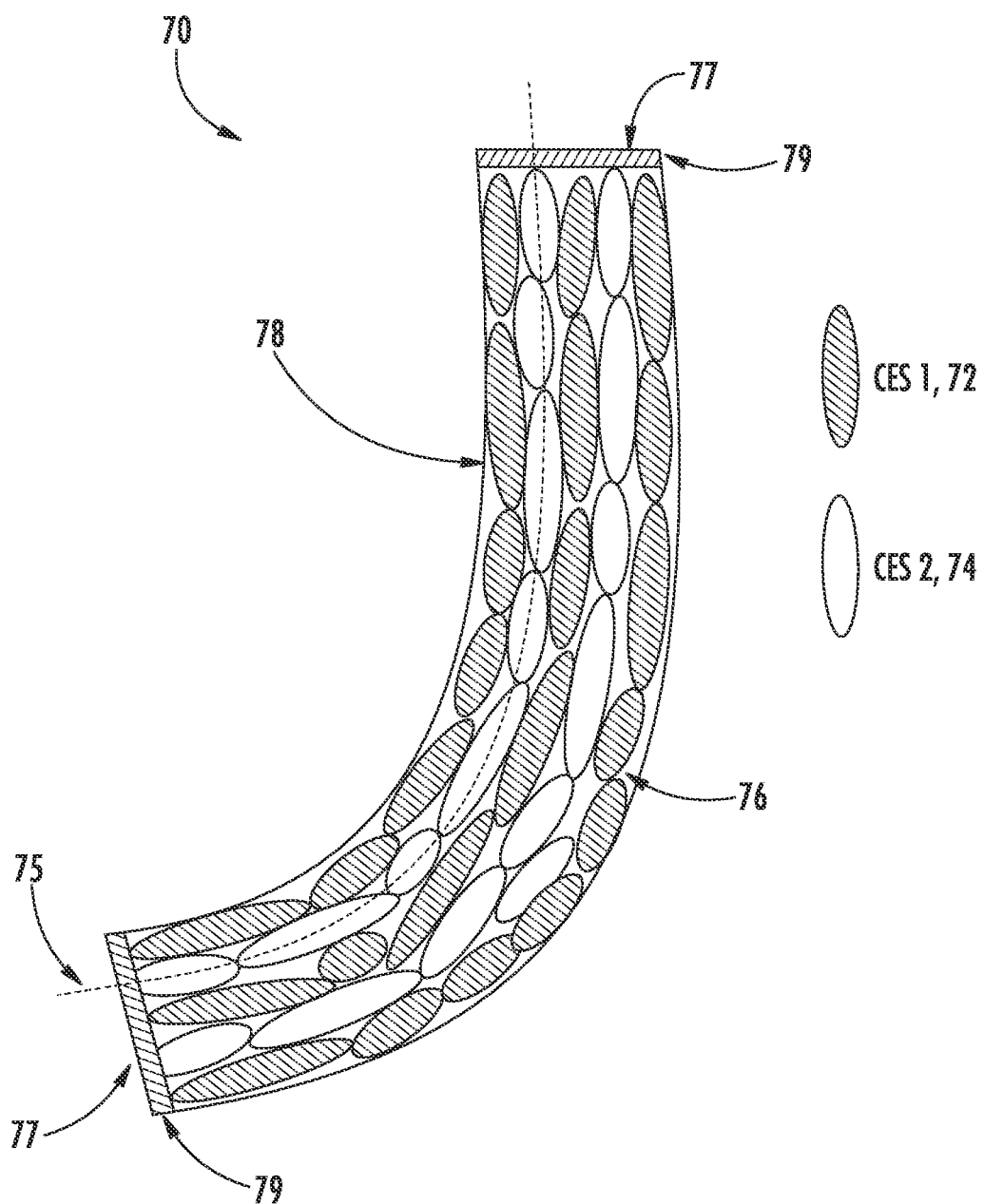
FIG. 7A illustrates a cutaway view of a flexible energy relay which achieves Transverse Anderson Localization by intermixing two component materials within an oil or liquid, in accordance with one embodiment of the present disclosure.

FIG. 7A illustrates a cutaway view of a flexible implementation 70 of a relay exhibiting the Transverse Anderson Localization approach using CES material type 1 (72) and CES material type 2 (74) with intermixing oil or liquid 76 and with the possible use of end cap relays 79 to relay the energy waves from a first surface 77 to a second surface 77 on either end of the relay within a flexible tubing enclosure 78 in accordance with one embodiment of the present disclosure. The CES material type 1 (72) and CES material type 2 (74) both have the engineered property of being elongated—in this embodiment, the shape is elliptical, but any other elongated or engineered shape such as cylindrical or stranded is also possible. The elongated shape allows for channels of minimum engineered property variation 75.

For an embodiment for visible electromagnetic energy relays, implementation 70 may have the bonding agent replaced with a refractive index matching oil 76 with a refractive index that matches CES material type 2 (74) and placed into the flexible tubing enclosure 78 to maintain flexibility of the mixture of CES material type 1 and CES material 2, and the end caps 79 would be solid optical relays to ensure that an image can be relayed from one surface of an end cap to the other. The elongated shape of the CES materials allows channels of minimum refractive index variation 75.

Multiple instances of 70 can be interlaced into a single surface in order to form a relay combiner in solid or flexible form.

In one embodiment, for visible electromagnetic energy relays, several instances of 70 may each be connected on one end to a display device showing only one of many specific tiles of an image, with the other end of the optical relay placed in a regular mosaic, arranged in such a way to display the full image with no noticeable seams. Due to the properties of the CES materials, it is additionally possible to fuse multiple the multiple optical relays within the mosaic together.

Figure 7B:
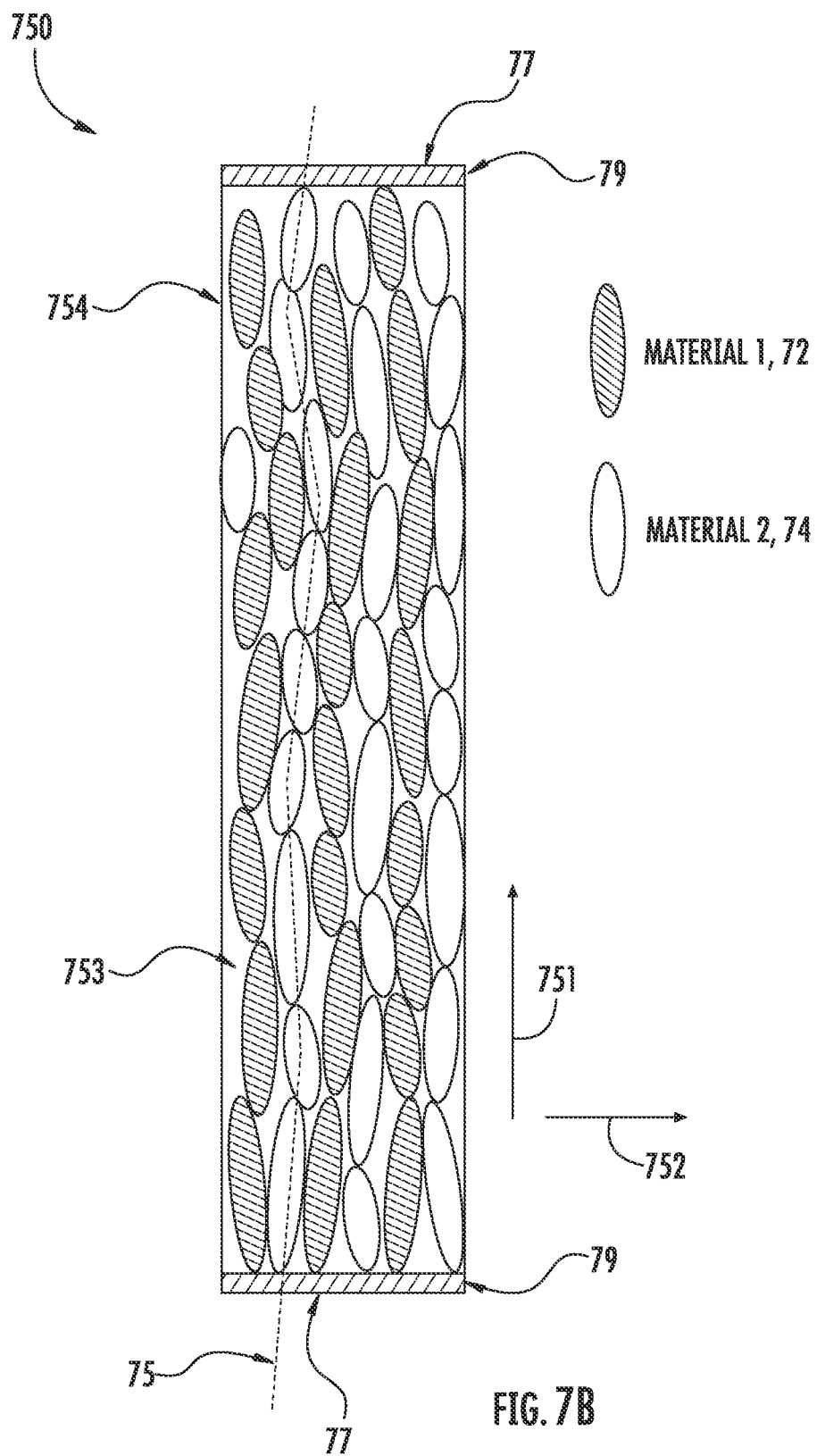
FIG. 7B illustrates a cutaway view of a rigid energy relay which achieves Transverse Anderson Localization by intermixing two component materials within a bonding agent, and in doing so, achieves a path of minimum variation in one direction for one critical material property, in accordance with one embodiment of the present disclosure.

FIG. 7B illustrates a cutaway view of a rigid implementation 750 of a CES Transverse Anderson Localization energy relay. CES material type 1 (72) and CES material type 2 (74) are intermixed with bonding agent 753 which matches the index of refraction of material 2 (74). It is possible to use optional relay end caps 79 to relay the energy wave from the first surface 77 to a second surface 77 within the enclosure 754. The CES material type 1 (72) and CES material type 2 (74) both have the engineered property of being elongated—in this embodiment, the shape is elliptical, but any other elongated or engineered shape such as cylindrical or stranded is also possible. Also shown in FIG. 7B is a path of minimum engineered property variation 75 along the longitudinal direction, which assists the energy wave propagation in this direction from one end cap surface 77 to the other end cap surface 77.

The initial configuration and alignment of the CESs can be done with mechanical placement, or by exploiting the EP of the materials, including but not limited to: electric charge, which when applied to a colloid of CESs in a liquid can result in colloidal crystal formation; magnetic moments which can help order CESs containing trace amounts of ferromagnetic materials, or relative weight of the CESs used, which with gravity helps to create layers within the bonding liquid prior to curing.

In one embodiment, for electromagnetic energy relays, the implementation depicted in FIG. 7B would have the bonding agent 753 matching the index of refraction of CES material type 2 (74), the optional end caps 79 would be solid optical relays to ensure that an image can be relayed from one surface of an end cap to the other, and the critical EP with minimal longitudinal variation would be refractive index, creating channels 75 which would assist the propagation of localized electromagnetic waves.

Figure 8:
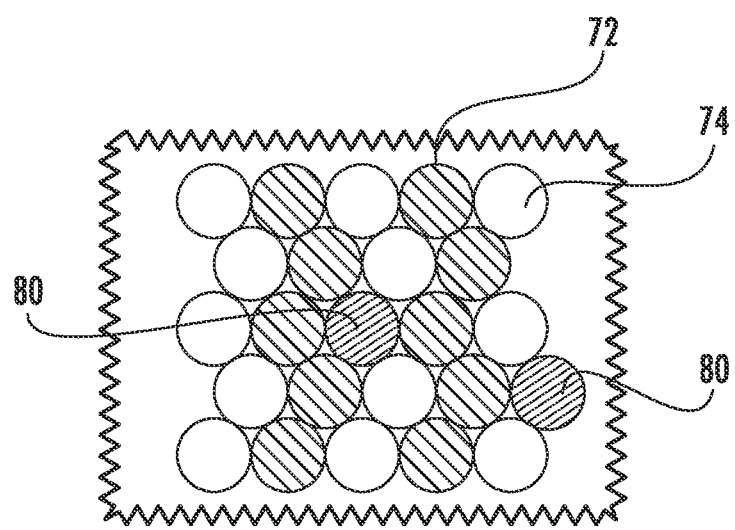
FIG. 8 illustrates a cutaway view in the transverse plane the inclusion of a DEMA (dimensional extra mural absorption) material in the longitudinal direction designed to absorb energy, in accordance with one embodiment of the present disclosure.

In an embodiment for visible electromagnetic energy relays, FIG. 8 illustrates a cutaway view in the transverse plane the inclusion of a DEMA (dimensional extra mural absorption) CES, 80, along with CES material types 72, 74 in the longitudinal direction of one exemplary material at a given percentage of the overall mixture of the material, which controls stray light, in accordance with one embodiment of the present disclosure for visible electromagnetic energy relays.

The additional CES materials that do not transmit light are added to the mixture(s) to absorb random stray light, similar to EMA in traditional optical fiber technologies, only the absorbing materials are included within a dimensional lattice and not contained within the longitudinal dimension, herein this material is called DEMA, 80. Leveraging this approach in the third dimension provides far more control than previous methods of implementation where the stray light control is much more fully randomized than any other implementation that includes a stranded EMA that ultimately reduces overall light transmission by the percent of the area of the surface of all the optical relay components, whereas the DEMA is intermixed in the dimensional lattice that effectively controls the light transmission in the longitudinal direction without the same reduction of light in the transverse. The DEMA can be provided in any ratio of the overall mixture. In one embodiment, the DEMA is 1% of the overall mixture of the material. In a second embodiment, the DEMA is 10% of the overall mixture of the material.

In an additional embodiment, the two or more materials are treated with heat and/or pressure to perform the bonding process and this may or may not be completed with a mold or other similar forming process known in the art. This may or may not be applied within a vacuum or a vibration stage or the like to eliminate air bubbles during the melt process. For example, CES with material type PS and PMMA may be intermixed and then placed into an appropriate mold that is placed into a uniform heat distribution environment capable of reaching the melting point of both materials and cycled to and from the respective temperature without causing damage/fractures due to exceeding the maximum heat elevation or declination per hour as dictated by the material properties.

For processes that require intermixing materials with additional liquid bonding agents, in consideration of the variable specific densities of each material, a process of constant rotation at a rate that prevents separation of the materials may be required.

High Density Energy Directing Device

In an embodiment, an energy directing device may comprises one or more energy locations and one or more energy relay elements, each of the one or more energy relay elements further comprising a first surface and a second surface. The second surfaces of each energy relay element may be arranged to form a singular seamless energy surface.

In embodiments of the present disclosure, the one or more energy locations may comprise a display technology including any of:

a) LCD, LED, laser, CRT, OLED, AMOLED, TOLED, pico projector, single chip, 3-chip, LCoS, DLP, Quantum Dots, monochrome, color, projection, backlit, directly emissive, reflective, transparent, opaque, coherent, incoherent, diffuse, direct, or any other illumination source sufficient to produce the desired pixel density; and b) wherein any reflective display technology may be directly bonded to the optical relay to provide an outdoor or ambient illumination display, and further, combined with other materials allows for the interaction of light with the relayed content for both 2D and light field applications; and c) a series of beamsplitters, prisms, or polarized elements and arranging each of the above devices within the optical system to provide a virtual energy surface that aggregates to include a completely seamless integration of all of the active area between the one or more devices even in consideration of the mechanical envelopes; and d) a series of parallel, converged, optically offset parallel and converged, on-axis, off-axis, radial, aligned or otherwise reflective or projection systems, each including a specified resolution and mechanical envelope but projecting onto a surface that is in aggregate smaller than the side-by-side footprint of all of the one or more reflective or projection systems combined.

In an embodiment, a separation between edges of any two adjacent second surfaces of the singular seamless energy surface may be less than a minimum perceptible contour as defined by the visual acuity of a human eye having better than 20/40 vision at a distance, greater than the lesser of a height of the singular seamless energy surface or a width of the singular seamless energy surface, from the singular seamless energy surface.

Creating a seamless energy surface from a plurality of separate independent energy sources presents a problem of significant seams between the active areas of the energy sources.

Figure 9:
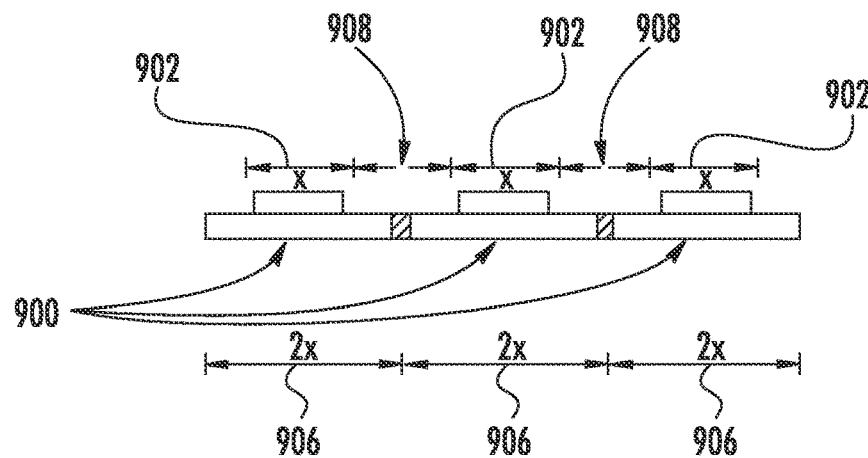
FIG. 9 illustrates a side view of three display devices which each comprise an active display area dimension and a mechanical envelope.

For example, for visible electromagnetic energy, FIG. 9 represents an example of the minimum separation possible between identical independent displays when mounted on flex cables. FIG. 9 illustrates a side view of three display devices 900, which each comprise an active display area dimension 902 and a mechanical envelope 906. Minimum gaps 908 highlight the minimum possible space between any two active imaging surfaces 902 of display devices 900. In the event that the active image to mechanical envelope ratio is less than 2:1 (e.g. the active area is 20 mm×10 mm and the mechanical envelope is less than 40 mm×10 mm), it is possible to use beam splitters or other similar optical and reflective materials to interleave two image surfaces to form one single contiguous plane.

Figure 10:
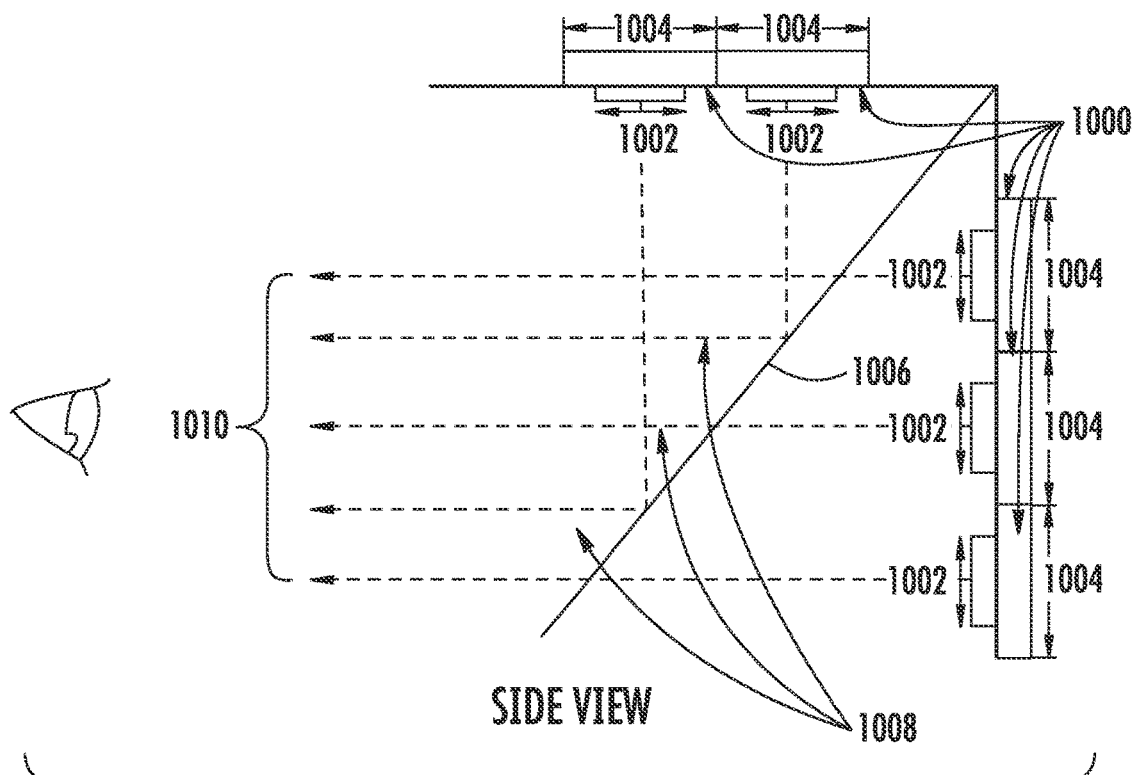
FIG. 10 features five display devices which each comprise active display areas and mechanical envelopes, used with a beam splitter.

FIG. 10 is a side view illustration which describes one such implementation of this methodology. FIG. 10 features five display devices 100 which each comprise active display areas 1002 and mechanical envelopes 1004. Beam splitter 1006 combines image light 1008 produced by display devices 1000 into a seamless image presentation 1010, which effectively masks the mechanical envelopes 1004 of the display devices 1000. It should be noted that a highly non-reflective dark surface is preferable at or near the display to mask out the non-image areas in order to avoid reflection of the electronics and other non-display regions.

Figure 11:
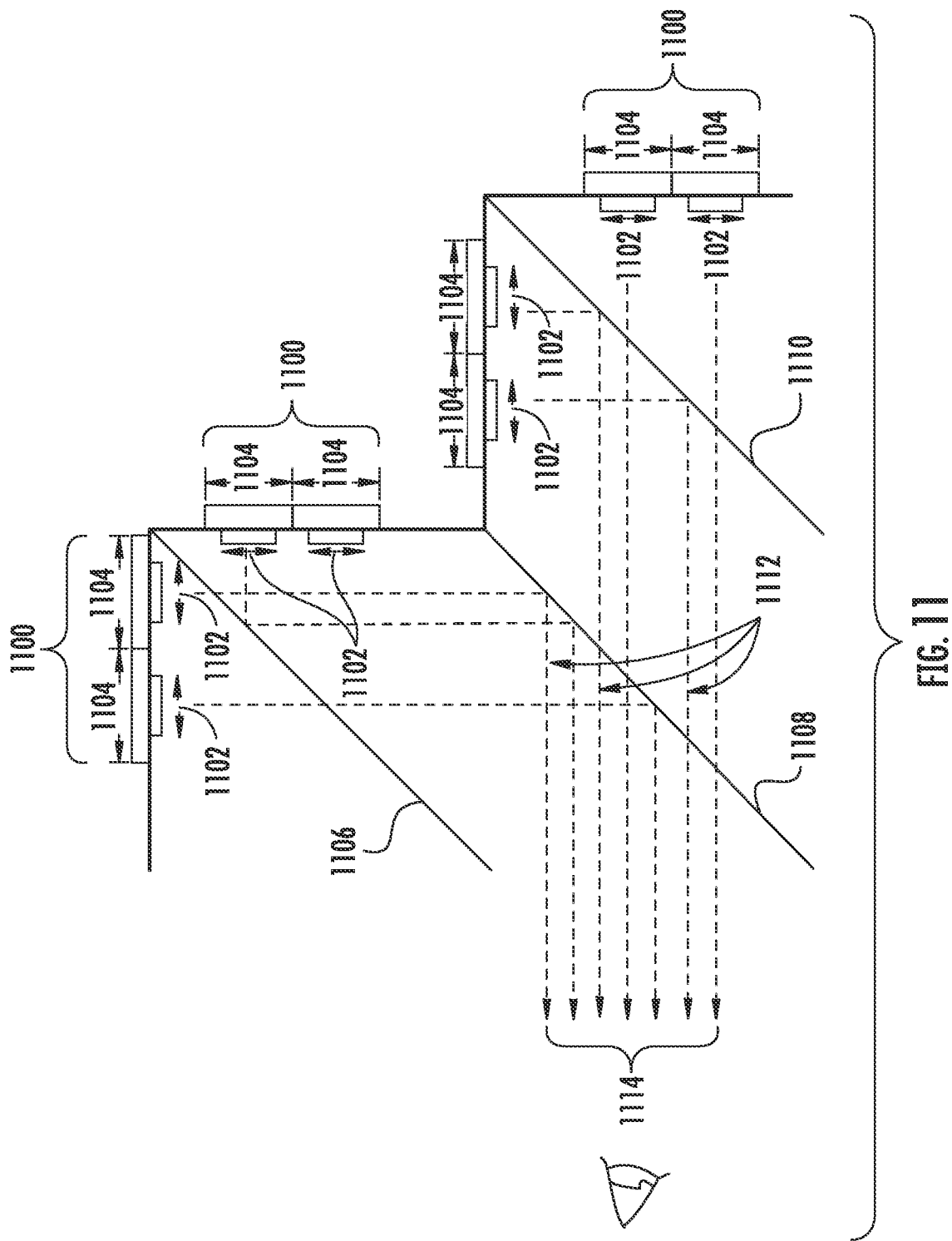
FIG. 11 is a side view illustration of a methodology where 3 beam splitters are leveraged to accommodate a mechanical envelope.

FIG. 11 is a side view illustration of a second methodology where 3 beam splitters are leveraged to accommodate a mechanical envelope that is a 4:1 ratio. FIG. 11 features eight display devices 1100 which each comprise active display areas 1102 and mechanical envelopes 1104. Three beam splitters 1106, 1108, and 1110 combine image light 1112 produced by the eight display devices 1100 into a seamless image presentation 1114, which effectively masks the mechanical envelopes 1104 of the display devices 1100.

It should be noted that while these methods can work, the mechanical accuracy may preferably be near perfect to avoid incorrect angular viewing of each overlapping display plane and the overall viewed brightness will decrease by the amount of light that is absorbed by the beam splitter in order to redirect the rays of light to each discreet reflected plane. In FIG. 11, the brightness of image light 1112 will only transmit at best 25% of actual display peak potential from display devices 1100 due to the loss of light from the overall system. Additionally, it should be noted that the size of the physical apparatus with multiple reflections becomes quite large very quickly depending on the size of the desired image surface.

It is also possible to consider projection technologies to aggregate multiple images into a larger overall display, however, this comes at the cost of great complexity for throw distance, minimum focus, optical quality, thermal consistency considerations over a temperature gradient over time, as well as image blending, alignment, size and form factor. For most practical applications, hosting tens or hundreds of these projection sources results in a design that is much larger and less reliable. With all of the above risks noted, all of the descriptions contained herein may also apply to any form of projection technology in addition to the disclosed panel methodologies.

An alternative methodology involves using many projectors in a tiled fashion to produce a seamless image surface in combination with a rear projection surface. This surface may include screens, diffusers, and optical relays in planar or non-planar surfaces. The regions between each individually addressed tile should ideally overlap slightly and blend the transition between each tile appropriately, although not explicitly required. The same concept of image area to mechanical envelope applies with some added complexity. We now introduce the concepts of maximum optical offset along image surface position which can be controlled by moving the optics of the projection system independently from that of the image source resulting in a non-keystoned shift of the image to the energy surface. High quality optics are desired for this to be successful and is often limited to less than the width of the projected image.

Additionally, when not using orthographic or collimated designs, we now have the challenge of minimum focus of the optics contained within the projection system. This can be addressed by increasing the overall projected image size per tile at the consequence of increasing the viewed distance to provide the desired pixel density as notated above.

Figure 12:
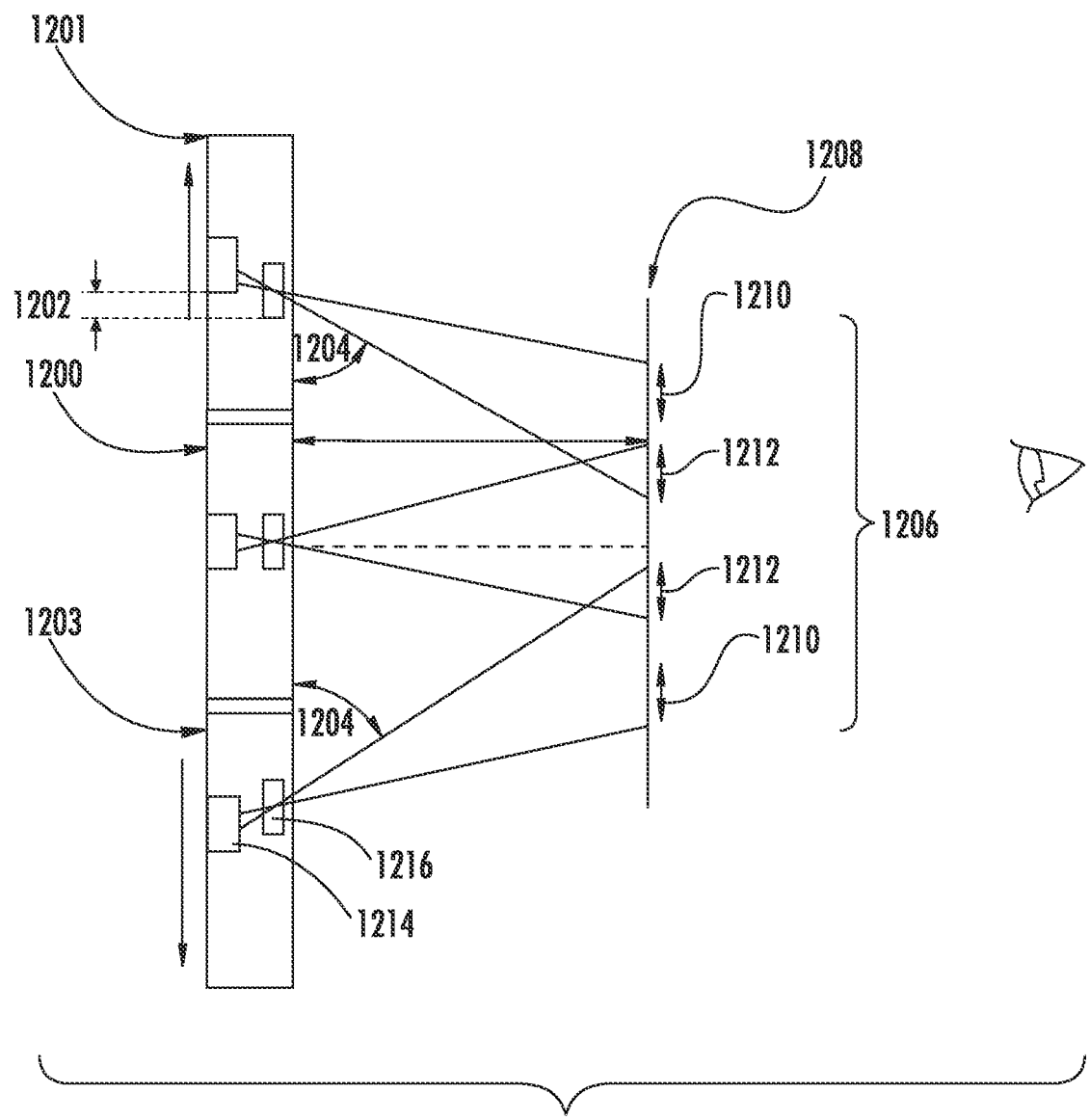
FIG. 12 highlights this relationship between the mechanical envelope ratio, the minimum focus distance and the maximum image offset as well as the percent of overlap between individual tiled images.

FIG. 12 highlights this relationship between the mechanical envelope ratio, the minimum focus distance and the maximum image offset as well as the percent of overlap between individual tiled images. FIG. 12 illustrates a top view of an embodiment with three projection devices: one centered projection device 1200, and two off-centered projection devises 1201, 1203. The mechanical envelope of each projection device 1200, 1201, 1203 creates a display offset which invites adjustment of the projection angle 1204 of each off-centered projection device 1201, 1203. FIG. 12 highlights the use of off-axis projection optics, where the display panel 1214 is displaced from the optical axis of the display lens 1216 by an amount 1202 in proportion to the display panel distance from the center of the array, allowing for the overlap of each of these images while maintaining a parallel array structure, and additionally avoid a keystone image correction. Image light projected from the projection devices 1200, 1201, 1203 forms a display image 1206 at image plane 1208. Image light from off-centered projection device 1201, 1203 will have an image offset 1210 and a fractional overlap 1212 at the image plane 1208.

In an embodiment, the singular seamless energy surface may be planar, faceted, or curved. It is also possible to form an arc of projectors at the expense of requiring keystone correction optically or computationally to form the singular energy surface. In an embodiment, three projection devices may be arranged in an arc. The projection devices may produce image light which propagates through a planar image plane. The image light may experience keystone effects.

Figure 13:
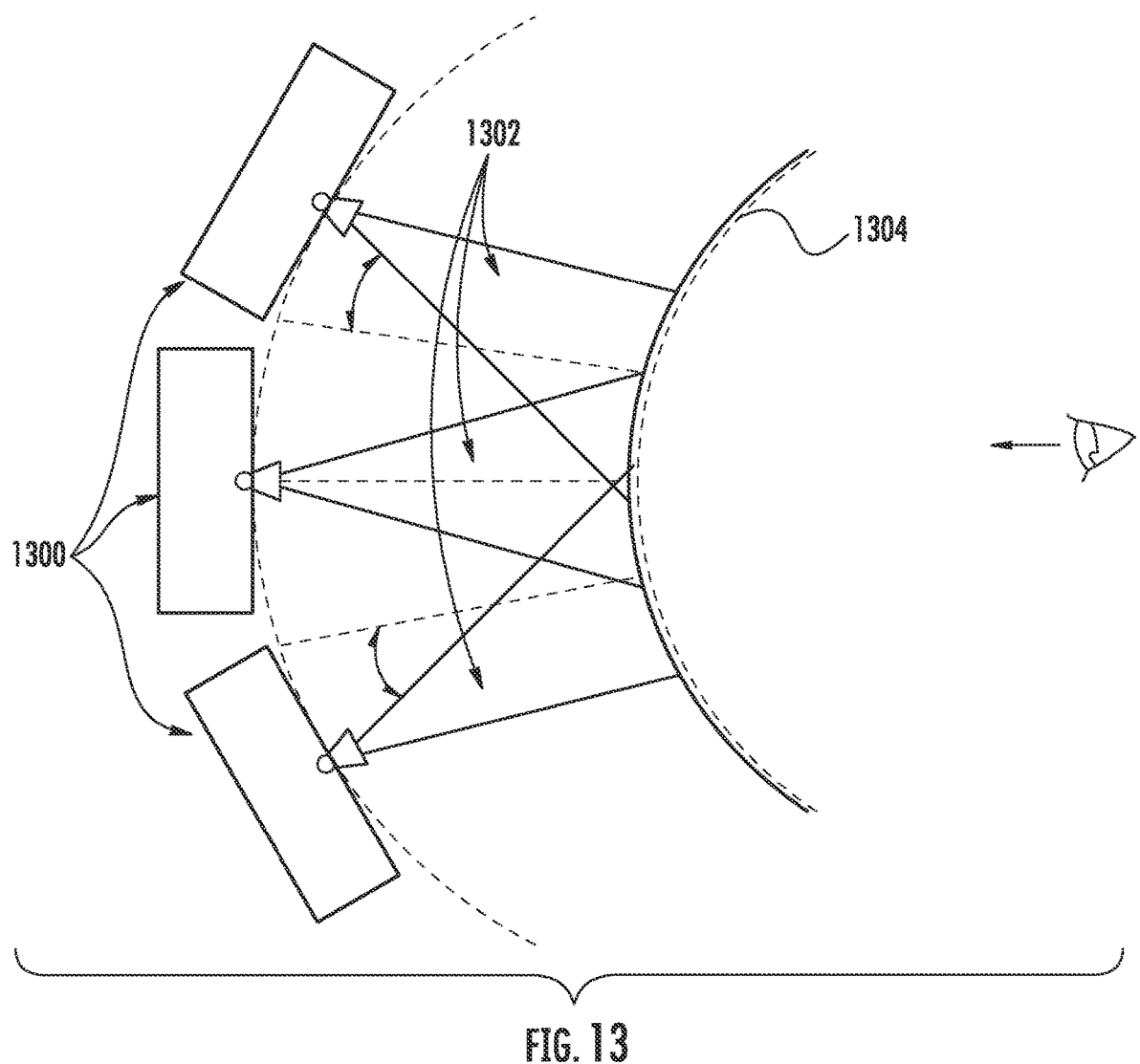
FIG. 13 is a top view illustration of an embodiment with three projection devices arranged in an arc.

Alternatively, non-planar surfaces may be designed in order to place each projector directly behind the corresponding tile of viewed energy surface. FIG. 13 is a top view illustration of an embodiment with three projection devices 1300 arranged in an arc. The projection devices 1300 produce image light 1302 which propagates through non-planar surface 1304. Image light 1302 may experience keystone effects that the embodiment of FIG. 12 avoids. For both of these approaches, the projectors do not necessarily need to be in a physically stacked configuration and may leverage reflectors or other optical methodologies in order to provide application specific mechanical designs.

Any combination of these approaches may be employed where both beam splitters and projection technologies can be leveraged simultaneously.

An additional embodiment of the system makes use of recent breakthroughs in energy relay technologies.

Tapered Energy Relays

In order to further solve the challenge of generating high resolution from an array of individual energy wave sources containing extended mechanical envelopes, the use of tapered energy relays can be employed to increase the effective size of each energy source. An array of tapered energy relays can be stitched together to form a singular contiguous energy surface, circumventing the limitation of mechanical requirements for those energy sources.

In an embodiment, the one or more energy relay elements may be configured to direct energy along propagation paths which extend between the one or more energy locations and the singular seamless energy surface.

For example, if an energy wave source's active area is 20 mm×10 mm and the mechanical envelope is 40 mm×20 mm, a tapered energy relay may be designed with a magnification of 2:1 to produce a taper that is 20 mm×10 mm (when cut) on the minified end and 40 mm×20 mm (when cut) on the magnified end, providing the ability to align an array of these tapers together seamlessly without altering or violating the mechanical envelope of each energy wave source.

Figure 14:
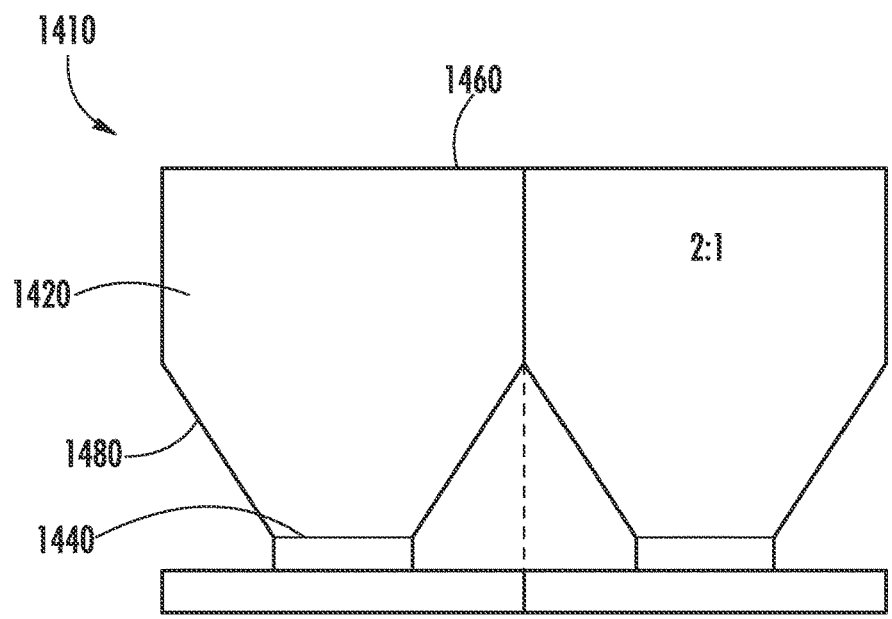
FIG. 14 illustrates a tapered energy relay mosaic arrangement.

FIG. 14 illustrates an orthogonal view of one such tapered energy relay mosaic arrangement 1410, in accordance with one embodiment of the present disclosure. In FIG. 14, the relay device 1410 may include two or more relay elements 1420, each relay element 1420 formed of one or more structures, each relay element 1420 having a first surface 1440, a second surface 1460, a transverse orientation (generally parallel to the surfaces 1440, 1460) and a longitudinal orientation (generally perpendicular to the surfaces 1440, 1410). The surface area of the first surface 1440 may be different than the surface area of the second surface 1460. For relay element 1420, the surface area of the first surface 1440 is less than the surface area of the second surface 1460. In another embodiment, the surface area of the first surface 1440 may be the same or greater than the surface area of the second surface 1460. Energy waves can pass from the first surface 1440 to the second surface 1460, or vice versa.

In FIG. 14, the relay element 1420 of the relay element device 1410 includes a sloped profile portion 1480 between the first surface 1440 and the second surface 1460. In operation, energy waves propagating between the first surface 1440 and the second surface 1460 may have higher transport efficiency in the longitudinal orientation than in the transverse orientation, and energy waves passing through the relay element 1420 may result in spatial magnification or spatial de-magnification. In other words, energy waves passing through the relay element 1420 of the relay element device 1410 may experience increased magnification or decreased magnification. In an embodiment, energy may be directed through the one or more energy relay elements with zero magnification. In some embodiments, the one or more structures for forming relay element devices may include glass, carbon, optical fiber, optical film, plastic, polymer, or mixtures thereof.

In one embodiment, the energy waves passing through the first surface have a first resolution, while the energy waves passing through the second surface have a second resolution, and the second resolution is no less than about 50% of the first resolution. In another embodiment, the energy waves, while having a uniform profile when presented to the first surface, may pass through the second surface radiating in every direction with an energy density in the forward direction that substantially fills a cone with an opening angle of +/−10 degrees relative to the normal to the second surface, irrespective of location on the second relay surface.

In some embodiments, the first surface may be configured to receive energy from an energy wave source, the energy wave source including a mechanical envelope having a width different than the width of at least one of the first surface and the second surface.

In an embodiment, energy may be transported between first and second surfaces which defines the longitudinal orientation, the first and second surfaces of each of the relays extends generally along a transverse orientation defined by the first and second directions, where the longitudinal orientation is substantially normal to the transverse orientation. In an embodiment, energy waves propagating through the plurality of relays have higher transport efficiency in the longitudinal orientation than in the transverse orientation and are spatially localized in the transverse plane due to randomized refractive index variability in the transverse orientation coupled with minimal refractive index variation in the longitudinal orientation via the principle of Transverse Anderson Localization. In some embodiments where each relay is constructed of multicore fiber, the energy waves propagating within each relay element may travel in the longitudinal orientation determined by the alignment of fibers in this orientation.

Mechanically, these tapered energy relays are cut and polished to a high degree of accuracy before being bonded or fused together in order to align them and ensure that the smallest possible seam gap between the relays. The seamless surface formed by the second surfaces of energy relays is polished after the relays are bonded. In one such embodiment, using an epoxy that is thermally matched to the taper material, it is possible to achieve a maximum seam gap of 50 um. In another embodiment, a manufacturing process that places the taper array under compression and/or heat provides the ability to fuse the elements together. In another embodiment, the use of plastic tapers can be more easily chemically fused or heat-treated to create the bond without additional bonding. For the avoidance of doubt, any methodology may be used to bond the array together, to explicitly include no bond other than gravity and/or force.

In an embodiment, a separation between the edges of any two adjacent second surfaces of the terminal energy relay elements may be less than a minimum perceptible contour as defined by the visual acuity of a human eye having better than 20/40 vision at a distance from the seamless energy surface that is greater than the lesser of a height of the singular seamless energy surface or a width of the singular seamless energy surface.

A mechanical structure may be preferable in order to hold the multiple components in a fashion that meets a certain tolerance specification. In some embodiments, the first and second surfaces of tapered relay elements can have any polygonal shapes including without limitation circular, elliptical, oval, triangular, square, rectangle, parallelogram, trapezoidal, diamond, pentagon, hexagon, and so forth. In some examples, for non-square tapers, such as rectangular tapers for example, the relay elements may be rotated to have the minimum taper dimension parallel to the largest dimensions of the overall energy source. This approach allows for the optimization of the energy source to exhibit the lowest rejection of rays of light due to the acceptance cone of the magnified relay element as when viewed from center point of the energy source. For example, if the desired energy source size is 100 mm by 60 mm and each tapered energy relay is 20 mm by 10 mm, the relay elements may be aligned and rotated such that an array of 3 by 10 taper energy relay elements may be combined to produce the desired energy source size. Nothing here should suggest that an array with an alternative configuration of an array of 6 by 5 matrix, among other combinations, could not be utilized. The array comprising of a 3×10 layout generally will perform better than the alternative 6×5 layout.

Energy Relay Element Stacks

While the most simplistic formation of an energy source system comprises of an energy source bonded to a single tapered energy relay element, multiple relay elements may be coupled to form a single energy source module with increased quality or flexibility. One such embodiment includes a first tapered energy relay with the minified end attached to the energy source, and a second tapered energy relay connected to the first relay element, with the minified end of the second optical taper in contact with the magnified end of the first relay element, generating a total magnification equal to the product of the two individual taper magnifications. This is an example of an energy relay element stack comprising of a sequence of two or more energy relay elements, with each energy relay element comprising a first side and a second side, the stack relaying energy from the first surface of the first element to the second surface of the last element in the sequence, also named the terminal surface. Each energy relay element may be configured to direct energy therethrough.

In an embodiment, an energy directing device comprises one or more energy locations and one or more energy relay element stacks. Each energy relay element stack comprises one or more energy relay elements, with each energy relay element comprising a first surface and a second surface. Each energy relay element may be configured to direct energy therethrough. In an embodiment, the second surfaces of terminal energy relay elements of each energy relay element stack may be arranged to form a singular seamless display surface. In an embodiment, the one or more energy relay element stacks may be configured to direct energy along energy propagation paths which extend between the one or more energy locations and the singular seamless display surfaces.

Figure 15:
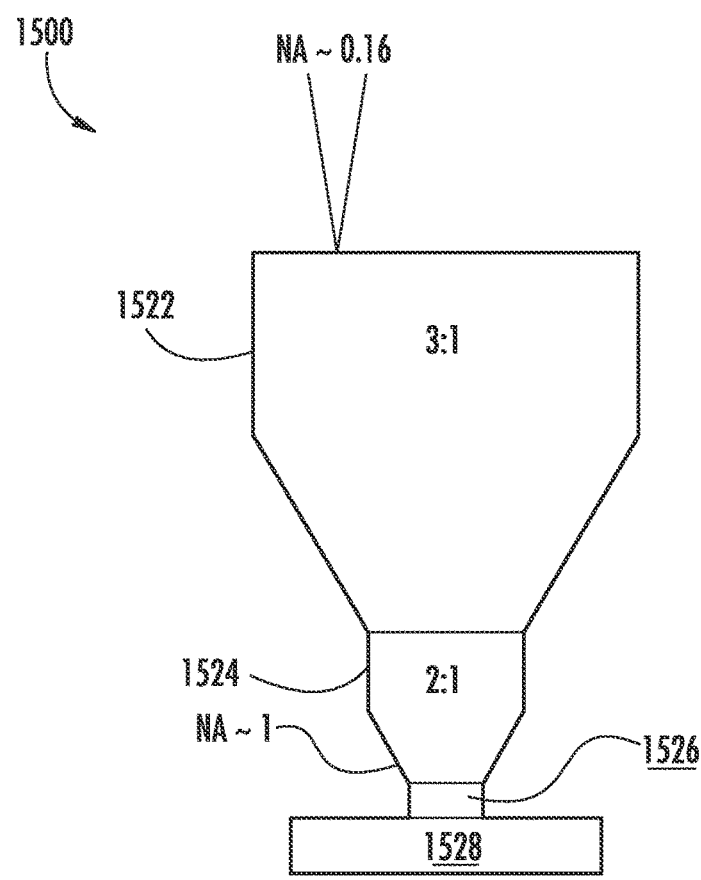
FIG. 15 illustrates a side view of an energy relay element stack comprising of two compound optical relay tapers in series.

FIG. 15 illustrates a side view of an energy relay element stack 1500 consisting of two compound optical relay tapers 1522, 1524 in series, both tapers with minified ends facing an energy source surface 1526, in accordance with an embodiment of the present disclosure. In FIG. 15, the input numerical aperture (NA) is 1.0 for the input of taper 1524, but only about 0.16 for the output of taper 1522. Notice that the output numerical aperture gets divided by the total magnification of 6, which is the product of 2 for taper 1524, and 3 for taper 1522. One advantage of this approach is the ability to customize the first energy wave relay element to account for various dimensions of energy source without alteration of the second energy wave relay element. It additionally provides the flexibility to alter the size of the output energy surface without changing the design of the energy source or the first relay element. Also shown in FIG. 15 is the energy source 1526 and the mechanical envelope 1528 containing the energy source drive electronics.

In an embodiment, the first surface may be configured to receive energy waves from an energy source unit (e.g., 1526), the energy source unit including a mechanical envelope having a width different than the width of at least one of the first surface and the second surface. In one embodiment, the energy waves passing through the first surface may have a first resolution, while the energy waves passing through the second surface may have a second resolution, such that the second resolution is no less than about 50% of the first resolution. In another embodiment, the energy waves, while having a uniform profile when presented to the first surface, may pass through the second surface radiating in every direction with an energy density in the forward direction that substantially fills a cone with an opening angle of +/−10 degrees relative to the normal to the second surface, irrespective of location on the second relay surface.

In one embodiment, the plurality of energy relay elements in the stacked configuration may include a plurality of faceplates (relays with unity magnification). In some embodiments, the plurality of faceplates may have different lengths or are loose coherent optical relays. In other embodiments, the plurality of elements may have sloped profile portions similar to that of FIG. 14, where the sloped profile portions may be angled, linear, curved, tapered, faceted or aligned at a non-perpendicular angle relative to a normal axis of the relay element. In yet another embodiment, energy waves propagating through the plurality of relay elements have higher transport efficiency in the longitudinal orientation than in the transverse orientation and are spatially localized in the transverse orientation due to randomized refractive index variability in the transverse orientation coupled with minimal refractive index variation in the longitudinal orientation. In embodiments where each energy relay is constructed of multicore fiber, the energy waves propagating within each relay element may travel in the longitudinal orientation determined by the alignment of fibers in this orientation.

Energy Directing Device

Figure 16:
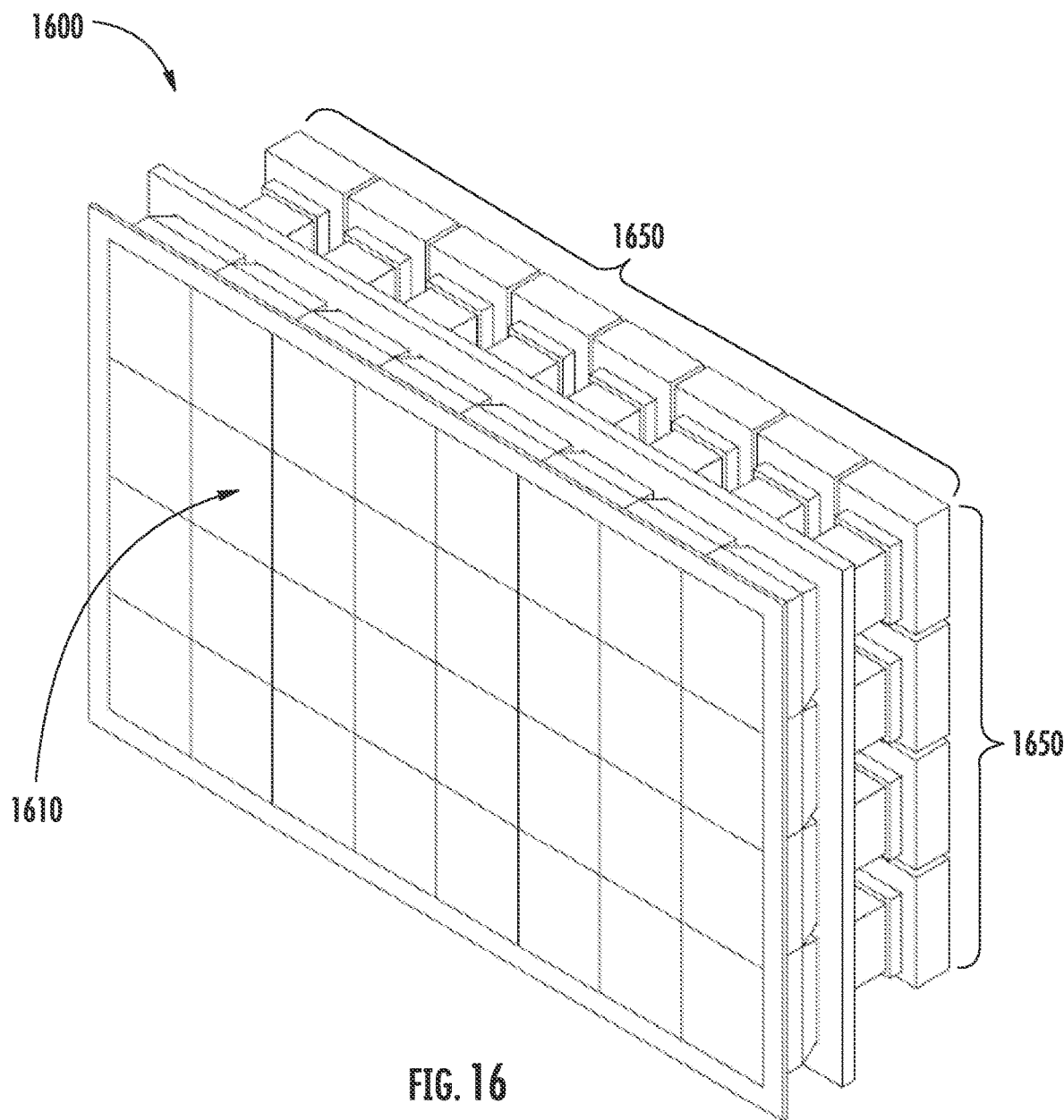
FIG. 16 illustrates a perspective view of an embodiment of an energy directing device where energy relay element stacks are arranged in an 8×4 array to form a singular seamless energy directing surface.

FIG. 16 illustrates a perspective view of an embodiment 1600 of an energy directing device where energy relay element stacks are arranged in an 8×4 array to form a singular seamless energy directing surface 1610 with the shortest dimension of the terminal surface of each tapered energy relay element stack parallel to the longest dimension of the energy surface 1610. The energy originates from 32 separate energy sources 1650; each bonded or otherwise attached to the first element of the energy relay element stacks.

In an embodiment, a separation between the edges of any two adjacent second surfaces of the terminal energy relay elements may be less than a minimum perceptible contour as defined by the visual acuity of a human eye having better than 20/100 vision at a distance, greater than the lesser of a height of the singular seamless display surface or a width of the singular seamless display surface, from the singular seamless display surface.

Figure 17:
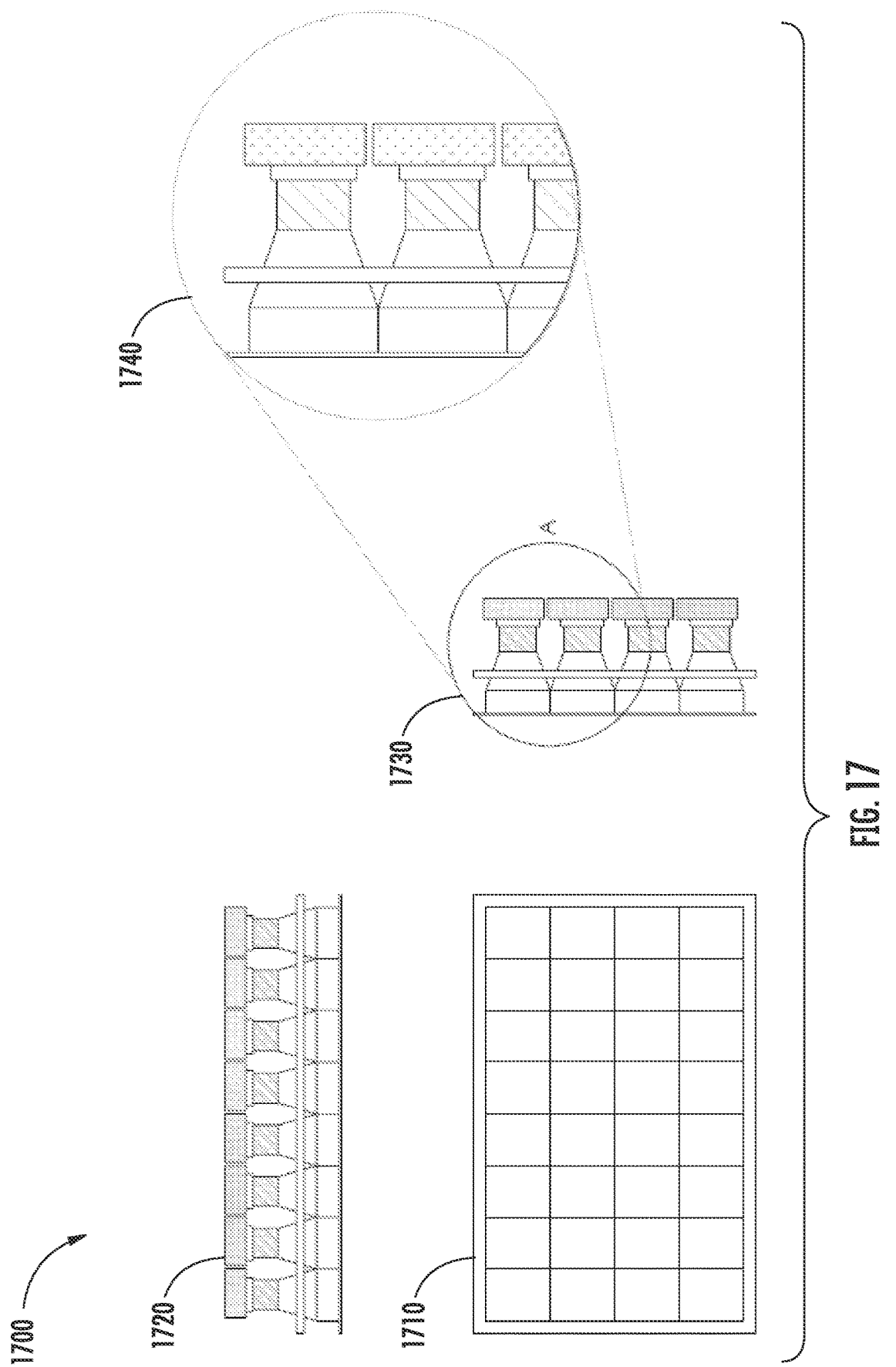
FIG. 17 contains several views of an energy directing device.

FIG. 17 contains the following views of embodiment 1600: a front view 1710, a top view 1710, a side view 1730, and a close-up side view 1740.

Figure 18:
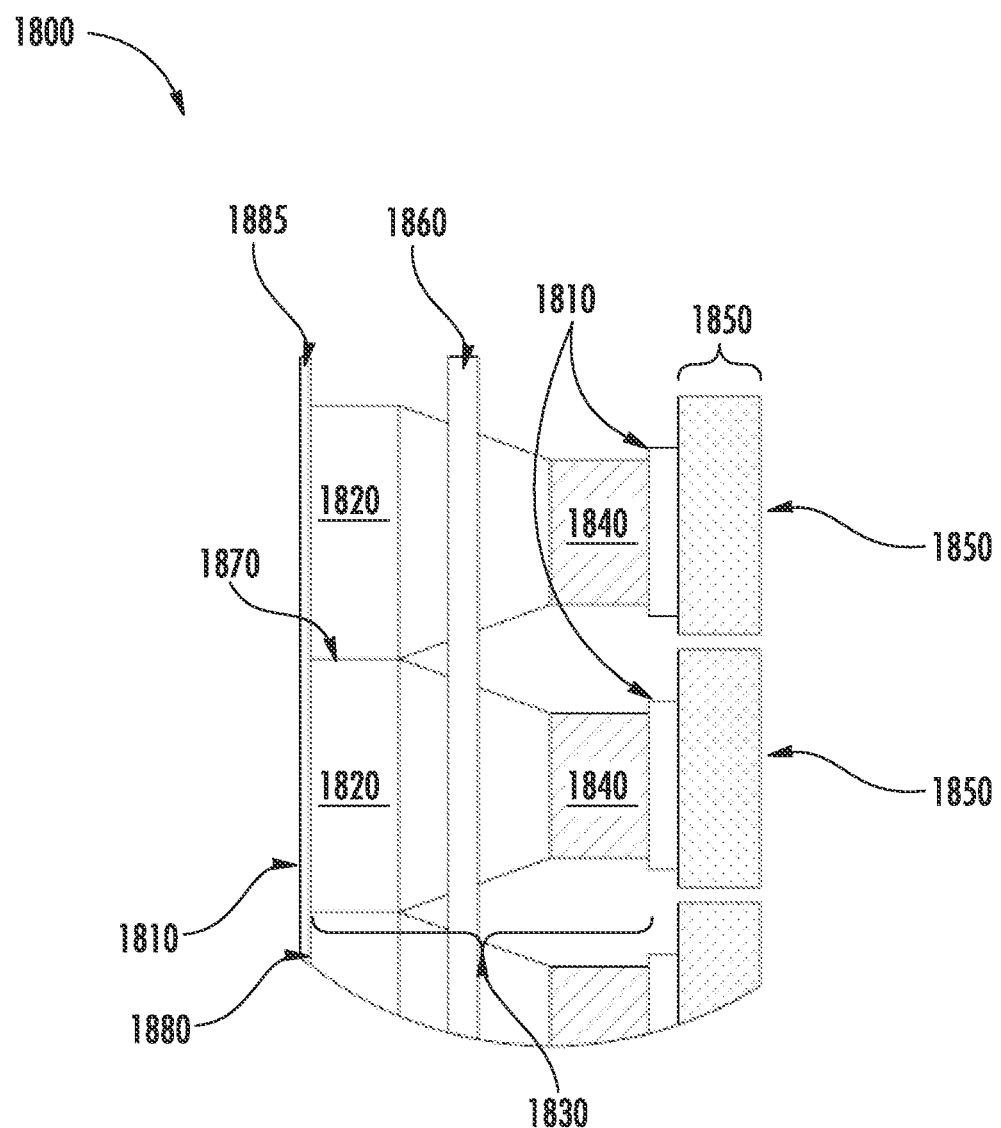
FIG. 18 contains a close-up view of the side view from FIG. 17 of the energy directing device.

FIG. 18 is the close-up view of the side view 1740 of the energy directing device 1600, consisting of a repeating structure comprised of energy relay element stacks 1830 arranged along a transverse orientation defined by first and second directions, used to propagate energy waves from the plurality of energy units 1850 to a single common seamless energy surface 1880 formed by the second surface of the energy relay element stacks. Each energy unit 1850 is composed of an energy source 1810 as well as the mechanical enclosure 1850 which houses the drive electronics. Each relay stack is composed of a faceplate 1840 with no magnification directly bonded to an energy source 1810 on one side, and a tapered energy relay on the other side, where the taper spatially magnifies the energy wave from the faceplate while propagating the energy to the seamless energy surface 1880. In one embodiment, the magnification of the tapered energy relay is 2:1. In one embodiment, tapered energy relays 1820 are held in place by a common base structure 1860, and each of these tapers are bonded to a faceplate 1840, which in turn is bonded to the energy unit 1850. Neighboring tapers 1820 are bonded or fused together at seam 1870 in order to ensure that the smallest possible seam gap is realized. All the tapered energy relays in the full 8×4 array are arranged in a seamless mosaic such that the second surface for each tapered energy relay forms a single contiguous energy surface 1880, which is polished during assembly to ensure flatness. In one embodiment, surface 1810 is polished to within 10 waves of flatness. Face plate 1885 has dimensions slightly larger than the dimensions of the surface 1880, and is placed in direct contact with surface 1880 in order to extend the field of view of the tapered energy surface 1880. The second surface of the faceplate forms the output energy surface 1810 for the energy directing device 1800.

In this embodiment of 1800, energy is propagated from each energy source 1810, through the relay stack 1830, and then substantially normal to the faceplate, defining the longitudinal direction, the first and second surfaces of each of the relay stacks extends generally along a transverse orientation defined by the first and second directions, where the longitudinal orientation is substantially normal to the transverse orientation. In one embodiment, energy waves propagating through at least one of the relay elements faceplate 1840, taper 1820, and faceplate 1885, have higher transport efficiency in the longitudinal orientation than in the transverse orientation and are localized in the transverse orientation due to randomized refractive index variability in the transverse orientation coupled with minimal refractive index variation in the longitudinal orientation. In some embodiments at least one of the relay elements faceplate 1840, taper 1820, and faceplate 1885 may be constructed of multicore fiber, with energy waves propagating within each relay element traveling in the longitudinal orientation determined by the alignment of fibers in this orientation.

In one embodiment, the energy waves passing through the first surface of 181640 have a first spatial resolution, while the energy waves passing through the second surface of tapered energy relay 1820 and through the face plate have a second resolution, and the second resolution is no less than about 50% of the first resolution. In another embodiment, the energy waves, while having a uniform profile at the first surface of the faceplate 1840, may pass through the seamless energy surfaces 1880 and 1810 radiating in every direction with an energy density in the forward direction that substantially fills a cone with an opening angle of +/−10 degrees relative to the normal to the seamless energy surface 1810, irrespective of location on this surface 1810.

In an embodiment, an energy directing device comprises one or more energy sources and one or more energy relay element stacks.

In an embodiment, each energy relay element of an energy directing device may comprise at least one of:
1. one or more optical elements exhibiting transverse Anderson Localization;
2. a plurality of optical fibers;
3. loose coherent optical fibers;
4. image combiners;
5. one or more gradient index optical elements;
6. one or more beam splitters;
7. one or more prisms;
8. one or more polarized optical elements;
9. one or more multiple size or length optical elements for mechanical offset;
10. one or more waveguides;
11. one or more diffractive, refractive, reflective, holographic, lithographic, or transmissive elements; and
12. one or more retroreflectors.

In an embodiment, a quantity of the one or more energy relay elements and a quantity of the one or more energy locations may define a mechanical dimension of the energy directing device. The quantity of optical relay elements incorporated into the system is unlimited and only constrained by mechanical considerations and the resultant seamless energy surface includes a plurality of lower resolution energy sources producing an infinite resolution energy surface only limited by the resolving power and image quality of the components included within the display device.

A mechanical structure may be preferable in order to hold the multiple relay components in a fashion that meets a certain tolerance specification. Mechanically, the energy relays that contain a second surface that forms the seamless energy surface are cut and polished to a high degree of accuracy before being bonded or fused together in order to align them and ensure that the smallest possible seam gap between the energy relays is possible. The seamless surface 1880 is polished after the relays 1820 are bonded together. In one such embodiment, using an epoxy that is thermally matched to the tapered energy relay material, it is possible to achieve a maximum seam gap of 50 um. In another embodiment, a manufacturing process that places the taper array under compression and/or heat provides the ability to fuse the elements together. In another embodiment, the use of plastic tapers can be more easily chemically fused or heat-treated to create the bond without additional bonding. For the avoidance of doubt, any methodology may be used to bond the array together, to explicitly include no bond other than gravity and/or force.

The energy surface may be polished individually and/or as a singular energy surface and may be any surface shape, including planar, spherical, cylindrical, conical, faceted, tiled, regular, non-regular, convex, concave, slanted, or any other geometric shape for a specified application. The optical elements may be mechanically mounted such that the optical axes are parallel, non-parallel and/or arranged with energy surface normal oriented in a specified way.

The ability to create various shapes outside of the active display area provides the ability to couple multiple optical elements in series to the same base structure through clamping structures, bonding processes, or any other mechanical means desired to hold one or more relay elements in place. The various shapes may be formed out of optical materials or bonded with additional appropriate materials. The mechanical structure leveraged to hold the resultant shape may be of the same form to fit over top of said structure. In one embodiment, an energy relay is designed with a square shape with a side that is equal to 10% of the total length of the energy relay, but 25% greater than the active area of the energy source in width and height. This energy relay is clamped with the matched mechanical structure and may leverage refractive index matching oil, refractive index matched epoxy, or the like. In the case of electromagnetic energy sources, the process to place any two optical elements in series may include mechanical or active alignment wherein visual feedback is provided to ensure that the appropriate tolerance of image alignment is performed. Typically, a display is mounted to the rear surface of the optical element prior to alignment, but this may or may not be desired depending on application.

In an embodiment, the second sides of terminal energy relay elements of each energy relay element stack may be arranged to form a singular seamless energy surface.

In an embodiment, the singular seamless energy surface formed by a mosaic of energy relay element stacks may be extended by placing a faceplate layer in direct contact with the surface, using a bonding agent, index matching oil, pressure, or gravity to adhere it to the energy surface. In one embodiment, the faceplate layer may be composed of a single piece of energy relay material, while in others it is composed of two or more pieces of energy relay material bonded or fused together. In one embodiment, the extension of a faceplate may increase the angle of emission of the energy waves relative to the normal to the seamless energy surface.

In an embodiment, the one or more energy relay element stacks may be configured to direct energy along propagation paths which extend between the one or more energy locations and the singular seamless energy surfaces.

In an embodiment, a separation between the edges of any two adjacent second surfaces of the terminal energy relay elements may be less than a minimum perceptible contour as defined by the visual acuity of a human eye having better than 20/40 vision at a distance, greater than the lesser of a height of the singular seamless energy surface or a width of the singular seamless energy surface, from the singular seamless energy surface.

In an embodiment, the energy relay elements of each energy relay element stack are arranged in an end-to-end configuration.

In an embodiment, energy may be directed through the one or more energy relay element stacks with zero magnification, non-zero magnification, or non-zero minification.

In an embodiment, any of the energy relay elements of the one or more energy relay element stacks may comprise an element exhibiting Transverse Anderson Localization, an optical fiber, a beam splitter, an image combiner, an element configured to alter an angular direction of energy passing therethrough, etc.

In an embodiment, energy directed along energy propagation paths may be electromagnetic energy defined by a wavelength, the wavelength belonging to a regime of the electromagnetic spectrum such as visible light, ultraviolet, infrared, x-ray, etc. In an embodiment, energy directed along energy propagation paths may be mechanical energy such as acoustic sound, tactile pressure, etc. A volumetric sound environment is a technology that effectively aspires to achieve holographic sound or similar technology. A dimensional tactile device produces an array of transducers, air emitters, or the like to generate a sensation of touching objects floating in midair that may be directly coupled to the visuals displayed in a light field display. Any other technologies that support interactive or immersive media may additionally be explored in conjunction with this holographic display. For the use of the energy directing device as a display surface, the electronics may be mounted directly to the pins of the individual displays, attached to the electronics with a socket such as a zero-insertion force (ZIF) connector, or by using an interposer and/or the like, to provide simplified installation and maintenance of the system. In one embodiment, display electronic components including display boards, FPGAs, ASICs, IO devices or similarly desired components preferable for the use of said display, may be mounted or tethered on flex or flexi-rigid cables in order to produce an offset between the display mounting plane and the location of the physical electronic package. Additional mechanical structures are provided to mount the electronics as desired for the device. This provides the ability to increase density of the optical elements, thereby reducing the optical magnification for any tapered optical relays and decreasing overall display size and/or weight.

Cooling structures may be designed to maintain system performance within a specified temperature range, wherein all mechanical structures may include additional copper or other similar material tubing to provide a liquid cooling system with a solid state liquid cooling system providing sufficient pressure on a thermostat regulator. Additional embodiments may include Peltier units or heat syncs and/or the like to maintain consistent system performance for the electronics, displays and/or any other components sensitive to temperature changes during operation or that may produce excess heat.

Figure 19:
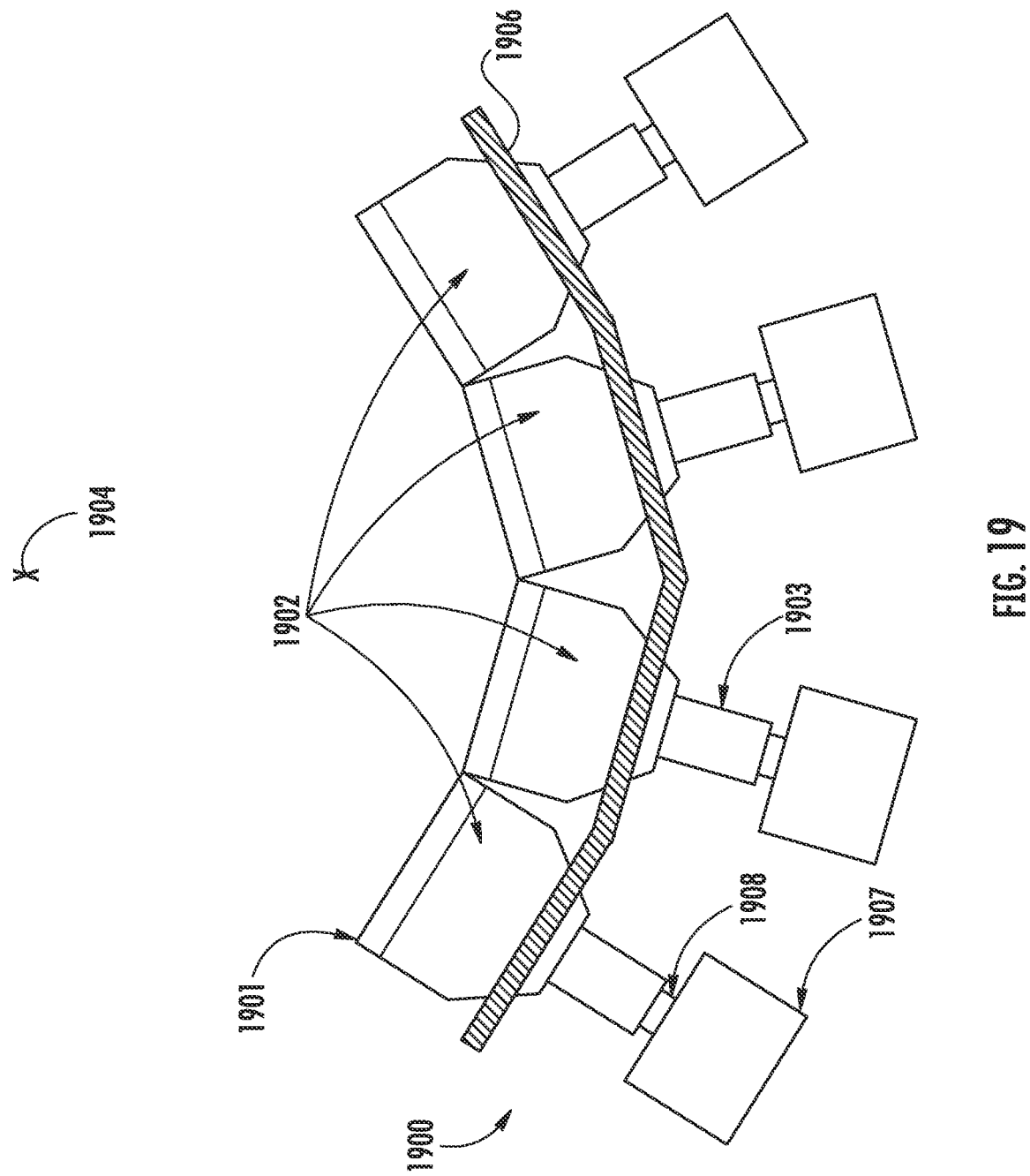
FIG. 19 illustrates a top view of an embodiment where energy relay element stacks are angled inward to a known point in space.
Figure 20:
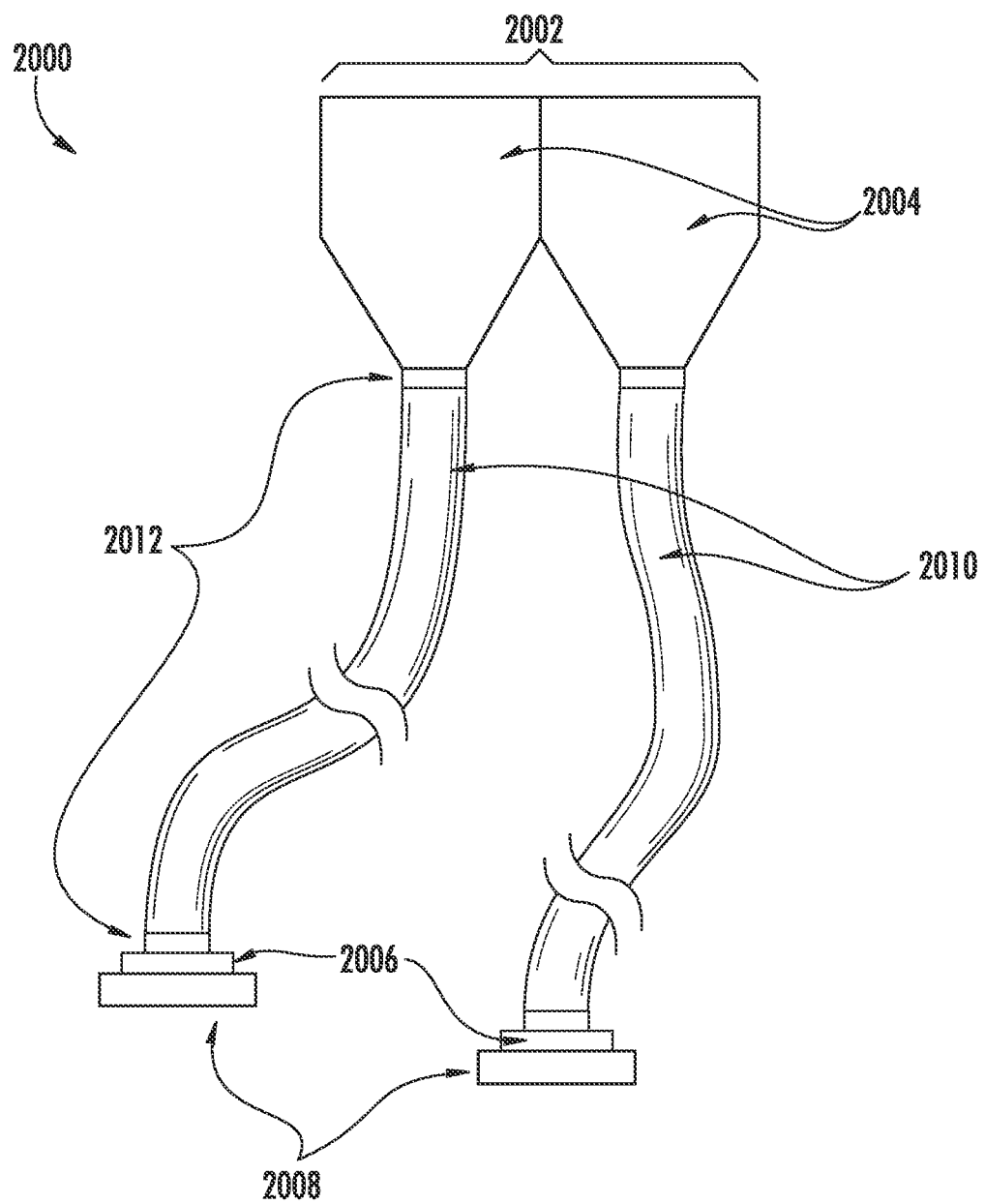
FIG. 20 is a top view illustration of an embodiment where the seamless energy surface is a display formed by tapered optical relays, while the display devices and the mechanical envelopes for the display electronics are located a distance away from the tapered relays.

FIG. 19 illustrates a top view of an embodiment 1900 where energy relay element stacks composed of elements 1902 and 1903 are angled inward to a known point in space 1904, directing energy to propagate from multiple sources 1908 through the seamless energy surface 1901. The base structure 1906 directly supports the tapered energy relays 1902, where each taper is in turn bonded to relay 1903. For an embodiment where the energy directing device 1900 is a display, tapered optical relay elements 1902 are angled inward to point the taper optical axes towards a fixed point in space 1904. The energy sources 1908 comprise of individual displays, with display electronics contained with the display mechanical envelope 1907.

In an embodiment, the optical relay may comprise loose coherent optical relays. Flexible optical elements, image conduits, and the like may additionally be leveraged in order to further offset display and display electronics from the seamless energy surface. In this fashion, it is possible to form an optical relay bundle including multiple loose coherent optical relays or other similar optical technology to connect two separate structures, with a first structure containing the seamless energy surface, and the second structure containing the display and display electronics.

One or more additional optical elements may be mounted in front of, or behind the ends of each loose coherent optical relay. These additional elements may be mounted with epoxies, pressure, mechanical structures, or other methods known in the art.

FIG. 2000 is a top view illustration of an embodiment where the seamless energy surface 2002 is a display formed by tapered optical relays 2004, while the display devices 2006 and the mechanical envelopes for the display electronics 2008 are located a distance away from the tapered relays 2004. Relaying light from display devices 2006 to the tapered optical relays 2004 are loose coherent optical relays 2010 each with end caps 2012 at either end. Embodiment 2000 allows the display devices 2006 to be disposed at the remote locations of 2008 away from the energy surface 2002 to ensure that a mechanical envelope of the display devices 2006 does not interfere with the positioning of energy surface 2002.

Optical elements may exhibit differing lengths to provide offset electronics as desired when formed in an alternating structure and provide the ability to increase density by the difference between the width of the electronic envelope minus the width of the optical element. In one such embodiment, a 5×5 optical relay mosaic contains two alternating optical relay lengths. In another embodiment, a 5×5 optical relay mosaic may contain 5 different optical relay lengths producing a pyramid-like structure, with the longest length at the center of the array, producing higher overall density for the resultant optical relay mosaic.

Figure 21:
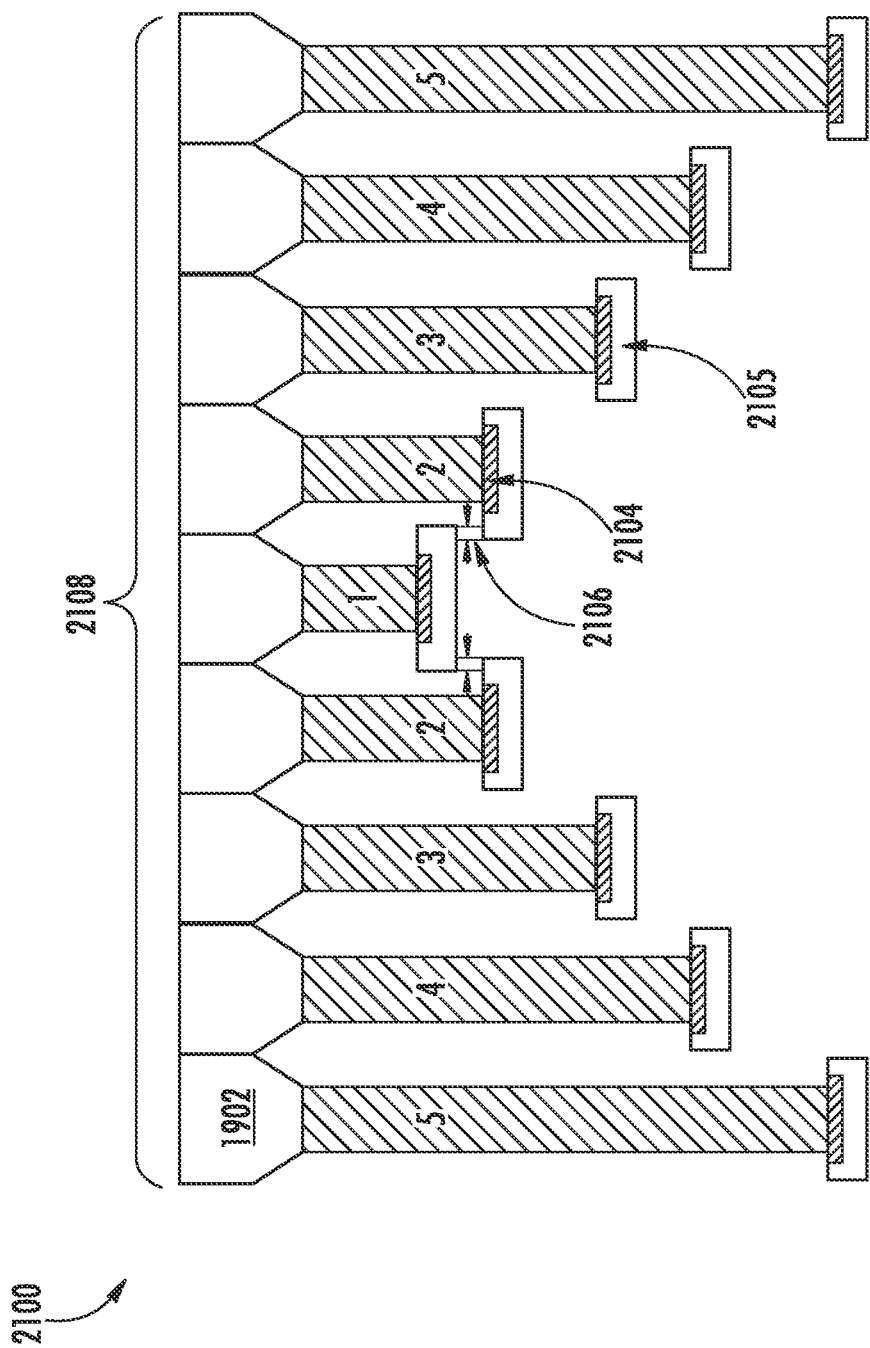
FIG. 21 is a side view illustration of an embodiment wherein a seamless display surface is composed of nine tapered optical relays.

FIG. 21 is a side view illustration of an embodiment 2100 wherein a seamless display surface 2108 is formed by nine tapered optical relays 2102, each associated with a display device 2104 through an *optical* face plate with one of five offset lengths 1, 2, 3, 4, or 5, such that no two adjacent display devices 2104 are connected to a face plate with the same offset length, providing sufficient clearance 2106 for respective mechanical envelopes 2105 for the display electronics.

Selective Propagation of Energy in Light Field and Holographic Waveguide Arrays

Figure 22:
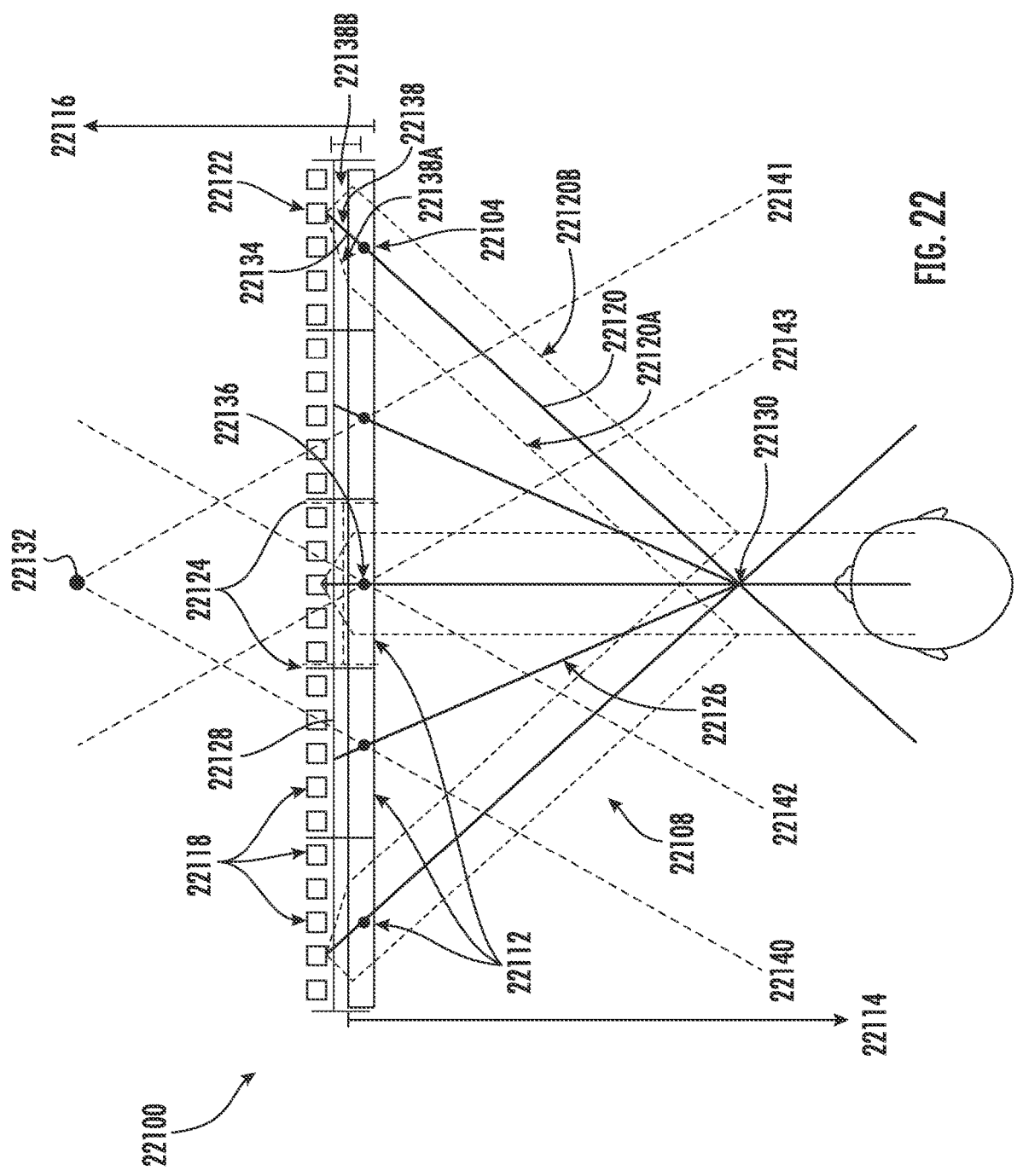
FIG. 22 illustrates a top-down perspective view of an embodiment of an energy waveguide system operable to define a plurality of energy propagation paths.

FIG. 22 illustrates a top-down perspective view of an embodiment of an energy waveguide system 22100 operable to define a plurality of energy propagation paths 22108. Energy waveguide system 22100 comprises an array of energy waveguides 22112 configured to direct energy therethrough along the plurality of energy propagation paths 22108. In an embodiment, the plurality of energy propagation paths 108 extend through a plurality of energy locations 22118 on a first side of the array 22116 to a second side of the array 22114.

Referring to FIG. 22 and FIG. 24A-H, in an embodiment, a first subset 24290 of the plurality of energy propagation paths 22108 extend through a first energy location 22122. The first energy waveguide 22104 is configured to direct energy along a first energy propagation path 22120 of the first subset 24290 of the plurality of energy propagation paths 22108. The first energy propagation path 22120 may be defined by a first chief ray 22138 formed between the first energy location 22122 and the first energy waveguide 22104. The first energy propagation path 22120 may comprise rays 22138A and 22138B, formed between the first energy location 22122 and the first energy waveguide 22104, which are directed by first energy waveguide 22104 along energy propagation paths 22120A and 22120B, respectively. The first energy propagation path 22120 may extend from the first energy waveguide 22104 towards the second side of the array 22114. In an embodiment, energy directed along the first energy propagation path 22120 comprises one or more energy propagation paths between or including energy propagation paths 22120A and 22120B, which are directed through the first energy waveguide 22104 in a direction that is substantially parallel to the angle propagated through the second side 22114 by the first chief ray 22138.

Embodiments may be configured such that energy directed along the first energy propagation path 22120 may exit the first energy waveguide 22104 in a direction that is substantially parallel to energy propagation paths 22120A and 22120B and to the first chief ray 22138. It may be assumed that an energy propagation path extending through an energy waveguide element 22112 on the second side 22114 comprises a plurality of energy propagation paths of a substantially similar propagation direction.

Figure 23:
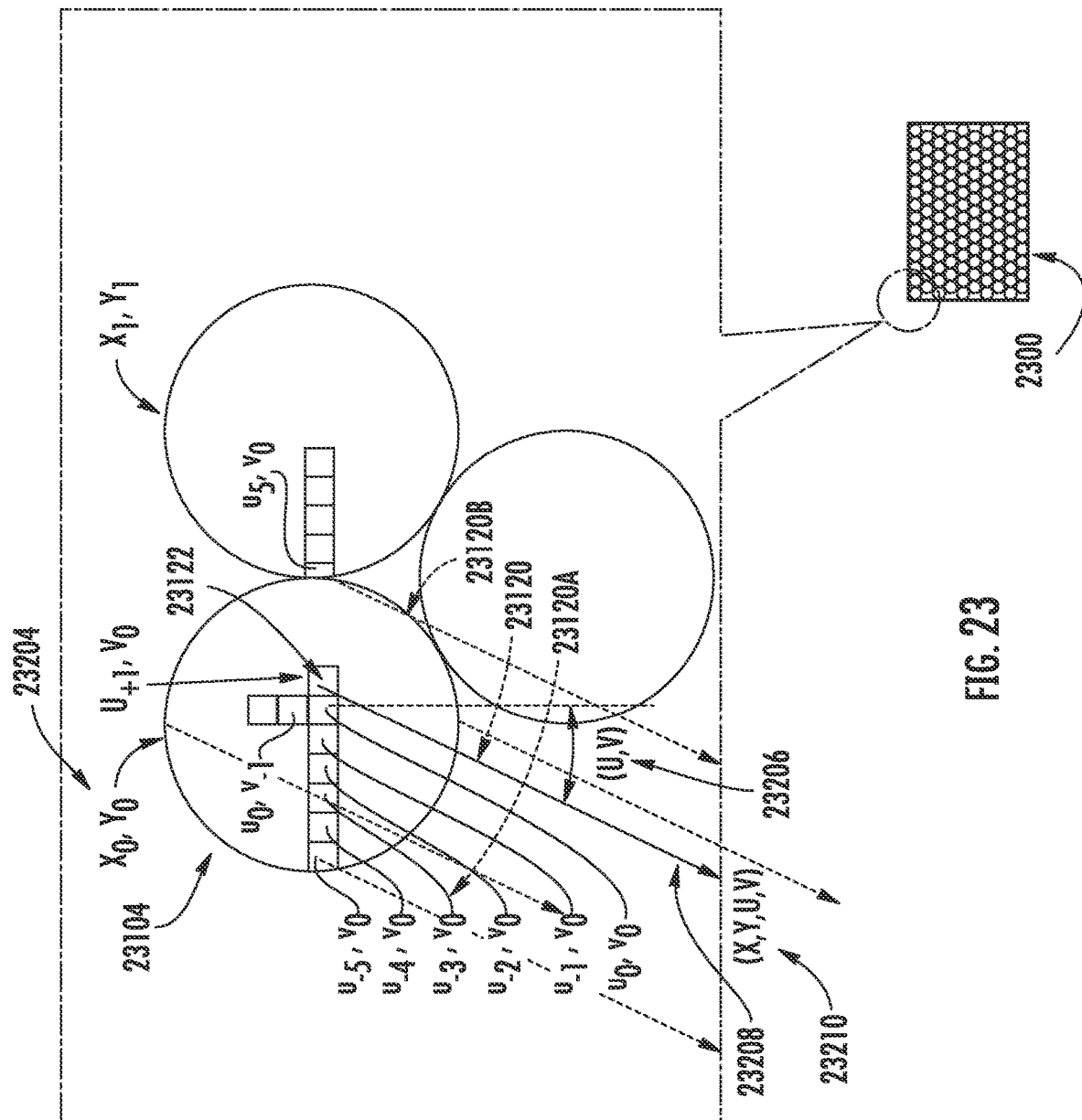
FIG. 23 illustrates a front perspective view of the embodiment shown in FIG. 22.

FIG. 23 is a front view illustration of an embodiment of energy waveguide system 23000. The first energy propagation path 23120 may extend towards the second side of the array in a unique direction 23208 extending from the first energy waveguide 23104, which is determined at least by the first energy location 23122. The first energy waveguide 23104 may be defined by a spatial coordinate 23204, and the unique direction 23208 which is determined at least by first energy location 23122 may be defined by an angular coordinate 23206 defining the directions of the first energy propagation path 23120. The spatial coordinate 23204 and the angular coordinate 23206 may form a four-dimensional plenoptic coordinate set 23210 which defines the unique direction 23208 of the first energy propagation path 23120.

Referring back to FIG. 22, in an embodiment, energy directed along the first energy propagation path 22120 through the first energy waveguide 22104 substantially fills a first aperture 22134 of the first energy waveguide 22104, and propagates along one or more energy propagation paths which lie between energy propagation paths 22120A and 22120B and are parallel to the direction of the first energy propagation path 22120. In an embodiment, the one or more energy propagation paths that substantially fill the first aperture 22134 may comprise greater than 50% of the first aperture 22134 diameter.

In a preferred embodiment, energy directed along the first energy propagation path 22120 through the first energy waveguide 22104 which substantially fills the first aperture 22134 may comprise between 50% to 80% of the first aperture 22134 diameter. In embodiments, the first energy propagation path 22120 through the first energy waveguide 22104 which substantially fills the first aperture 22134 may comprise a different degree of the first aperture 22134 diameter.

Turning again to FIGS. 22 and 24A-H, in an embodiment, the energy waveguide system 22100 may further comprise an energy inhibiting element 22124 positioned to limit propagation of energy between the first side 22116 and the second side 22114 and to inhibit energy propagation between adjacent waveguides 22112. In an embodiment, the energy inhibiting element is configured to inhibit energy propagation along a portion of the first subset 24290 of the plurality of energy propagation paths 22108 that do not extend through the first aperture 22134. In an embodiment, the energy inhibiting element 22124 may be located on the first side 22116 between the array of energy waveguides 22112 and the plurality of energy locations 22118. In an embodiment, the energy inhibiting element 22124 may be located on the second side 22114 between the plurality of energy locations 22118 and the energy propagation paths 22108. In an embodiment, the energy inhibiting element 22124 may be located on the first side 22116 or the second side 22114 orthogonal to the array of energy waveguides 22112 or the plurality of energy locations 22118.

In an embodiment, energy directed along the first energy propagation path 22120 may converge with energy directed along a second energy propagation path 22126 through a second energy waveguide 22128. The first and second energy propagation paths may converge at a location 22130 on the second side 22114 of the array 22112. In an embodiment, a third and fourth energy propagation paths 22140, 22141 may also converge at a location 22132 on the first side 22116 of the array 22112. In an embodiment, a fifth and sixth energy propagation paths 22142, 22143 may also converge at a location 22136 between the first and second sides 22116, 22114 of the array 22112.

In an embodiment, the energy waveguide system 22100 may comprise structures for directing energy such as: a structure configured to alter an angular direction of energy passing therethrough, for example a refractive, diffractive, reflective, gradient index, holographic, or other optical element; a structure comprising at least one numerical aperture; a structure configured to redirect energy off at least one internal surface; an optical relay; etc. It is to be appreciated that the waveguides 22112 may include any one or combination of bidirectional energy directing structure or material, such as:

a) refraction, diffraction, or reflection;

b) single or compound multilayered elements;
c) holographic optical elements and digitally encoded optics;
d) 3D printed elements or lithographic masters or replicas;
e) Fresnel lenses, gratings, zone plates, binary optical elements;
f) retro reflective elements;
g) fiber optics, total internal reflection or Anderson Localization;
h) gradient index optics or various refractive index matching materials;
i) glass, polymer, gas, solids, liquids;
j) acoustic waveguides;
k) micro & nano scale elements; or
l) polarization, prisms or beam splitters.

In an embodiment, the energy waveguide systems propagate energy bidirectionally. In an embodiment, the energy waveguides are configured for propagation of mechanical energy. In an embodiment, the energy waveguides are configured for propagation of electromagnetic energy. In an embodiment, by interlacing, layering, reflecting, combining, or otherwise provisioning the appropriate material properties within one or more structures within an energy waveguide element, and within one or more layers comprising an energy waveguide system, the energy waveguides are configured for simultaneous propagation of mechanical, electromagnetic and/or other forms of energy.

In an embodiment, the energy waveguides propagate energy with differing ratios for u and v respectively within a 4D coordinate system. In an embodiment, the energy waveguides propagate energy with an anamorphic function. In an embodiment, the energy waveguides comprise multiple elements along the energy propagation path. In an embodiment, the energy waveguides are directly formed from optical fiber relay polished surfaces. In an embodiment, the energy waveguide system comprises materials exhibiting Transverse Anderson Localization. In an embodiment, the energy waveguide system propagates hypersonic frequencies to converge tactile sensation in a volumetric space.

FIGS. 24A-H are illustrations of various embodiments of energy inhibiting element 22124. For the avoidance of doubt, these embodiments are provided for exemplary purposes and in no way limiting to the scope of the combinations or implementations provided within the scope of this disclosure.

Figure 24A:
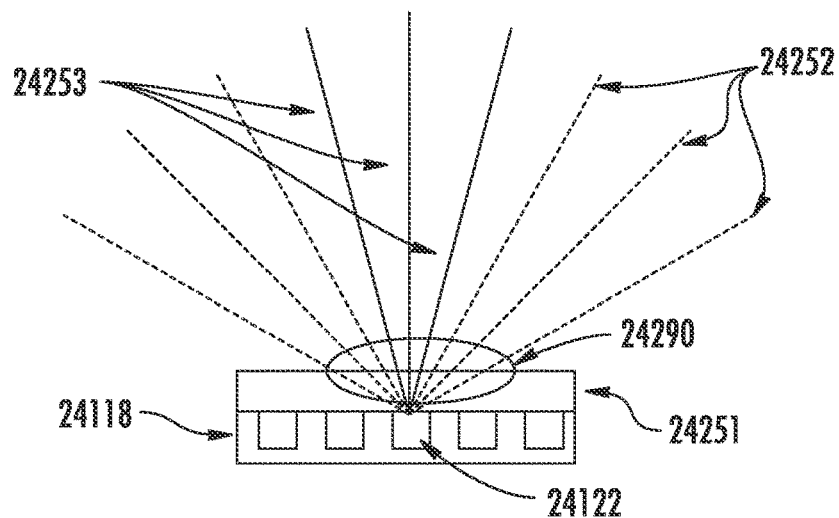
FIGS. 24A-H illustrate various embodiments of an energy inhibiting element.

FIG. 24A illustrates an embodiment of the plurality of energy locations 24118 wherein an energy inhibiting element 24251 is placed adjacent to the surface of the energy locations 24118 and comprises a specified refractive, diffractive, reflective, or other energy altering property. The energy inhibiting element 24251 may be configured to limit the first subset of energy propagation paths 24290 to a smaller range of propagation paths 24253 by inhibiting propagation of energy along energy propagation paths 24252. In an embodiment, the energy inhibiting element is an energy relay with a numerical aperture less than 1.

Figure 24B:
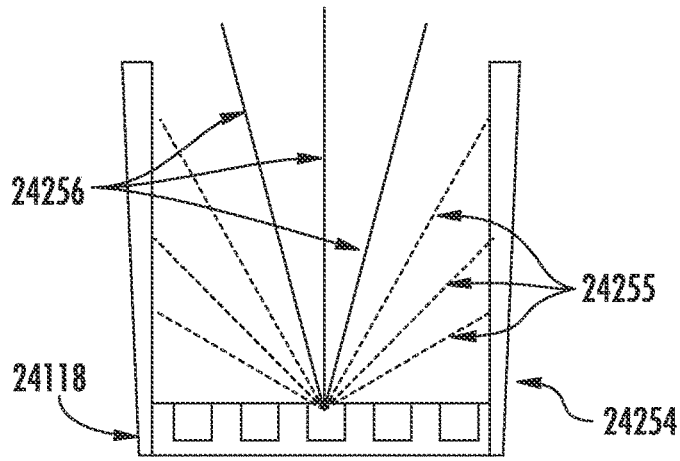

FIG. 24B illustrates an embodiment of the plurality of energy locations 24118 wherein an energy inhibiting structure 24254 is placed orthogonal between regions of energy locations 24118, and wherein the energy inhibiting structure 24254 exhibits an absorptive property, and wherein the inhibiting energy structure 24254 has a defined height along an energy propagation path 24256 such that certain energy propagation paths 24B255 are inhibited. In an embodiment, the energy inhibiting structure 24254 is hexagonal in shape. In an embodiment, the energy inhibiting structure 24254 is round in shape. In an embodiment, the energy inhibiting structure 24254 is non-uniform in shape or size along any orientation of the propagation path. In an embodiment, the energy inhibiting structure 24254 is embedded within another structure with additional properties.

Figure 24C:
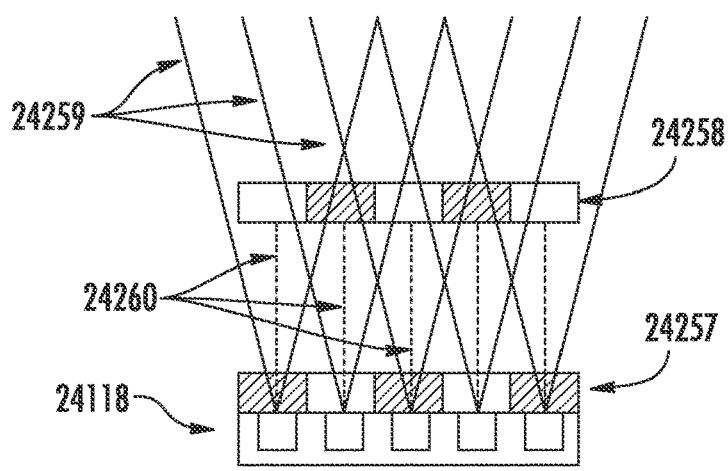

FIG. 24C illustrates the plurality of energy locations 24118, wherein a first energy inhibiting structure 24257 is configured to substantially orient energy 24259 propagating therethrough into a first state. A second energy inhibiting structure 24258 is configured to allow energy 24259, which is substantially oriented in the first state, to propagate therethrough, and to limit propagation of energy 24260 oriented substantially dissimilarly to the first state. In an embodiment, the energy inhibiting element 24257, 24258 is an energy polarizing element pair. In an embodiment, the energy inhibiting element 24257, 24258 is an energy wave band pass element pair. In an embodiment, the energy inhibiting element 24257, 24258 is a diffractive waveguide pair.

Figure 24D:
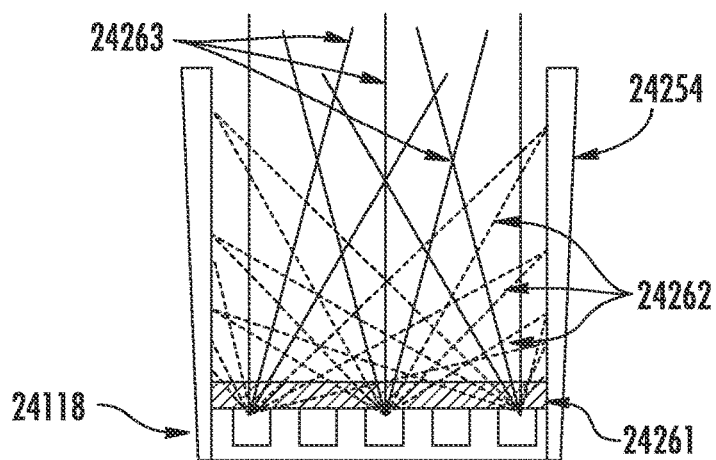

FIG. 24D illustrates an embodiment of the plurality of energy locations 24118, wherein an energy inhibiting element 24261 is structured to alter energy propagation paths 24263 to a certain extent depending upon which of the plurality of energy locations 24118 the energy propagation paths 24263 extends through. Energy inhibiting element 24261 may alter energy propagation paths 24263 in a uniform or non-uniform way along energy propagation paths 24263 such that certain energy propagation paths 24262 are inhibited. An energy inhibiting structure 24254 is placed orthogonal between regions of energy locations 24118, and wherein the energy inhibiting structure 24254 exhibits an absorptive property, and wherein the inhibiting energy structure 24254 has a defined height along an energy propagation path 24263 such that certain energy propagation paths 24262 are inhibited. In an embodiment, an inhibiting element 24261 is a field lens. In an embodiment, an inhibiting element 24261 is a diffractive waveguide. In an embodiment, an inhibiting element 24261 is a curved waveguide surface.

Figure 24E:
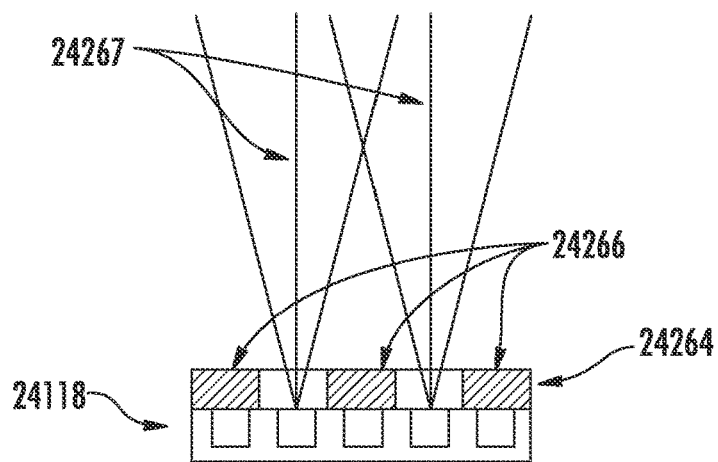

FIG. 24E illustrates an embodiment of the plurality of energy locations 24118, wherein an energy inhibiting element 24264 provides an absorptive property to limit the propagation of energy 24266 while allowing other propagation paths 24267 to pass.

Figure 24F:
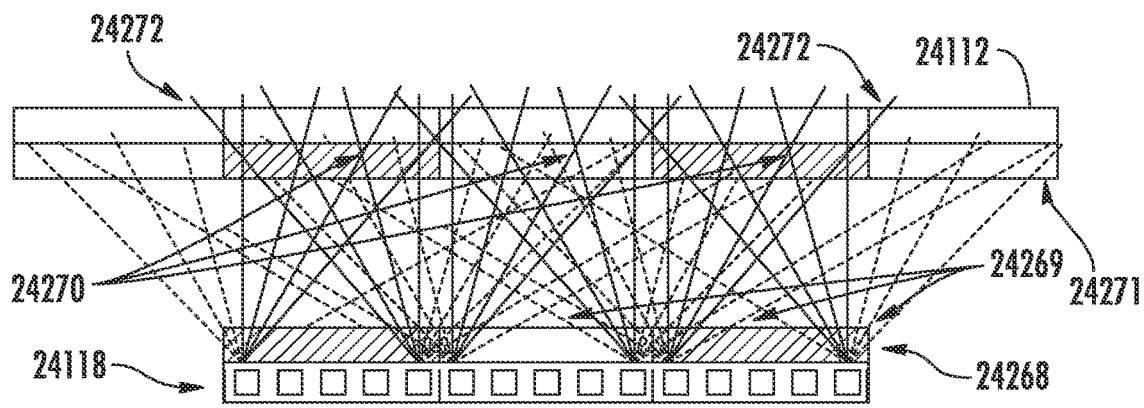

FIG. 24F illustrates an embodiment of the plurality of energy locations 24118, and the plurality of energy waveguides 24112, wherein a first energy inhibiting structure 24268 is configured to substantially orient energy 24270 propagating therethrough into a first state. A second energy inhibiting structure 24271 is configured to allow energy 24270, which is substantially oriented in the first state, to propagate therethrough, and to limit propagation of energy 24269 oriented substantially dissimilarly to the first state. In order to further control energy propagation through a system, exemplified by the stray energy propagation 24272, energy inhibiting structures 24268, 24271 may require a compound energy inhibiting element to ensure energy propagation maintains accurate propagation paths.

Figure 24G:
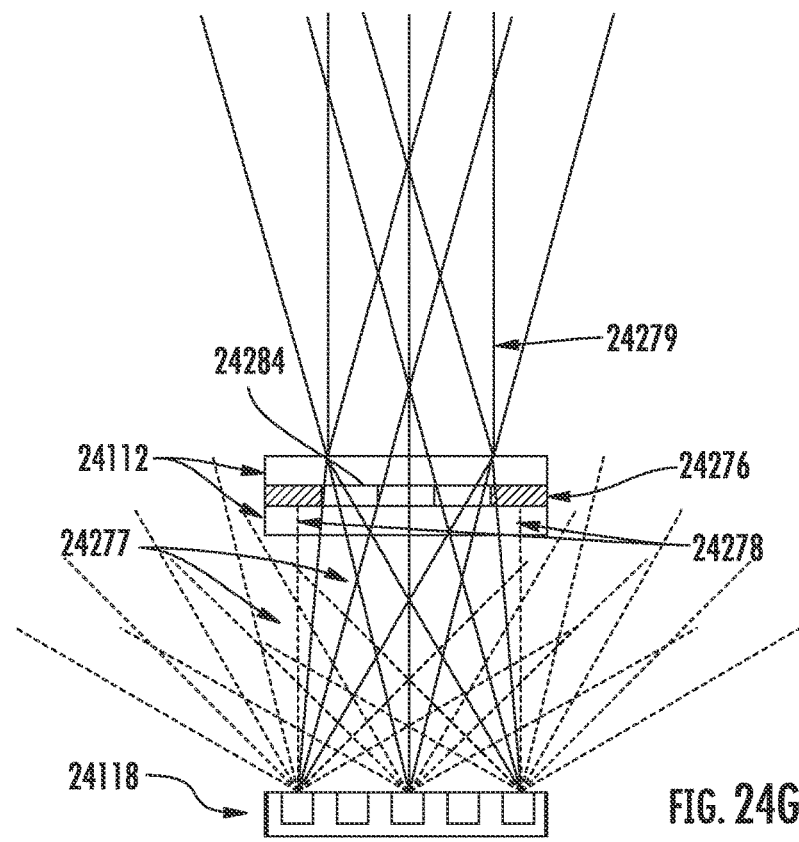

FIG. 24G illustrates an embodiment of the plurality of energy locations 24118, and wherein an energy inhibiting element 24276 provides an absorptive property to limit the propagation of energy along energy propagation path 24278 while allowing other energy along energy propagation path 24277 to pass through a pair of energy waveguides 24112 for an effective aperture 24284 within the array of waveguides 24112. In an embodiment, energy inhibiting element 24276 comprises black chrome. In an embodiment, energy inhibiting element 24276 comprises an absorptive material. In an embodiment, energy inhibiting element 24276 comprises a transparent pixel array. In an embodiment, energy inhibiting element 24276 comprises an anodized material.

Figure 24H:
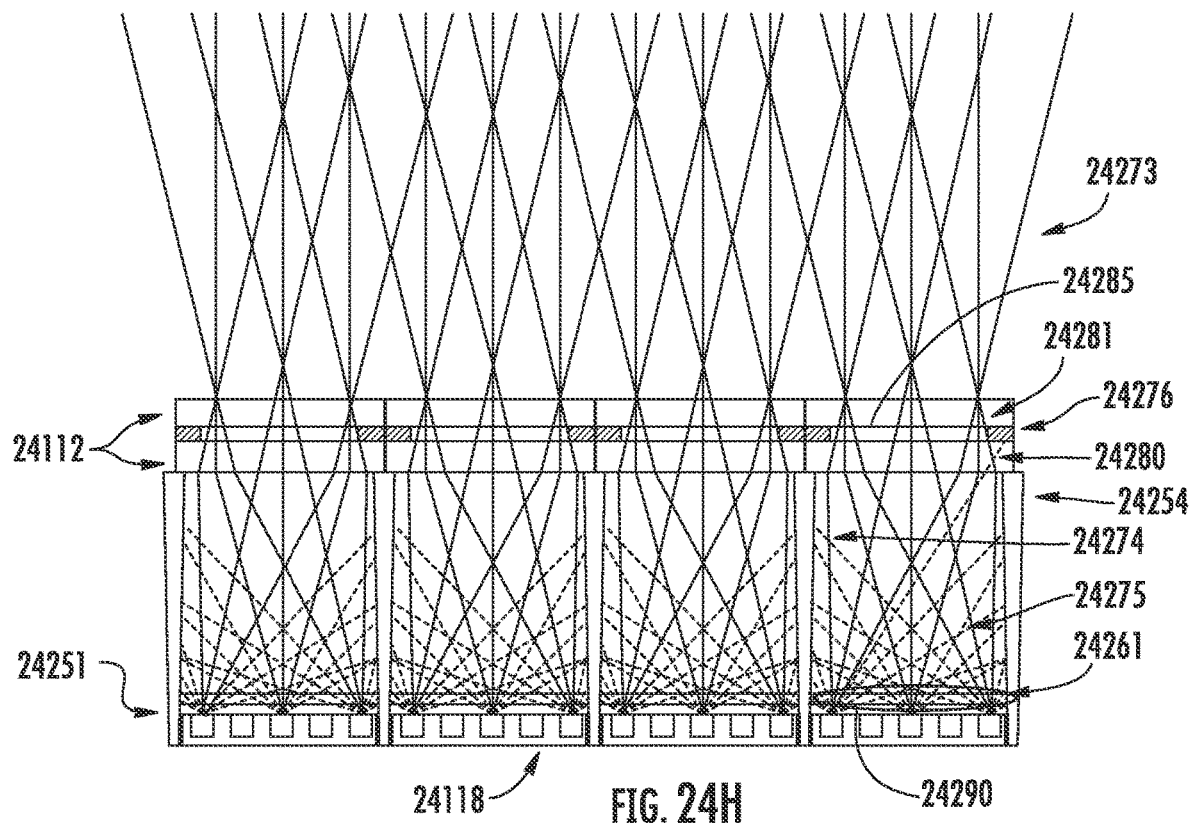

FIG. 24H illustrates an embodiment comprising a plurality of energy locations 24118, and a plurality of energy waveguides 24112, wherein a first energy inhibiting structure 24251 is placed adjacent to the surface of the energy locations 24118 and comprises a specified refractive, diffractive, reflective, or other energy altering property. The energy inhibiting structure 24251 may be configured to limit the first subset of energy propagation paths 24290 to a smaller range of propagation paths 24275 by inhibiting propagation of energy along energy propagation paths 24274. A second energy inhibiting structure 24261 is structured to alter energy propagation paths 24275 to a certain extent depending upon which of the plurality of energy locations 24118 the energy propagation paths 24275 extend through. Energy inhibiting structure 24261 may alter energy propagation paths 24275 in a uniform or non-uniform way such that certain energy propagation paths 24274 are inhibited. A third energy inhibiting structure 24254 is placed orthogonal between regions of energy locations 24118. The energy inhibiting structure 24254 exhibits an absorptive property, and has a defined height along an energy propagation path 24275 such that certain energy propagation paths 24274 are inhibited. An energy inhibiting element 24276 provides an absorptive property to limit the propagation of energy 24280 while allowing energy 24281 to pass through. A compound system of similar or dissimilar waveguide elements 24112 are positioned to substantially fill an effective waveguide element aperture 24285 with energy from the plurality of energy locations 24118 and to alter the propagation path 24273 of energy as defined by a particular system.

In an embodiment, the energy inhibiting element 24276 may comprise a structure for attenuating or modifying energy propagation paths. In an embodiment, the energy inhibiting element 24276 may include one or more energy absorbing elements or walls positioned within the system to limit propagation of energy to or from the waveguides 24112. In an embodiment, the energy inhibiting element 24276 may include a specified numerical aperture, positioned within the system to limit the angular distribution of energy to and from waveguide 24112.

In an embodiment, the energy inhibiting element 24276 may include one or more energy blocking walls, structures, metal, plastic, glass, epoxy, pigment, liquid, display technologies or other absorptive or structural material, with a determined thickness between a plane of energy locations 24122 and a waveguide array plane with voids or structures that are up to the pitch of a waveguide aperture diameter.

In an embodiment, the energy inhibiting structure 24254 is located proximate the first energy location 22122 and comprises an optical relay faceplate adjacent to the first energy location 22122. In an embodiment, the energy inhibiting element 24276 may include an optical relay faceplate comprising one or more spatially consistent or variable numerical apertures, wherein the numerical aperture value meaningfully limits the angular distribution of energy to and from the waveguide 24112. For example, an embodiment of the numerical aperture may be designed to provide an angular distribution that is at or near two times the field of view formed between the energy location and perpendicular to the center of the effective waveguide element size, entrance pupil, aperture, or other physical parameter for energy propagation, to provide off-axis fill factor for the specified waveguide aperture 24285.

In an embodiment, the energy inhibiting element 24276 may include a binary, gradient index, Fresnel, holographic optical element, zone plate or other diffractive optical element that alters the path of energy waves through the system to decrease scatter, diffusion, stray light, or chromatic aberration. In an embodiment, the energy inhibiting element 24276 may include a positive or negative optical element at or around the location wherein the energy propagation path is altered to further increase the fill factor of the waveguide aperture 24285 or decrease stray light. In an embodiment, the energy inhibiting element 24276 may include an active or passive polarized element combined with a second active or passive polarized element designed to provide spatial or time multiplexed attenuation of defined regions of the energy location 22122, waveguide aperture 24285, or other regions. In an embodiment, the energy inhibiting element 24276 may include an active or passive aperture stop barrier designed to provide spatial or time multiplexed attenuation of defined regions of the energy location 24122, waveguide aperture 24276 or other regions. In an embodiment, the energy inhibiting element 24276 many include any one the following or any combination thereof:

a) physical energy baffle structures;
b) volumetric, tapered or faceted mechanical structures;
c) aperture stops or masks;
d) optical relays and controlled numerical apertures;
e) refraction, diffraction, or reflection;
f) retro reflective elements;
g) single or compound multilayered elements;
h) holographic optical elements and digitally encoded optics;
i) 3D printed elements or lithographic masters or replicas;
j) Fresnel lenses, gratings, zone plates, binary optical elements;
k) fiber optics, total internal reflection or Anderson localization;
l) gradient index optics or various refractive index matching materials;
m) glass, polymer, gas, solids, liquids;
n) milli, micro & nano scale elements; and
o) polarization, prisms or beam splitters In an embodiment, the energy inhibiting structure 24254 may be constructed to include hexagonally packed energy blocking baffles constructed to form voids that are tapered along the Z axis, decreasing in void size as the aperture stop location for the waveguide system is reached. In another embodiment, the energy inhibiting structure 24254 may be constructed to include hexagonally packed energy blocking baffles bonded to an optical relay face plate. In another embodiment, the energy inhibiting structure 24254 may be constructed to include hexagonally packed energy blocking baffles filled with a prescribed refractive index to further alter the path of energy wave projection to and from the energy waveguide array. In another embodiment, a diffractive or refractive element may be placed, attached or bonded to the energy blocking baffle with a defined waveguide prescription to further alter the path of energy projection to and from the waveguide elements 24112. In another example, the energy inhibiting structure 24254 may be formed into a single mechanical assembly, and the energy waveguide array 24254 may be placed, attached or bonded to the assembled energy inhibiting element 24254. It is to be appreciated that other implementations may be leveraged to enable other energy waveguide configurations or super-resolution considerations.

In an embodiment, the energy inhibiting structure 24254 may be located proximate the first energy location 22122 and generally extend towards the first energy waveguide 24104. In an embodiment, the energy inhibiting structure 24254 may be located proximate the first energy waveguide 24104 and generally extend towards the first energy location 22122.

In an embodiment, the energy inhibiting elements are configured for inhibiting electromagnetic energy. In an embodiment, the energy inhibiting elements are configured for inhibiting mechanical energy. In an embodiment, by interlacing, layering, reflecting, combining, or otherwise provisioning the appropriate material properties within one or more structures within an energy inhibiting element, and within one or more layers comprising an energy waveguide system, the energy inhibiting elements are configured for simultaneous attenuation of mechanical, electromagnetic and/or other forms of energy.

Figure 28:
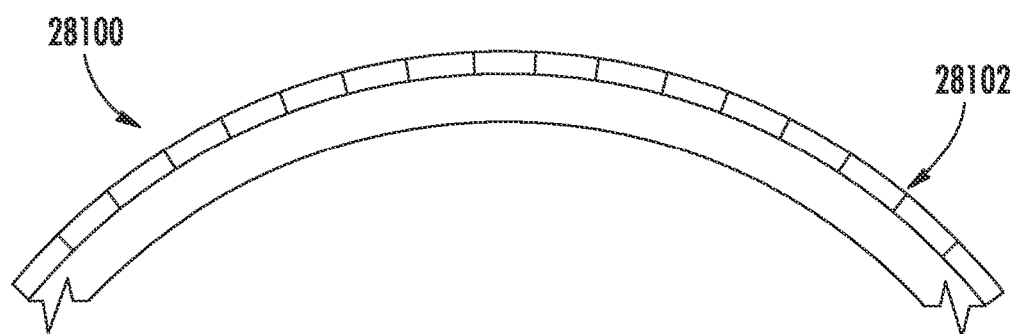
FIG. 28 illustrates an embodiment featuring an array of energy waveguides arranged in a curved configuration.

In an embodiment, an array of energy waveguides may be arranged to form a planar surface, or a curved surface of a desirable shape. FIG. 28 is an illustration of an embodiment 28100 featuring an array of energy waveguides 28102 arranged in a curved configuration.

Embodiments of the present disclosure may be configured to direct energy of any wavelength belonging to the electromagnetic spectrum, including visible light, ultraviolet, infrared, x-ray, etc. The present disclosure may also be configured to direct other forms of energy such as acoustic sound vibrations and tactile pressure waves.

Figure 25:
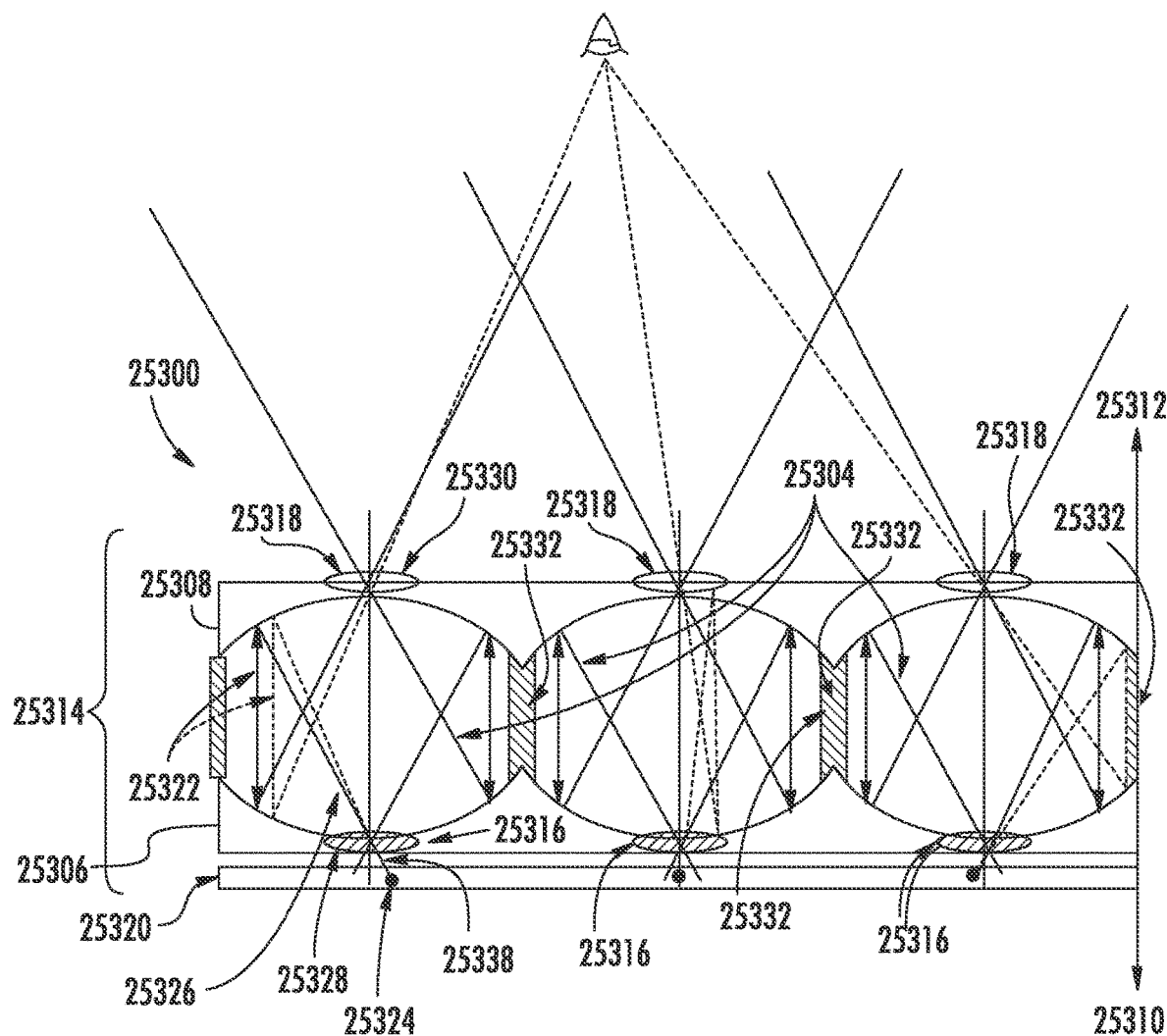
FIG. 25 illustrates an additional embodiment of an energy waveguide system.

FIG. 25 is an illustration of an additional embodiment of an energy waveguide system 25300. The energy waveguide system 25300 may define a plurality of energy propagation paths 25304, and may comprise a reflector element 25314 comprising a first reflector 25306 located on a first side 25310 of the reflector element 25314, the first reflector 25306 comprising one or more aperture stops 25316 formed therethrough, and a second reflector 25308 located on a second side 25312 of the reflector element 25314, the second reflector 25308 comprising one or more aperture stops 25318 formed therethrough. The first and second reflectors 25306, 25308 are configured to direct energy along a plurality of energy propagation paths 25304 extending through the aperture stops of the first and second reflectors 25316, 25318 and a plurality of energy locations 25320 on the first side 25310 of the reflector element 25314. A first subset 25322 of the plurality of energy propagation paths 25304 extend through a first energy location 25324. The reflector element 25314 is configured to direct energy along a first energy propagation path 25326 of the first subset 25322 of the plurality of energy propagation paths 25304.

In an embodiment, the first energy propagation path 25326 may be defined by a first chief ray 25338 formed between the first energy location 25324 and a first aperture stop 25328 of the first reflector 25306. The first energy propagation path 25326 may extend from a first aperture stop 25330 of the second reflector 25308 towards the second side 25312 of the reflector element 25314 in a unique direction extending from the first aperture stop 25330 of the second reflector 25308, which is determined at least by the first energy location 25324.

In an embodiment, energy directed along the first energy propagation path 25326 substantially fills the first aperture stop 25328 of the first reflector 25306 and the first aperture stop 25330 of the second reflector 25308.

In an embodiment, an energy inhibiting element 25332 may be positioned to limit propagation of energy along a portion 25350 of the first subset 25322 of the plurality of energy propagation paths 25304 that do not extend through the first aperture stop 25328 of the first reflector 25306.

In an embodiment in which the energy is light and the energy waveguide is operable to direct said light, with a perfect parabolic structure, any ray that passes through, or from, the focus of the first reflector will reflect parallel to the optical axis, reflect off of the second reflector, and then relay at the same angle in the inverse orientation.

In an embodiment, the first reflector and second reflector have differing focal lengths, in order to produce varied magnification of the energy information and/or to alter angular field of view coverage as a viewer from above the surface of the second reflector would view the reflected information. The aperture stops may be of differing sizes for varied design purposes in collaboration with the varied focal lengths.

An additional embodiment is provided where both reflective surfaces are conical, faceted, curved in a non-linear shape or otherwise. The design of this curvature is critical to ensuring that the display information and the viewed information may have a non-linear relationship to change or simplify signal processing.

In an embodiment, the energy waveguides comprise flexible reflective surfaces capable of altering the reflective surface profile dynamically to change the propagation path of energy through the energy waveguide system.

Figure 26:
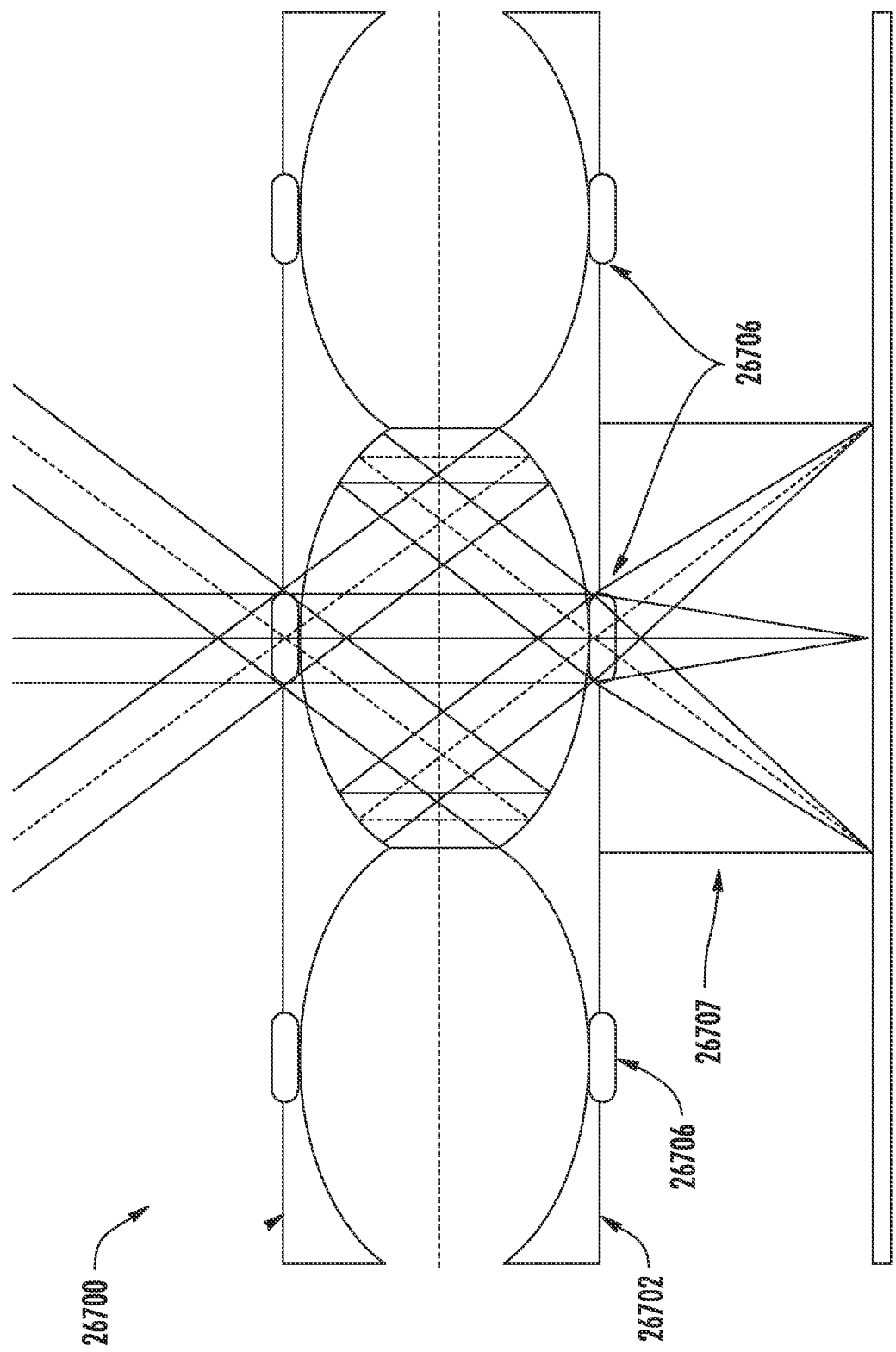
FIG. 26 illustrates an additional embodiment of an energy waveguide system.

In an embodiment, additional waveguides, including but not limited to reflective or optical elements, birefringent materials, liquid lenses, refractive, diffractive, holographic, or the like, may be located anywhere within the energy propagation path. With this approach, one such embodiment provides a design such that when viewed, the view angles are at significantly different position than the aperture stop and focal length would have provided otherwise. FIG. 26 demonstrates one such application of this approach.

FIG. 26 is an illustration of an embodiment of an energy waveguide system 26700. Energy waveguide system 26700 comprises first and second reflectors 26702 and 26704, respectively. Positioned at the focus of the first reflector 26702 are additional optical elements 26706 and an energy inhibitor 26707 perpendicular to the energy location 26708. The additional optical elements are designed to affect energy propagation paths of energy propagating through energy waveguide system 26700. Additional waveguide elements may be included within the energy waveguide system 26700, or additional energy waveguide systems may be placed into the energy propagation path.

Figure 27:
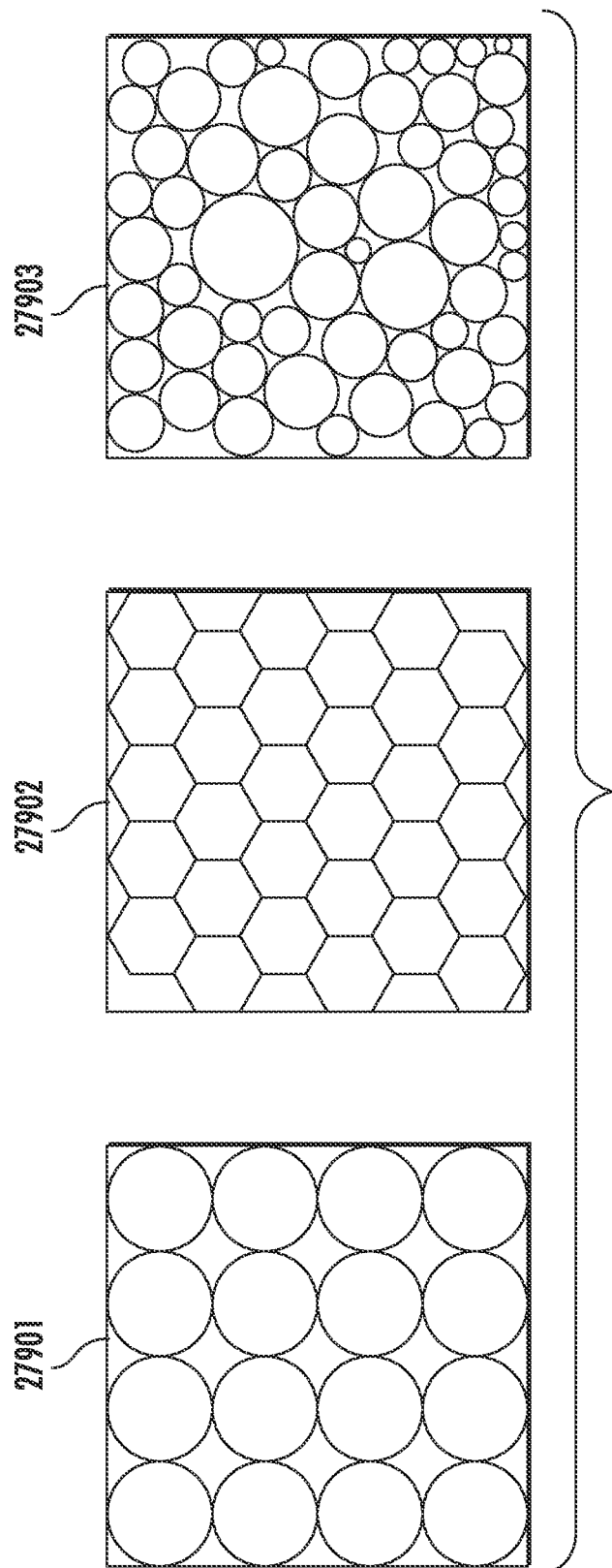
FIG. 27 highlights the differences between square packing, hex packing and irregular packing for energy waveguide design considerations.

In an embodiment, the array of energy waveguide elements may include:
   a) A hexagonal packing of the array of energy waveguides;
   b) A square packing of the array of energy waveguides;
   c) An irregular or semi-regular packing of the array of energy waveguides;
   d) Curved or Non-planar array of energy waveguides;
   e) Spherical array of energy waveguides;
   f) Cylindrical array of energy waveguides;
   g) Tilted regular array of energy waveguides;
   h) Tilted irregular array of energy waveguides;
   i) Spatially varying array of energy waveguides;
   j) Multi-layered array of energy waveguides;

FIG. 27 highlights the differences between square packing 27901, hex packing 27902 and irregular packing 27903 of an array of energy waveguide elements.

Several different geometries for CES particles and material pre-forms have been illustrated thus far. One important aspect of the present disclosure is that any arrangement or geometry of materials may be leveraged, so long as they abide by the criteria for ordered distributions previously discussed. However, the pre-fused relay material geometry may have a significant impact on the efficiency of the localization and energy propagation properties of the materials. Certain geometries, known as convex uniform tilings, may provide advantageous distributions of relay materials by arranging the materials in efficient configurations.

The Laves tilings have vertices at the centers of the regular polygons, and edges connecting centers of regular polygons that share an edge. The tiles of the Laves tilings are called planigons including 3 regular tiles (triangle, square and pentagon) and 8 irregular ones. Each vertex has edges evenly spaced around it. Three dimensional analogues of the planigons are called stereohedrons.

All reflectional forms can be made by Wythoff constructions, represented by Wythoff symbols, or Coxeter-Dynkin diagrams, each operating upon one of three Schwarz triangle (4,4,2), (6,3,2), or (3,3,3), with symmetry represented by Coxeter groups: [4,4], [6,3], or [3[3]]. Only one uniform tiling can't be constructed by a Wythoff process, but can be made by an elongation of the triangular tiling. An orthogonal mirror construction [∞,2, ∞] also exists, seen as two sets of parallel mirrors making a rectangular fundamental domain. If the domain is square, this symmetry can be doubled by a diagonal mirror into the [4,4] family. We disclose within this provisional the geometries that may be leveraged.

A percolation model is to take a regular lattice, like a square lattice, and make it into a random network by randomly "occupying" sites (vertices) or bonds (edges) with a statistically independent probability p. At a critical threshold pc, large clusters and long-range connectivity first appears, and this is called the percolation threshold. Depending on the method for obtaining the random network, one distinguishes between the site percolation threshold and the bond percolation threshold. More general systems have several probabilities p1, p2, etc., and the transition is characterized by a critical surface or manifold. One can also consider continuum systems, such as overlapping disks and spheres placed randomly, or the negative space.

When the occupation of a site or bond is completely random, this is the so-called Bernoulli percolation. For a continuum system, random occupancy corresponds to the points being placed by a Poisson process. Further variations involve correlated percolation, such as percolation clusters related to Ising and Potts models of ferromagnets, in which the bonds are put down by the Fortuin-Kasteleyn method. In bootstrap or k-sat percolation, sites and/or bonds are first occupied and then successively culled from a system if a site does not have at least k neighbors. Another important model of percolation, in a different universality class altogether, is directed percolation, where connectivity along a bond depends upon the direction of the flow.

Simply duality in two dimensions implies that all fully triangulated lattices (e.g., the triangular, union jack, cross dual, martini dual and asanoha or 3-12 dual, and the Delaunay triangulation) all have site thresholds of ½, and self-dual lattices (square, martini-B) have bond thresholds of ½.

Leveraging tiled structures may have the result of altering the respective holographic pixel aspect ratio, while providing variation in field of view spatially and/or volumetrically.

Reduction in moiré or repeating patterns may also provide increased effective resolution and simultaneously provides higher potential levels of accuracy (increase in depth of field) by virtue of the various convergence locations that may be addressed. Increased efficiency of resolution may also be achieved by packing more effective resolution in potential dimensions that are more ideal for applications by not necessarily leveraging a repeating single orientation or pattern.

Energy waveguides may be fabricated on a glass or plastic substrate to specifically include optical relay elements if desirable and may be designed with glass or plastic optical elements to specifically include optical relays as well as desired. Furthermore, the energy waveguide may be faceted for designs that provide multiple propagation paths or other column/row or checkerboard orientations, specifically considering but not limited to multiple propagation paths separated by beam-splitters or prisms, or tiled for waveguide configurations that allow for tiling, or a singular monolithic plate, or tiled in a curved arrangement (e.g. faceted cylinder or spherical with geometry alterations to the tiles to mate accordingly), curved surfaces to include but not limited to spherical and cylindrical or any other arbitrary geometry as required for a specific application.

In an embodiment where the array of energy waveguides comprises a curved configuration, the curved waveguide may be produced via heat treatments or by direct fabrication onto curved surfaces to include optical relay elements.

In an embodiment, the array of energy waveguides may abut other waveguides and may cover entire walls and/or ceilings and or rooms depending on specific application. The waveguides may be designed explicitly for substrate up or substrate down mounting. The waveguide may be designed to mate directly to an energy surface or be offset with an air gap or other offset medium. The waveguide may include an alignment apparatus to provide the ability to focus the plane actively or passively either as a permanent fixture or a tooling element. The purposes of the geometries described is to help optimize the angle of view defined by the normal of the waveguide element and the represented imagery. For a very large energy surface planar surface, the majority of the angular samples at the left and right-most of the surface are mainly outside of the viewing volume for an environment. For that same energy surface, with a curved contour and a curved waveguide, the ability to use more of these propagating rays to form the converging volume is increased significantly. This is however at the expense of usable information when off-axis. The application specific nature of the design generally dictates which of the proposed designs will be implemented. Furthermore, a waveguide may be designed with regular, graduated, or regional element structures that are fabricated with an additional waveguide element to tilt the element towards a predetermined waveguide axis.

In embodiments where the energy waveguides are lenses, the embodiments may include both convex and concave lenslets, and may include the fabrication of the lenses directly onto an optical relay surface. This may involve destructive or additive lenslet fabrication processes to include removal of material to form or stamp and lenslet profile, or the direct replica fabricated directly to this surface.

An embodiment may include a multiple layered waveguide design that provides additional energy propagation optimizations and angular control. All of the above embodiments may be combined together independently or in conjunction with this approach. In an embodiment, a multiple layered design may be envisioned with tilted waveguide structures on a first waveguide element and a regionally varying structure for a second waveguide element.

An embodiment includes the design and fabrication of a per element, or per region liquid lens waveguide joined together as a single waveguide. An additional design of this approach includes a single birefringent or liquid lens waveguide electrical cell that can modify an entire waveguide array simultaneously. This design provides the ability to dynamically control the effective waveguide parameters of the system without redesigning the waveguide.

In an embodiment configured to direct light, with any combination of the disclosures provided herein, it is possible to generate a wall mounted 2D, light field or holographic display. The wall mounted configuration is designed such that a viewer is looking at an image that may float in front, at or behind of the designed display surface. With this approach, the angular distribution of rays may be uniform, or provided with increased density at any particular placement in space depending on specific display requirements. In this fashion, it is possible to configure the waveguides to alter angular distribution as a function of surface profile. For example, for a given distance perpendicular to the display surface and a planar waveguide array, an optically perfect waveguide would provide increased density at the perpendicular center of the display with a gradual increase in ray separation distance along a given perpendicular distance to the display. Conversely, if viewing the rays radially about the display where a viewer maintains a distance between the eyes and the center point of the display, the viewed rays would maintain consistent density across the entire field of view. Depending on the anticipated viewing conditions, the properties of each element may be optimized by altering the waveguide functions to produce any potential distribution of rays to optimize the viewing experience for any such environment.

Figure 29:
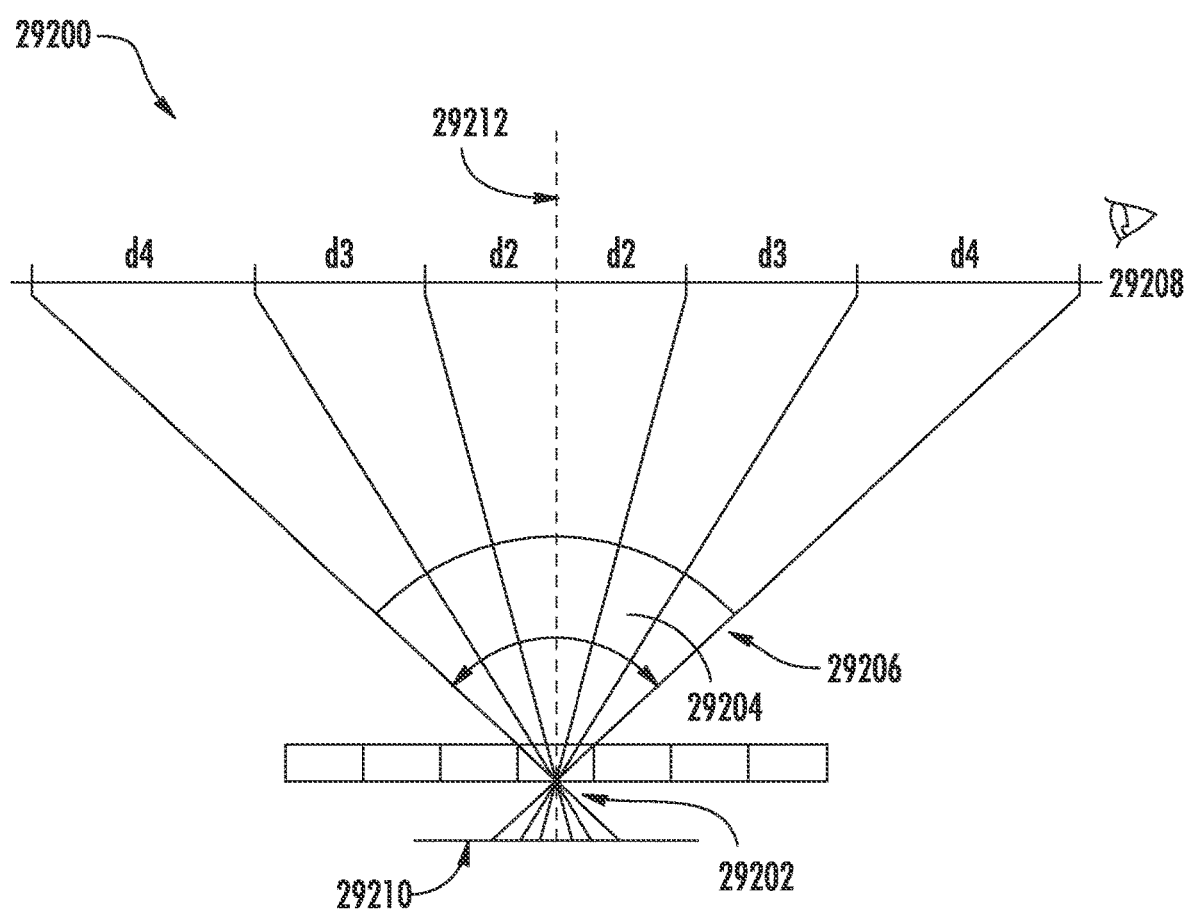
FIG. 29 illustrates an embodiment that highlights how a waveguide element may affect a spatial distribution of energy passing therethrough.

FIG. 29 is an illustration of an embodiment 29200 which highlights how a single waveguide element function 29202 may produce identical distribution of energy 29204 across a radial viewing environment 29206, whereas the same waveguide element function 29202 when propagated at a distance 29208 that is constant and parallel to the waveguide surface 29210 will appear to exhibit increased density at the waveguide element center 29212 of the waveguide surface and decreased density further from the center 29212 of the waveguide surface.

Figure 30:
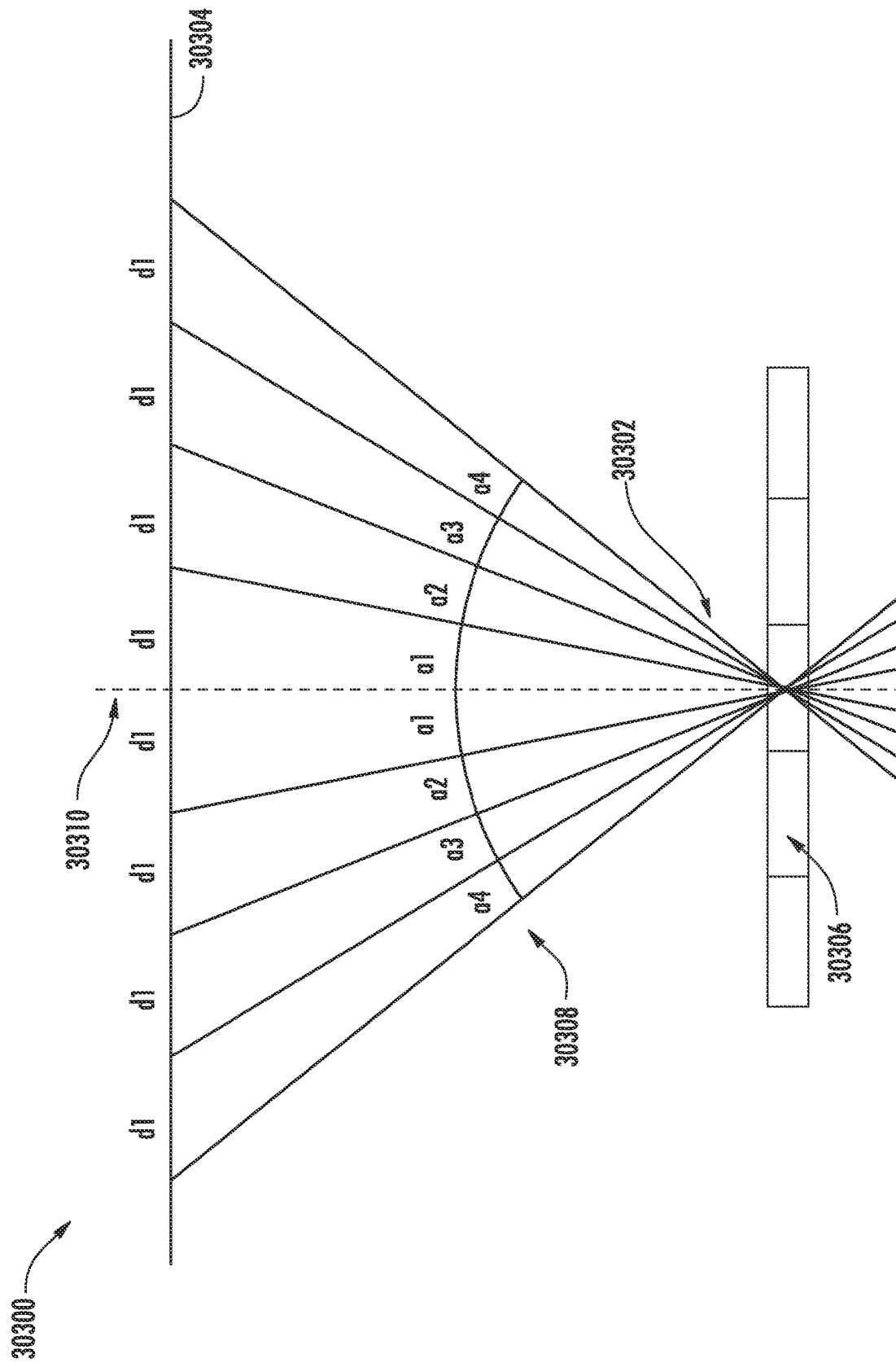
FIG. 30 illustrates an additional embodiment which further highlights how a waveguide element may affect a spatial distribution of energy passing therethrough.

FIG. 30 is an illustration of an embodiment 30300 which illustrates configuring the waveguide element functions 30302 to exhibit uniform density at a constant distance 30304 parallel to the waveguide surface 30306 that simultaneously produces apparent lower density at the center 30310 of the waveguide surface 30306 when measured about a radius 30308 about the center of the waveguide surface 30306.

The ability to generate a waveguide function that varies sampling frequency over field distance is a characteristic of various waveguide distortions and known in the art. Traditionally, the inclusion of distortions are undesirable in a waveguide function, however, for the purposes of waveguide element design, these are all characteristics that are claimed as benefits to the ability to further control and distribute the propagation of energy depending on the specific viewing volume required. It may require the addition of multiple functions or layers or a gradient of functions across the entirety of the waveguide array depending on the viewing volume requirements.

In an embodiment, the functions are further optimized by curved surfaces of the energy surface and/or the waveguide array. The variation of the normal of the chief ray angle in relation to the energy surface itself may further increase efficiency and require a different function than a planar surface, although the gradient, variation and/or optimization of the waveguide function still applies.

Further, leveraging the resultant optimized waveguide array in consideration of waveguide stitching methodologies, it is possible to further increase the effective size of the waveguide by tiling each of the waveguides and systems to produce any size or form-factor desired. It is important to note that the waveguide array may exhibit a seam artifact unlike the energy surface by virtue of reflections produced between any two separate substrates, the apparent contrast differential at the mechanical seam, or due to any form of non-square grid packing schema. To counteract this effect, either a larger singular waveguide may be produced, refractive matching materials may be leveraged between the edges of any two surfaces, or regular waveguide grid structures may be employed to ensure that no elements are split between two waveguide surfaces, and/or precision cutting between energy inhibiting elements and seaming along a non-square waveguide grid structure may be leveraged.

With this approach, it is possible to produce room scale 2D, light field and/or holographic displays. These displays may be seamless across large planar or curved walls, may be produced to cover all walls in a cubic fashion, or may be produced in a curved configuration where either a cylindrical-type shape, or a spherical-type shape is formed to increase view angle efficiency of the overall system.

Alternatively, it is possible to design a waveguide function that warps the propagated energy to virtually eliminate the region that is not desired in the required angle of view resulting in a non-uniform distribution of energy propagation. To accomplish this, one may implement a torus shaped optical profile, annular lens, concentric prism array, a Fresnel or diffractive function, binary, refractive, holographic, and/or any other waveguide design may allow for a larger aperture and shorter focal length (herein will be referred to as a "Fresnel lenslet") to provide the ability to practically form a single or multi element (or multiple sheets) Fresnel waveguide array. This may or may not be combined with additional optics, including an additional waveguide array, depending on waveguide configuration.

In order to produce wide energy propagation angles (e.g. 180 degrees) a very low effective f/number (e.g. <f/0.5) is required and in order to ensure that no 4D "Disk Flipping" occurs (the ability for the ray from one waveguide element to see undesired energy locations underneath of any second waveguide element), it is further required that the focal length be appropriately matched closely to the angle of view required. This means that in order to produce a ~160 degree viewing volume, an ~f/0.17 lens and a nearly matched ~0.17 mm focal length is required.

Figure 31:
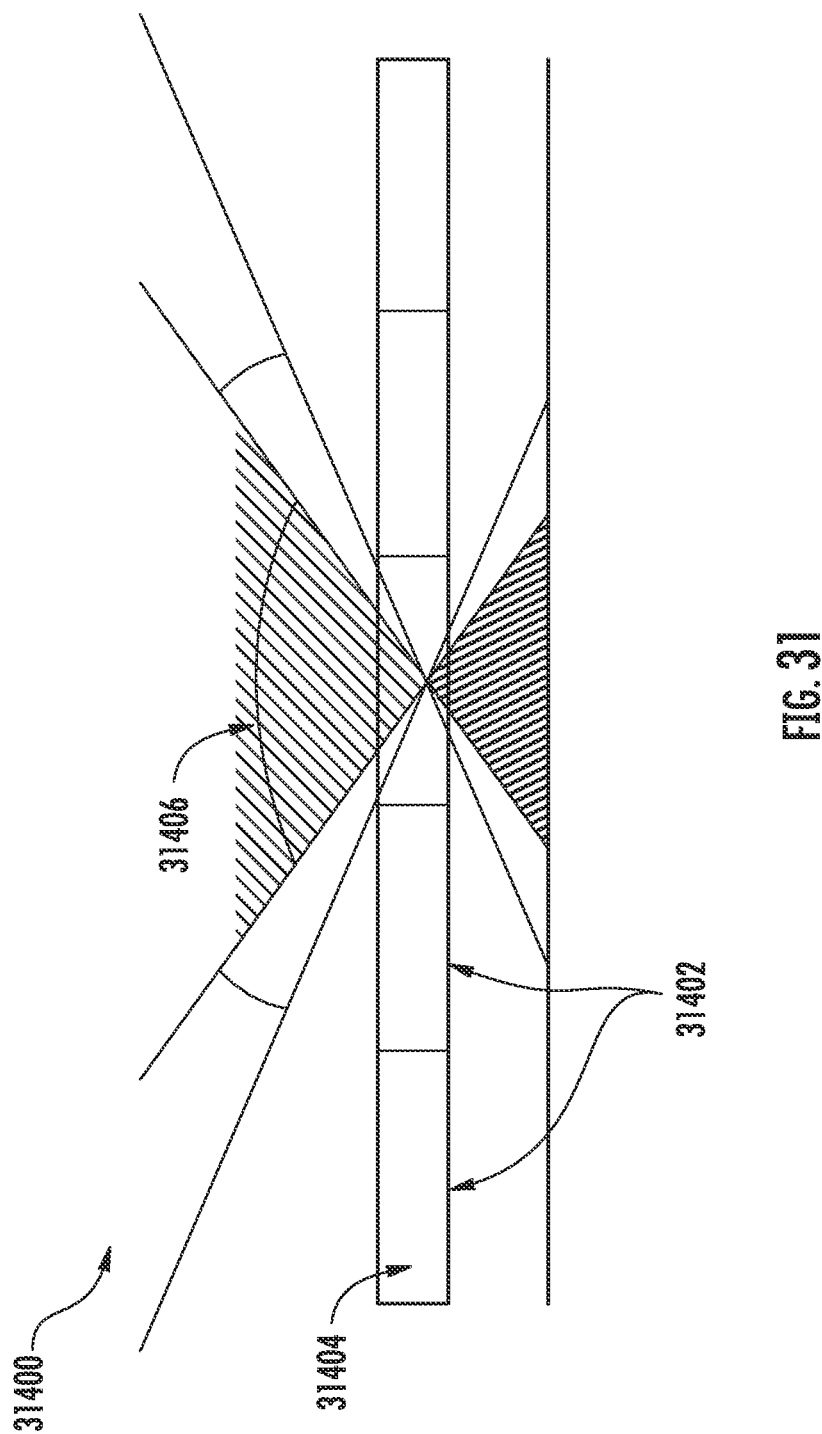
FIG. 31 illustrates an embodiment wherein the plurality of energy waveguides comprise diffractive waveguide elements.

FIG. 31 illustrates an embodiment 31400 wherein the plurality of energy waveguides comprise diffractive waveguide elements 31402, and demonstrates one proposed structure for a modified Fresnel waveguide element structure 31404 that produces an effectively extremely short focal length and low f/number while simultaneously directing rays of energy to explicitly defined locations 31406.

Figure 32:
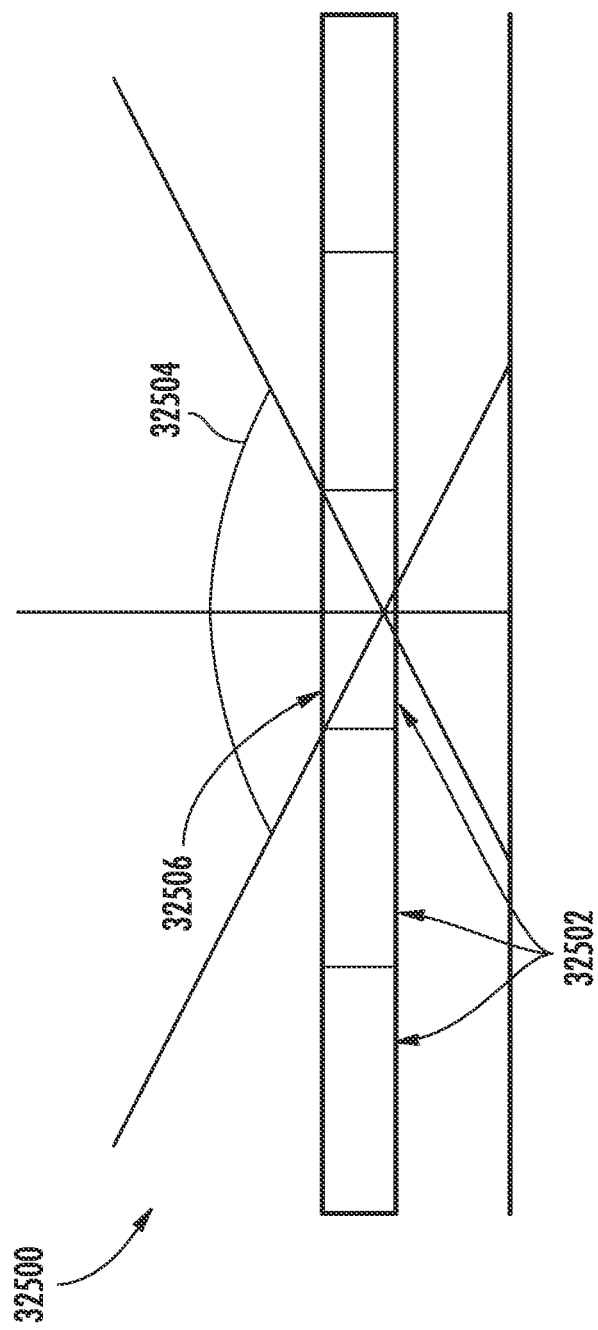
FIG. 32 illustrates a lenslet configuration used to provide full density of ray illumination for the desired angle of view.

FIG. 32 illustrates an embodiment 32500 wherein the plurality of energy waveguides comprise elements 32502, and demonstrates how such a waveguide configuration 32506 may be used in an array to provide full density of ray propagation for the desired viewing volume 32504.

A further embodiment of the proposed modified waveguide configuration provides for a method to produce radially symmetric or spiraling rings or gradient of two or more materials along either or both of a transverse or longitudinal orientation with a refractive index separated by a predetermined amount with a per ring pitch with a diameter of X, where X may be constant or variable.

In a further embodiment, equal or non-linear distribution of all of the rays are produced with or without the modified waveguide configurations for wall-mounted and/or table-mounted waveguide structures as well as all room or environment based waveguide structures where multiple waveguides are tiled.

With a waveguide array, it is possible to produce planes of projected light that converge in space at a location that is not located at the surface of the display itself. By ray-tracing these rays, one can clearly see the geometry involved and how converging rays may appear both in-screen (away from the viewer) as well as off-screen (towards viewer) or both simultaneously. As planes move away from the viewer on planar displays with traditional waveguide array designs, the planes tend to grow with the frustum of the viewpoint and may become occluded by the physical frame of the display itself depending on the number of contributing illumination sources. By contrast, as planes move toward the viewer on planar displays with traditional waveguide array designs, the planes tend to shrink with the frustum of the viewpoint but are viewable from all angles at the specified location as long as the viewer is at an angle presenting energy to the eye and the virtual plane does not move beyond the angle created between the viewer and the far edge of the active display area.

In one embodiment, the viewed 2D image or images are presented off of the screen. In another embodiment, the viewed 2D image or images are presented in screen. In another embodiment, the viewed 2D image or images are presented simultaneously both in and/or off screen. In another embodiment, the viewed 2D image or images are presented in combination with other volumetric elements or presented as text for other graphic design or interactive reasons.

In another embodiment, the viewed 2D image or images are presented with higher effective 2D resolution than the physical number of X and Y waveguide elements would otherwise suggest due to the ability for rays to converge with higher density in space than physical elements.

The novelty of this approach is that it is entirely possible to manufacture a holographic display that produces both volumetric imaging capabilities, as well as extremely high resolution 2D imagery such that there is no further mechanical or electronic apparatus or alterations necessary to the waveguides in the display to move seamlessly between flat and volumetric imagery or produce other interesting effects.

With this property, it is possible to programmatically isolate certain illumination sources to present to a viewer that is only visible at explicit angles to the display.

In one embodiment, a single pixel or group of pixels are illuminated under each waveguide element at an angle that triangulates to the viewer's eye and presents an image that is only viewable from that viewer's position in space.

In another embodiment, a second illumination source or group of illumination sources are presented simultaneously to triangulate to a position that is only viewable by a second viewer and contains an image that may be the same or different than the first image presented to the first viewer. For the avoidance of doubt, this may be X addressable viewpoints where X represents the number of individually addressable viewpoints which may be one or more.

In another embodiment, these images are presented with eye, retinal, object or the like tracking leveraging sensors and algorithms known in the art, to dynamically vary the illuminated pixel location to present imagery dynamically to a triangulated location between the viewer and the pixels under each waveguide element. This may be applied to one or more viewers. The tracking may be performed as a 2D process or as a 3D/stereoscopic process, or leveraging other depth sensing technologies known in the art.

In one embodiment, the first region and second region are both parabolic in profile, with the first region focus located at the apex of the second region and the second region focus located at the apex of the first region and the display surface located at an opening located at the apex of the second region and an opening equivalent to the diameter of the display surface presented to the apex of the second region located at the apex of the first region. With this approach, the display surface image will appear to float above a surface without any physical surfaces as the viewed rays that pass through the focus of the second region from an off-axis viewpoint will reflect off of the second region surface and parallel off of the first surface and then at the same angle from the viewed position in the inverse orientation from the first region to the display surface.

In an embodiment, a dual parabolic relay system that includes two reflective regions each with a focus located at the apex of the alternate reflector, the display surface located at the apex of the second region, and an opening equivalent to the diameter of the presented display surface located at the first region producing a virtual image of the display surface. In the event that a waveguide array, holographic or light field display are leveraged, the viewed imagery will retain the nature of the holographic data as well as appearing to float in space without a physical display surface.

In another embodiment, the focus location of region two is differing to produce magnification or minification. In a second embodiment, the regions have matched focal lengths and are offset by a distance greater than the focal length in order to produce a virtual image with increased magnification.

In another embodiment, the parabolic profiles are manufactured to accommodate a specific shape that results in differing viewed positions from the display to accommodate various display surface geometries or other required viewing angle or condition.

In another embodiment, the regions contain multiple facets in order to independently propagate rays of light by facet region rather than as a singular surface.

In another embodiment, the reflective surface are formed of energy relays such that the "Chief Ray Angle" CRA of the energy surface exceeds the view angle possible from the curve applied to one or more surface(s) wherein the first surface that would have otherwise been a reflective surface has a certain geometric profile and the second surface at the alternate end of the waveguide element has a certain geometric profile, and cumulatively they have a CRA that reflects energy from a viewer's position and the addition of energy surface panels at the second surface may be implemented thereby providing energy information that is not viewable from the viewer's direct position but may provide energy information indirectly through one or more reflective surfaces and the associated calibration process required to compute the reflected imaging data in relation to the ultimately viewed data.

Figure 33A:
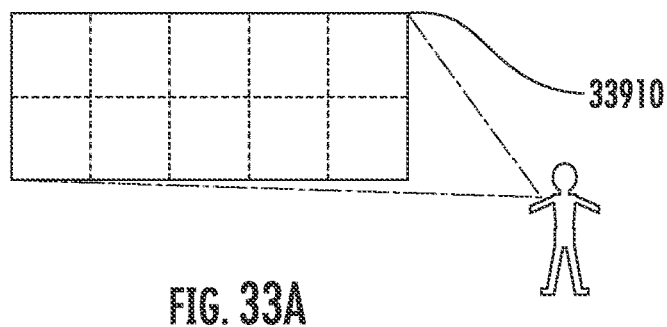
FIGS. 33A-33D illustrate four perspective views of tiling multiple energy systems to form a seamless environment, in accordance with four embodiments of the present disclosure.
Figure 33B:
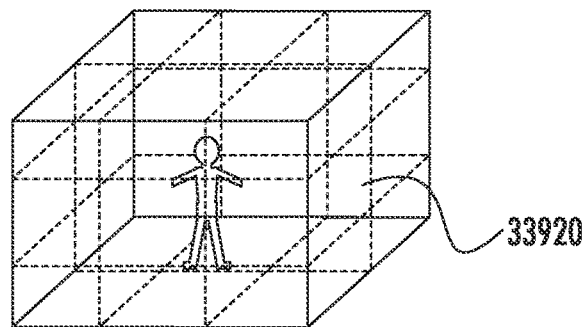
Figure 33C:
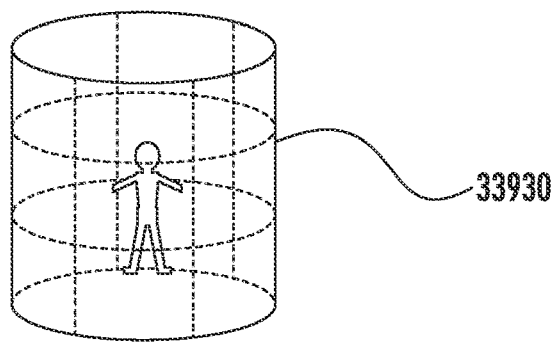
Figure 33D:
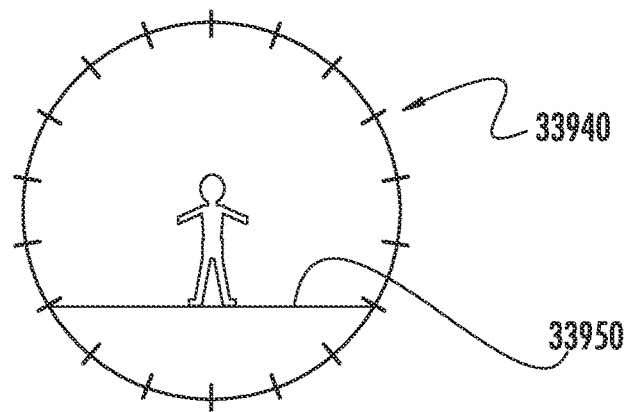

Configurations for Bi-Directional Seamless Energy Surfaces to Propagate Two-Dimensional, Light Field and Holographic Energy FIGS. 33A-33D illustrate four perspective views of tiling multiple energy waveguide systems to form a seamless environment in different shapes, in accordance with four embodiments of the present disclosure. FIG. 33A illustrates a perspective view of a large format aggregated seamless energy surface 33910. FIG. 33B illustrates a perspective view of a six-sided aggregated seamless surface environment 33920. FIG. 33C illustrates a perspective view of a cylindrical aggregated energy environment 33930. FIG. 33D illustrates a perspective view of a spherical aggregated energy surface environment 33940 with a transparent platform 33950 within.

Leveraging the resultant optimized energy system energy waveguide and surface seaming processes, it is possible to further increase the effective size of the system by tiling each of the energy surfaces and waveguide elements to produce any size, shape, or form-factor desired. It is important to note that the waveguide element may exhibit a seam artifact by virtue of non-square grid waveguide element packing schema. To counter this effect, either a larger singular waveguide may be produced, refractive matching materials may be leveraged between the edges of any two surfaces and cut to the angle required for a specified environment (e.g. systems placed at 90 degrees of each other may require a 45 degree bezel cut for simplified bonding, although other methodologies may be leveraged), and/or regular waveguide grid structures may be employed to ensure that no waveguide elements are split between two waveguide surfaces. Further, it is possible to leverage non-square grid waveguide element structures and form a complex mechanical seam that follows the contour of the non-square grid pattern and aligns to the light inhibiting elements within the waveguide structures to provide a seam at the location of a non-energy transmitting location of the waveguide element.

Figure 33E:
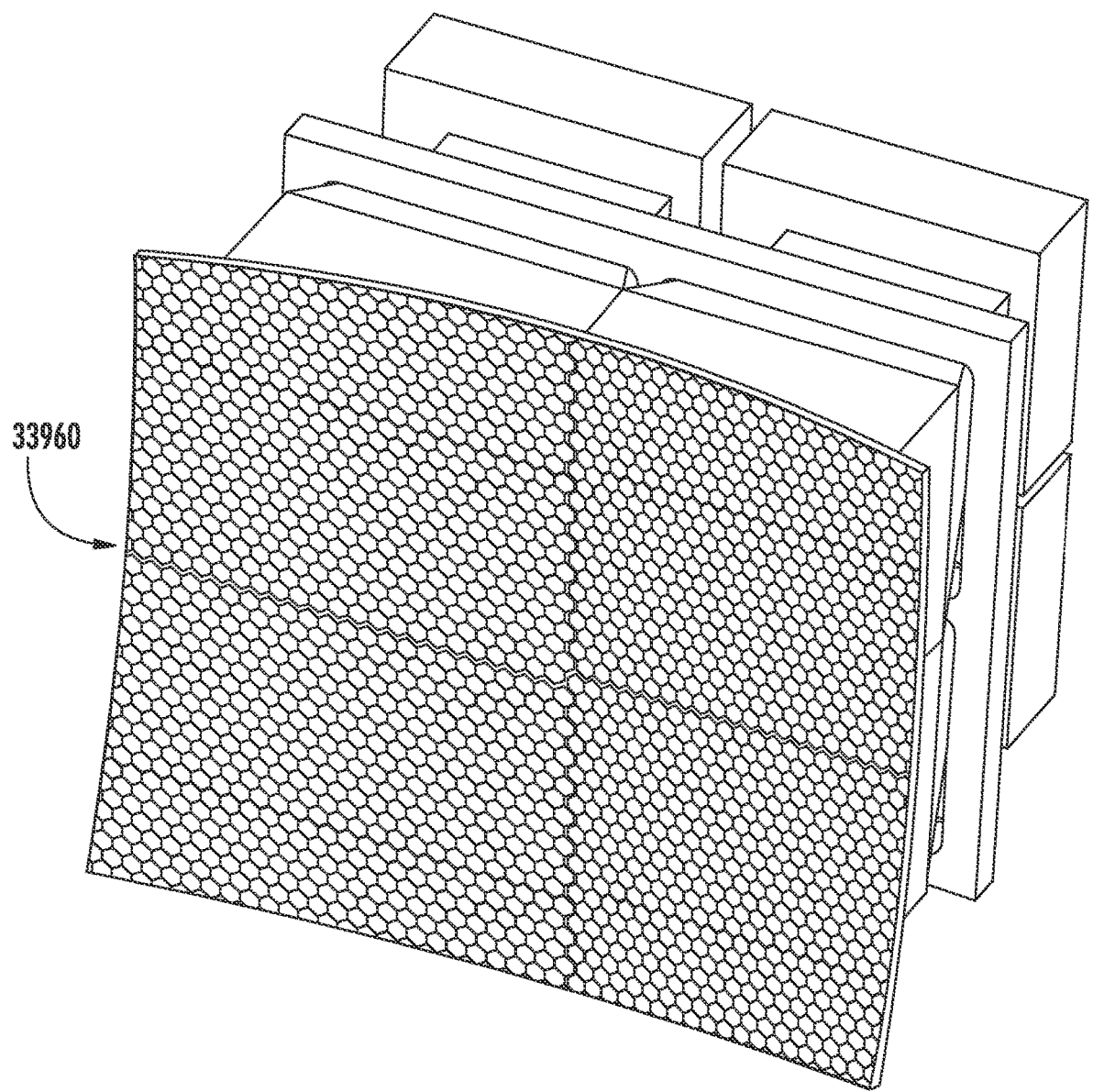
FIG. 33E illustrates the curved waveguide surface and energy devices of an energy waveguide system, in accordance with one embodiment of the present disclosure.

FIG. 33E illustrates, in one embodiment, one such tiled curved waveguide and energy surface 33960 wherein the mechanical seam follows the structure of the edge of the walls of the light inhibiting elements within the waveguide structures and leverages a bonding, mechanical alignment, fusing, or the like process between the adjacent walls of both of the energy surfaces and waveguide surfaces to form the seamless energy waveguide system. As shown in the figure, the curved waveguide and energy surface 33960 includes four separate systems where waveguide seams can be seen prior to bonding, but may become seamless once bonded. It will be appreciated by one skilled in the art that there can be more or fewer than four separate systems and that the energy surface can have any sizes depending on application.

In an embodiment, a tiled array of seamless energy systems are constructed to form a room scale 2D, light field and/or holographic display. These displays may be seamless across large planar or curved walls, may be produced to cover all walls in a cubic fashion, or may be produced in a curved configuration where either a cylindrical-type shape, or a spherical-type shape is formed to increase view angle efficiency of the overall system. Nothing in this description should assume that it is not possible to directly construct a room sized device directly, this embodiment is disclosed as a variation to fabrication methodologies and to further expand the utilization of a single product line into larger devices through tiling, fusing, bonding, attaching, and/or stitching. Further, nothing in this description should be interpreted to limit the room sizes, scales, shapes designs or any other limiting attribute to the ability to generate arbitrary tiled shapes to generate a completely immersive energy environment.

As further embodiments of the above, the energy waveguide systems and the energy relay systems may be assembled in any combination to form various aggregated seamless surfaces. For example, FIG. 33A illustrates a cinema/wall sized large screen planar seamless energy surface, FIG. 33B illustrates a rectangular room with four walls and/or six surfaces to additionally comprise the ceiling and/or floor covered with planar and tiled seamless energy surfaces, FIG. 33C illustrates a tiled curved surface that produces a cylindrically shaped seamless environment, and FIG. 33D illustrates a spherical or dome environment designed from the curved surfaces of each individual energy surfaces and tiled to form the seamless spherical environment.

In some embodiments, a plurality of energy waveguide systems and the energy relay systems, similar to those discussed above, may be formed into an aggregation system, where the plurality of energy systems are assembled to form a single planar or curved surface to create a seamless aggregate surface oriented in a perpendicular configuration with respect to a floor surface, similar to the aggregated seamless energy surface 33910 shown in FIG. 33A.

In other embodiments, a plurality of energy waveguide systems and the energy relay systems, similar to those discussed above, may be formed into an aggregation system, where the plurality of energy systems are assembled to form a single planar or curved surface to create a seamless aggregate surface oriented in a parallel configuration with respect to a floor surface, similar to the transparent platform 33950 as shown in FIG. 33D.

In some embodiments, a plurality of energy waveguide systems and the energy relay systems, similar to those discussed above, may be formed into an aggregation system, where the plurality of energy systems are assembled to form two or more planar or curved surfaces to create a seamless aggregate surface across any combination of objects including tables, walls, ceiling, floor or other surfaces.

In other embodiments, a plurality of energy waveguide systems and the energy relay systems, similar to those discussed above, may be formed into an aggregation system, where the plurality of energy systems are assembled to form three planar or curved surfaces to create a seamless aggregate surface across three adjacent walls.

In some embodiments, a plurality of energy waveguide systems and the energy relay systems, similar to those discussed above, may be formed into an aggregation system, where the plurality of energy systems are assembled to form four planar or curved surfaces to create a seamless aggregate surface across four enclosed walls.

In other embodiments, a plurality of energy waveguide systems and the energy relay systems, similar to those discussed above, may be formed into an aggregation system, where the plurality of energy systems are assembled to form five planar or curved surfaces to create a seamless aggregate surface across any combination of objects including tables, walls, ceiling, floor or other surfaces.

In some embodiments, a plurality of energy waveguide systems and the energy relay systems, similar to those discussed above, may be formed into an aggregation system, where the plurality of energy systems are assembled to form six planar or curved surfaces to create a seamless aggregate surface across four objects including tables, walls, ceiling, floor or other surfaces, in an enclosed environment, similar to the aggregated seamless energy surface 33920 shown in FIG. 33B.

In other embodiments, a plurality of energy waveguide systems and the energy relay systems, similar to those discussed above, may be formed into an aggregation system, where the plurality of energy systems are assembled to form a planar or curved surface to create a seamless aggregate cylindrical surface across any range of angles, volumes and combinations of objects including tables, walls, ceiling, floor or other surfaces, similar to the aggregated seamless energy surface 33930 shown in FIG. 33C.

In some embodiments, a plurality of energy waveguide systems and the energy relay systems, similar to those discussed above, may be formed into an aggregation system, where the plurality of energy systems are assembled to form a planar or curved surface to create a seamless aggregate spherical or domed surface across any range of angles, volumes and combinations of objects including tables, walls, ceiling, floor or other surfaces, similar to the aggregated seamless energy surface 33940 shown in FIG. 33D.

As depicted in FIGS. 33A-33D, each system may further include an assembly of the systems having tiled, light field optomechanical systems, and each system may be configured for light field display and other bidirectional energy emission, reflection, or sensing. Each system may comprise a base structure, one or more components forming an energy surface, one or more elements forming a waveguide capable of altering the path of energy waves transmitted to or received from the energy surface, one or more energy devices emitting or receiving energy waves to or from the energy surface, and one or more electronic components. In an embodiment, the energy surface, the waveguide, the energy devices, and the electronic components are secured to the base structure. And in another embodiment, the assembly is arbitrarily shaped to form a seamless, tiled optomechanical display.

In one embodiment, the energy relay system may further include relay elements including faceplates and optical tapers. In another embodiment, the array of energy waveguides may be bonded into a single waveguide component. In some embodiments, the energy relay system may be aligned and calibrated to the singular seamless energy surface passively or actively with up to pixel-by-pixel rectification leveraging an external calibration tooling station or alignment hardware.

In one embodiment, the energy waveguide system may be mounted parallel to the base structure. In another embodiment, the singular seamless energy surface may be mounted orthogonal to the base structure.

In one embodiment, the one or more relay elements includes fused or tiled mosaics, where any seams between adjacent fused or tiled mosaics are separated by or are less than the minimum perceptible contour as defined by the visual acuity of a human eye having better than 20/40 vision at a distance at or greater than the width or height of the singular seamless energy surface.

In operation, the energy system may be configured to relay light to form 2D, stereoscopic, multiview, plenoptic, 4D, volumetric, light field, holographic, or any other visual representation of light. In other embodiments, the energy system may be operable to emit, reflect or converge frequencies to induce tactile sensation or volumetric haptic feedback.

In some embodiments, the array of energy waveguide is designed to project rays up to 360 degrees along a horizontal axis with additional rays in a vertical axis, and limiting rays perpendicular to the singular seamless energy surface. In other embodiments, the energy system is configured for a floor-mounted assembly or a ceiling-mounted assembly, and optionally includes a transparent surface above the floor-mounted assembly.

Figure 36:
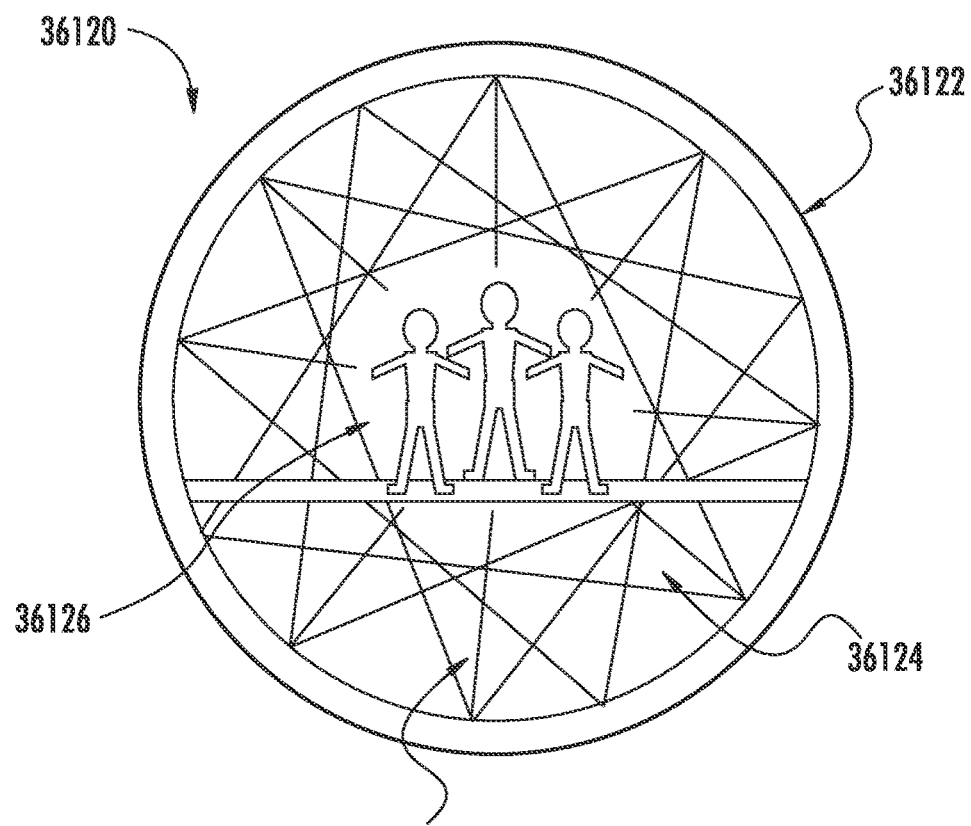
FIG. 36 illustrates an orthogonal view of a spherical structure where a viewing volume is surrounded by tiled energy waveguide systems, in accordance with one embodiment of the present disclosure.

Reference is now made to FIG. 36, which is a further embodiment of FIG. 33D, wherein an orthogonal view of a spherical structure 36120 illustrates where viewers are surrounded by tiled and curved energy surfaces 36122 and are elevated above the bottom floor surface on a transparent platform 36124, in accordance with one embodiment of the present disclosure. FIG. 36 exemplifies the approach of decreasing angle of view requirements when placing a viewer within a central environment volume wherein a viewer or series of viewers exist within a range of volume (e.g., central viewing volume 36126) and demonstrates the relative angles of view required for each waveguide element for a given central viewing range (e.g., range of space that the viewers may move around without loss of energy resolution).

A further embodiment of the above where equal or non-linear distribution of the rays are produced with or without Fresnel, diffractive, gradient index, holographic optical element, digitally encoded or otherwise customized waveguide configurations for wall-mounted and/or table-mounted energy waveguide structures as well as all room or environment based energy surface structures where multiple systems are tiled.

A further embodiment where a completely spherical or near-spherical or conical, cubic or other surrounding geometry, tiled energy structures are produced and viewers walk on a transparent platform 36124 such that the energy surfaces 36122 are viewable in a radius surrounding the viewing volume 36126. In such a case, the rays propagate more normal to the radial waveguide surface 36128 and leverage wall-mounted type waveguide structures 36122 with distribution including perpendicular angles in relation to the normal of the curved surface in the required AOV.

FIG. 36 further illustrates spherical, conical and any non-planar enveloping surface where the viewing volume exists within a certain relative energy focus position from the energy surfaces, resulting in the possible optimization of a reduction of required angles of view from each respective waveguide. This phenomenon is produced by virtue of the normal of the waveguide maintaining a much tighter relationship between the viewer and the energy surface thus reducing the necessity for increased angles of view that are traditionally required for planar surfaces. FIG. 36 exemplifies this approach wherein a viewer or series of viewers exist within a range of volume and demonstrates the relative angles of view required for each waveguide for a given central viewing range (range of space that the viewers may move around without loss of energy propagation).

It is additionally possible to include multiple focus positions by altering the waveguide prescription or by stacking multiple waveguides or both to produce multiple regions of density along the z-axis when directed to target specific regions in space for specific applications. It is additionally possible to layer multiple transmissive and/or one non-transmissive and multiple transmissive energy surfaces wherein the waveguide provides the ability to increase effective resolution through various means of time sequential, spatial, or spatiotemporal super resolution, and may comprise two or more surfaces focused at differing positions resulting in a change in propagation angle per energy surface and/or altering the physical location of the energy surface in relation to each other to produce angular dependencies in resultant energy values.

FIGS. 36, 33C and 33D additionally may include curved waveguides commensurate with the curvature of the energy surface. The ability to generate a waveguide function that varies sampling frequency over field distance is a characteristic of various distortions and known in the art. Traditionally, the inclusion of distortions are undesirable in a waveguide profile, however, for the purposes of curved waveguide element design, these are all characteristics that further control and distribute the rays of light depending on the specific viewing conditions desired. It may require the addition of multiple prescriptions, elements, layers or a gradient of prescriptions across the entirety of the waveguide depending on the application and environment requirements.

An additional embodiment of the above where the prescriptions are further optimized by the curved surfaces of the energy surface and/or the waveguide element. The variation of the normal of the chief ray angle (CRA) in relation to the energy surface itself may further increase efficiency and require a different prescription than a planar waveguide, although the gradient, variation and/or optimization of the waveguide element still applies.

In a similar fashion as described for the variation of waveguide prescription to produce different energy ray densities depending on distance and desired density as a function of spatial location, it is additionally possible to further refine the prescription to generate a horizontally viewable table-mounted waveguide.

Figure 34A:
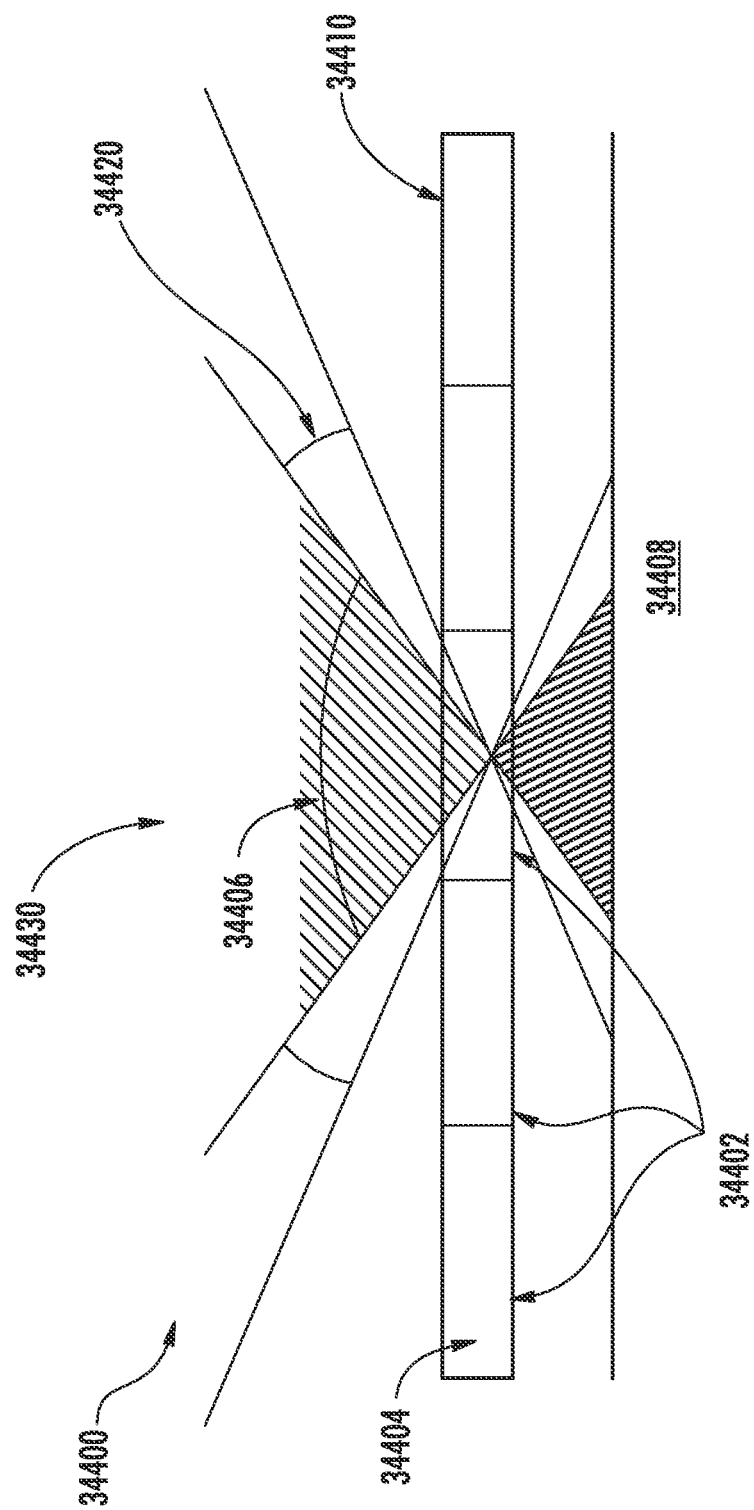
FIG. 34A illustrates a waveguide element exhibiting a non-regular distribution of energy, in accordance with one embodiment of the present disclosure.

Moving on to FIG. 34A illustrates a waveguide system 34400 having a waveguide element that exhibits a non-regular distribution of energy designed to redistribute energy from a perpendicular orientation in relation to waveguide surface to steeper angles throughout the element. In this embodiment, the plurality of energy waveguides may include diffractive waveguide elements 34402, and demonstrates one proposed structure for a modified Fresnel waveguide element structure 34404 on a seamless energy surface 34408 that produces an effectively extremely short focal length and low f/number while simultaneously directing rays of energy to explicitly defined locations 34406. In another embodiment, the waveguide system 34400 includes non-regular waveguides 34410. In operation, there may be energy propagation within a first region 34420 while there may be no energy propagation within a second region 34430.

FIG. 34B illustrates an orthogonal view of a table-mounted energy surface 34450 leveraging the waveguide elements from FIG. 34A, in accordance with one embodiment of the present disclosure. FIG. 34B illustrates the variables to consider with a table-mounted energy surface to help articulate how it is possible to identify the specific system requirements. The considerations and goals for any such system design are to produce an optimal distribution of energy for a given environment.

For example, the energy surface 34450 may be oriented parallel to a ground plane and for a given range of vertical and horizontal locations, configured to distribute energy with density appropriate for a desired vertical and horizontal field of view 34455. In one embodiment, a table-mounted energy system requires the horizontal AOV to be 180 degrees and the vertical to be 45 degrees. In a second embodiment, a table-mounted energy system requires the horizontal AOV to be 360 degrees and the vertical to be 60 degrees. These embodiments are presented for exemplary purposes only and in no way intended to limit the scope of the numerous variations of system specifications that may be designed.

As FIG. 34B illustrates, everything outside of the desired field of view is un-utilized space. Taking the 360-degree example provided, while the full 360 horizontal degrees require sufficient energy density, there are potentially 30 degrees of vertical locations that are not required. While one may simply provide no energy to these regions in space, a design with a waveguide function that provides information across 180×180 degrees (when positioned perpendicular on a wall, 360 by 90 degrees when placed parallel on a table), this is generally not efficient and results in energy densities that may not be practical based upon the target markets.

FIG. 34B illustrates an embodiment wherein the optomechanical assembly comprises a waveguide exhibiting non-regular distribution of energy providing 360 degrees in a horizontal axis and a limited distribution in a vertical axis with the energy surface parallel to a ground plane, by redirecting rays that would have otherwise been projected perpendicular to the energy surface. The assembly may be configured for a floor-mounted assembly or a ceiling-mounted assembly, and optionally includes a transparent platform above the floor-mounted assembly similar to those discussed above.

In one embodiment, the energy surface 34450 may include modified waveguides having a viewing volume 34470 with a horizontal field of view 34455. In this embodiment, the rays 34460 may be limited by the modified waveguides on the energy surface 34450.

Figure 34C:
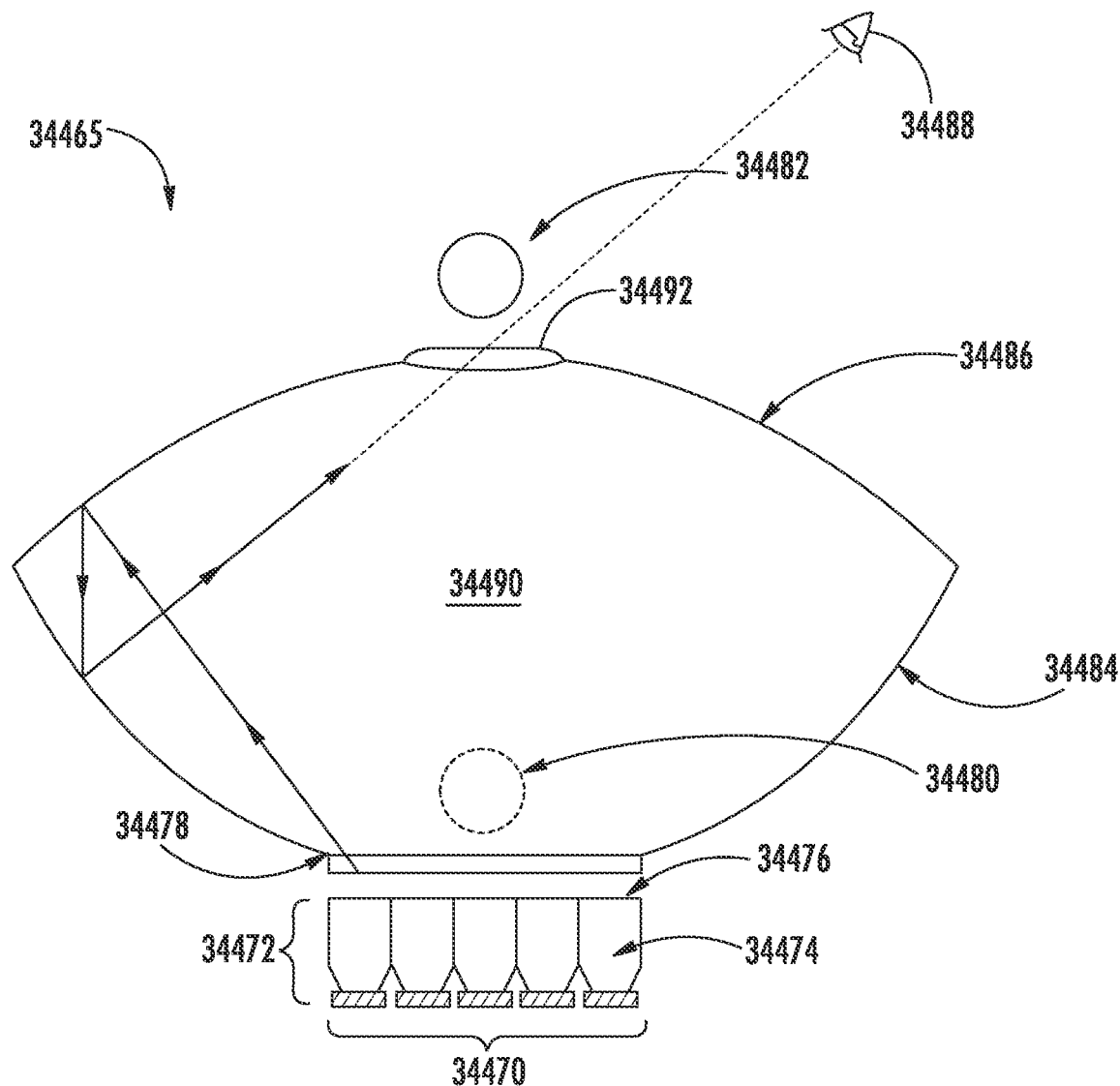
FIG. 34C illustrates an orthogonal view of a table-mounted waveguide system with an additional reflective waveguide elements, in accordance with one embodiment of the present disclosure.

FIG. 34C illustrates an embodiment of the table-mounted waveguide system of FIG. 34B comprising additional reflective waveguide elements having an aperture to allow relayed converging energy from a first surface to a second offset surface, and wherein the second surface is virtual. In one embodiment, the system further includes a reflective waveguide element having an aperture to relay converging energy from the singular seamless energy surface to virtual space.

In one embodiment, the waveguide system 34465 includes five energy waveguides 34470. Although five energy waveguides 34470 are shown, it will be understood that there can be more or fewer waveguides. The energy waveguides 34470 may be coupled to a plurality of energy relays 34474 to form a seamless energy surface 34476 in similar fashion as described above. In one embodiment, the height 34472 of the energy waveguides 34470, the energy relays 34474 and the seamless energy surface 34476 may vary in relation to the object or focus as can be appreciated and understood by one of ordinary skill in the art.

In some embodiments, the table-mounted waveguide system 34465 may include an additional reflective waveguide element 34490 having a first reflector surface 34486 and a second reflector surface 34484. The reflective waveguide element 34490 may include an aperture 34492 such that converging energy from the seamless energy surface 34476 may be relayed from the first reflector surface 34486 to the second reflector surface 34484 through the aperture 34492 to a viewer 34488. In other words, a first virtual object 34480 may be relayed and converged at a virtual space to form a second virtual object 34482.

As depicted in the various embodiments of this disclosure, an optomechanical assembly may comprise energy relays inducing transverse Anderson localization and/or energy relays with two or more first or second surfaces for bidirectional propagation of energy.

Figure 35:
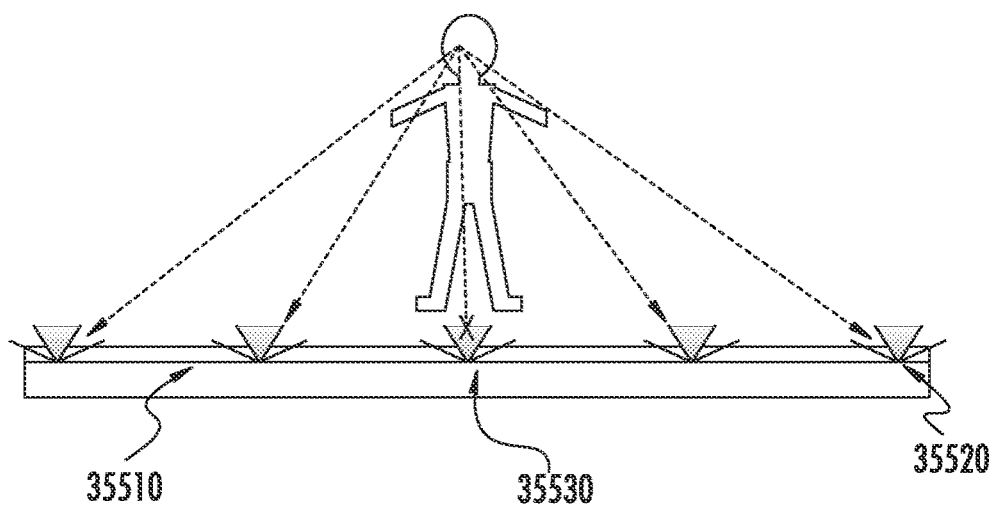
FIG. 35 illustrates an orthogonal view of a floor-mounted tiled energy waveguide system, in accordance with one embodiment of the present disclosure.

FIG. 35 illustrates an orthogonal view of a floor-mounted tiled energy surface 35510 with a non-linear distribution of rays, in accordance with one embodiment of the present disclosure. FIG. 35 exemplifies the floor-mounted tiled assembly 35510 with the non-linear distribution of rays that tend to exclude the perpendicular rays to the energy surface. While it may be possible to configure the floor mounted tiled assembly 35510 in the same waveguide structure as the other environment surfaces where perpendicular rays and off-axis rays are provided with even, or some form of, distribution, however, with the proposed table mounted approach placed at or approximate to the feet of a standing position (or above or below depending on the requirements for the system), it is possible to further optimize the waveguide configuration as no rays directly perpendicular to the floor assembly 35510 surface may need to be represented as one will be self-occluding these rays with their body and/or feet. As shown in FIG. 35, in the event of a multiple viewer experience, the perpendicular rays will not be viewable by other participants as the rays presented in a perpendicular orientation, unlike walls or ceilings, are occluded or not at the correct view angle to produce artifacts. In other words, the floor assembly 35510 may be configured with modified waveguide elements 35520 such that certain rays may not be visible due to self-occlusion 35530.

Figure 37:
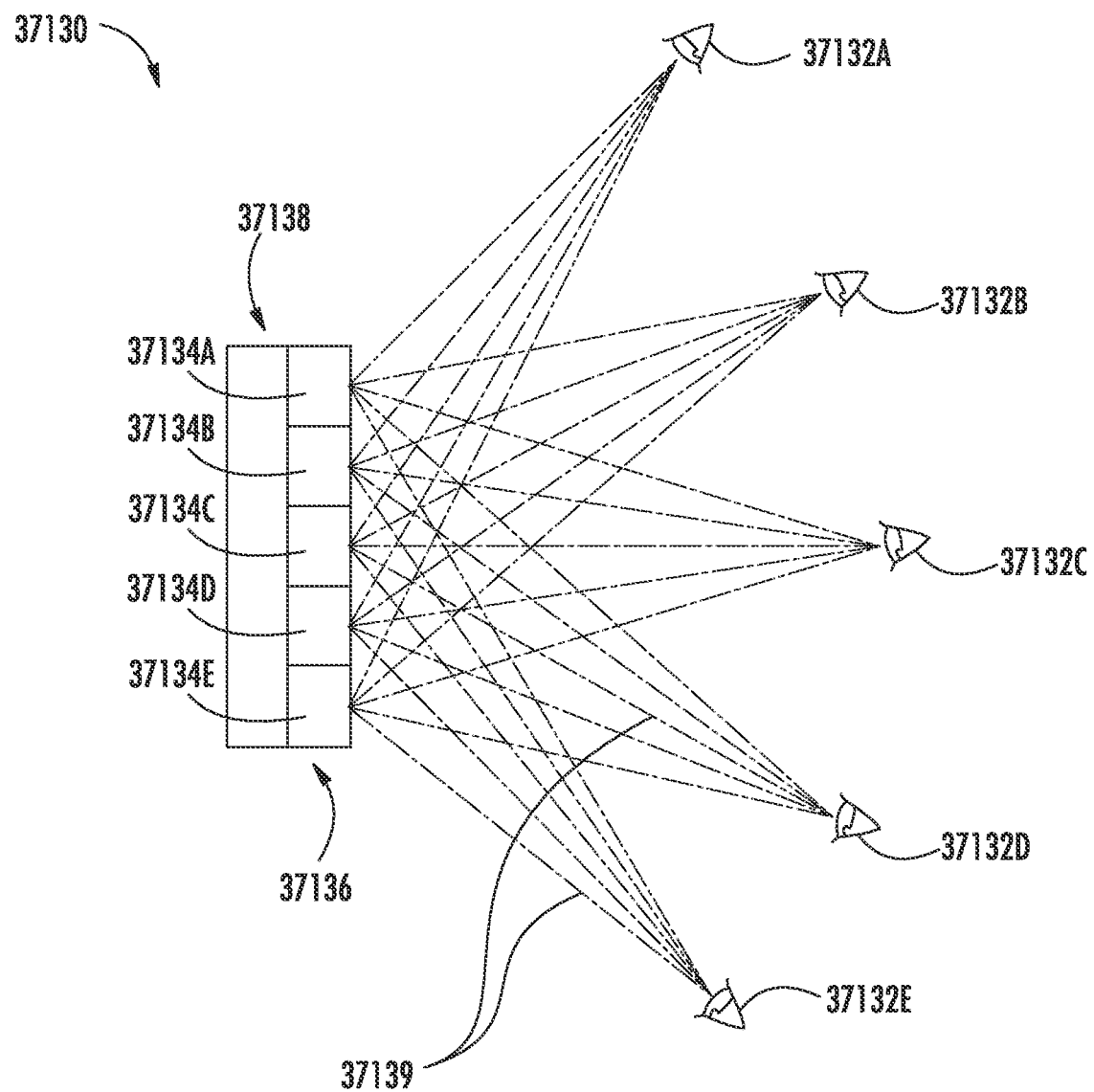
FIG. 37 illustrate an orthogonal view of five viewer locations within a viewing volume and five energy coordinates under each waveguide to propagate a plurality of rays to each viewer location that is unique to a single viewer location, in accordance with one embodiment of the present disclosure.

FIG. 37 illustrates an orthogonal view of a system 37130 of five viewer locations 37132 and five corresponding energy locations 37134 under each waveguide element 37136 to present a single ray bundle to each viewer that is unique to a single viewer location, in accordance with one embodiment of the present disclosure. FIG. 37 illustrates five viewer locations 37132A, 37132B, 37132C, 37132D, 37132E and five energy locations 37134A, 37134B, 37134C, 37134D, 37134E under each waveguide element 37136 and an energy surface 37138. These ray bundles propagated to the viewer locations are a direct result of the waveguide element functions. In this fashion, all energy is propagated up to simultaneously addressing each of the specified viewer locations without additional knowledge of said locations. It is additionally possible to configure the energy system of FIG. 37 to include depth sensing devices and algorithms known in the art to dynamically vary the energy location information propagated to each of the specified viewer locations. This may be applied to one or more viewers. The tracking may be performed as a 2D process or as a 3D/stereoscopic process, or leveraging other depth sensing technologies known in the art. As will be appreciated by one skilled in the art, because of the different viewer locations 37132 and the different energy locations 37134, unique plurality of rays 37139 may be provided to each viewer at his or her respective viewer locations 45132.

Figure 38A:
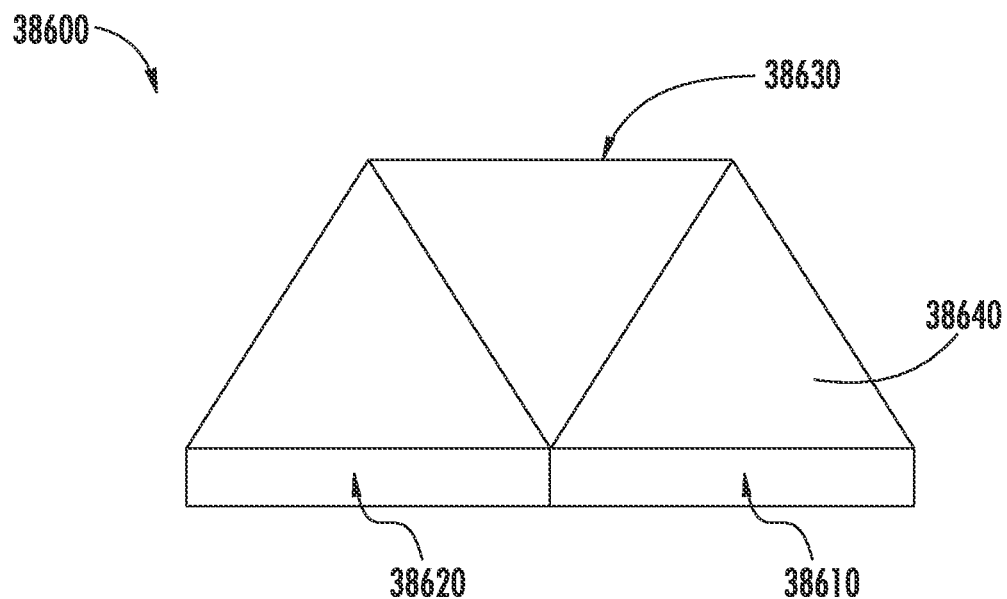
FIG. 38A illustrates an energy relay combining device, in accordance with one embodiment of the present disclosure.

FIG. 38A illustrates an energy relay combining element 38600 that comprises a first surface and two interwoven second surfaces 38630 wherein the second surface 38630 having both an energy emitting device 38610 and an energy sensing device 38620. A further embodiment of FIG. 38A includes an energy relay structure 38640 having two or more sub-structure components 38610, 38620 for at least one of two or more second relay surfaces 38630, that exhibits different engineered properties between the sub-structure components of the two or more second relay surfaces 38630, including sub-structure diameter, wherein the sub-structure diameter for each of the one or more second surfaces 38630 is substantially similar to the wavelength for a determined energy device and energy frequency domain.

Figure 38B:
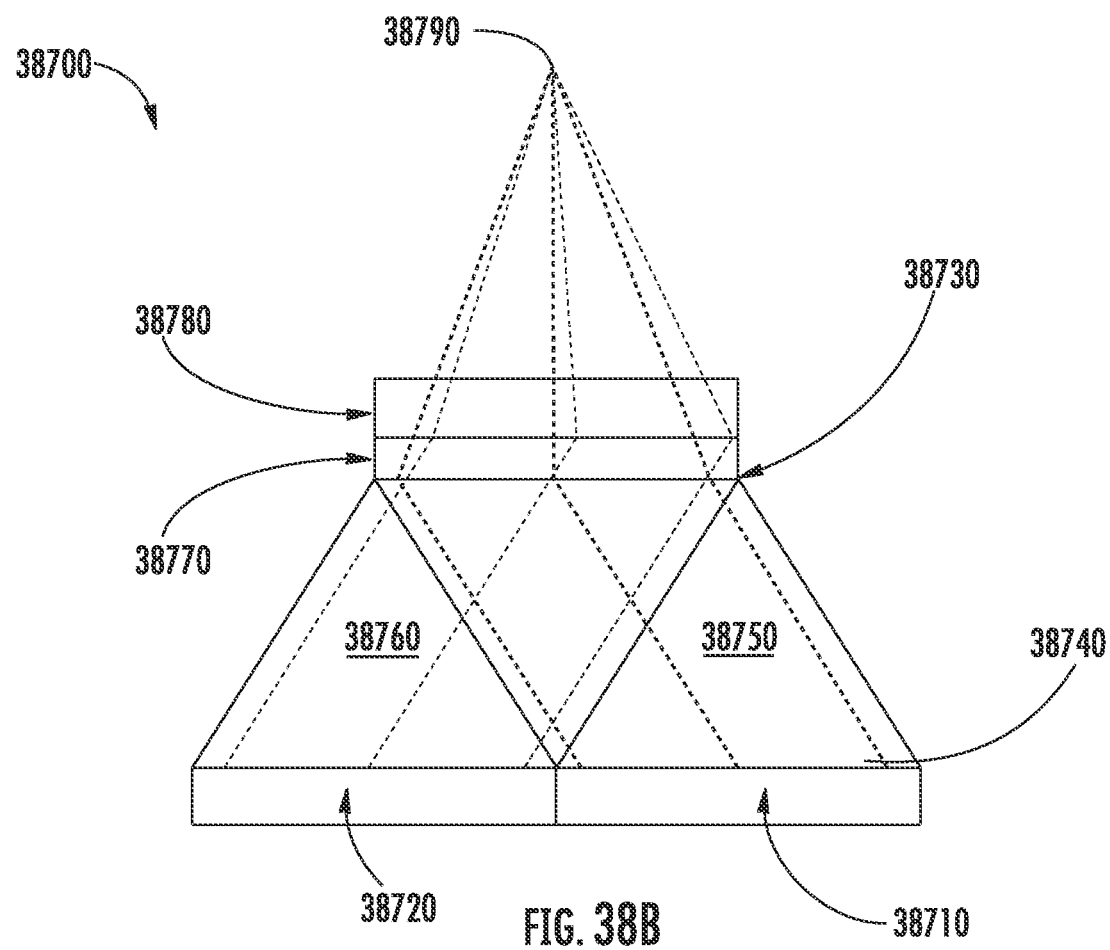
FIG. 38B illustrates a further embodiment of FIG. 38A, in accordance with one embodiment of the present disclosure.

FIG. 38B illustrates a further embodiment of FIG. 38A wherein the energy waveguide 38700 includes one or more element types 38710, 38720 within one or more waveguide element surfaces 38730 and properties, where each of the element types 38710, 38720 are designed to alter the propagation path 38750, 38760 of a wavelength within the commensurate energy frequency domain. In one embodiment, the energy waveguide 38700 may include an electromagnetic energy emitting device 38710 and a mechanical energy emitting device 38720, each device 38710, 38720 configured to alter an electromagnetic energy relay path 38750 and a mechanical energy relay path 38760, respectively.

In another embodiment, the wavelengths of any second energy frequency domain may be substantially unaffected by the first energy frequency domain. The combination of multiple energy devices on the two or more second surfaces of the energy relay and the one or more element types within the one or more waveguide elements provides the ability to substantially propagate one or more energy domains through the energy devices, the energy relays, and the energy waveguides substantially independently as required for a specified application.

In one embodiment, the energy waveguide 38700 may further include an electromagnetic energy waveguide 38770 and a mechanical energy waveguide 38780 assembled in a stacking configuration and coupled to a simultaneously integrated seamless energy surface 38730 similar to that described above. In operation, the energy waveguide 38700 is able to propagate energy paths such that all the energy is able to converge about a same location 38790.

In some embodiments, this waveguide 38700 may be a single relay element with a bidirectional energy surface, one interlaced segment to propagate energy, and a second interlaced segment to receive energy at the energy surface. In this fashion, this may be repeated for every energy relay module in the system to produce a bidirectional energy surface.

Figure 38C:
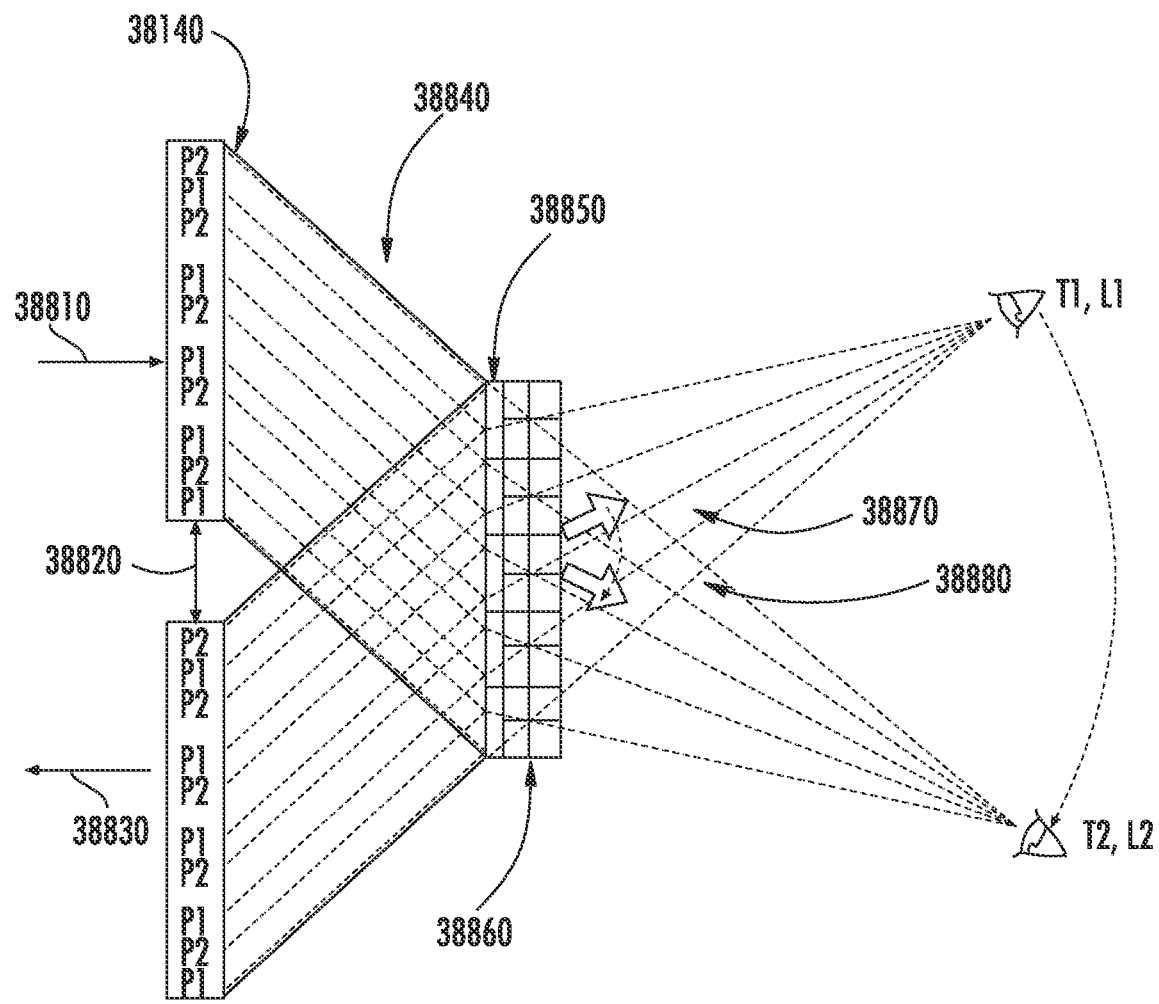
FIG. 38C illustrates an orthogonal view of an implementation of an energy waveguide system, in accordance with one embodiment of the present disclosure.

FIG. 38C illustrates an orthogonal view of an implementation 38140 as a further embodiment of FIG. 37 and comprises the energy relay of FIG. 38A with a viewer at location L1 and time T1, with converging rays along a path through a waveguide and to energy coordinates P1, and where a viewer moves to location L2 at time T2, with rays converging along a path through a waveguide and to energy coordinates P2, and where each of the plurality of energy coordinates P1 and P2 are formed on a first side of an energy relay surface and includes two interwoven second relay surfaces and provides a first energy sensing device and a second energy emitting device to both sense movement and interaction within the viewing volume through the energy waveguide as well as emit energy through the same energy relay and energy waveguide resulting in the visible change to energy emitted from time and location T1, L1 to T2, L2, in accordance with one embodiment of the present disclosure.

In one embodiment, the system 38140 may include energy devices 38820 where one set of energy devices are configured for energy emission 38810 and another set of energy devices are configured for energy sensing 38830. This embodiment may further include a plurality of relay combining elements 38840 configured to provide a single seamless energy surface 38850. Optionally, a plurality of waveguides 38860 may be disposed in front of the energy surface 38850. In operation, as discussed above, the system 38840 may provide simultaneous bi-directional energy sensing or emission with interactive control with the propagated energy at T1 38870, and modified propagated energy at T2 38880, in response to sensed movement between T1, L1 and T2, L2.

Further embodiments of FIG. 38C include compound systems wherein the energy relay system having more than two second surfaces, and wherein the energy devices may be all of a differing energy domain, and wherein each of the energy devices may each receive or emit energy through a first surface of the energy relay system.

Figure 39:
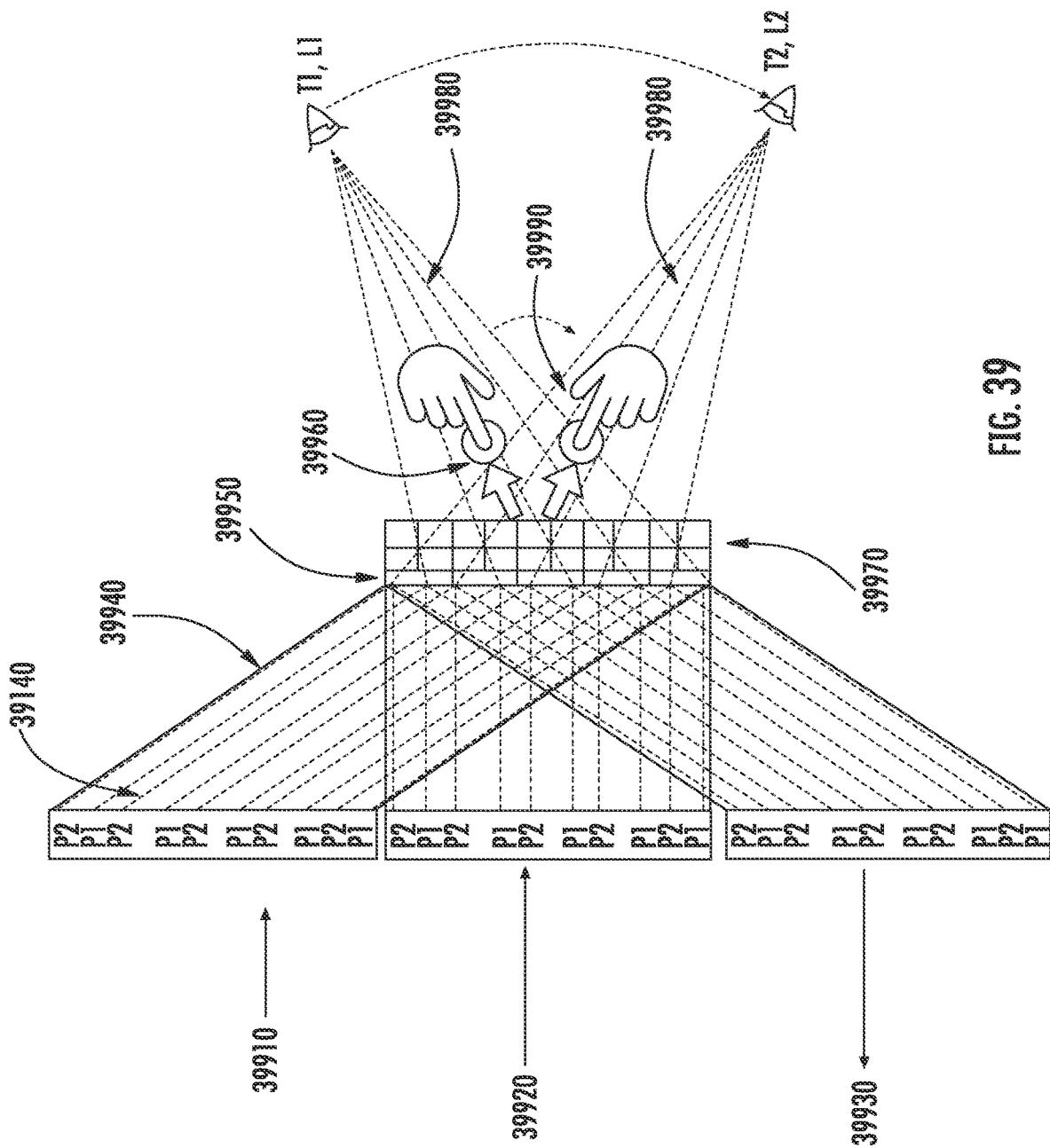
FIG. 39 illustrates an orthogonal view of another implementation of an energy waveguide system, in accordance with one embodiment of the present disclosure.

FIG. 39 illustrates a further compound system 38140 of FIG. 38A (represented in FIG. 39 as 39140) with an orthogonal view of an embodiment where a viewer is at location L1 at time T1, with converging rays along a path through a waveguide and to energy coordinates P1, and wherein a viewer moves to location L2 at time T2, with rays converging along a path through a waveguide and to energy coordinates P2, and wherein each of the plurality of energy coordinates P1 and P2 are formed on a first side of an energy relay surface and comprises three second relay surfaces having a first mechanical energy emitting device, a second energy emitting device and a third energy sensing device, wherein the energy waveguide emits both mechanical and energy through the first surface of the energy relay allowing the third energy sensing device to detect interference from the known emitted energy to the sensed received data, and wherein the mechanical energy emission results in the ability to directly interact with the emitted energy, the mechanical energy converging to produce tactile sensation, the energy converging to produce visible illumination, and the energy emitted at T1, L1 to T2, L2 is modified to respond to the tactile interaction between the viewer and the emitted energy, in accordance with one embodiment of the present disclosure.

In one embodiment, the system 38140 may include an ultrasonic energy emission device 39910, an electromagnetic energy emission device 39920, and an electromagnetic sensing device 39930. This embodiment may further include a plurality of relay combining elements 39940 configured to provide a single seamless energy surface 39950. Optionally, a plurality of waveguides 39970 may be disposed in front of the energy surface 39950.

The one or more energy devices may be independently paired with two-or-more-path relay combiners, beam splitters, prisms, polarizers, or other energy combining methodology, to pair at least two energy devices to the same portion of the energy surface. The one or more energy devices may be secured behind the energy surface, proximate to an additional component secured to the base structure, or to a location in front and outside of the FOV of the waveguide for off-axis direct or reflective projection or sensing. The resulting energy surface provides for bidirectional transmission of energy and the waveguide converge energy waves onto the energy device to sense relative depth, proximity, images, color, sound, and other energy, and wherein the sensed energy is processed to perform machine vision related tasks including, but not limited to, 4D eye and retinal tracking through the waveguide array, energy surface and to the energy sensing device.

In operation, as discussed above, the system 39140 may provide simultaneous bi-directional energy sensing or emission with interactive control with the propagated energy at T1 39960, propagated haptics at T1 39980, and modified propagated energy at T2 39990, in response to sensed interference of propagated energy emission from sensed movement and ultrasonic haptic response between T1, L1 and T2, L2.

Figure 40:
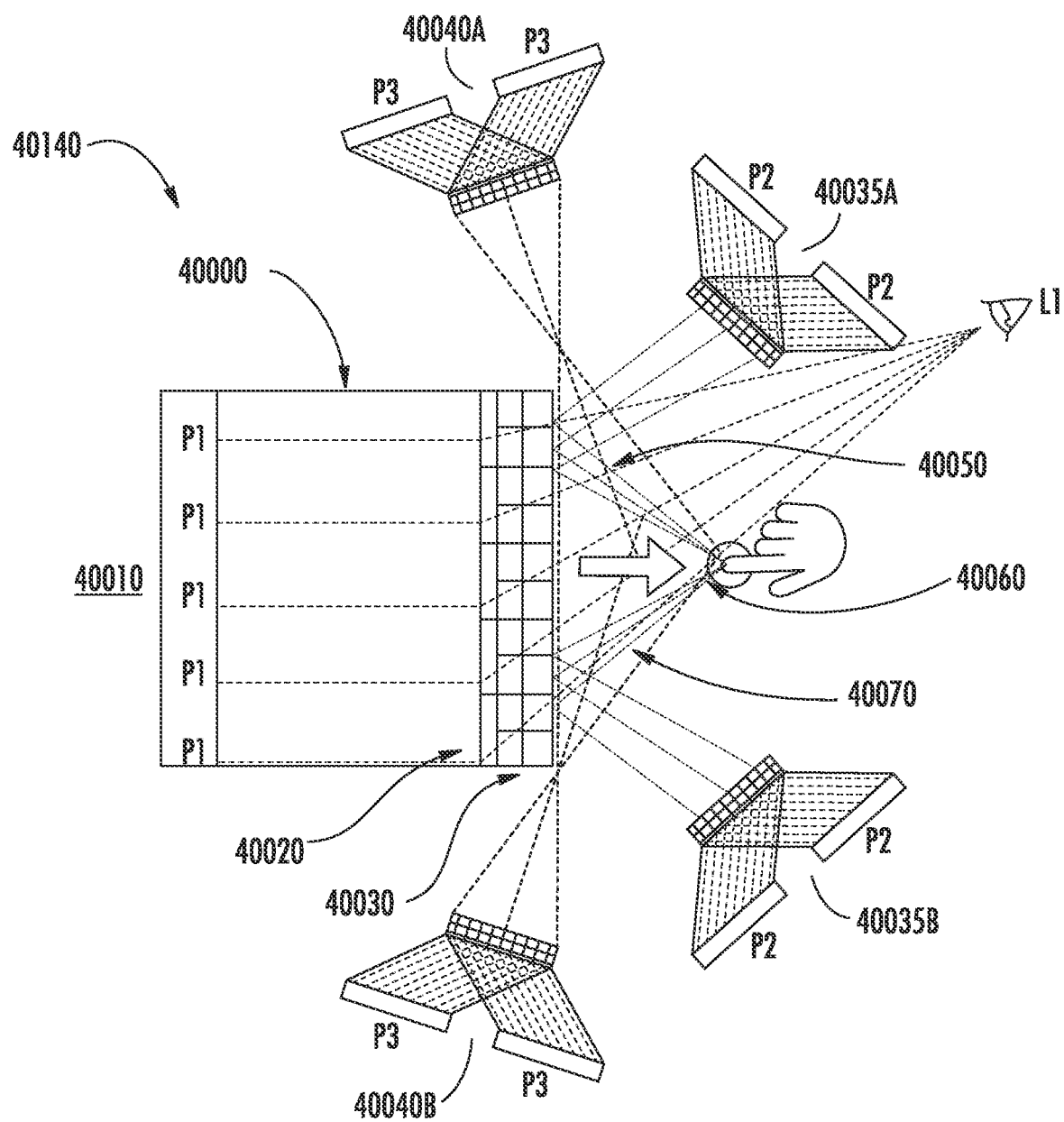
FIG. 40 illustrates an orthogonal view of yet another implementation, in accordance with one embodiment of the present disclosure.

FIG. 40 illustrates an embodiment of pairing one or more energy devices 40010 to additional components (e.g., relay elements 40000 configured to form a single seamless energy surface 40020) where a viewer is at location L1, with converging rays along a path through a waveguide 40030 and to energy coordinates P1, and where each of the plurality of energy coordinates P1 are formed on a first side of an energy relay surface 40020 corresponding to one or more devices E1, and where the waveguide or relay surface provides an additional reflective or diffractive property and propagated haptics 40060, where the reflective or diffractive property substantially does not affect the propagation of rays at coordinates P1.

In one embodiment, the reflective or diffractive property commensurate for the energy of additional off-axis energy devices E2 40035A, 40035B, each of devices E2 40035A, 40035B containing an additional waveguide and energy relay, each additional energy relay containing two or more second surfaces, each with a sensing or emitting device respectively with corresponding energy coordinates P2 propagating through a similar volume as P1. In one embodiment, reflective or diffractive energy can propagate through the devices of E2 40050.

In another embodiment, an additional system out of the field of view in respect to the first E1 and second E2 waveguide elements comprise an additional system E3 40040A, 40040B having additional waveguide and relay elements, the relay elements having two second surfaces and one first surface, the second surfaces receiving energy from both focused emitting and sensing energy devices.

In one embodiment, the E3 waveguide elements 40040A, 40040B are configured to propagate energy 40070 directly through a desired volume, the desired volume corresponding to the path of energy coordinates P1 and P2, and forming additional energy coordinates P3 passing through the E3 system 40040A, 40040B, each of the E1, E2 and E3 sensing and emitting devices configured to detect interference from the known emitted energy to the sensed received data.

In some embodiments, the mechanical energy emission results in the ability to directly interact with the emitted energy, the mechanical energy converging to produce tactile sensation, the energy converging to produce visible illumination, and the energy emitted is modified to respond to the tactile interaction between the viewer and the emitted energy, in accordance with one embodiment of the present disclosure.

Various components within the architecture may be mounted in a number of configurations to include, but not limit, wall mounting, table mounting, head mounting, curved surfaces, non-planar surfaces, or other appropriate implementation of the technology.

FIGS. 38A, B, C, 39 and 40 illustrate an embodiment wherein the energy surface and the waveguide may be operable to emit, reflect, diffract or converge frequencies to induce tactile sensation or volumetric haptic feedback.

FIGS. 38A, B, C, 39 and 40 illustrates a bidirectional energy surface comprising (a) a base structure; (b) one or more components collectively forming an energy surface; (c) one or more energy devices; and (d) one or more energy waveguides. The energy surface, devices, and waveguides may mount to the base structure and prescribe an energy waveguide system capable of bidirectional emission and sensing of energy through the energy surface.

In an embodiment, the resulting energy display system provides for the ability to both display and capture simultaneously from the same emissive surface with waveguides designed such that light field data may be projected by an illumination source through the waveguide and simultaneously received through the same energy device surface without additional external devices.

Further, the tracked positions may actively calculate and steer light to specified coordinates to enable variable imagery and other projected frequencies to be guided to prescribed application requirements from the direct coloration between the bidirectional surface image and projection information.

In one embodiment of embodiment of FIGS. 38A, B, C, 39 and 40 the one or more components are formed to accommodate any surface shape, including planar, spherical, cylindrical, conical, faceted, tiled, regular, non-regular, or any other geometric shape for a specified application.

In one embodiment of FIGS. 38A, B, C, 39 and 40 the one or more components comprise materials that induce transverse Anderson localization.

In one embodiment, an energy system configured to direct energy according to a four-dimensional (4D) plenoptic function includes a plurality of energy devices; an energy relay system having one or more energy relay elements, where each of the one or more energy relay elements includes a first surface and a second surface, the second surface of the one or more energy relay elements being arranged to form a singular seamless energy surface of the energy relay system, and where a first plurality of energy propagation paths extend from the energy locations in the plurality of energy devices through the singular seamless energy surface of the energy relay system. The energy system further includes an energy waveguide system having an array of energy waveguides, where a second plurality of energy propagation paths extend from the singular seamless energy surface through the array of energy waveguides in directions determined by a 4D plenoptic function. In one embodiment, the singular seamless energy surface is operable to both provide and receive energy therethrough.

In one embodiment, the energy system is configured to direct energy along the second plurality of energy propagation paths through the energy waveguide system to the singular seamless energy surface, and to direct energy along the first plurality of energy propagation paths from the singular seamless energy surface through the energy relay system to the plurality of energy devices.

In another embodiment, the energy system is configured to direct energy along the first plurality of energy propagation paths from the plurality of energy devices through the energy relay system to the singular seamless energy surface, and to direct energy along the second plurality of energy propagation paths from the singular seamless energy surface through the energy waveguide system.

In some embodiments, the energy system is configured to sense relative depth, proximity, images, color, sound and other electromagnetic frequencies, and where the sensed energy is processed to perform machine vision related to 4D eye and retinal tracking. In other embodiments, the singular seamless energy surface is further operable to both display and capture simultaneously from the singular seamless energy surface with the energy waveguide system designed such that light field data may be projected by the plurality of energy devices through the energy waveguide system and simultaneously received through the same singular seamless energy surface.

Vision Correction

Many people have less than perfect vision, and can have trouble seeing or focusing their vision on far-away objects or reading up-close lettering. A variety of conditions can negatively impact a person's ability to see, including, but not limited to farsightedness or hyperopia, nearsightedness or myopia, astigmatism, and presbyopia. Glasses were developed as a way to "correct" for a person's vision, by re-focusing the light entering a person's eyes to sharpen their view of previously blurry or out-of-focus objects. Contact lenses employ the same concept. Vision-correction surgery also operates along the same principle of altering how light is focused on the photoreceptors in the back of our eyes.

Lenses used in glasses operate by bending light in a controlled and predictable way. The lens equation is often used to describe a relationship useful for vision correction between three objects. It is $1/(f)=1/(dO)+(1/dI)$, where f is the focal length of the lens, dO is the distance from the lens to the object, and dI is the distance from the lens to the photo site. Using this equation, a corrective prescriptive function for contact lenses or eyeglasses can be determined that allows light to be refocused into our eyes. In the present disclosure, we propose that the same concept can be applied to a system utilizing holographic display technology according to the principles disclosed herein.

Vision correction may be achieved using holographic light field display systems. In the present disclosure, it is described how calibration and ray tracing, as well as the 4D functions used herein, may be applied to vision correction.

Understanding how light field and 4D computational processing works, a novel implementation for a light field display not only creates holographic projections and content, but also provides the ability to calibrate the projections and content for a specified viewer's eyesight. Vision-calibration parameters can also be stored as a display profile in some embodiments to allow every single viewer to experience in-focus, optically correct images leveraging a high fidelity light field display utilizing appropriate calibration sequences—as disclosed herein—and appropriate processing algorithms.

In addition to holographic imaging, these concepts can also be leveraged for 2D mediums in some embodiments so that any image viewed on a display that is 4D enabled may also provide for the dioptric corrections required for a user's vision—all without a visit to the optometrist, and without prescription eyewear.

The proposed system provides at least for the following within the disclosure:
  a 4D light field display system
  an interactive control system capable of providing an eye exam from a 4D display for one or more users and storing the results in a data storage system for later use
  a calibration system that leverages the results from the vision tests
  a processor capable of reading the vision results and the calibration files on a storage device and processing the results in real time or offline to provide individualized optical corrections
  a methodology for eye/retinal tracking to provide visual corrections for two or more separate eye profiles, or more than a single user at a time
  a user interface to dynamically switch between various detected or manually input users
  a method to switch between 4D and 2D modes Some embodiments of the 4D display system of this disclosure can perform the calibration process for individual user or, even for each eye of the individual users.

In some embodiments, the process goes through a series of:
  object positions at x diopters+ or − the display surface (and at the display surface);
  object focus for each of the previous object positions at each step location, increasing or decreasing the number of diopters used within the calculation for the projection of the object (e.g., to normal vision, will get out of focus in front and behind of the focus point);
  other vision related calibrations may be included for color variation, eye to eye variation, etc.

For each position within the vision calibration sequence, in some embodiments, the viewer will indicate if the results are better or worse, much like a traditional eye exam. The results from the calibration process will be individually prepared and rendered for that viewer to correct for any visual anomalies without the requirement for the viewer to get prescription glasses. This provides the viewer the ability to update the calibration of a display anytime the viewer feels the need. Further, this may apply to all content, not just holographic content. This may also be leveraged as a security setting on a display, as when initiated, images will appear blurry or out of focus to other individuals looking at the display.

Figure 41:
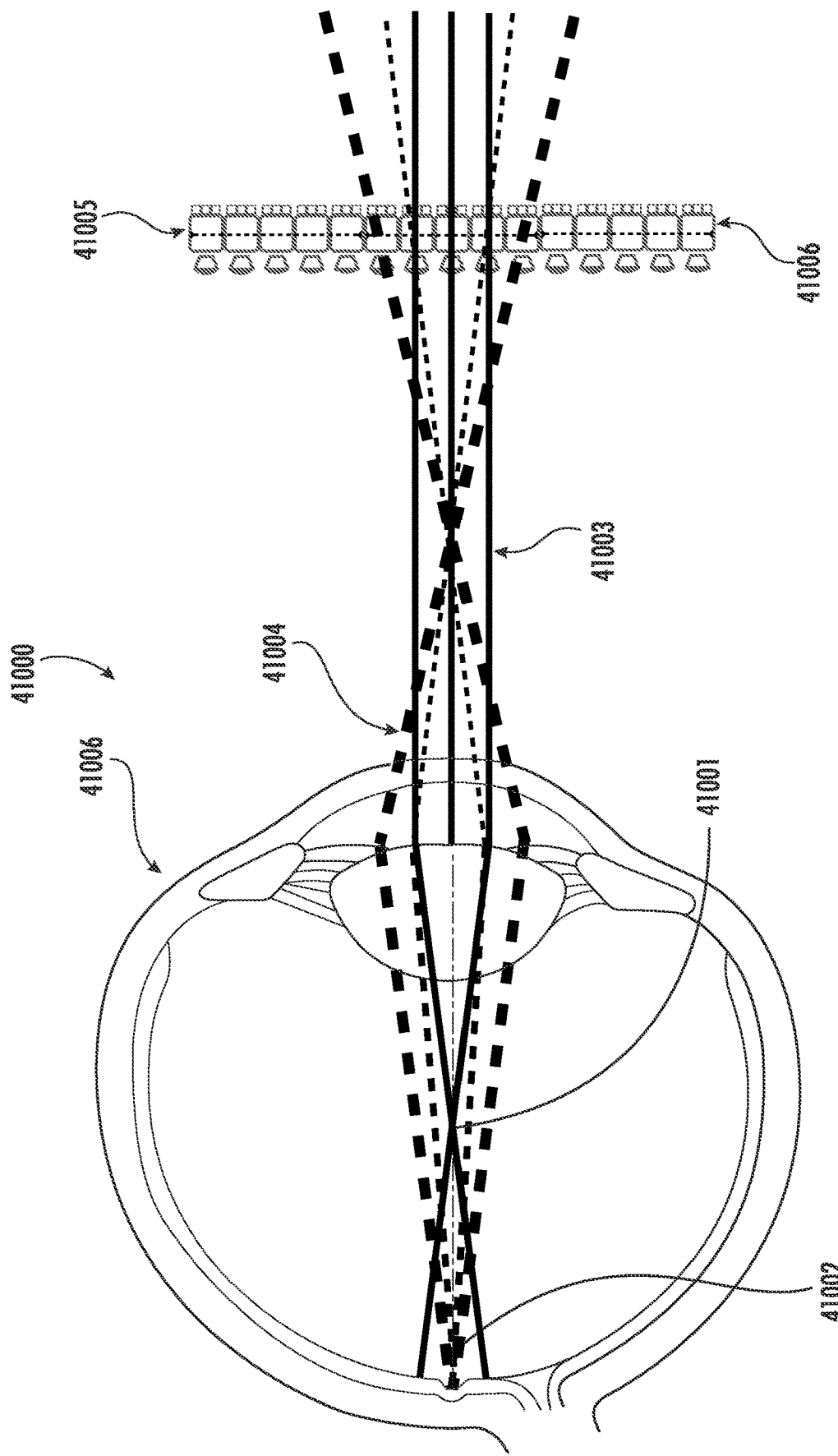
FIG. 41 illustrates a system for correcting vision in a nearsighted viewer.

FIG. 41 illustrates a system 41000 for correcting vision in a nearsighted viewer. An eye of the viewer is represented at 41006. Near the back of the eye, original image rays 41003 converge at an incorrect location 41001, which causes the viewer to see an incorrect image. Through use of a device having a 4D virtual pixel plane 41005 and a virtual display which, in some embodiments may include a plane of projection waveguides 41006, it is possible to create a corrected group of rays leveraging calibration results at 41004. Corrected rays 41004 can be seen converging at the correct location 41002 on the back surface of eye 41006, resulting in the viewer seeing an "in focus" image.

Figure 42:
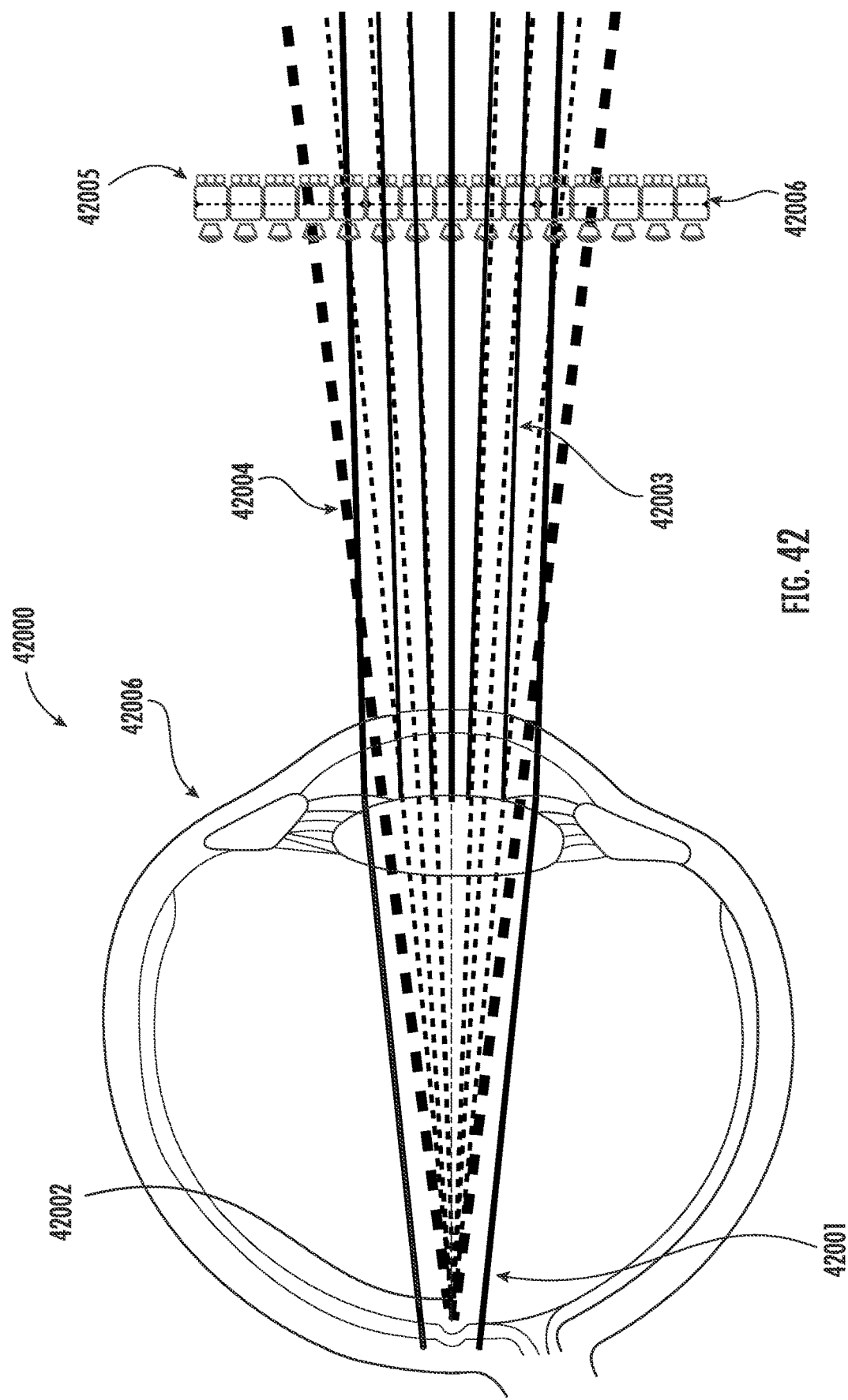
FIG. 42 illustrates a system for correcting vision in a farsighted viewer.

FIG. 42 illustrates a system 42000 for correcting vision in a farsighted viewer. An eye of the viewer is represented at 42006. Image rays 42003 converge at an incorrect location behind the back surface of the eye 420006 due to incorrect focus 42001. This produces a distorted image for the viewer. Through use of a device having a 4D virtual pixel plane 42005 and a virtual plane of projection waveguides 42006, it is possible to create a corrected group of rays leveraging calibration results at 42004. Corrected rays 42004 can be seen converging at the correct location 42002 on the back surface of eye 42006, resulting in the viewer seeing an "in focus" image.

FIG. 43 illustrates a comparison between the perceived images seen by viewers with uncorrected nearsightedness 43001, uncorrected farsightedness 43002, and with a 4D correction applied, or a person with correct vision at 43003.

Figure 44:
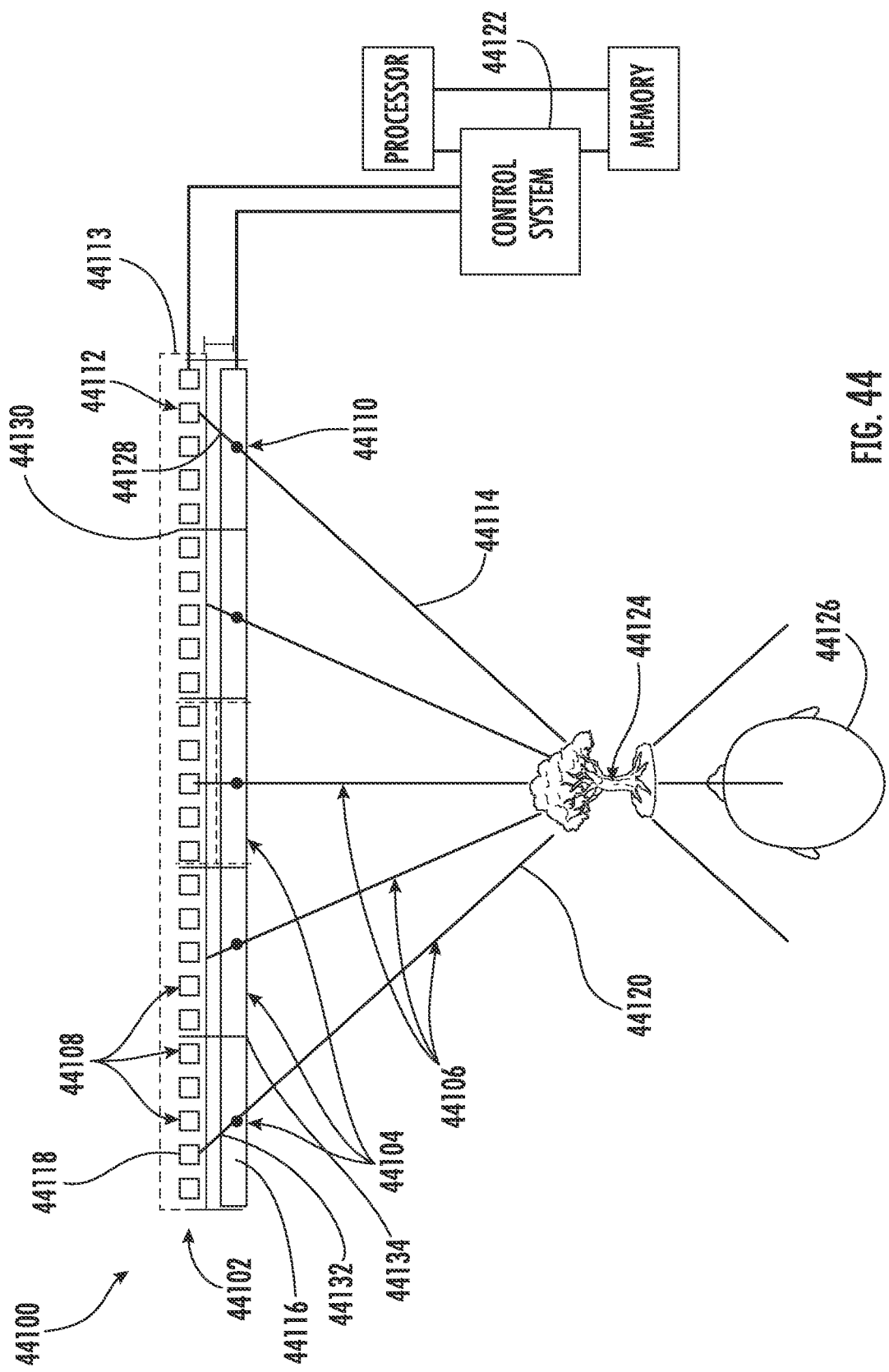
FIG. 44 illustrates an embodiment of a vision-correction device calibrated to project a holographic object.

FIG. 44 depicts one embodiment of a vision-corrective device 44100 of this disclosure. However, the vision-corrective device 44100 disclosed herein is not limited to the one depicted in FIG. 44, and there are other possible embodiments. As shown in FIG. 44, the vision-correction device 44100 includes a light-directing system 44102. The light-directing system 44102 may include any light-directing system of this disclosure or others known in the art. Some embodiments of a vision-corrective device include a light-source system 44113. In an embodiment the light-source system 44113 may include a plurality of light sources. In an embodiment the light sources may provide light energy to one or more light locations 44108. In an embodiment the light locations 44108 are located at the same location as the light sources. In an embodiment, one or more light locations 44108 may be located at the surface of the light sources. In some embodiments, the light-source system 44113 may further include a relay system like that depicted in FIG. 3 for guiding energy from an energy source 310 through the relay to the plurality of light locations on a surface 350 of the relay. As will be appreciated, the light-source system may include other relays in other embodiments including but not limited to the relays depicted in FIGS. 3-5, 7A, 7B, 14-16, 20-21, and 38A-C. Other relays known in the art may also be used in certain embodiments.

Different embodiments may employ different light sources, or different combinations of light sources. Any energy source described elsewhere in this disclosure may be used in different embodiments as well as other energy sources known in the art. Some examples include, but are not limited to LCD, LED, laser, CRT, OLED, AMOLED, TOLED, pico projector, single chip, 3-chip, LCoS, DLP, Quantum Dots, monochrome, color, projection, backlit, directly emissive, reflective, transparent, opaque, coherent, incoherent, diffuse, direct, or any other illumination source sufficient to produce the desired pixel density as discussed elsewhere in this disclosure.

In an embodiment, the light-directing system 44102 may include an array of waveguides 44104. Different embodiments may have different waveguide structures including the waveguides of this disclosure; however, other embodiments may not utilize waveguides 44104 as a component of the light-directing system 44102. A person of ordinary skill in the art will appreciate that there are also alternative embodiments that are consistent with the disclosures made herein that may utilize alternative light-directing systems.

FIG. 44 depicts an embodiment where light emitted by the plurality of light sources is directed by the array of waveguides 44104 along a plurality of light propagation paths 44106. FIG. 44 is for demonstrative purposes only and does not limit the embodiments disclosed herein. And, additional light propagation paths may be present in additional embodiments as depicted and discussed elsewhere in this disclosure.

One side of each of the propagation paths 44106 extends through one of a plurality of light locations 44108 in the embodiment depicted in FIG. 44. A first waveguide 44110 of the array of waveguides 44104 may be configured to direct light from a first light location 44112 of the plurality of light locations 44108 along a first propagation path 44114 of the plurality of propagation paths 44106. The first propagation path 44114 extends from the first waveguide 44110 in a unique direction. In other words, the first propagation path is the only propagation path that extends from the first waveguide 44110 in that direction. The unique direction of the first propagation path 44114 is determined at least by the first light location 44112. But, it should be appreciated that in some embodiments there may be additional, or other, factors that determine the unique direction. Different types of waveguides 44104 may be utilized in different embodiments. Some embodiment may also combine different types of waveguides. And, this embodiment of the vision-correction device may be combined with the other embodiments of this disclosure unless explicitly stated otherwise including but not limited to the waveguide structures depicted in FIGS. 23-26 and 28-32.

Some embodiments will also include a second waveguide 44116 of the array of waveguides 44104 that is configured to direct light from a second light location 44118 of the plurality of light locations 44108 along a second propagation path 44120 of the plurality of propagation paths 44108. The second propagation path 44120 extends from the second waveguide 44116 in a second unique direction. Similar to the relationship between the first propagation path 44114 and the first waveguide 44110, the second propagation path 44120 is the only propagation path that extends from the second waveguide 44116 in that direction. The second unique direction of the second propagation path 44120 is determined at least by the second light location 44118. And, as mentioned above, in some embodiments there may be additional, or other, factors that may determine the unique direction. A person of ordinary skill in the art will also recognize that some embodiments will also have additional waveguides and propagation paths that extend from a waveguide in a unique direction that is determined at least by a light location. These unique directions provide a means to identify and independently control the propagation paths that extend from the waveguides helping to allow the vision-correction device to make the kinds of specific adjustments needed to tailor the device for an individual user, or in some embodiments, multiple users.

In an embodiment, the vision-corrective device 44100 depicted in FIG. 44 includes a control system 44122. The control system 44122 is configured to operate the plurality of light sources to direct light through the light-directing system 44102 to project a first holographic object 44124 along the plurality of propagation paths 44106 according to a four-dimensional ("4D") light field function. The 4D light field function is determined to account for an uncorrected visual acuity of a first user. Some embodiments may also include a processor, which is discussed elsewhere in this disclosure. Other embodiments may also include a memory, which is discussed elsewhere in this disclosure.

In some embodiments, the unique direction can be determined at least by a first light location 44112. Some embodiments allow the first waveguide 44110 to define a two-dimensional (2D) spatial coordinate wherein the unique direction determined at least by the first light location 44112 includes a two-dimensional (2D) angular coordinate, and whereby the 2D spatial coordinate and the 2D angular coordinate form a 4D light field coordinate set. Energy waveguide systems allowing these types of embodiments have been discussed previously in this disclosure using at least FIGS. 22-26 and 28-32 as non-limiting demonstrative illustrations. Some embodiments of the light-directing system 44100 of FIG. 44 include an energy waveguide system 44102 that allows 2D spatial coordinate and the 2D angular coordinate form a 4D light field coordinate set as illustrated in FIG. 23.

In an embodiment, light directed along the first propagation path 44114 through the first waveguide 44110 substantially fills a first aperture 44128 of the first waveguide 44110. In an embodiment, the waveguides of the vision-correction device 44100 may include different waveguides including but not limited to those discussed in reference to FIGS. 22-32. Some embodiments may also employ more than one waveguide. Other embodiments may use other waveguide structures known in the art in combination with waveguides of this disclosure, or instead of the waveguides of this disclosure.

In an embodiment, the light-directing system 44102 includes a first light-inhibiting element 44130 positioned to limit propagation of light along a portion of the plurality of propagation paths that do not extend through the first aperture 44128. In an embodiment, the first light-inhibiting element 44130 includes a baffle structure for attenuating or modifying the portion of propagation paths that do not extend through the first aperture. In an embodiment, the first light-inhibiting element 44130 may include any kind of light-inhibiting element referenced in this disclosure or known in the art.

In an embodiment, light directed along the second propagation path 44120 through the second waveguide 44116 substantially fills a second aperture 44132 of the second waveguide 44116. Furthermore, as mentioned above, in different embodiments, the waveguides of the vision-correction device, including the first, second, and any additional waveguides, may include the different waveguides of this disclosure including but not limited to those discussed in reference to FIGS. 24-26 and 28-32. Some embodiments may also employ more than one waveguide of this disclosure. Other embodiments may use other waveguide structures known in the art in combination with waveguides of this disclosure, or instead of the waveguides of this disclosure.

In an embodiment, the light-directing system 44102 includes a second light-inhibiting element 44134 positioned to limit propagation of light along a portion of the plurality of propagation paths that do not extend through the second aperture 44132. In an embodiment, the second light-inhibiting element 44134 includes a baffle structure for attenuating or modifying the portion of propagation paths that do not extend through the second aperture 44132. In some embodiments, the second light-inhibiting element 44134 may include any kind of light-inhibiting element referenced in this disclosure or known in the art.

In some embodiments, additional propagation paths extending from waveguides in unique directions may also substantially fill additional apertures of the additional waveguides. The additional waveguides may also include additional light-inhibiting elements positioned to limit propagation of light along a portion of propagation paths that do not extend through any aperture, and may include baffles in some instances. However, the light-inhibiting elements may also include any of the other light-inhibiting elements referenced in this disclosure. Unless explicitly stated otherwise, embodiments of the vision-correction device including waveguides, apertures, light-inhibiting elements, and baffles, may be combined with the other embodiments of this disclosure. In an embodiment, light directed along the first propagation path 44114 may converge with light directed along the second propagation path 44120. Additional propagation paths extending in unique directions from additional waveguides may also converge rays of energy or light in space as described elsewhere in this disclosure.

Figure 45A:
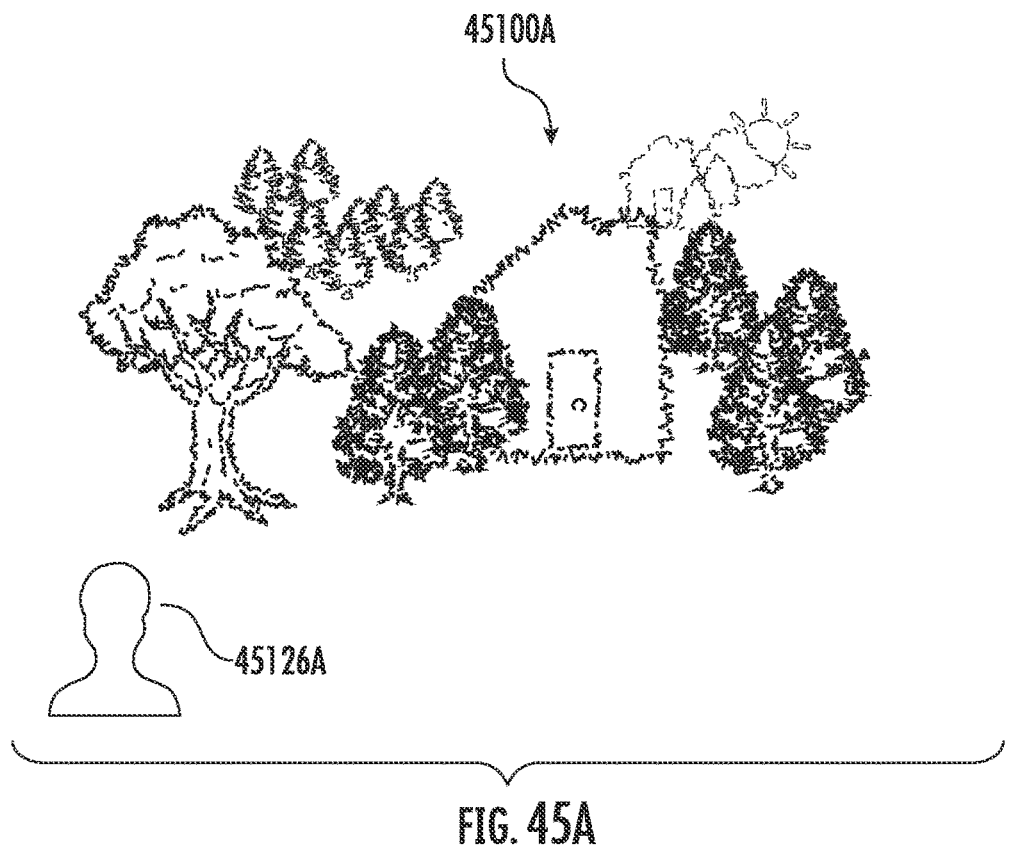
FIG. 45A illustrates an uncorrected visual acuity of a person in the real world.

FIG. 45A depicts an uncorrected visual acuity 45100A, which represents how a user with an uncorrected visual acuity perceives the real world without any corrective lenses or visual adjustments. It should be appreciated that uncorrected visual acuities will vary by individual so there are a multitude of possible uncorrected visual acuities. FIG. 45A is included for demonstrative purposes and a 4D light field function can be determined for the vision-correction device 44100 to account for many different uncorrected visual acuities, as described elsewhere in this disclosure.

Figure 45B:
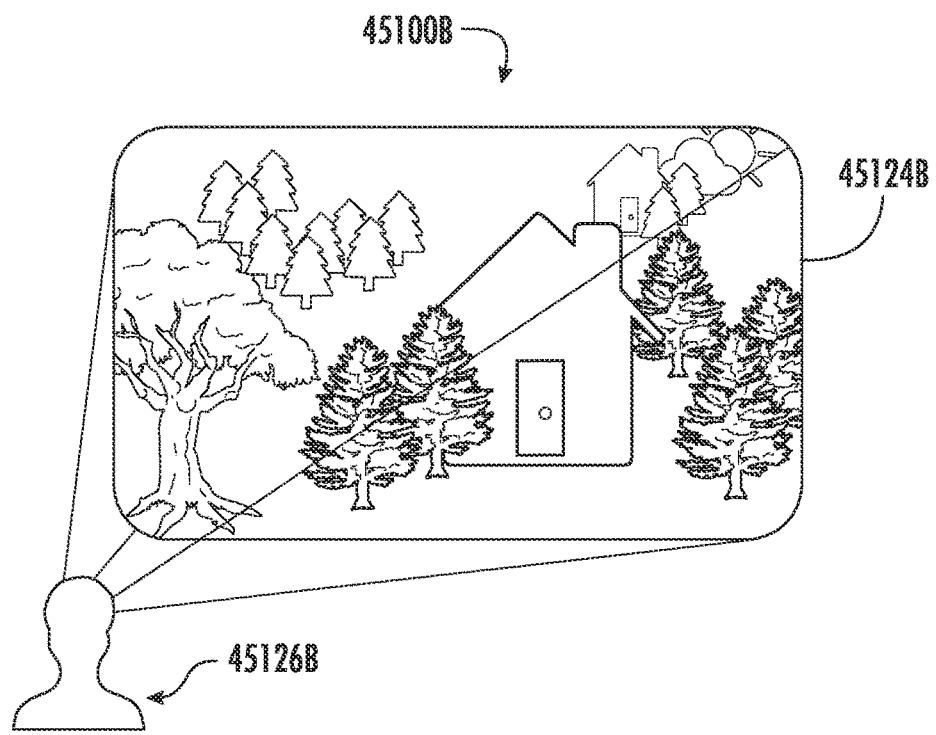
FIG. 45B illustrates a corrected visual acuity of a user viewing a holographic objected projected according to a 4D light field function determined to account for an uncorrected visual acuity.

FIG. 45B illustrates a corrected visual acuity of a user viewing a holographic objected projected according to a 4D light field function determined to account for an uncorrected visual acuity. The 4D light field function tailors the projection of the first holographic object 45124B for the first user 45126B so he or she can view the first holographic object 45124B with a first corrected visual acuity 45100B. This allows the first user 45126B to see the first holographic object 45124B clearly without the use of prescriptive lenses or other visual aids. Embodiments allowing users to perceive objects with corrected visual acuities can be combined with the other embodiments described herein unless explicitly stated otherwise.

Figure 46B:
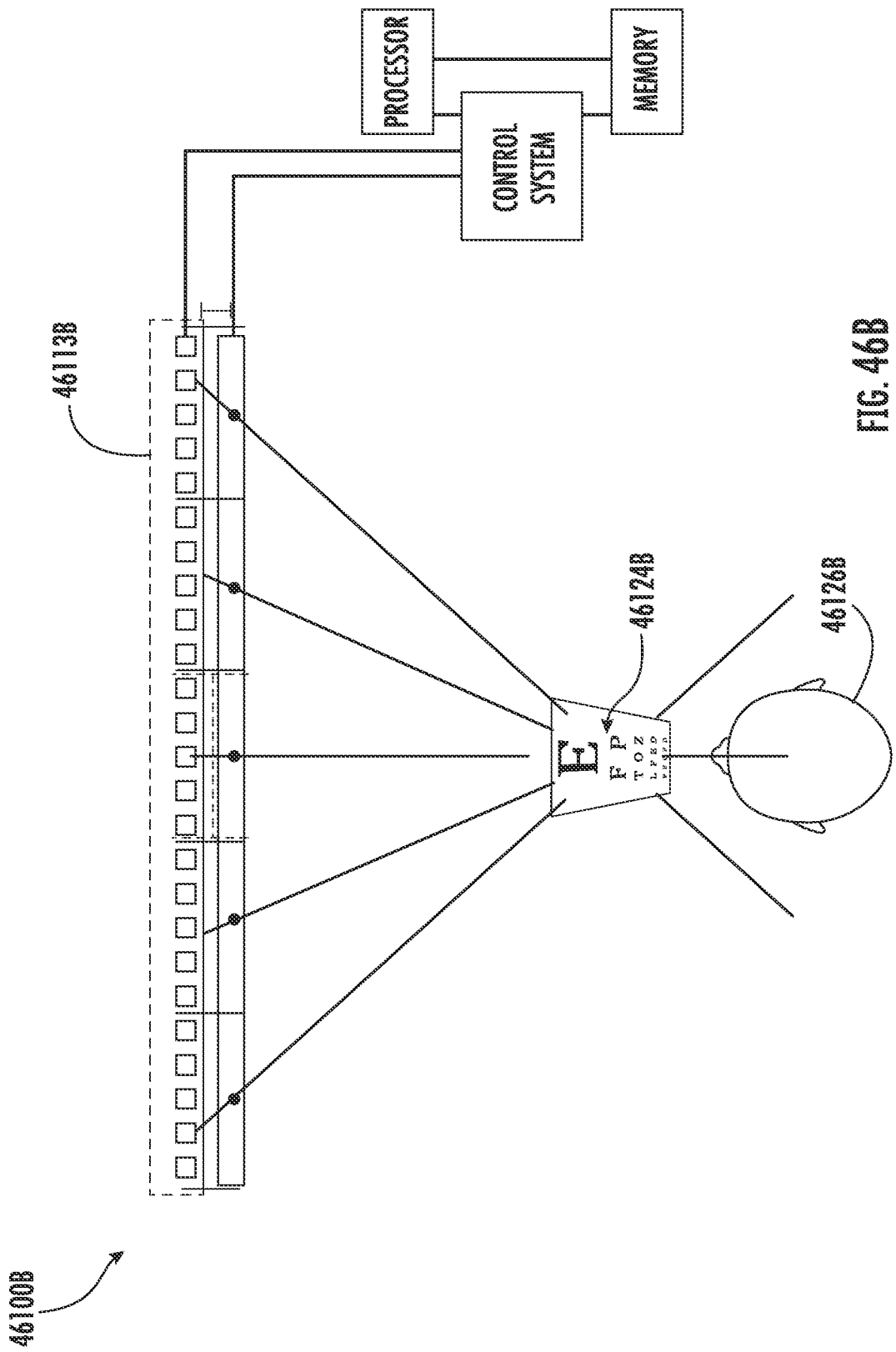
FIG. 46B illustrates an embodiment of a vision-correction device calibrated to project a Snellen eye chart.

Some embodiments of the vision-correction device 46100A allow additional types of objects to be projected other than holographic objects. Referring to FIG. 46A, in some embodiments, the control system 46122A can operate the plurality of light sources of the light-source system 46113A to direct light through the light-directing system 46102A to project a two-dimensional object 46124A according to a 4D light field function determined to account for an uncorrected visual acuity of a first user 46126A. This allows the first user 46126A to perceive the 2D object with a corrected visual acuity without the aid of corrective lenses. The 2D object 46124A can include a page from a book as depicted in FIG. 46A. This embodiment allows a user to clearly see a page of a book without corrected lenses when the same user would need corrective lenses or other visual aids to enjoy the book without the vision-corrective device of this disclosure. In some embodiments, successive pages of a book can be projected as successive 2D objects allowing a user to read a book without corrective lenses.

A variety of techniques known in the art can be employed in different embodiments either in isolation or in combination to allow the user to move from page to page of a book. Some illustrative examples include, but are not limited to touch screens, remote controls, audio controls, and motion sensing, among others. Any other 2D objects can also be projected, including, but not limited to a Snellen eye chart 46124B, as depicted in the embodiment of the vision-correction device 46100B shown FIG. 46B. Embodiments of the vision-correction device 46100B allow simultaneous projection of 2D objects and holographic objects. Embodiments of the vision-correction device 46100B that allow projections of 2D objects can be combined with the other embodiments of this disclosure unless explicitly stated otherwise including but not limited the energy waveguide system 44100.

Referring to FIG. 47, in some embodiments of the vision-correction system 47100 of this disclosure, the control system 47122 can operate the plurality of light sources of the light-source system 47113 to direct light through the light-directing system 47102 to project a stereoscopic object 47124 according to a 4D light field function determined to account for an uncorrected visual acuity of a first user 47126. This allows the first user 47126 to perceive the stereoscopic object with a corrected visual acuity without the aid of corrective lenses. In such embodiments, the user may use polarized glasses 47144, or other means known in the art to view the stereoscopic object 47124. Some embodiments of the vision-correction device may allow simultaneous projection of any combination of holographic, 2D, or stereoscopic objects. Embodiments of the vision-correction device 47100 that allow projection of a stereoscopic object 47124 can also be combined with the other embodiments of this disclosure unless explicitly stated otherwise including but not limited the energy-waveguides of FIGS. 23-26 and 28-32.

It should also be appreciated by one skilled in the art that in addition to static, fixed objects, the vision-correction device may also allow for successive projections of 2D, stereoscopic or holographic images or clips. In doing so this may allow viewers to watch 2D, stereoscopic, or holographic movies, television shows or other video content without corrective lenses or other visual aids.

Embodiments of the vision-correction device described herein may allow many different types of imperfections to be corrected independently or simultaneously. This gives the vision-correction device advantages over traditional corrective lenses. The teachings disclosed herein allow holographic, 2D, stereoscopic of other types of objects to be projected according to a 4D light field function determined to account for an uncorrected visual acuity. The 4D light field function can account for users suffering from myopia, hyperopia, astigmatisms, presbyopia or other vision problems and project a holographic, 2D, or stereoscopic object that allows such users to perceive holographic, 2D, or stereoscopic objects with a corrected visual acuity.

However, many people may have more than one type of vision problem. For example, a user may have myopia and astigmatism. Another user may have myopia and presbyopia. Still another user may have vision that requires a different power of dioptric adjustment at different depths to correct their vision. For example, a single user's vision may require one optical power adjustment to correct objects at a distance of 40 feet, but require a second optical power adjustment to correct objects at a distance of 60 feet. A single-vision lens cannot account for more than one vision problem at a time. Bifocal and multifocal lenses can help correct more than one type of vision problem. But, multifocal lens can only address a limited number of visual problems and can cause image jumping when a user focuses through different areas of the multifocal lenses.

Embodiments of the vision-correction device disclosed herein do not face the same shortcomings because the vision-correction device may allow control over the content of the light field projected by the vision-corrective device at the source of the light field rather than attempting to introduce an outside element, like a lens, into an existing light field to manipulate how the existing light field is received by the user into her or his eye.

Figure 48A:
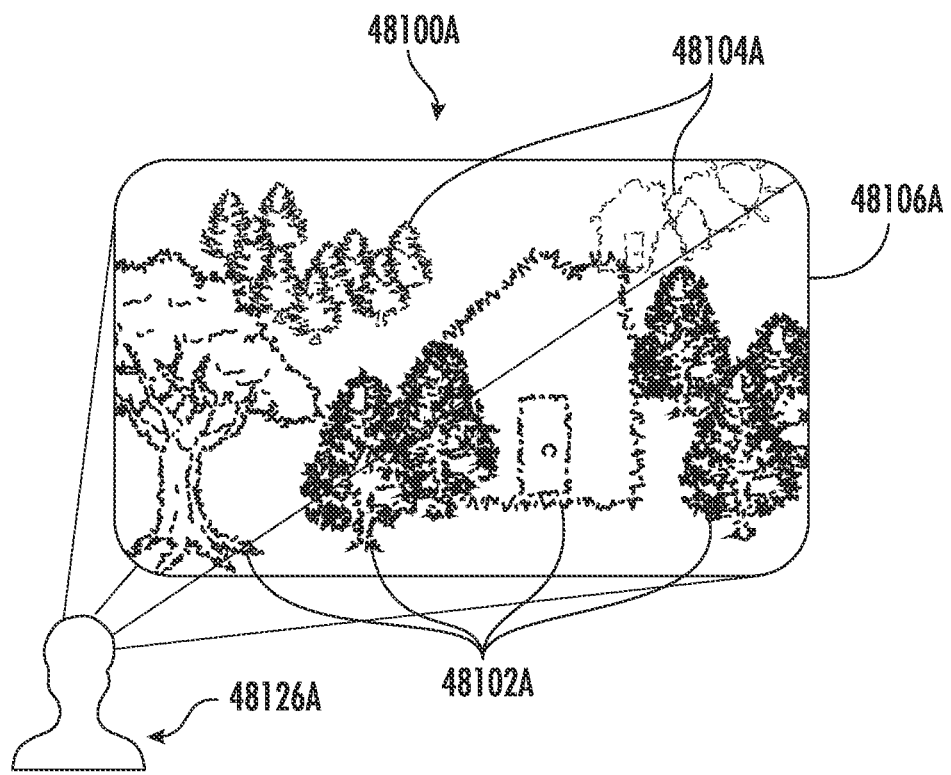
FIG. 48A illustrates a projected object as perceived by a user with an uncorrected visual acuity.
Figure 48B:
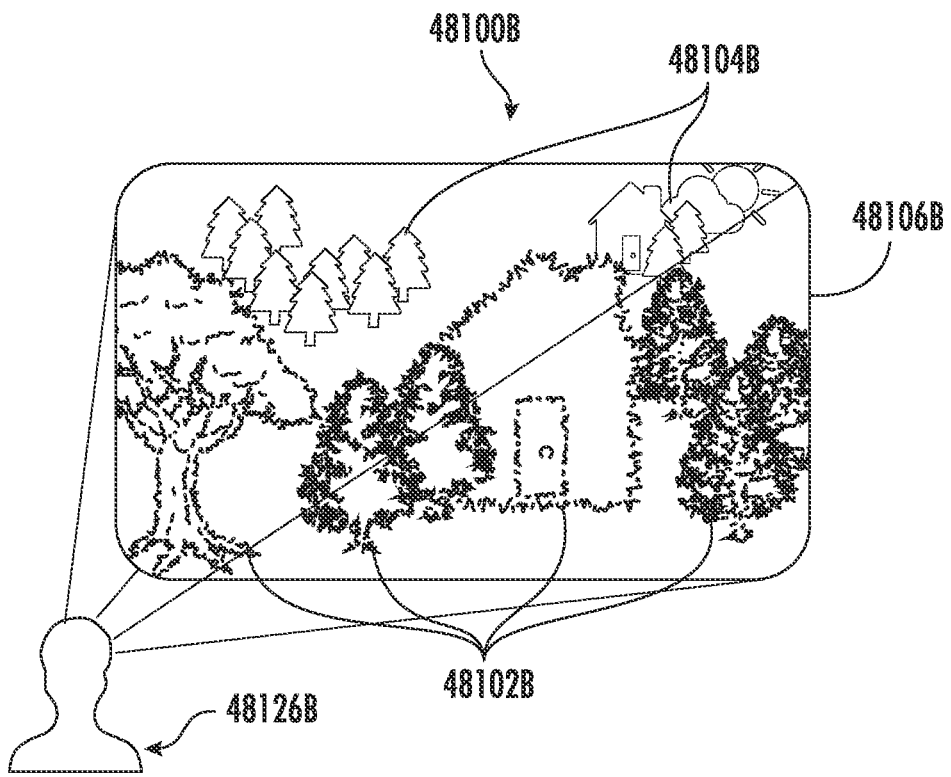
FIG. 48B illustrates a projected object as perceived by a user with a partially corrected visual acuity.

FIG. 48A helps demonstrate this principle. The user 48126A has an uncorrected visual acuity 48100A. The projected object 48106A includes foreground objects 48102A and background objects 48104A. As depicted, both appear blurry to the user 48126A. A single-vision lens may only correct for a vision problem at one of these two depths so either the foreground or the background may still appear blurry to users. FIG. 48B demonstrates a partially-corrected acuity 48100B where background objects 48104B are clear and foreground objects 48102B remain unclear in the projected object 48106B to user 48126B. Another optical adjustment may produce a visual acuity where foreground objects are clear and background objects are unclear.

Figure 48C:
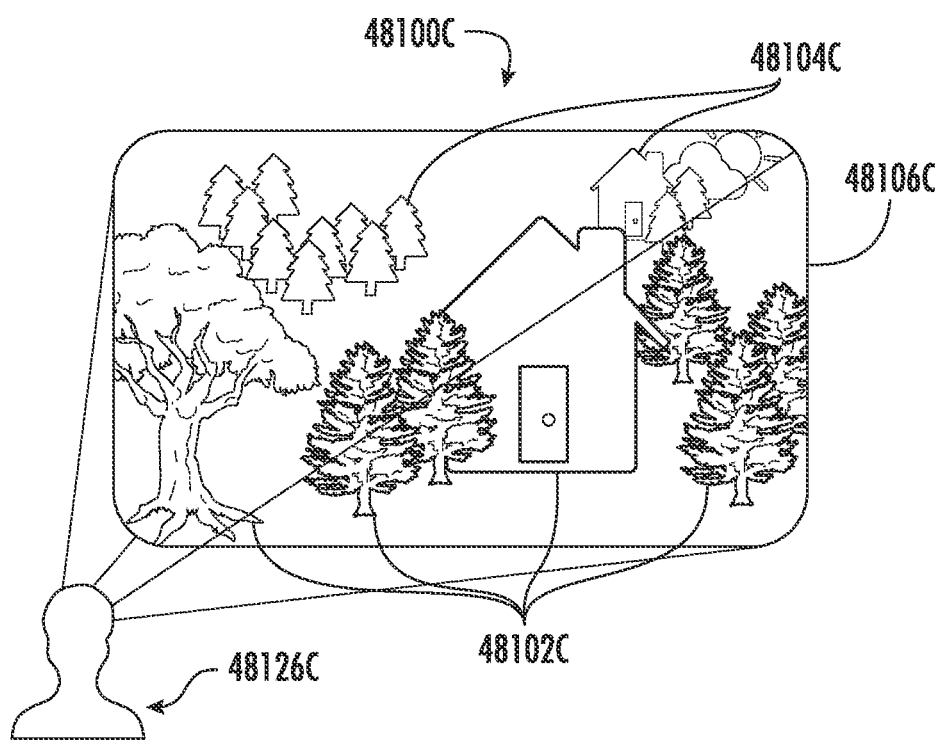
FIG. 48C illustrates a projected object as perceived by a user with a corrected visual acuity.

To help a user with multiple vision problems at multiple depths more than one optical-power adjustment may be required, which is not possible for a single-focus lens. This is also problematic for a multi-focal lens because of image jumping, limited lens space for different optical powers, and manufacturing considerations. However, embodiments of the vision-correction device of this disclosure allow control over the projected light that forms the foreground objects 48102C and the background objects 48104C of a projected object 48106C for user 48126C. This control allows the vision-correcting device to simultaneously make independent adjustments at both depths according to the 4D light field function determined to account for user's vision problems. This yields a corrected visual acuity 48100C, as depicted in FIG. 48C, where the user 48126C is able to perceive both the foreground 48102C and the background 48104C clearly. In some embodiments, the vision-correction device of this disclosure can therefore allow for simultaneous, independent adjustments to correct for multiple vision problems like myopia, hyperopia, astigmatism, and presbyopia. In one embodiment, the 4D light field function can account for the uncorrected visual acuity of the user, where the uncorrected visual acuity includes correction by an optical power correction. In some embodiments, the vision-correction device may also allow for simultaneous optical-power corrections at multiple depths. Unless explicitly stated to the contrary, these embodiments may be combined with other embodiments described herein.

In an embodiment, the vision-correction device may also simultaneously correct for different problems in different eyes. Individuals may need different vision corrections for their left and right eyes. And, in many cases, the eye prescription needed to correct a person's vision may have different optical power adjustments for left and right eyes. The 4D light field function can be determined to account for corrective needs that vary from eye to eye and use eye-tracking technology, as described elsewhere in this disclosure, to ensure that each eye receives light information that allows a user to see a projected object with a corrected visual acuity in each eye as depicted in FIG. 49. The vision-correction device 49100 can project a left object 49124L corrected for the specific visual problems of the user's 49126 left eye. And, the vision-correction device 49100 can project a right object 49124R corrected for the specific visual problems of the user's 49126 right eye. These embodiments can be combined with embodiments that allow for simultaneous correction of multiple vision problems and simultaneous correction at multiple depths so the vision-corrective device can simultaneously correct multiple vision problems at multiple depths in each eye. And, unless explicitly stated otherwise, these embodiments can be combined with the other embodiments of this disclosure.

Figure 50A:
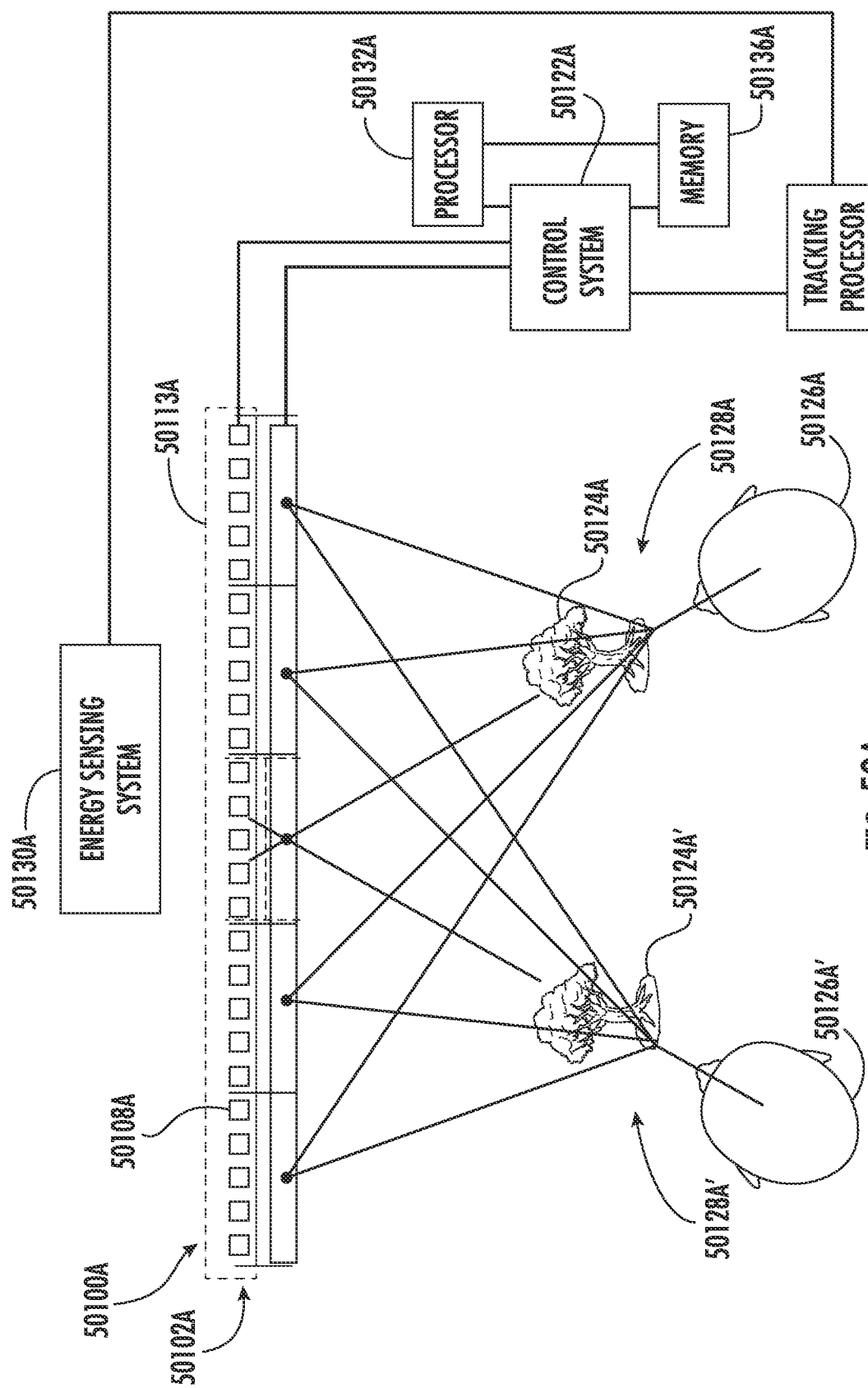
FIG. 50A illustrates an embodiment of a vision-correcting device that projects different objects to different users.

Embodiments of the vision-corrective device 50100A also allow projection of a second 2D, holographic, or stereo object. As depicted in FIG. 50A the control system 50122A can be configured to operate the plurality of light sources to direct light through the light-directing system 50102A to project a first 2D, stereoscopic, or holographic object 50124A to a first user 50126A, as already been described, and a second 2D, stereoscopic, or holographic 50124A' object according to a second 4D light field function that has been determined to account for an uncorrected visual acuity of a second user 50126A'. This allows the second user 50126A' to perceive the second holographic object 50124A' with a corrected visual acuity. Embodiments that allow the projection of a second holographic object 50124A' can also be combined with other embodiments of the vision-correcting device disclosed herein to allow the second 4D light field function to simultaneously account for multiple vision problems, simultaneously correct for vision problems that vary by depth, and simultaneously correct vision problems that vary from the right eye of the second user from the left eye of the second user.

The second 4D light field function may account for myopia, hyperopia, presbyopia, astigmatism and other eye conditions. These embodiments can also be combined with embodiments discussed above that allow projection of 2D objects, or stereoscopic objects. Like the 2D objects referenced above, the second 2D object can also comprise pages of a book, or a Snellen eye chart. In some embodiments, the vision-correction device 50100A allows the projection of a first holographic, 2D or stereoscopic object that is perceived by a first user with a first corrected visual acuity tailored for the first user, and simultaneous projection of a second holographic, 2D, or stereoscopic object that can be perceived by the second user with a second corrected visual acuity tailored to the second user. These embodiments also allow the vision-correction device 50100A to project multiple, additional holographic, 2D, or stereoscopic objects that are determined by multiple, additional 4D light field functions to account for additional uncorrected visual acuities of multiple, additional users whereby the multiple, additional holographic, 2D, or stereoscopic images are perceivable by the multiple, additional viewers with corrected visual acuities. Embodiments allowing projection of a second-holographic object may also be combined with embodiments discussed elsewhere in this disclosure wherein there are second, and additional propagation paths extending from additional waveguides that substantially fill apertures of the waveguides. Combination with waveguides that further comprise light-inhibiting elements such as baffles is also allowed by this disclosure, and the discussions and drawings relevant to the aforementioned embodiments are incorporated herein. Finally, unless explicitly stated to the contrary, these embodiments can be combined with the embodiments of this disclosure.

As depicted in FIG. 50A, in an embodiment the control system 50122A may operate the plurality of light sources of the light-source system 50113A to direct light through the light-directing system 50102A to project a first holographic, 2D, or stereoscopic object 50124A, according to a first 4D light field function, to a first-viewing zone 50128A, and to project a second holographic, 2D, or stereoscopic object 50124A', according to a second 4D light field function, to a second-viewing zone 50128A'. This may allow the first user 50126A to perceive the first holographic object, 2D, or stereoscopic object 50124A with a corrected visual acuity when the first user 50126 is located in the first-viewing zone 50128A. Further, it may also allow the second user 50126A' to perceive the second holographic, 2D or stereoscopic object 50124A' with a corrected visual acuity when the second user 50126A' is located in the second-viewing zone 50128A'.

In an embodiment, the first 4D light field function is able to account for the location of the first user 50126A so that the first holographic, 2D or stereoscopic object 50124A can be perceived by the first user 50126A with the first corrected visual acuity when the first user 50126A is at one of a continuum of distances for vision correction. In other words, the first 4D light field function is able to do this continuously regardless of the distance of the first-viewing zone 50128A from the light-directing system 50102A. Likewise, in an embodiment, the second 4D light field function is able to account for the location of the second user 50126A' so that the second holographic, 2D or stereoscopic object 50124A' can be perceived by the second user 50126A' with the second corrected visual acuity when the second user 50126A' is at one of a continuum of distances for vision correction. In other words, the second 4D light field function is able to do this continuously regardless of the distance of the second-viewing zone 50128A' from the light-directing system 50102A.

In some instances, the second holographic, 2D, or stereoscopic object 50124A' may look blurry to the first user 50126A if the first user 50126A is viewing the second holographic, 2D, or stereoscopic object 50124A' from the second-viewing zone 50128A', assuming that the first user and second user require differing corrections of visual acuity. This is because the second 4D light field function is determined to account for the uncorrected visual acuity of the second user 50126A' and will not account for the uncorrected visual acuity of the first user 50126A.

Likewise, the first holographic, 2D or stereoscopic object 50124A may look blurry to the second user 50126A', if the second user 50126A' is viewing the first holographic, 2D, or stereoscopic object 50124A from the first-viewing zone 50128A. This is because the first 4D light field function is determined to account for the uncorrected visual acuity of the first user 50126A and may not account for the uncorrected visual acuity of the second user 50126A'. This can also provide a measure of security because holographic, 2D, or stereoscopic object projections can be specifically calibrated for the vision of a specific user so they can perceive the holographic, 2D, or stereoscopic object with a corrected visual acuity.

In operation, each of first user 50126A and second user 50126A' may be sitting in their respective viewing zones 50128A and 50128A' while each views the object tailored to their own vison. The first object 50124A and the second object 50124A' can include alternate versions of the same content that may be individually calibrated for the vision of the first user 50126A and the second user 50126A', respectively. In the alternative, the first object 50124A and the second objects 50124A' can include separate content that the first user 50126A and the second user 50126A' can perceive while sitting side-by-side. In some embodiments, the vision-correction device may include multiple, additional viewing zones for the projection of multiple, additional objects as determined by multiple, additional 4D light field functions to account for various, uncorrected visual acuities of multiple, additional users.

In an embodiment, the energy-sensing system may include an eye tracking system having an energy sensor 50130A as well as eye tracking software run on the processor 50132A. The energy sensor 50130A of the eye tracking system or energy-sensing system may be a single camera, more multiple cameras, a depth sensor, another type of imaging device, or any combination of these devices, or other devices known in the art. The energy sensor 50130A may be external to the display, as shown in FIG. 50A, as a device which may be placed on top of the display, to the side of the display, or be integrated into the display as a bidirectional energy surface that simultaneously projects a light field and senses light from the environment in front of the display surface, shown as 50130B in FIG. 50B. In such an embodiment, the tracking processor 50132B may be configured to determine the location of the first user 50126B and the second user 50126B' based on data received from the eye tracking system energy sensor 50130B. The tracking processor 50132B may leverage algorithms knowns in the art to analyze and process information generated by the eye tracking system or energy-sensing system to track the location of the user 50126B, 50126B'. In some embodiments, the tracking processor 50132B may allow eye and retinal tracking of any users to allow targeted projections of light energy.

In some embodiments, the location of the first-viewing zone 50128A and the location of the second-viewing zone 50128A' may be determined by the positions of the first user 50126A and second user 50126A', respectively, which as discussed above, may be determined by an energy-sensing system, which may optionally include an eye-tracking system. In other embodiments, the location of the first-viewing zone 50128A and the second-viewing zone 50128A' may move as the first user 50126A and the second user 50126A' is moving. The viewing zones may follow the users as they move and allows the first 50124A and second 50124A' holographic, 2D, or stereoscopic objects to be projected to the appropriate user. In other words, the tracking processor is able to dynamically track the location of the first user and the second user based on energy data received from an energy-sensing system, and where the location of the first-viewing zone 50128A may follow movement of the first user 50126A while the location of the second-viewing zone 50128A' may follow movement of the second user 50126A'. In other words, the tracking processor is able to do this whether the users 50126A, 50126A' are moving closer or further away from the vision-correction device.

In some embodiments, the vision-correction device may include multiple, additional objects and multiple, additional users with multiple, additional corresponding viewing zones that follow the respective multiple, additional users, as they move about. These embodiments can also be combined with the other embodiments of this disclosure. For example, the 4D light field functions can each be determined to simultaneously account for multiple vision problems, vision problems that vary by depth or by eye as discussed elsewhere in this disclosure. These embodiments can also be combined with the energy waveguides and all the light-inhibiting elements of this disclosure. Unless explicitly stated, all these embodiments may be combined with the other embodiments of this disclosure. FIG. 50A is provided for descriptive purposes only and does not limit the embodiments of this disclosure.

As discussed above, the eye-tracking system energy sensor or energy-sensing system 50130A may include a plurality of cameras for capturing image data. In an embodiment, the energy-sensing system 50130A may be a single camera. In another embodiment, the energy-sensing system 50130A may include multiple cameras for capturing images at multiple angles. In such embodiments, the tracking processor may analyze data captured by the camera or cameras 50130A to determine the location of the first, second or any additional users so the vision-correcting device can project a holographic, 2D, or stereoscopic object according to a 4D light field function determined to account for the uncorrected visual acuities of each of the users to a viewing zone for that user so each user can perceive the object with a corrected visual acuity. Additionally, the viewing zones may dynamically follow the users as the user moves about as described elsewhere in this disclosure.

In an embodiment, the eye-tracking energy sensor or energy-sensing system 50130A may include at least one depth sensor. In operation, the tracking processor may analyze data generated by the depth sensor to determine the location of the first, second or any additional multiple users so the vision-correcting device can project a holographic, 2D, or stereoscopic object according to a 4D light field function determined to account for the uncorrected visual acuities of each of the users to a viewing zone for that user so each user can perceive the object with a corrected visual acuity. In some embodiments, the eye-tracking energy sensor or energy-sensing system 50130A may include a combination of one or more cameras and one or more depth sensors.

Figure 50B:
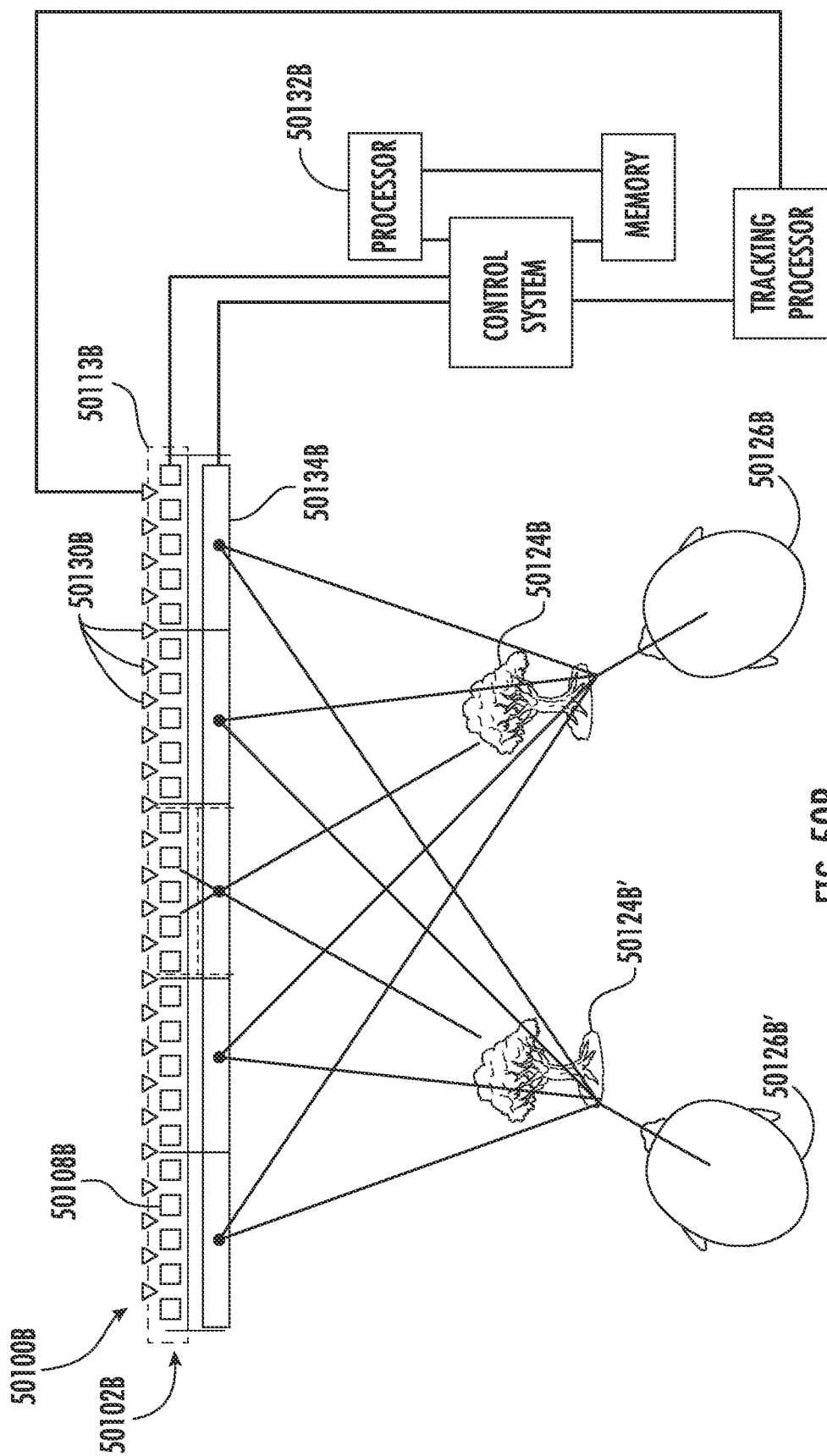
FIG. 50B illustrates another embodiment of a vision-correcting device that projects different objects to different users.

In operation, the eye-tracking system energy sensor or energy-sensing system 50130B may be configured to generate data describing a 4D light field function by sensing light received at the array of waveguides 50134B as shown in FIG. 50B. In an embodiment, the display surface may be a bi-directional energy surface configured to simultaneously sense imaging data and project holographic, 2D, and stereoscopic objects. Like above, the light-source system and light sensor locations may be behind the waveguides 50134B within the light-directing system 50102B. The tracking processor 50133A can analyze the data describing the 4D light field to determine the location of the first 50126B, second 50126B' or any additional users so the vision-correcting device can project a holographic, 2D, or stereoscopic object 50124B, 50124B' according to one or more 4D light field functions determined to account for the individual uncorrected visual acuity of each of the users.

Similar to above, the vision-correction device of FIG. 50B may include a processor 50132B having a tracking processor, the processor 50132B and the tracking processor being distinctive units. And like above, the viewing zones maybe dynamically tracked as the users are moving via the eye-tracking energy sensor 50130B having one or more camera or depth sensor, and configured to sense energy received at the interface of the array of waveguides 50134B. These embodiments may be combined with other energy-sensing system, energy waveguide system and light-inhibiting elements as disclosed herein allowing for a single user or single viewing zone or for multiple users and multiple viewing zones.

As depicted in FIGS. 50A-50B, the vision-correcting device 50100 may also include a memory 50136 in communication with the control system 50122. In some embodiments, the control system 50122 stores the 4D light field function in the memory 50136. The memory 50136 allows the vision-correcting device 50100 to store 4D light field functions that account for an individual user's 50126 uncorrected visual acuity. This allows the vision-correction device 50100 to access a 4D function light field function calibrated for a specific user 50126 so that user can view holographic, 2D, or stereoscopic objects 50124 with a corrected visual acuity. In some embodiments, multiple 4D light field functions that correspond to multiple users can be stored on the memory 50136. And, data describing the 4D light field function can be received by the vision-correction device 50100 from any data-transfer method known in the art. For example, data describing the 4D light field function can be uploaded from the Internet, a USB, or manually entered into a user interface. Additionally, the 4D light field function can be calculated by the vision-correction device 50100 as described in more detail elsewhere in this disclosure. Unless explicitly noted otherwise, embodiments of the vision-correction device that include a memory can be combined with the other embodiments described herein, e.g., memory processor for carrying out the instructions for storing data and information, among others.

In one embodiment, a processor with the memory 50136 can be configured to instruct the memory 50136 to store at least one additional 4D light field function where the at least one additional 4D light field function is determined to account for a first uncorrected visual acuity of at least one additional user, and where the processor is configured to instruct the memory 50136 to associate at least one of a user name of the least one additional user, a user profile of the least one additional user, and a user identification of the least one additional user with the least one additional 4D light field function stored in the memory 50136.

In some embodiments, the vision-correction device 50100 may include relay systems as described elsewhere throughout this disclosure and will not be elaborated further herein. In an embodiment, the relay system may include one or more relay elements, where each relay element has first and second surfaces and configured to direct light emitted by the plurality of light sources along the plurality of propagation paths through the first and second surfaces to the plurality of light locations. In some instances, like above, the second surfaces of the relay elements may be arranged to form a singular seamless energy surface.

Figure 51A:
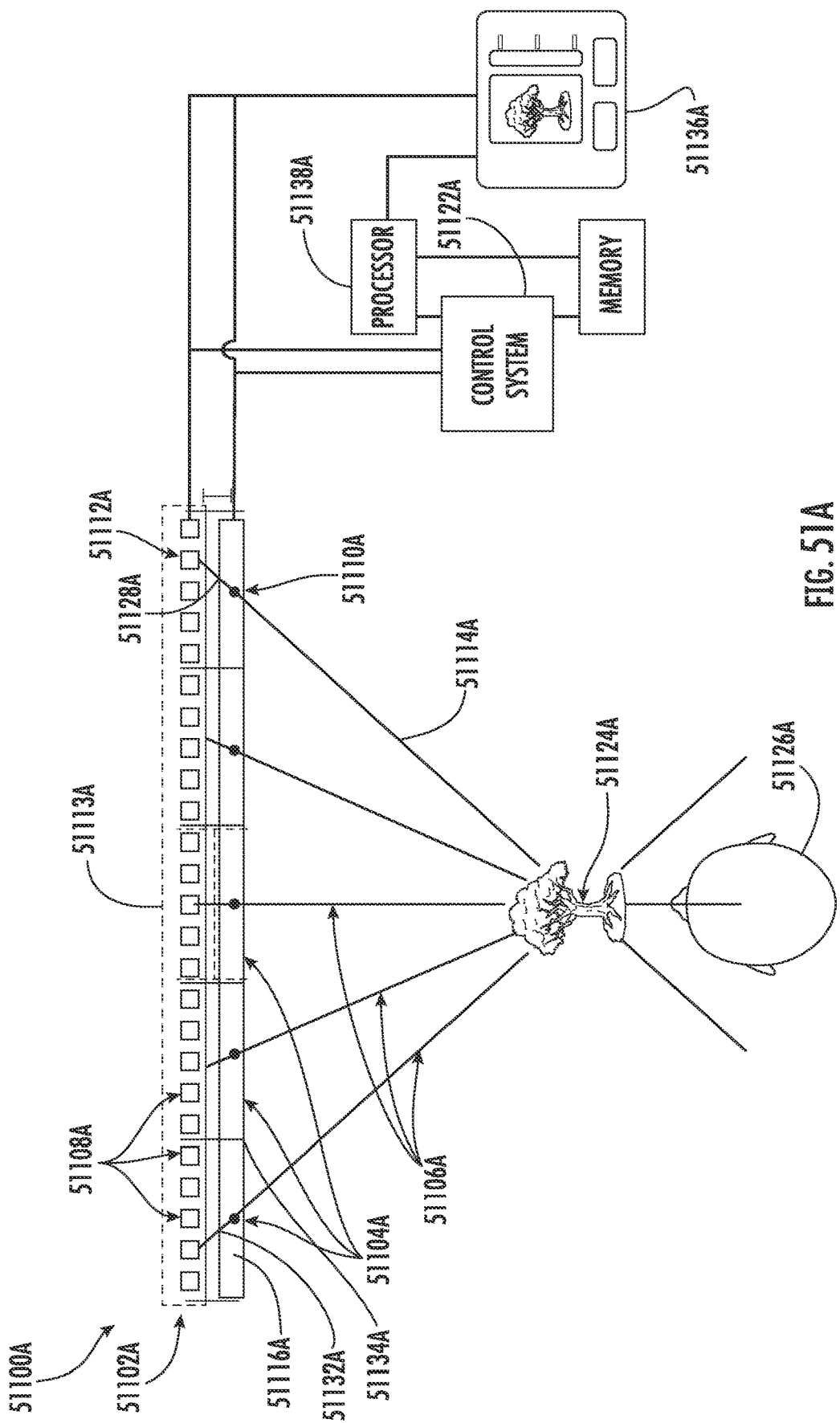
FIG. 51A illustrates an embodiment of a vision-correcting device that generates a 4D light field function determined to account for an uncorrected visual acuity of a user.

As discussed above, the vision-corrective device may calculate the 4D light field function(s). An example of one such device is depicted in FIG. 51A. In an embodiment, the vision-correction device 51100A includes a light-source system 51113A having a plurality of light sources similar to other embodiments of this disclosure. As can be appreciated by a person of ordinary skill in the art, a variety of different types of light sources, as discussed elsewhere in this disclosure, may be used.

In an embodiment, the vision-correction device 51100A includes a light-directing system 51102A having an array of waveguides 51104A. In some embodiments, the vision-correction device 51100A may or may not utilize waveguides as a component of the light directing system 51102A. And, as a person of ordinary skill in the art will appreciate, there may be alternative embodiments that are consistent with the disclosures made herein that may be used as the light-direction system.

In operation, light sources of the light-source system 51113A may be directed from the array of waveguides 51104A along a plurality of light propagation paths 51106A. Each propagation path 51106A extends through one of a plurality of light locations 51108A of the light-source system 51113A. In an embodiment, a first waveguide 51110A of the array of waveguides 51104A is configured to direct light from a first light location 51112A of the plurality of light locations 51108A along a first propagation path 51114A of the plurality of propagation paths 51106A. The first propagation path 51114A extends from the first waveguide 51110A in a unique direction meaning it is the only propagation path to extend from the first waveguide 51110A in that direction. The unique direction is determined at least by the first light location 51112A. But, it should be appreciated that in other embodiments there may be additional, or other, factors that determine the unique direction. It should also be noted that FIG. 51A represents a demonstrative example and does not limit the embodiments of this disclosure. Additional embodiments with additional propagation paths, waveguides, and propagation paths extending from additional unique directions may be used.

In one embodiment, the vision-correction device of FIG. 51A also includes a control system 51122A configured to operate the plurality of light sources of the light source system 51113A to direct light through the light-directing system 51102A to project a test object 51124A along the plurality of propagation paths 51106A. And like above, the device may include a processor 51138A configured to generate a 4D light field function from the progression of user inputs that is determined to account for an uncorrected visual acuity of the user 51126A.

In an embodiment, the device includes an interactive user interface 51136A. In some embodiments, the interactive user interface 51136A may include any types known in the art including but not limited to touch screens, keyed inputs, voice recognition, tactile or gesture tracking, among others. The user interface 51136A may be configured to receive a progression of inputs from a user 51126A for ranking the user's perception of the visual clarity of the test object 51124A.

Figure 51C:
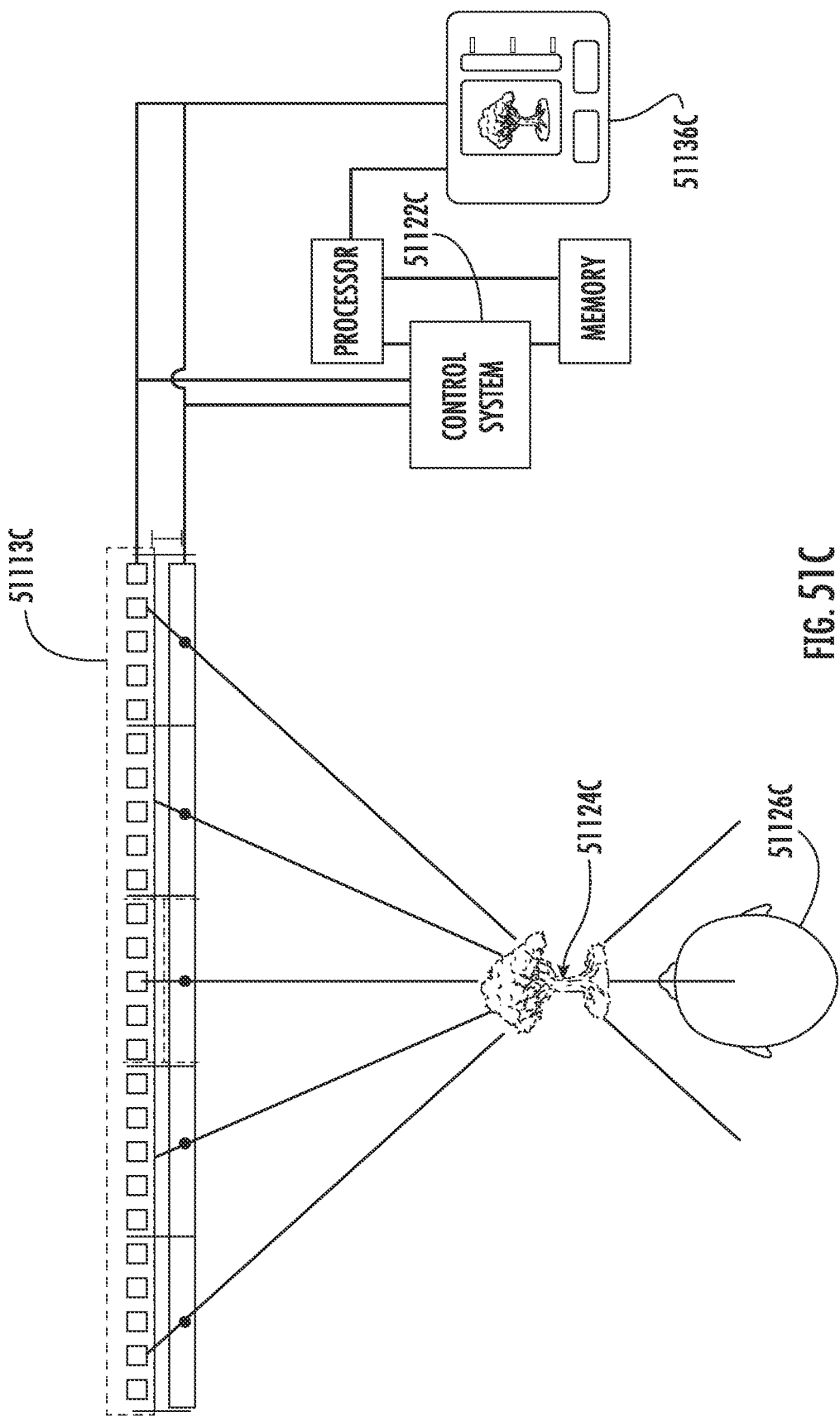
FIG. 51C illustrates a second iteration of a test object.

In operation, the control system 51122A may be configured to iteratively adjust the test object 51124A as the user enters input into the user interface 51136 ranking the visual clarity of the test object 51124A. Adjustments can include successive diopter and astigmatism corrections determined by the progression of user inputs ranking the visual clarity of the test object 51124A. FIGS. 51A, 51B, and 51C demonstrate an example of the iterative process.

FIG. 51B shows a first iteration of the test object 51124B as perceived by the user 51126B. The user 51126B inputs data into the user interface 51136B ranking the clarity of the first iteration of the test object 51124B. If the user input indicates that adjustment is necessary, the control system 51122B uses the input to make diopter or astigmatism corrections to the test object 51124B to produce a second iteration of the test object 51124C as shown in FIG. 51C. Next, the user 51126C ranks the clarity of the second iteration of the test object 51124C. If further adjustment is necessary, the control system 51122C will make additional diopter or astigmatism corrections as determined by the user input via the user interface 51136C, and this process will continue until the user perceives the test object 51124A as sufficiently clear, as shown in FIG. 51A. The processor 51138A then uses the progression of user inputs ranking the visual clarity of the iterations of the test object 51124A to generate a 4D light field function determined to account for the eyesight of the user 51126A that accounts for the uncorrected visual acuity of that user. Embodiments of the vision-correction device 51100A that allow the vision-correction device 51100A to calculate a 4D light field function determined to account for the eyesight of a user—including embodiments with an interactive user interface—can be combined with the other embodiments of this disclosure unless specifically denoted otherwise. This includes but is not limited to waveguide energy systems, light inhibiting elements, and vision-correction devices that allow projection of holographic, 2D, or stereoscopic objects that are perceivable by a user, or users, with a corrected visual acuity or acuities.

Different ranking schemes can be utilized. In an embodiment, a user is allowed to rank the test object 51124A with each eye independently. And the control system 51122A can make adjustments and independently run the iterative process described above for each eye to create a progression of user input that allows the processor 51138A to generate a 4D light field function that can simultaneously account for an uncorrected visual acuity for each of a user's 51126A two eyes. In other embodiments, the uncorrected visual acuity includes a left uncorrected visual acuity for the left eye of the first user, and a right uncorrected visual acuity for the right eye of the first user, and the 4D light field function further simultaneously accounts for the left uncorrected visual acuity and for the right uncorrected visual acuity.

Figure 52:
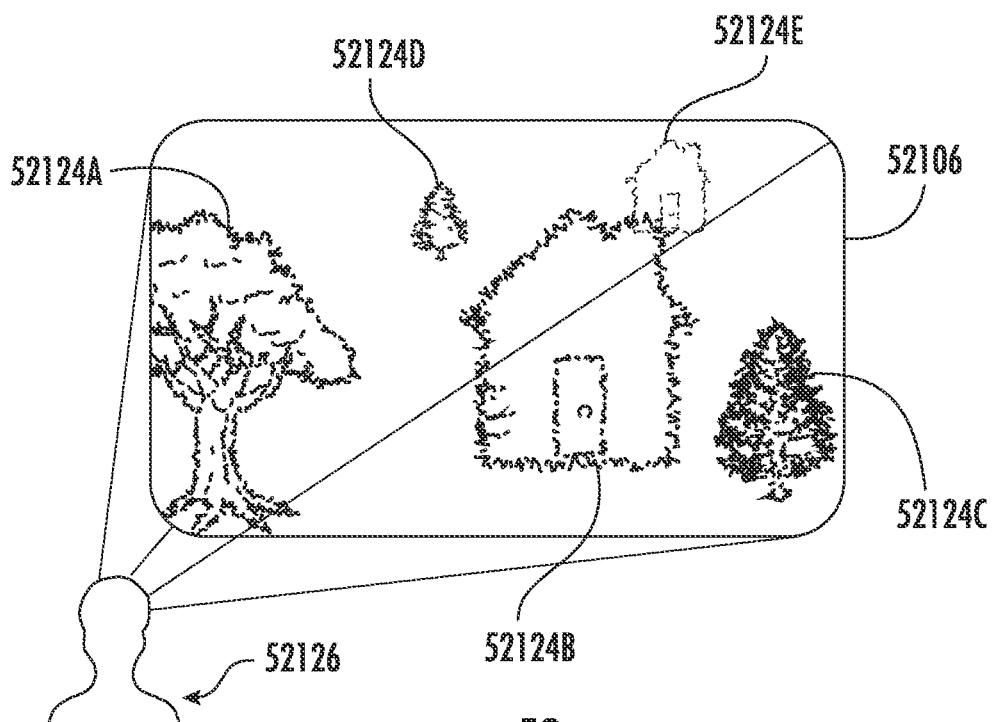
FIG. 52, FIG. 53, and FIG. 54 illustrate how a 4D light field function can be generated to account for multiple uncorrected visual acuities.
Figure 53:
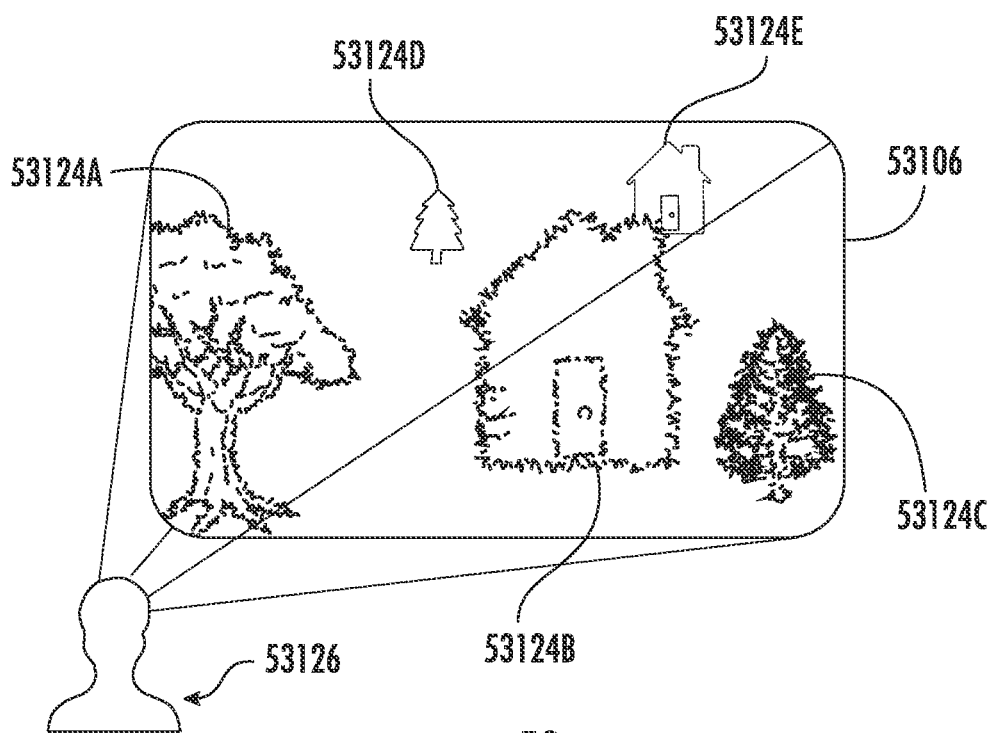
Figure 54:
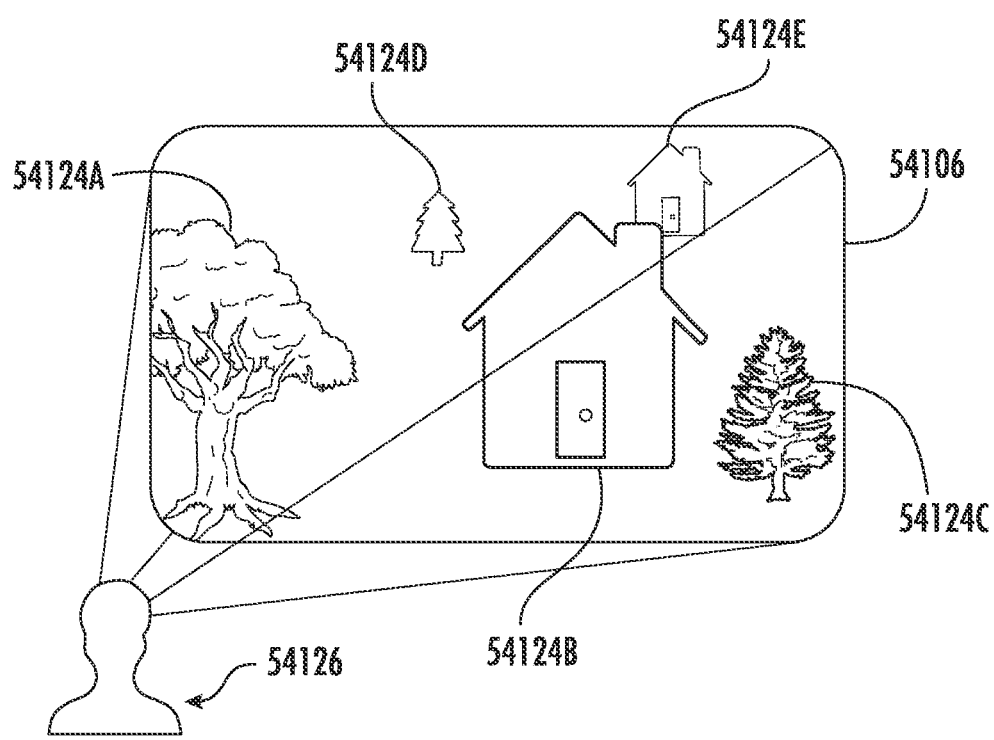

Some ranking schemes may also allow the vision-correction device 51100A to calculate a 4D light field function to account for multiple visual imperfections that may occur at different depths, or visual imperfections that vary from the right and left eye of a user. As shown in FIG. 52, the test object 52106 may include a plurality of sub-objects 52124A-52124E located at different depths, e.g., distances. The user can then rank the visual clarity of each sub-object 52124A-52124E. And, as described above, the control system can iteratively adjust each sub-object 52124A-52124E until each sub-object 52124A-52124E is sufficiently clear as shown in FIGS. 53-54. The progressive user input collected during the iterative adjustments allow the processer to generate a 4D light field function determined to account for more than one vision problem, and vision problems that vary at different distances. In some embodiments, each sub-object may iteratively be adjusted one at a time. And, in other embodiments, the user may rank all the sub-objects in a single iteration of the test object. The next iteration may include a test object where all the sub-objects have been adjusted. In another embodiment, the first test object may include a plurality of sub-objects perceivable to the first user at a corresponding plurality of perceived distances, where the progression of user inputs from the first user ranks the visual clarity of the plurality of sub-objects. In other words, in an embodiment, the uncorrected visual acuity may include a plurality of uncorrected visual sub-acuities or sub-objects of a user where the user perceives all visible objects equidistant to the user with the same uncorrected visual sub-acuity or sub-object, and where the 4D light field function further simultaneously accounts for the plurality of uncorrected visual sub-acuities or sub-objects by a plurality of simultaneous optical power corrections, each optical power correction corresponding to an uncorrected visual sub-acuity or sub-object.

Embodiments ranking sub-objects or sub-acuities may be combined with the other embodiments disclosed herein unless explicitly stated otherwise. For example, embodiments that allow the user to rank the clarity of the test object for each eye may also allow the user to rank the clarity of a plurality of sub-objects for each eye to create a progression of user inputs that allow the processor to generate a 4D light field function that simultaneously accounts for multiple vision imperfections for each eye that can vary at different depths.

Figure 55:
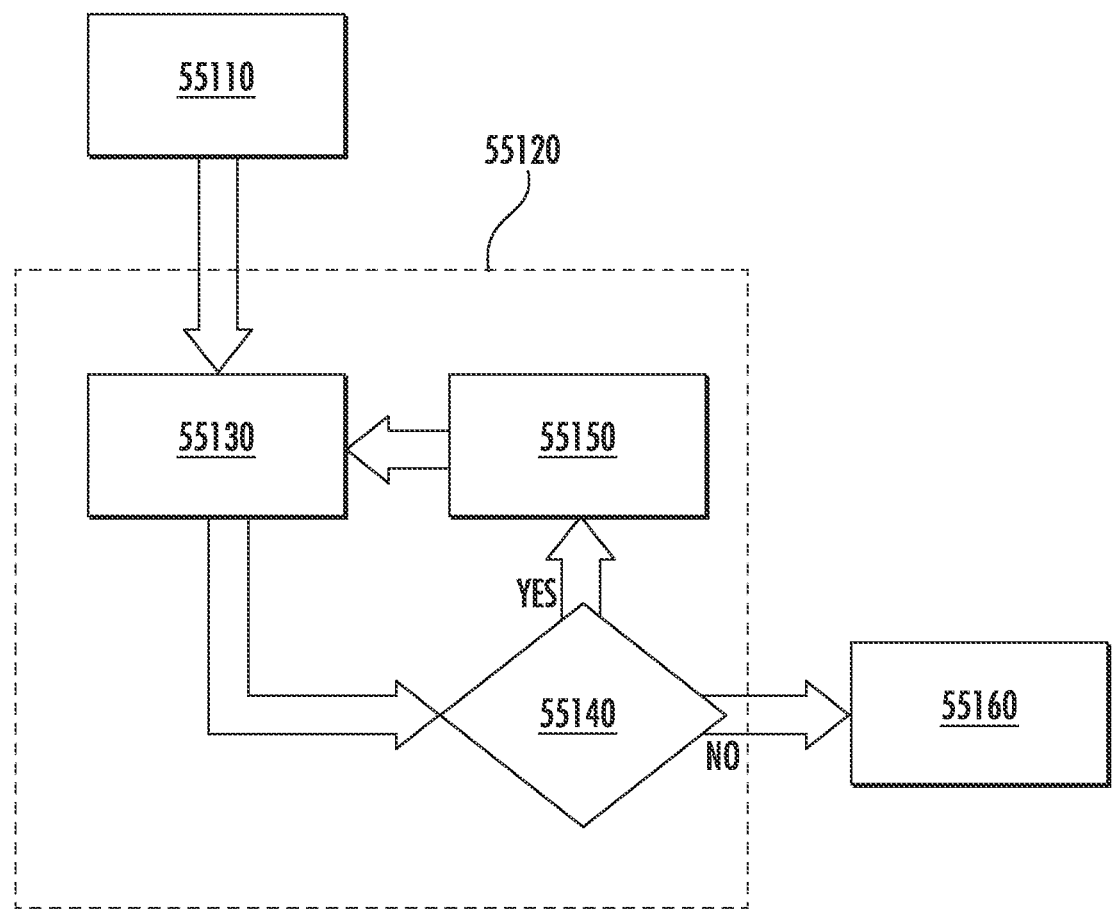
FIG. 55 illustrates a method for calibrating a 4D light field display.

In an embodiment, a method for calibrating a four dimensional (4D") light field display operable to project a 2D, stereoscopic, or holographic object according to a 4D light field function for a user with an uncorrected visual acuity is disclosed herein as depicted in FIG. 55. In one example, the method may include the use of a 4D light field display to project a test object 55110. The test object may include a 2D, stereoscopic, or holographic object, among other. Next, the method may include a step 55120 to iteratively adjust the projection of the test object according to a progression of user inputs evaluating the clarity of the test object. A user evaluates 55130 the clarity of the test object and inputs data into an interactive user interface. In step 55140 it is determined whether the test object needs to be adjusted according to the user input entered in that iteration. If yes, then the test object is adjusted in step 55150 and the user evaluates 55130 the adjusted test object again. This iterative process continues until it is determined in step 55140 that no more adjustments are needed and a 4D light field function is generated 55160 from the progression of user inputs. In operation, the 4D light field display employs the corrected 4D light field function to calibrate holographic, 2D, or stereoscopic projections to correct for any vision problems of the user.

In an embodiment, adjusting the test object includes a progression of successive diopter and astigmatism corrections. The test object can include a 2D or stereoscopic object. In some embodiments the test object may be a Snellen eye chart. In operation, the user evaluates the clarity of the test object by reading lines from the Snellen eye chart. The test object can also include a plurality of sub-objects, each sub-object being projected at a unique depth in the user's field of view. In other embodiments, evaluating the clarity of the test object includes evaluating the clarity of each sub-object. The 4D light field function can be generated to account for myopia, hyperopia, astigmatism or presbyopia in the uncorrected visual acuity of the user. In some embodiments, the 4D light field function can account for a user with a plurality of visual imperfections in the uncorrected visual acuity of the user, among others. In other embodiment, the method may be repeated for additional users to project additional holographic objects calibrated to account for vision problems of the additional users.

The uncorrected visual acuity can include a left uncorrected visual acuity for the left eye of the user, and a right uncorrected visual acuity for the right eye of the user. In such cases, the 4D light field function may simultaneously accounts for the left uncorrected visual acuity and for the right uncorrected visual acuity. In some embodiments, the 4D light field function accounts for the uncorrected visual acuity of the user, where the uncorrected visual acuity may be correctable by an optical power correction. In other embodiments, the 4D light field function accounts for an uncorrected visual acuity of a user with a plurality of optical power adjustments that account for a plurality of uncorrected visual sub-acuities of the user corresponding to vision at a plurality of different distances.

While various embodiments in accordance with the principles disclosed herein have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

It will be understood that the principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically, and by way of example, although the headings refer to a "Field of Invention," such claims should not be limited by the language under this heading to describe the so-called technical field. Further, a description of technology in the "Background of the Invention" section is not to be construed as an admission that technology is prior art to any invention (s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. In general, but subject to the preceding discussion, a numerical value herein that is modified by a word of approximation such as "about" may vary from the stated value by at least ±1, 2, 3, 4, 5, 6, 7, 10, 12 or 15%.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result. Words relating to relative position of elements such as "near," "proximate to," and "adjacent to" shall mean sufficiently close to have a material effect upon the respective system element interactions. Other words of approximation similarly refer to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature.

The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A device for vision correction, the device comprising:
a light-source system configured to provide light to a plurality of light locations and comprising a plurality of light sources;
a light-directing system comprising;
an array of waveguides configured to direct light emitted by the plurality of light sources along a plurality of propagation paths wherein each propagation path extends through one of the plurality of light locations; and
wherein a first waveguide of the array of waveguides is configured to direct light from a first light location through the first waveguide along a first propagation path of the plurality of propagation paths wherein the first propagation path extends from the first waveguide in a unique direction determined at least by the first light location; and
a control system configured to operate the plurality of light sources to direct light through the light-directing system to project a first holographic object along the plurality of propagation paths according to a four-dimensional ("4D") light field function that has been determined to account for an uncorrected visual acuity of a first user, whereby the first holographic object is perceivable by the first user with a first corrected visual acuity.

2. The device of claim 1, wherein the first waveguide defines a two-dimensional ("2D") spatial coordinate, and wherein the unique direction determined at least by the first light location comprises a two-dimensional angular coordinate, whereby the 2D spatial coordinate and the 2D angular coordinate form a 4D light field coordinate set.

3. The device of claim 1, wherein the control system is further configured to operate the plurality of light sources to direct light through the light-directing system to project a first 2D object according to the 4D light field function that has been determined to account for the uncorrected visual acuity of the first user, whereby the projected object is perceivable by the first user with the first corrected visual acuity.

4. The device of claim 3, wherein the first 2D object comprises at least one of a page of a book and a Snellen eye chart.

5. The device of claim 1, wherein the control system is further configured to operate the plurality of light sources to direct light through the light-directing system to project a first stereoscopic object according to the 4D light field function that has been determined to account for the uncorrected visual acuity of the first user, whereby the first stereoscopic object is perceivable by the first user with the first corrected visual acuity.

6. The device of claim 1, wherein the 4D light field function accounts for at least one of myopia, hyperopia, astigmatism, presbyopia, and a plurality of visual imperfections in the uncorrected visual acuity of the first user.

7. The device of claim 1, wherein the uncorrected visual acuity comprises a plurality of uncorrected visual sub-acuities of the first user wherein the first user perceives all visible objects equidistant to the first user with the same uncorrected visual sub-acuity, and further wherein the 4D light field function simultaneously accounts for the plurality of uncorrected visual sub-acuities by a plurality of simultaneous optical power corrections, each optical power correction corresponding to an uncorrected visual sub-acuity.

8. The device of claim 1, further comprising:
an energy-sensing system configured to sense energy data; and
a tracking processor configured to determine the location of the first user based on the energy data received from the energy-sensing system.

9. The device of claim 8, wherein the 4D light field function has also been determined to account for the location of the first user so the first holographic object is perceivable by the first user with the first corrected visual acuity when the first user is at one of a continuum of distances from the device for vision correction.

10. The device of claim 8, wherein the tracking processor tracks the location of the eyes of the one or more users.

11. The device of claim 10, wherein the uncorrected visual acuity comprises a left uncorrected visual acuity for the left eye of a first user, and a right uncorrected visual acuity for the right eye of a first user wherein the 4D light field function accounts for the left uncorrected visual acuity and the right uncorrected visual acuity.

12. The device of claim 1, wherein the control system is configured to operate the plurality of light sources to direct light through the light-directing system to project a second holographic object according to a second 4D light field function that has been determined to account for an uncorrected visual acuity of a second user, whereby the second holographic object is perceivable by the second user with a second corrected visual acuity.

13. The device of claim 12, wherein the control system is configured to project the first holographic object to a first-viewing zone and project the second holographic object to a second-viewing zone.

14. The device of claim 13, wherein the location of the first-viewing zone and the location of the second-viewing zone are determined by the location of the first user and the second user.

15. The device of claim 13, wherein a tracking processor is configured to dynamically track the location of the first and second users based on energy data received from an energy-sensing system and wherein the location of the first-viewing zone follows the movement of the first user, and the location of the second-viewing zone follows the movement of the second user.

16. The device of claim 12, further comprising:
an energy-sensing system configured to sense energy data; and
a tracking processor configured to determine the location of the first and second users based on the energy data received from the energy-sensing system.

17. The device claim of 16, wherein the energy-sensing system comprises a plurality of cameras that capture image data, and further wherein the tracking processor analyzes the image data to determine the location of the first and second users.

18. The device of claim 16, wherein the second 4D light field function has also been determined to account for the location of the second user so the second holographic object is perceivable by the second user with the second corrected visual acuity when the second user is at one of a continuum of distances from the device for vision correction.

19. The device claim of 16, where the energy-sensing system comprises at least one depth sensor, and further wherein the tracking processor analyzes data generated by the depth sensor to determine the location of the first and second users.

20. The device of claim 16, wherein the energy-sensing system is configured to generate data describing a 4D light field by sensing light received at an interface, and further wherein the tracking processor analyzes the data describing a 4D light field to determine the location of the first and second users.

21. The device of claim 16, wherein the tracking processor tracks the location of the eyes of the first and second users.

22. The device of claim 21, wherein the uncorrected visual acuity comprises a left uncorrected visual acuity for the left eye of the first user, and a right uncorrected visual acuity for the right eye of the first user, further wherein the 4D light field function simultaneously accounts for the left uncorrected visual acuity and for the right uncorrected visual acuity.

23. The device of claim 1 wherein the light-source system further comprises a relay system, wherein the relay system comprises one or more relay elements, wherein each of the one or more relay elements comprises a first surface and a second surface, and wherein the plurality of light sources are disposed at the second surface of the one or more relay elements, the one or more relay elements configured to direct light emitted by the plurality of light sources through the first and second surfaces to the plurality of light locations.

* * * * *